(12) United States Patent
Guo et al.

(10) Patent No.: US 9,725,433 B2
(45) Date of Patent: *Aug. 8, 2017

(54) COMPOUNDS AS TYROSINE KINASE MODULATORS

(71) Applicant: Allergan, Inc., Irvine, CA (US)

(72) Inventors: Xialing Guo, San Clemente, CA (US); Zhen Zhu, Foothill Ranch, CA (US)

(73) Assignee: ALLERGAN, INC., Irvine, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/269,612

(22) Filed: Sep. 19, 2016

(65) Prior Publication Data

US 2017/0066738 A1    Mar. 9, 2017

Related U.S. Application Data

(63) Continuation of application No. 14/793,913, filed on Jul. 8, 2015, now Pat. No. 9,475,801, which is a continuation of application No. 14/054,444, filed on Oct. 15, 2013, now Pat. No. 9,328,103, which is a continuation of application No. 12/875,218, filed on Sep. 3, 2010, now Pat. No. 8,614,234.

(60) Provisional application No. 61/239,603, filed on Sep. 3, 2009, provisional application No. 61/306,616, filed on Feb. 22, 2010, provisional application No. 61/356,699, filed on Jun. 21, 2010, provisional application No. 61/360,531, filed on Jul. 1, 2010.

(51) Int. Cl.
| | |
|---|---|
| *C07D 401/04* | (2006.01) |
| *A61K 31/4427* | (2006.01) |
| *C07D 401/14* | (2006.01) |
| *C07D 405/14* | (2006.01) |
| *C07D 409/04* | (2006.01) |
| *C07D 409/14* | (2006.01) |
| *C07D 413/14* | (2006.01) |
| *C07D 405/00* | (2006.01) |

(52) U.S. Cl.
CPC ......... *C07D 401/04* (2013.01); *C07D 401/14* (2013.01); *C07D 405/00* (2013.01); *C07D 405/14* (2013.01); *C07D 409/04* (2013.01); *C07D 409/14* (2013.01); *C07D 413/14* (2013.01)

(58) Field of Classification Search
None
See application file for complete search history.

(56) References Cited

U.S. PATENT DOCUMENTS

| | | | |
|---|---|---|---|
| 4,966,849 A | 10/1990 | Vallee et al. | |
| 5,217,999 A | 6/1993 | Levitzki et al. | |
| 5,302,606 A | 4/1994 | Spada et al. | |
| 5,330,992 A | 7/1994 | Eissenstat et al. | |
| 5,792,783 A | 8/1998 | Tang et al. | |
| 5,834,504 A | 11/1998 | Tang et al. | |
| 5,883,113 A | 3/1999 | Tang et al. | |
| 5,883,116 A | 3/1999 | Tang et al. | |
| 5,886,020 A | 3/1999 | Tang et al. | |
| 6,541,504 B1 | 4/2003 | Andrews et al. | |
| 6,747,025 B1 | 6/2004 | Andrews et al. | |
| 6,765,012 B2 | 7/2004 | Andrews et al. | |
| 8,614,234 B2 | 12/2013 | Guo et al. | |
| 8,906,944 B2 | 12/2014 | Guo et al. | |
| 9,328,103 B2 | 5/2016 | Guo et al. | |
| 2006/0287343 A1 | 12/2006 | Saavedra et al. | |
| 2007/0197537 A1 | 8/2007 | Blake et al. | |
| 2008/0064718 A1 | 3/2008 | Saavedra et al. | |
| 2008/0312232 A1 | 12/2008 | Kim et al. | |
| 2009/0264440 A1 | 10/2009 | Claridge et al. | |
| 2009/0286984 A1 | 11/2009 | Raeppel et al. | |

FOREIGN PATENT DOCUMENTS

| | | |
|---|---|---|
| EP | 0039051 | 11/1981 |
| JP | 2004528379 A | 9/2004 |
| JP | 2006511518 A | 6/2006 |
| JP | 2008528520 A | 7/2008 |
| JP | 2008533151 A | 11/2012 |

(Continued)

OTHER PUBLICATIONS

18572 Canadian Patent Application No. 2,772,718, Preliminary Amendment, dated Apr. 26, 2012.
18572 European Patent Application No. 10760159.3-2117, Communication pursuant to Rules 161(1) and 162 EPC, dated Apr. 27, 2012.
18572 European Patent Application No. 10760159.3-2117, Publication, dated Jun. 13, 2012.
18572 Japanese Patent Application No. 2012-528084, 2nd Office Action, dated Jan. 7, 2015.
18572 Japanese Patent Application No. 2012-528084, Office Action, dated Aug. 4, 2014.
18572 Japanese Patent Application No. 2012-528084, Response to Office Action, dated Nov. 10, 2014.
Bolen, Joseph, Nonreceptor Tyrosine Protein Kinases, Oncogene, 1993, 2025-2031, 8.

(Continued)

*Primary Examiner* — Zinna Northington Davis
(74) *Attorney, Agent, or Firm* — Jonathan Bass

(57) ABSTRACT

The present invention is directed to novel compounds of Formula I. The compounds of the present invention are potent tyrosine kinase modulators, and are suitable for the treatment and prevention of diseases and conditions related to abnormal activities of tyrosine kinase receptors.

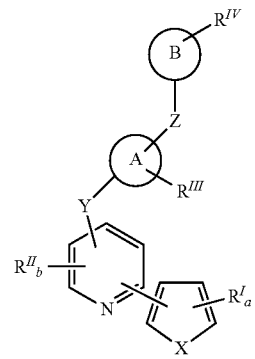

Formula I

10 Claims, 4 Drawing Sheets

(56) References Cited

FOREIGN PATENT DOCUMENTS

| WO | 9115495 | 10/1991 |
| WO | 9220642 | 11/1992 |
| WO | 9221660 | 12/1992 |
| WO | 9403427 | 2/1994 |
| WO | 9414808 | 7/1994 |
| WO | 9920617 | 4/1999 |
| WO | 0290352 | 11/2002 |
| WO | 2004052884 | 6/2004 |
| WO | 2006067446 | 6/2006 |
| WO | 2006081389 | 8/2006 |
| WO | 2006081391 | 8/2006 |
| WO | 2006099379 | 9/2006 |
| WO | 2006116713 A1 | 11/2006 |
| WO | 2006133006 A2 | 12/2006 |
| WO | 2007071455 | 6/2007 |
| WO | 2008046003 A2 | 4/2008 |
| WO | 2009103778 | 8/2009 |
| WO | 2011028995 | 3/2011 |

OTHER PUBLICATIONS

Ciulla, Thomas A., Diabetic Retinopathy and Diabetic Macular Edema, Diabetes Care, 2003, 2653-2654, 26 (9).

Communications to the Editor, A Novel Solution-Stable. Water-Soluble Prodrug Type for Drugs Containing a Hydroxyl or an NH-Acidic Group, Journal of Medicinal Chemistry, Dec. 1989, 2503-2507, 32 (12).

Edelman, Jeffrey et al., Corticosteroids Inhibit VEGF-Induced Vascular Leakage in a Rabbit Model of Blood-Retinal and Blood-Aqueous Barrier Breakdown, Experimental Eye Research, 2005, 249-258, 80.

Edelman, Jeffrey et al., Quantitative Image Analysis of Laser-induced Chorodial Neovascularization in Rat, Exp. Eye Res. 2000, 71: 523-533.

International Search Report and Written Opinion mailed on Dec. 20, 2010 for PCT/US10/47800 filed Sep. 3, 2010 in the name of Allergan, Inc.

International Search Report and Written Opinion mailed on Feb. 17, 2014 for PCT/US13/69337 filed Nov. 8, 2013 in the name of Allergan, Inc.

Jellinek, Derek et al, Inhibition of Receptor Binding by High-Affinity RNA Ligands to Vascular Endothelial Growth Factor, Biochemistry, 1994, 10450-10456, 33.

Kendall, Richard et al, Inhibition of Vascular Endothelial Cell Growth Factor Activity by an Endogenously Encoded Soluble Receptor, Proc. Natl. Acad. Sci., Nov. 1993, 10705-10709, 90.

Kim, Jin et al, Inhibition of Vascular Endothelial Growth Factor-Induced Angiogenesis Suppresses Tumour Growth in Vivo, Nature, Apr. 29, 1993, 841-844, 362(6423).

Kinsella, J.L. et al, Protein Kinase C Regulates Endothelial Cell Tube Formation on Basement Membrane Matrix, Matrigel, Experimental Cell Research, 1992, 56-62, 199.

Mariani, M. et al., Inhibition of Angiogenesis by FCE 26806, A Potent Tyrosine Kinase Inhibitor, Proceedings of the American Association for Cancer Research, Mar. 1994, Abstract 2268, 35.

Plowman, Gregory et al, Receptor Tyrosine Kinases as Targets for Drug Intervention, Drug News & Perspectives, Aug. 1994, 334-339, 7(6).

Silverman, Richard B., Prodrugs and Delivery Systems (Chapter 8), The Organic Chemistry of Drug Delivery and Drug Design and Drug Action Second Edition, 2004, 496-557.

Takano, S. et al, Inhibition of Angiogenesis by a Novel Diaminoanthraquinone that Inhibits Protein Kinase C, Protein Kinases, Wednesday 1993, 2072-2077, Abstract 2 pages, 358a, 2076.

Wright, Paul et al, Inhibition of Angiogenesis in Vitro and in Ovo with an inhibitor of Cellular Protein Kinases, MDL 27032, Journal of Cellular Physiology, Sep. 1992, 448-457, 152(3).

COMPOUNDS AS TYROSINE KINASE MODULATORS

CROSS REFERENCE TO RELATED APPLICATIONS

This application is a continuation of U.S. application Ser. No. 14/793,913, filed Jul. 8, 2015, which is a continuation of U.S. application Ser. No. 14/054,444, filed on Oct. 15, 2013, now U.S. Pat. No. 9,328,103 issued May 3, 2016, which is a continuation of U.S. application Ser. No. 12/875,218, filed on Sep. 3, 2010, now U.S. Pat. No. 8,614,234, issued Dec. 24, 2013, which claims the benefit of U.S. Provisional Application Nos. 61/239,603, filed on Sep. 3, 2009, 61/306,616, filed on Feb. 22, 2010, 61/356,699 filed on Jun. 21, 2010 and 61/360,531 filed on Jul. 1, 2010, all of each which are incorporated herein by reference in their entireties.

FIELD OF THE INVENTION

The present invention is directed to novel compounds with multiple aromatic components capable of modulating, regulating and/or inhibiting tyrosine kinase signal transduction. The present invention is also directed to methods of prevention and/or treatment of disorders related to unregulated tyrosine kinase signal transduction, including but not limited to, cell growth disorders, metabolic disorders, blood vessel proliferative disorders, inflammatory disorders, neurodegenerative diseases and immune disorders.

BACKGROUND OF THE INVENTION

Protein tyrosine kinases ("PTKs") play an important role in the control of cell growth and differentiation. PTKs comprise a large and diverse class of proteins having enzymatic activity. PTKs can be of the receptor-type (having extracellular, transmembrane and intracellular domains) or the non-receptor type (being wholly intracellular). For example, signal transduction mediated by receptor tyrosine kinases ("RTKs") is initiated by extracellular interaction with a specific growth factor (i.e., a ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to RTKs, it has been shown also that tyrosine phosphorylation sites function as high-affinity binding sites for SH2 (src homology) domains of signaling molecules. Several intracellular substrate proteins that associate with RTKs have been identified and are divided into two principal groups: (1) substrates which have a catalytic domain; and (2) substrates which lack a catalytic domain but serve as adapters and associate with catalytically active molecules. The specificity of the interactions between receptors or proteins and SH2 domains of their substrates is determined by the amino acid residues immediately surrounding the phosphorylated tyrosine residue. Differences in binding affinities between SH2 domains and the amino acid sequences surrounding the phosphotyrosine residues on particular receptors are consistent with the observed differences in their substrate phosphorylation profiles. These observations suggest that the function of each RTK is determined not only by its pattern of expression and ligand availability, but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

The RTKs comprise a large family of transmembrane receptors with diverse biological activities. The intrinsic function of RTKs is activated upon ligand binding, which results in phophorylation of the receptor and multiple cellular substrates, and subsequently in a variety of cellular responses. At present, at least nineteen distinct RTK subfamilies have been identified. One RTK subfamily, designated the HER subfamily, is believed to be comprised of EGFR, HER2, HER3 and HER4. Ligands to the HER subfamily of receptors include epithelial growth factor (EGF), TGF-α, amphiregulin, HB-EGF, betacellulin and heregulin. The second subfamily of RTKs, designated the insulin subfamily, is comprised of the INS-R, the IGF-1R and the IR-R. The third RTK subfamily, the "PDGF" family, includes the PDGF α and β receptors, CSFIR, c-kit and FLK-II. Another subfamily of RTKs, identified as the FLK family, is believed to be comprised of the kinase insert domain-receptor fetal liver kinase-1 (KDR/FLK-1), the fetal liver kinase 4 (FLK-4) and the fms-like tyrosine kinase 1 (flt-1). Each of these receptors was initially believed to be a receptor for hematopoietic growth factors. Two other subfamilies of RTKs have been designated as the FGF receptor family (FGFR1, FGFR2, FGFR3 and FGFR4) and the Met subfamily (c-met and Ron). Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs, and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the protein tyrosine kinases (PTKs), whether an RTK or non-receptor tyrosine kinase, have been found to be involved in cellular signaling pathways leading to cellular signal cascades and pathogenic conditions such as cancer, psoriasis and hyper immune responses. In view of the importance of PTKs to the control, regulation and modulation of cell proliferation and the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (Kendall & Thomas, 1994, Proc. Nat'l Acad. Sci 90: 10705-09; Kim, et al, 1993, Nature 362: 841-844), RNA ligands (Jellinek, et al, Biochemistry 33: 10450-56); Takano, et al, 1993, Mol. Bio. Cell 4:358A; Kinsella, et al, 1992, Exp. Cell Res. 199: 56-62; Wright, et al, 1992, J. Cellular Phys. 152: 448-57) and tyrosine kinase inhibitors (U.S. Pat. No. 5,330,992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinyleneazaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

In addition, other small molecules were studied as tyrosine kinase inhibitors, such as the compounds disclosed in U.S. Pat. Nos. 6,765,012; 6,541,504; 6,747,025; 5,792,783; 5,834,504; 5,883,113; 5,883,116 and 5,886,020, all of which are incorporated by reference in their entireties.

The identification and use of compounds which specifically inhibit signal transduction by modulating the activity of receptor and non-receptor tyrosine is one aspect of the present invention.

SUMMARY OF THE INVENTION

The present invention is directed to compounds represented by Formula I capable of modulating, regulating and/or inhibiting tyrosine kinase signal transduction, and uses of the compounds and compositions incorporating the compounds for disease treatment and prevention.

The compounds of the present invention can be found in general Formula I:

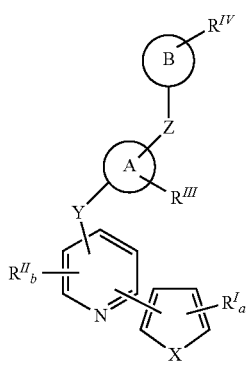

Formula I wherein
X is selected from the group consisting of $NR^1$, O, $S(O)_n$;
n is 0 or an integer of from 1 to 2;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered heterocyclic ring with N;

$R^I$ is selected from the group consisting of hydrogen, halogen, $C_1$ to $C_8$ alkyl, $S(O)_fR^4$, $(CR^5R^6)_dC(O)OR^4$, $S(O)_f(CR^5R^6)_dC(O)OR^4$, $(CR^5R^6)_dAr$, $NR^4(CR^5R^6)_d$ Ar, $O(CR^5R^6)_dAr$, $S(O)_f(CR^5R^6)_dAr$, $(CR^5R^6)_dS(O)_f$ $R^4$, $NR^4(CR^5R^6)_dS(O)_fR^4$, $O(CR^5R^6)_d S(O)_fR^4$, $S(O)_f$ $(CR^5R^6)_eS(O)_fR^4$, $(CR^5R^6)_dC(O)N(R^4)_2$, $NR^4$ $(CR^5R^6)_d C(O)N(R^4)_2$, $O(CR^5R^6)_dC(O)N(R^4)_2$, $S(O)_f$ $(CR^5R^6)_eC(O)N(R^4)_2$, $(CR^5 R^6)_dOR^4$, $S(O)_f(CR^5R^6)_d$ $OR^4$, $(CR^5 R^6)_dOSO_2R^4$, $S(O)_f(CR^5 R^6)_eOSO_2R^4$, $(CR^5 R^6)_dP(O)(OR^4)_2$, $S(O)_f(CR^5 R^6)_eP(O)(OR^4)_2$, $OC(O)(CR^5R^6)_dN(R^4)_2$, $C(O)(CR^5R^6)_dN(R^4)_2$, $C(O)$ $N=S(O)R^5 R^6$, $NR^2C(O)(CR^5R^6)_dN(R^4)_2$, $(CR^5R^6)_d$ $R^5$, $S(O)_f(CR^5R^6)_dR^5$, $HNC(O)R^4$, $HN-C(O)OR^4$, $(CR^5R^6)_dN(R^4)_2$, $S(O)_f(CR^5R^6)_dN(R^4)_2$, $OC(O)OR^4$, $(CR^5R^6)_dC(O)(CR^5R^6)_dR^4$, $(CR^5R^6)_dC(O)(CR^5R^6)_d$ $OR^4$, and $(CR^5R^6)_dC(O)(CR^5R^6)_dN(R^4)_2$, wherein each $R^4$ is independently selected from the group consisting of hydrogen, hydroxyl, $C_1$-$C_8$ alkyl, aryl, $C_1$-$C_8$ hydroxyalkyl, $C_1$-$C_8$ alkoxyalkyl, $(CR^5R^6)_d$ and $N(R^4)_2$ may form a 3-7 membered heterocyclic ring, comprising of aziridine, azetidine, pyrrolidine, 5-fluoropyrrolidine, piperidine, 6-fluoropiperidine, N-methylpiperazine, morpholine, 2,6-dimethylmorpholine, thiomorpholine, and wherein said heterocyclic ring may be optionally substituted with up to three of $R^5$; wherein $R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, sulfonate and $CR^5R^6$ may represent a carbocyclic or heterocyclic ring of from 5 to 6 carbons or alternatively, $(CR^5R^6)_d$ and $(CR^5R^6)_e$ may form a 3-7 membered carbocyclic or heterocyclic ring, wherein the ring may be optionally substituted with up to three of hydroxyl, halo, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl and sulfonate;

a is 0 or an integer of from 1 to 3;
d is 0 or an integer of from 1 to 5;
e is an integer of from 1 to 4;
f is 0 or an integer of from 1 to 2;
$R^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, $(NR^2R^3)$ alkoxy, $(NR^2R^3)$alkenyl, $(NR^2R^3)$alkyl, $(NR^2R^3)$carbonylalkenyl, and $(NR^2R^3)$carbonylalkyl, wherein $R^2$ and $R^3$ are independently selected from the group consisting of hydrogen, alkyl, alkylcarbonyl, alkylsulfonyl, arylsulfonyl, haloalkylsulfonyl, and heterocyclylsulfonyl; alternatively $R^2$ and $R^3$ and may be taken together to form a 5-7 membered heterocyclic ring with N;
b is 0 or an integer of from 1 to 2;
Y is selected from the group consisting of:
(1') —$(CH_2)g$-O—$(CH_2)h$-;
(2') —$(CH_2)g$-$NR^1$—$(CH_2)h$-;
(3') —$(CH_2)g$-$S(O)_n$—$(CH_2)h$-;
(4') —$(CH_2)g$-$SO_2N$ $R^2$—$(CH_2)h$-;
(5') —$(CH_2)g$-$NR^2SO_2$—$(CH_2)h$-;
(6') —$(CH_2)g$-CO—$(CH_2)h$-;
(7') —$(CH_2)g$-$C(O)NR^2$—$(CH_2)h$-;
(8') —$(CH_2)g$-$NR^2C(O)$—$(CH_2)h$-;
(9') —$(CH_2)g$-C≡C—$(CH_2)h$-;
(10') —$(CH_2)g$-$NR^2C(O)NR^3$—$(CH_2)h$-;
(11') —$(CH_2)g$-$(CH_2)h$-;

(12') —(CH$_2$)g-CF$_2$—(CH$_2$)h-;
(13') —(CH$_2$)g-CCl$_2$—(CH$_2$)h-;
(14') —(CH$_2$)g-CHF—(CH$_2$)h-;
(15') —(CH$_2$)g-CH(OH)—(CH$_2$)h-;
(16') —(CH$_2$)g-CR$^2$R$^3$—(CH$_2$)h-;
(17') —(CH$_2$)g-C≡C—(CH$_2$)h-;
and (18') a single bond;

wherein
g is 0 or an integer of from 1 to 3;
h is 0 or an integer of from 1 to 3;
R$^1$ is independently selected from the group consisting of hydrogen, alkenyl, alkoxyalkyl, CF$_3$, alkyl, alkylcarbonyl, alkoxycarbonyl, aryl, heterocycloalkyl, hydroxyalkyl, and alkyl(N R$^2$R$^3$), wherein R$^2$ and R$^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively R$^2$ and R$^3$ and may be taken together to form a 5-7 membered heterocyclic ring with N;
R$^2$ and R$^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively R$^2$ and R$^3$ and may be taken together to form a 5-7 membered cyclic ring;
Ring A is selected from the group consisting of:

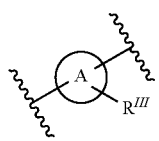

(i) Phenyl;
(ii) Naphthyl;
(iii) A 5 or 6 membered monocyclic heteroaryl group which have 1-5 heteroatoms independently selected from the group consisting of O, N and S;
and (iv) An 8 to 10 membered bicyclic heteroaryl group which have 1-6 heteroatoms independently selected from the group consisting of O, N and S;
Ring A can be illustrated but not limited to the following:

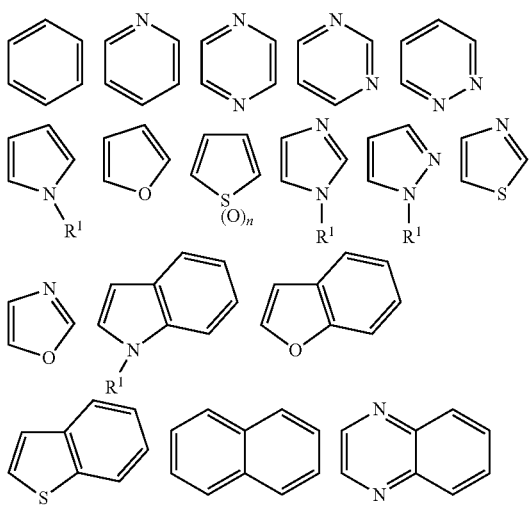

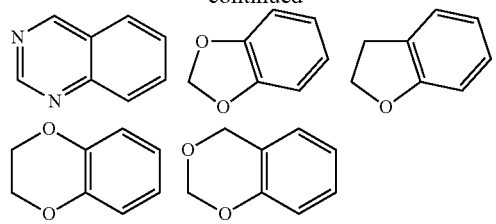

wherein
R$^1$ is independently selected from the group consisting of hydrogen, alkenyl, alkoxyalkyl, CF$_3$, alkyl, alkylcarbonyl, alkoxycarbonyl, aryl, heterocycloalkyl, hydroxyalkyl, and alkyl(N R$^2$R$^3$), wherein R$^2$ and R$^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively R$^2$ and R$^3$ and may be taken together to form a 5-7 membered heterocyclic ring with N;
R$^{III}$ represents optionally 1-3 substituents independently selected from the group consisting of C$_1$-C$_5$ linear or branched alkyl, C$_1$-C$_5$ linear or branched haloalkyl, C$_1$-C$_5$ alkoxy, hydroxy, amino, C$_1$-C$_5$ alkylamino, C1-C6 dialkylamino, halogen, cyano, and nitro;
Z is selected from the group consisting of
  (1') (CH$_2$)$_i$N(R$^7$)C(O)N(R$^8$)(CH$_2$)$_j$;
  (2') (CH$_2$)$_i$N(R$^7$)C(S)N(R$^8$)(CH$_2$)$_j$;
  (3') (CH$_2$)$_i$N(R$^7$)C(O);
  (4') C(O)N(R$^8$)(CH$_2$)$_j$;
  (5') (CH$_2$)$_i$N(R$^7$)S(O)$_2$;
  and (6') S(O)$_2$N(R$^8$)(CH$_2$)$_j$;
wherein
  i is 0 or 1;
  j is 0 or 1;
  R$^7$ and R$^8$ are independently selected from the group consisting of hydrogen and alkyl.
Ring B is selected from the group consisting of:

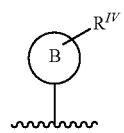

(i') Phenyl;
(ii') Naphthyl;
(iii') A 5 or 6 membered monocyclic heteroaryl group which have 1-3 heteroatoms independently selected from the group consisting of O, N and S;
and (iv') An 8 to 10 membered bicyclic heteroaryl group which have 1-3 heteroatoms independently selected from the group consisting of O, N and S;
Ring B can be illustrated but not limited to the following:

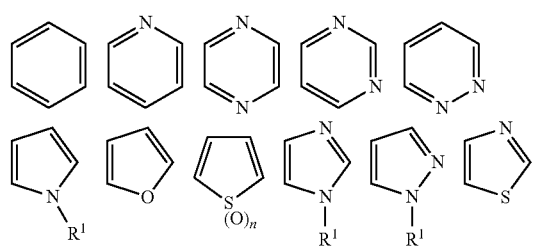

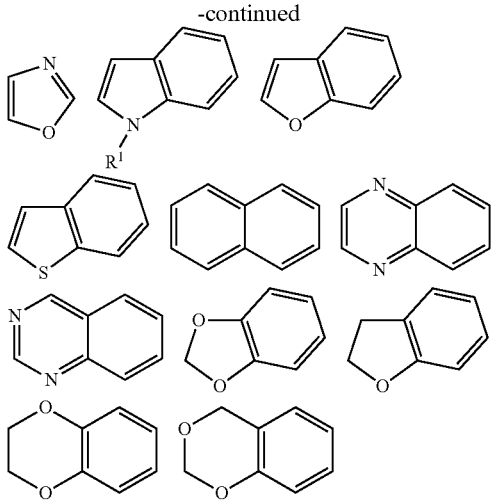

wherein

R¹ is independently selected from the group consisting of hydrogen, alkenyl, alkoxyalkyl, CF₃, alkyl, alkylcarbonyl, alkoxycarbonyl, aryl, heterocycloalkyl, hydroxyalkyl, and alkyl(N R²R³), wherein R² and R³ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively R² and R³ and may be taken together to form a 5-7 membered heterocyclic ring with N;

$R^{IV}$ represents optionally 1-3 substituents, independently selected from the group consisting of alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —NR⁹R¹⁰, wherein R⁹ and R¹⁰ are independently selected from the group consisting of hydrogen, alkyl, alkylcarbonyl, aryl, arylalkyl, cycloalkyl, cycloalkylalkyl, heterocyclyl, and heterocyclylalkyl.

Some embodiments of the present invention are included in the following paragraphs:

(1) A compound according to Formula I, including any tautomer, stereoisomer, diastereoisomeric form, polymorphic form, crystal form, a solvate, a hydrate, a metabolite, a pharmaceutically acceptable salt or prodrug, mixture of different stereoisomers, and any mixture of different crystal forms.

(2) A compound of Formula I in the form of a prodrug.

(3) The compound according to paragraph 1, wherein Z is selected from the group consisting of (CH₂)ᵢN(R⁷)C(O), C(O)N(R⁸)(CH₂)ⱼ, (CH₂)ᵢN(R⁷)S(O)₂ and S(O)₂N(R⁸)(CH₂)ⱼ.

(4) The compound according to paragraphs 1-3, wherein Y is selected from the group consisting of —(CH₂)g-O—(CH₂)h-; —(CH₂)g-NR¹—(CH₂)h-; —(CH₂)g-S(O)ₙ—(CH₂)h-; —(CH₂)g-SO₂N R²—(CH₂)h-; —(CH₂)g-NR²SO₂—(CH₂)h-; —(CH₂)g-CO—(CH₂)h-; —(CH₂)g-C(O)NR²—(CH₂)h-; —(CH₂)g-NR²C(O)—(CH₂)h-; —(CH₂)g-C≡C—(CH₂)h-; —(CH₂)g-NR²C(O)NR³—(CH₂)h and a single bond.

(5) The compound according to paragraphs 1-4, wherein Ring A and Ring B are independently selected from the group consisting of

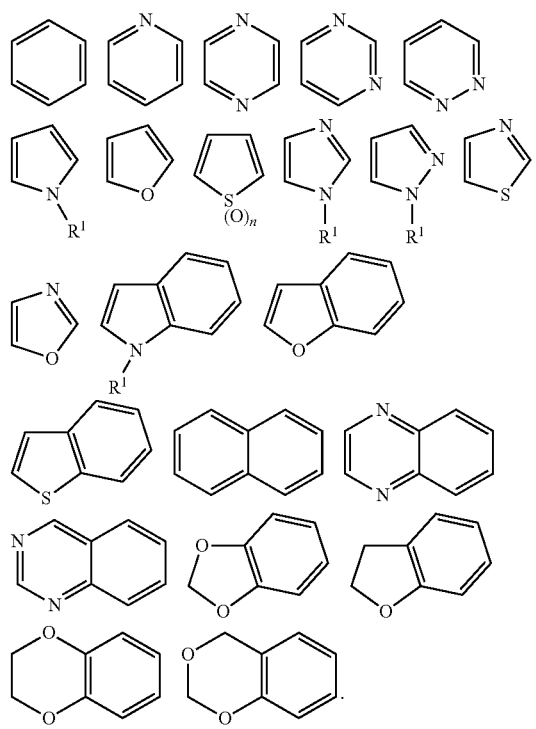

(6) The compound according to paragraphs 1-5, wherein Y is selected from the group consisting of —(CH₂)g-(CH₂)h-; —(CH₂)g-CF₂—(CH₂)h-; —(CH₂)g-CCl₂—(CH₂)h-; —(CH₂)g-CHF—(CH₂)h-; —(CH₂)g-CH(OH)—(CH₂)h-; —(CH₂)g-CR²R³—(CH₂)h-; and —(CH₂)g-C≡C—(CH₂)h-.

(7) The compound according to paragraphs 1-6, wherein X is NH.

(8) A compound selected from the group consisting of (1') [({5-[4-(2-fluoro-5-{[(2-fluoro-5-methylphenyl)amino]carbonyl}phenoxy)pyridin-2-yl]-1H-pyrrol-3-yl}carbonyl)amino]acetic acid;

(2') methyl [({5-[4-(2-fluoro-5-{[(2-fluoro-5-methylphenyl)amino]carbonyl}phenoxy)pyridin-2-yl]-1H-pyrrol-3-yl}carbonyl)amino]acetate;

(3') ({[5-(4-{3-[(3-methyl-2-furoyl)amino]phenoxy}pyridin-2-yl)-1H-pyrrol-3-yl]carbonyl}amino)acetic acid;

(4') methyl ({[5-(4-{3-[(3-methyl-2-furoyl)amino]phenoxy}pyridin-2-yl)-1H-pyrrol-3-yl]carbonyl}amino)acetate;

(5') 5-[4-({3-[(3-methyl-2-furoyl)amino]phenyl}amino)pyridin-2-yl]-1H-pyrrole-3-carboxylic acid;

(6') methyl 5-[4-({3-[(3-methyl-2-furoyl)amino]phenyl}amino)pyridin-2-yl]-1H-pyrrole-3-carboxylate;

(7') 5-[4-(2-fluoro-5-{[(2-fluoro-5-methylphenyl)amino]carbonyl}phenoxy)pyridin-2-yl]-N-hydroxy-1H-pyrrole-3-carboxamide;

(8') 4-fluoro-N-(2-fluoro-5-methylphenyl)-3-[(2-{4-[(3-hydroxypiperidin-1-yl)carbonyl]-1H-pyrrol-2-yl}pyridin-4-yl)oxy]benzamide;

(9) N-(2,3-dihydroxypropyl)-5-[4-(3-{[(2-fluoro-5-methylphenyl)amino]carbonyl}phenoxy)pyridin-2-yl]-1H-pyrrole-3-carboxamide;

(10) N-(2-fluoro-5-methylphenyl)-3-[(2-{4-[(3-hydroxypyrrolidin-1-yl)carbonyl]-1H-pyrrol-2-yl}pyridin-4-yl)oxy]benzamide;

(11') 5-[4-(3-{[(2-fluoro-5-methylphenyl)amino]carbonyl}phenoxy)pyridin-2-yl]-N-hydroxy-1H-pyrrole-3-carboxamide;
(12') methyl 5-[4-(2-fluoro-5-{[(2-fluoro-5-methylphenyl)amino]carbonyl}phenoxy)pyridin-2-yl]-1H-pyrrole-3-carboxylate;
(13') 5-[4-(2-fluoro-5-{[(2-fluoro-5-methylphenyl)amino]carbonyl}phenoxy)pyridin-2-yl]-1H-pyrrole-3-carboxylic acid;
(14') N-ethyl-5-(4-{3-[(3-methyl-2-furoyl)amino]phenoxy}pyridin-2-yl)-1H-pyrrole-3-carboxamide;
(15') N-(2,3-dihydroxypropyl)-5-(4-{3-[(3-methyl-2-furoyl)amino]phenoxy}pyridin-2-yl)-1H-pyrrole-3-carboxamide;
(16') 5-(4-{3-[(3-methyl-2-furoyl)amino]phenoxy}pyridin-2-yl)-1H-pyrrole-3-carboxamide;
(17') N-hydroxy-5-(4-{3-[(3-methyl-2-furoyl)amino]phenoxy}pyridin-2-yl)-1H-pyrrole-3-carboxamide;
(18') N-(3-{[2-(4-{[(3R)-3-hydroxypyrrolidin-1-yl]carbonyl}-1H-pyrrol-2-yl)pyridin-4-yl]oxy}phenyl)-3-methyl-2-furamide;
(19') 5-[4-(3-{[(2-fluoro-5-methylphenyl)amino]carbonyl}phenoxy)pyridin-2-yl]-1H-pyrrole-3-carboxylic acid;
(20') methyl 5-[4-(3-{[(2-fluoro-5-methylphenyl)amino]carbonyl}phenoxy)pyridin-2-yl]-1H-pyrrole-3-carboxylate;
(21') 2,3-dihydroxypropyl 5-(4-{3-[(3-methyl-2-furoyl)amino]phenoxy}pyridin-2-yl)-1H-pyrrole-3-carboxylate;
(22') 5-[4-(3-{[(3-methylphenyl)amino]carbonyl}phenoxy)pyridin-2-yl]-1H-pyrrole-3-carboxylic acid;
(23') methyl 5-[4-(3-{[(3-methylphenyl)amino]carbonyl}phenoxy)pyridin-2-yl]-1H-pyrrole-3-carboxylate;
(24') 2-hydroxyethyl 5-[4-(3-{[(3-methyl-2-thienyl)carbonyl]amino}phenoxy)pyridin-2-yl]-1H-pyrrole-3-carboxylate;
(25') 2-hydroxyethyl 5-(4-{3-[(3-methyl-2-furoyl)amino]phenoxy}pyridin-2-yl)-1H-pyrrole-3-carboxylate;
(26') 5-[4-(3-{[(3-methyl-2-thienyl)carbonyl]amino}phenoxy)pyridin-2-yl]-1H-pyrrole-3-carboxylic acid;
(27') methyl 5-[4-(3-{[(3-methyl-2-thienyl)carbonyl]amino}phenoxy)pyridin-2-yl]-1H-pyrrole-3-carboxylate;
(28') 5-(4-{4-fluoro-3-[(3-methyl-2-furoyl)amino]phenoxy}pyridin-2-yl)-1H-pyrrole-3-carboxylic acid;
(29') methyl 5-(4-{4-fluoro-3-[(3-methyl-2-furoyl)amino]phenoxy}pyridin-2-yl)-1H-pyrrole-3-carboxylate;
(30') N-[dimethyl(oxido)-lambda~4~-sulfanylidene]-5-(4-{3-[(3-methyl-2-furoyl)amino]phenoxy}pyridin-2-yl)-1H-pyrrole-3-carboxamide;
(31') N-(3-{[2-(4-{[(3S)-3-hydroxypyrrolidin-1-yl]carbonyl}-1H-pyrrol-2-yl)pyridin-4-yl]oxy}phenyl)-3-methyl-2-furamide;
(32') 5-(4-{3-[(3-methyl-2-furoyl)amino]phenoxy}pyridin-2-yl)-1H-pyrrole-3-carboxylic acid;
(33') methyl 5-(4-{3-[(3-methyl-2-furoyl)amino]phenoxy}pyridin-2-yl)-1H-pyrrole-3-carboxylate;
(34') 3-methyl-N-(3-{[2-(1H-pyrrol-2-yl)pyridin-4-yl]oxy}phenyl)-2-furamide;
(35') methyl 4-(4-{3-[(3-methyl-2-furoyl)amino]phenoxy}pyridin-2-yl)-1H-pyrrole-2-carboxylate;
(36') 2-fluoro-5-methyl-N-(4-{[2-(1H-pyrrol-2-yl)pyridin-4-yl]oxy}phenyl)benzamide;
and (37') 3-methyl-N-(4-{[2-(1H-pyrrol-2-yl)pyridin-4-yl]oxy}phenyl)-2-furamide.

(9) The compound according to paragraph 1, wherein Z is $(CH_2)_iN(R^7)C(O)N(R^8)(CH_2)_j$ or $(CH_2)_iN(R^7)C(S)N(R^8)(CH_2)_j$, provided that when Ring B is pyrazole, $R^{IV}$ is not a phenyl or substituted phenyl.
(10) The compound according to paragraph 9, wherein Y is selected from the group consisting of —$(CH_2)g$-O—$(CH_2)h$-; —$(CH_2)g$-$NR^1$—$(CH_2)h$-; —$(CH_2)g$-$S(O)_n$—$(CH_2)h$-; —$(CH_2)g$-$SO_2N R^2$—$(CH_2)h$-; —$(CH_2)g$-$NR^2SO_2$—$(CH_2)h$-; —$(CH_2)g$-CO—$(CH_2)h$-; —$(CH_2)g$-$C(O)NR^2$—$(CH_2)h$-; —$(CH_2)g$-$NR^2C(O)$—$(CH_2)h$-; —$(CH_2)g$-C≡C—$(CH_2)h$-; —$(CH_2)g$-$NR^2C(O)NR^3$—$(CH_2)h$, and a single bond.
(11) The compound according to paragraph 9, wherein Y is selected from the group consisting of —$(CH_2)g$-$(CH_2)h$-; —$(CH_2)g$-$CF_2$—$(CH_2)h$-; —$(CH_2)g$-$CCl_2$—$(CH_2)h$-; —$(CH_2)g$-CHF—$(CH_2)h$-; —$(CH_2)g$-CH(OH)—$(CH_2)h$-; —$(CH_2)g$-$CR^2R^3$—$(CH_2)h$-; and —$(CH_2)g$-C≡C—$(CH_2)h$-.
(12) The compound according to paragraphs 9-11, wherein Ring A and Ring B are independently selected from the group consisting of

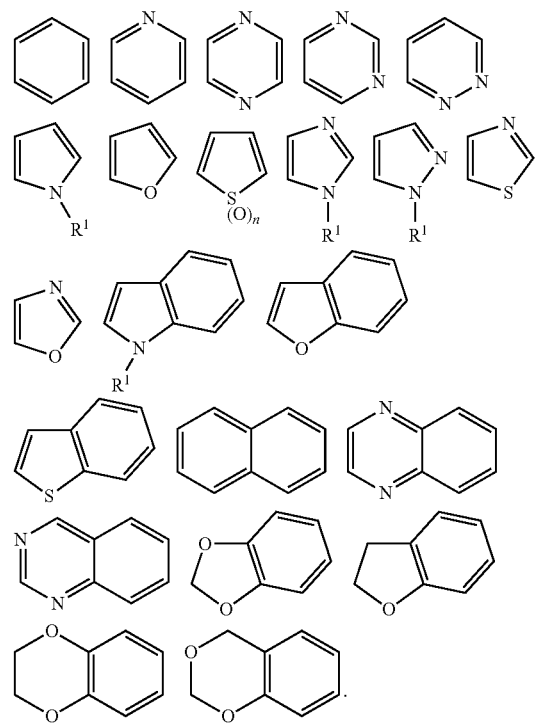

(13) The compound according to paragraphs 9-12, wherein X is NH.
(14) The compound according to paragraphs 9-12, wherein X is S.
(15) The compound according to paragraphs 9-14, wherein $R^I$ is selected from the group consisting of hydrogen, halogen, $C_1$ to $C_8$ alkyl, $(CR^5R^6)_dC(O)OR^4$, $(CR^5R^6)_dAr$, $NR^4(CR^5R^6)_dAr$, $(CR^5R^6)_dC(O)N(R^4)_2$, $NR^4(CR^5R^6)_dC(O)N(R^4)_2$, $O(CR^5R^6)_dC(O)N(R^4)_2$, $(CR^5R^6)_dOR^4$, $OC(O)(CR^5R^6)_dN(R^4)_2$, $C(O)(CR^5R^6)_dN(R^4)_2$, $C(O)N=S(O)R^5 R^6$, $NR^2C(O)(CR^5R^6)_dN(R^4)_2$, $HNC(O)R^4$, $HN—C(O)OR^4$, $(CR^5R^6)_dN(R^4)_2$, $S(O)_f(CR^5R^6)_dN(R^4)_2$, $OC(O)OR^4$, $(CR^5R^6)_dC(O)(CR^5R^6)_dR^4$, $(CR^5R^6)_dC(O)(CR^5R^6)_dOR^4$, and $(CR^5R^6)_dC(O)(CR^5R^6)_dN(R^4)_2$, wherein each R⁴ is independently selected from the group consisting of hydrogen, hydroxyl, $C_1$-$C_8$ alkyl, aryl, $C_1$-$C_8$ hydroxyalkyl, $C_1$-$C_8$ alkoxyalkyl, $(CR^5R^6)_d$ and $N(R^4)_2$ may form a 3-7 membered heterocyclic ring, comprising of aziridine, azetidine, pyrrolidine, 5-fluoropyrrolidine, piperidine, 6-fluoropiperidine, N-methylpiperazine, morpholine, 2,6-dimethylmorpholine, thiomorpholine, and wherein said heterocyclic ring may be optionally substituted with up to three of $R^5$; wherein $R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonyl, alkoxycarbonyl, hydroxycarbonyl, hydroxycarbonylalkyl, amide, alkylamide, amidoalkyl, sulfonate and $CR^5R^6$ may represent a carbocyclic or heterocyclic ring of from 5 to 6 carbons or alternatively, $(CR^5R^6)_d$ and $(CR^5R^6)_e$ may form a 3-7 membered carbocyclic or heterocyclic ring, wherein the ring may be optionally substituted with up to three of hydroxyl, halo, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl and sulfonate.

(16) A compound of Formula II:

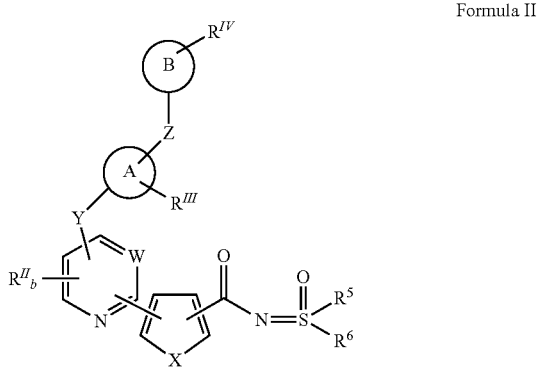

Formula II wherein
W is C or N;
X is selected from the group consisting of $NR^1$, O, and $S(O)_n$;
n is 0 or an integer of from 1 to 2;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered heterocyclic ring with N;
$R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, sulfonate;
$R^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, $(NR^2R^3)$alkoxy, $(NR^2R^3)$alkenyl, $(NR^2R^3)$alkyl, $(NR^2R^3)$carbonylalkenyl, and $(NR^2R^3)$carbonylalkyl, wherein $R^2$ and $R^3$ are independently selected from the group consisting of hydrogen, alkyl, alkylcarbonyl, alkyl sulfonyl, arylsulfonyl, haloalkylsulfonyl, and heterocyclylsulfonyl; alternatively $R^2$ and $R^3$ and may be taken together to form a 5-7 membered heterocyclic ring with N;
b is 0 or an integer of from 1 to 2;
Y is selected from the group consisting of:
 (1') —(CH₂)g-O—(CH₂)h-;
 (2') —(CH₂)g-NR¹—(CH₂)h-;
 (3') —(CH₂)g-S(O)ₙ—(CH₂)h-;
 (4') —(CH₂)g-SO₂N R²—(CH₂)h-;
 (5') —(CH₂)g-NR²SO₂—(CH₂)h-;
 (6') —(CH₂)g-CO—(CH₂)h-;
 (7') —(CH₂)g-C(O)NR²—(CH₂)h-;
 (8') —(CH₂)g-NR²C(O)—(CH₂)h-;
 (9') —(CH₂)g-C═C—(CH₂)h-;
 (10') —(CH₂)g-NR²C(O)NR³—(CH₂)h-;
 (11') —(CH₂)g-(CH₂)h-;
 (12') —(CH₂)g-CF₂—(CH₂)h-;
 (13') —(CH₂)g-CCl₂—(CH₂)h-;
 (14') —(CH₂)g-CHF—(CH₂)h-;
 (15') —(CH₂)g-CH(OH)—(CH₂)h-;
 (16') —(CH₂)g-CR²R³—(CH₂)h-;
 (17') —(CH₂)g-C≡C—(CH₂)h-;
 and (18') a single bond;
wherein
g is 0 or an integer of from 1 to 3;
h is 0 or an integer of from 1 to 3;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered heterocyclic ring with N;
$R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered cyclic ring;
Ring A is selected from the group consisting of:

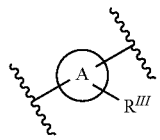

(i) Phenyl;
(ii) Naphthyl;
(iii) A 5 or 6 membered monocyclic heteroaryl group which have 1-5 heteroatoms independently selected from the group consisting of O, N and S;
and (iv) An 8 to 10 membered bicyclic heteroaryl group which have 1-6 heteroatoms independently selected from the group consisting of O, N and S;
Ring A can be illustrated but not limited to the following:

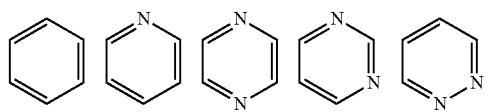

-continued

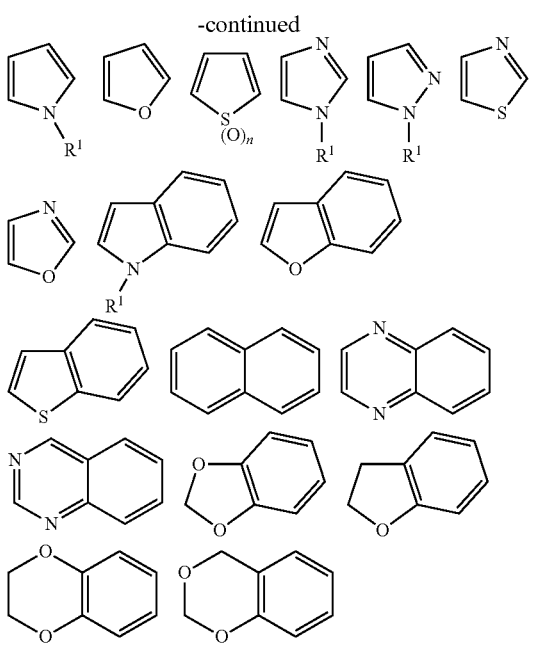

wherein
R¹ is independently selected from the group consisting of hydrogen, alkenyl, alkoxyalkyl, CF₃, alkyl, alkylcarbonyl, alkoxycarbonyl, aryl, heterocycloalkyl, hydroxyalkyl, and alkyl(N R²R³), wherein R² and R³ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively R² and R³ and may be taken together to form a 5-7 membered heterocyclic ring with N;

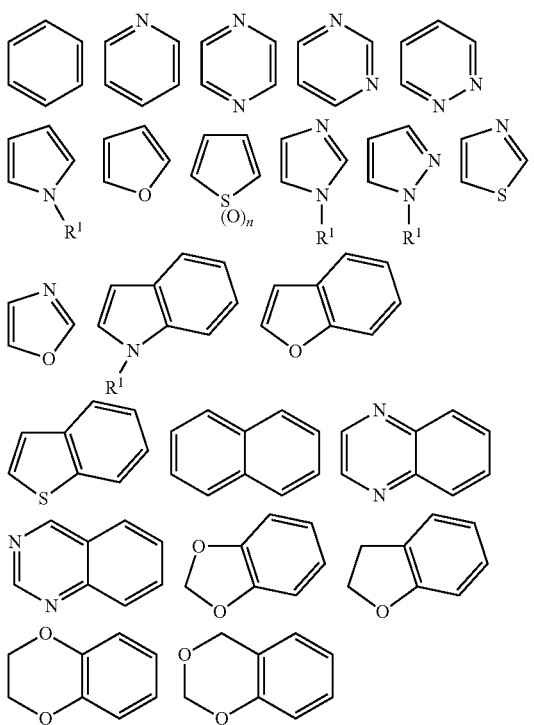

$R^{III}$ represents optionally 1-3 substituents independently selected from the group consisting of $C_1$-$C_5$ linear or branched alkyl, $C_1$-$C_5$ linear or branched haloalkyl, $C_1$-$C_5$ alkoxy, hydroxy, amino, $C_1$-$C_5$ alkylamino, C1-C6 dialkylamino, halogen, cyano, and nitro;

Z is selected from the group consisting of
(1') $(CH_2)_iN(R^7)C(O)N(R^8)(CH_2)_j$;
(2') $(CH_2)_iN(R^7)C(S)N(R^8)(CH_2)_j$;
(3') $(CH_2)_iN(R^7)C(O)$;
(4') $C(O)N(R^8)(CH_2)_j$;
(5') $(CH_2)_iN(R^7)S(O)_2$;
and (6') $S(O)_2N(R^8)(CH_2)_j$;

wherein
i is 0 or 1;
j is 0 or 1;
$R^7$ and $R^8$ are independently selected from the group consisting of hydrogen and alkyl;

Ring B is selected from the group consisting of:

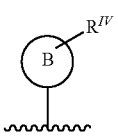

(i') Phenyl;
(ii') Naphthyl;
(iii') A 5 or 6 membered monocyclic heteroaryl group which have 1-3 heteroatoms independently selected from the group consisting of O, N and S;
and (iv') An 8 to 10 membered bicyclic heteroaryl group which have 1-3 heteroatoms independently selected from the group consisting of O, N and S;

Ring B can be illustrated but not limited to the following:
wherein
R¹ is independently selected from the group consisting of hydrogen, alkenyl, alkoxyalkyl, CF₃, alkyl, alkylcarbonyl, alkoxycarbonyl, aryl, heterocycloalkyl, hydroxyalkyl, and alkyl(N R²R³), wherein R² and R³ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively R² and R³ and may be taken together to form a 5-7 membered heterocyclic ring with N;

$R^{IV}$ represents optionally 1-3 substituents, independently selected from the group consisting of alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^9R^{10}$; wherein $R^9$ and $R^{10}$ are independently selected from the group consisting of hydrogen, alkyl, alkylcarbonyl, aryl, arylalkyl, cycloalkyl, cycloalkylalkyl, heterocyclyl, and heterocyclylalkyl;

and any pharmaceutical acceptable salt or prodrug.

(17) The compound according to paragraph 16, wherein Z is selected from the group consisting of $(CH_2)_iN(R^7)C(O)$, $C(O)N(R^8)(CH_2)_j$, $(CH_2)_iN(R^7)C(O)N(R^8)(CH_2)_j$ and $(CH_2)_iN(R^7)C(S)N(R^8)(CH_2)_j$.

(18) The compound according to paragraphs 16-17, wherein Y is selected from the group consisting of —$(CH_2)g$-O—$(CH_2)h$-; —$(CH_2)g$-NR¹—$(CH_2)h$-; —$(CH_2)g$-S(O)$_n$—$(CH_2)h$-; —$(CH_2)g$-SO$_2$N R²—$(CH_2)h$-; —$(CH_2)g$-NR²SO$_2$—$(CH_2)h$-; —$(CH_2)g$-CO—$(CH_2)h$-; —$(CH_2)g$-C(O)NR²—$(CH_2)h$-;

—(CH$_2$)g-NR$^2$C(O)—(CH$_2$)h-;  —(CH$_2$)g-C≡C—(CH$_2$)h-;  —(CH$_2$)g-NR$^2$C(O)NR$^3$—(CH$_2$)h and a single bond.

(19) The compound according to paragraphs 16-18, wherein Ring A and Ring B are independently selected from the group consisting of

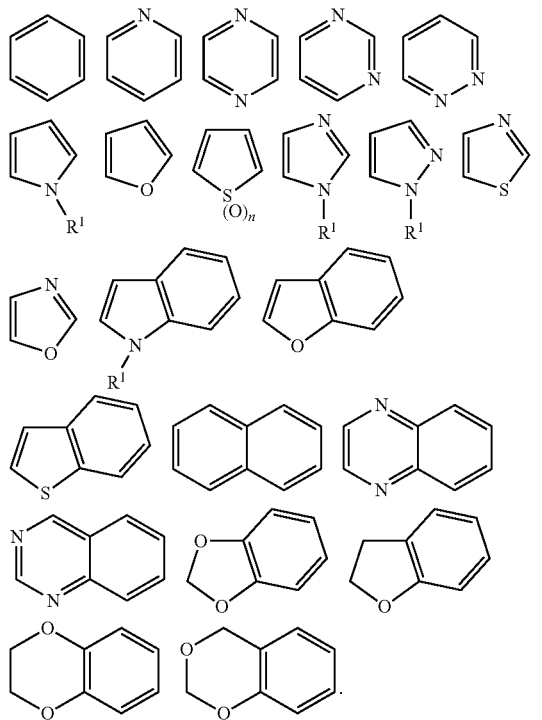

(20) The compound according to paragraphs 16-19, wherein W is C.

(21) A method of use of the compounds of paragraphs 1-20, wherein the compounds are used as tyrosine kinase modulators;

(22) Use of the compounds of paragraphs 1-20 in the preparation of a medicament for the treatment or prevention of diseases or conditions related with unregulated tyrosine kinase activities, comprising administering a therapeutically effective amount of the compound of paragraphs 1-20 together with a pharmaceutically acceptable carrier;

(23) The use of paragraph 22, wherein the diseases or conditions are selected from the group consisting of cell growth and metabolic disorders, blood vessel proliferative disorders, inflammatory disorders, neurodegenerative diseases, and immune disorders.

(24) The use of paragraphs 22-23 wherein the diseases or conditions are selected from the group consisting of colorectal cancer, lung cancer, hematological cancer, renal cancer, liver cancer, breast cancer, diabetic retinopathy, macular degeneration, age-related macular degeneration, retinopathy of prematurity, ocular angiogenesis, retinal edema, retinal ischemia, diabetic macular edema, cystoid macular edema, retinal vein occlusion, branch vein occlusion, preretinal neovascularization, laser-induced choroidal neovascularization, neovascularization associated with keratoplasty, glaucoma and ocular tumors, arthritis, restenosis, hepatic cirrhosis, atherosclerosis, psoriasis, diabetes mellitus, wound healing, inflammation, neurodegenerative diseases and immune disorders.

(25) The use of paragraphs 22-23 wherein the conditions and diseases are wound healing or to alleviate transplant rejection.

(26) A pharmaceutical composition comprising a therapeutic effective amount of a compound according to paragraphs 1-20 together with a pharmaceutically acceptable carrier which is suitable for systematic, parenteral, local or topical delivery.

(27) The pharmaceutical composition of paragraph 26, which are in the form selected from the group comprising of tablets, capsules, intravenous injections, intramuscular injections, local injections, topical creams, gels and ointments, eye drops, ophthalmic solutions, ophthalmic suspensions, ophthalmic emulsions, intravitreal injections, subtenon injections, ophthalmic biodrodible implant, and non-bioeordible ophthalmic inserts or depots.

(28) Use of the compounds of paragraphs 1-20 in the preparation of a medicament for the treatment of diseases and conditions, wherein the medicament contains pharmaceutical acceptable composition according to paragraphs 26 and 27.

DETAILED DESCRIPTION OF THE INVENTION

Figure 1:
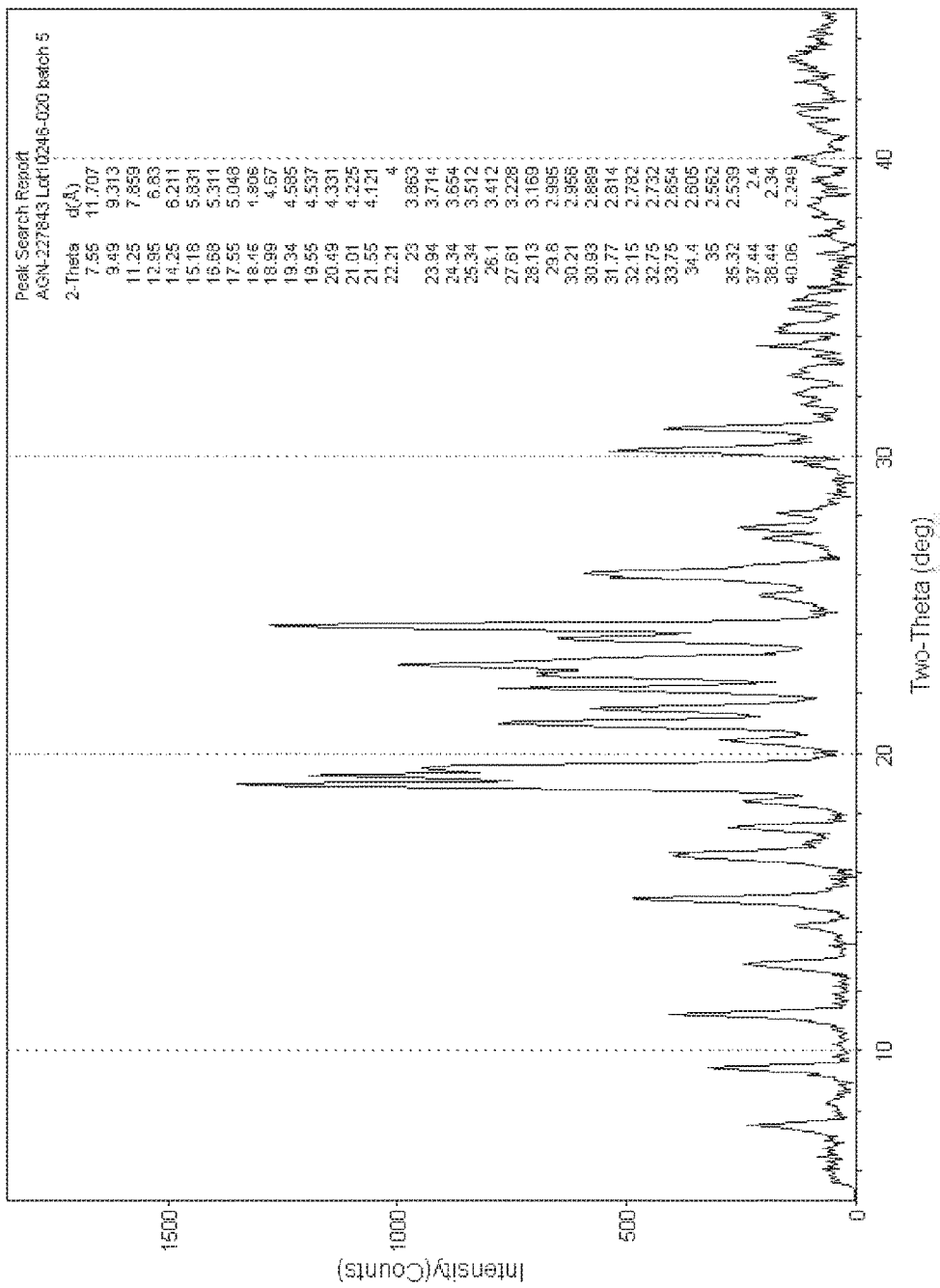
FIG. 1 shows a powder X-Ray Diffraction (XRPD) of Example 78.
Figure 2:
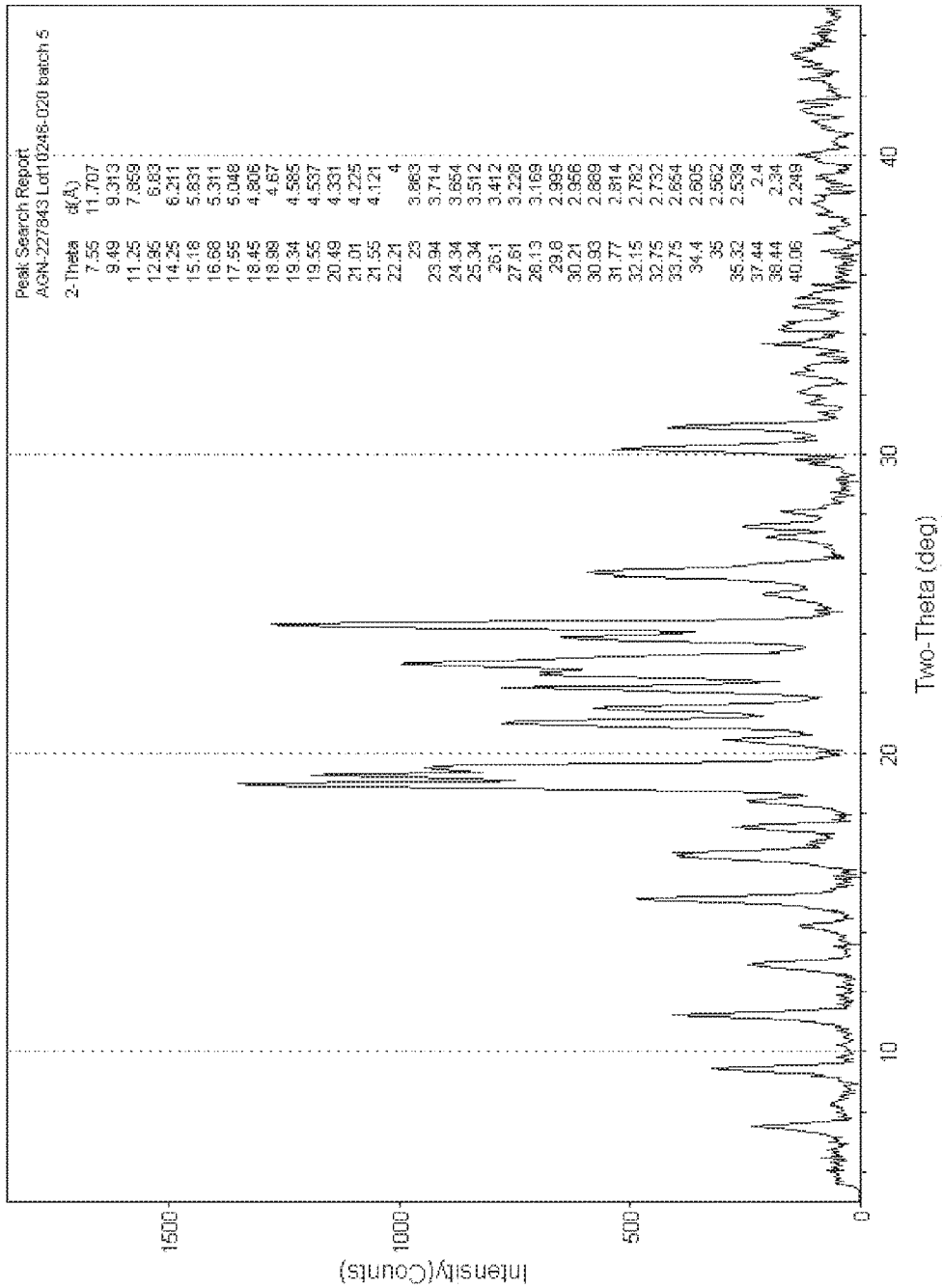
FIG. 2 shows a powder X-Ray Diffraction (XRPD) of Example 69.
Figure 3:
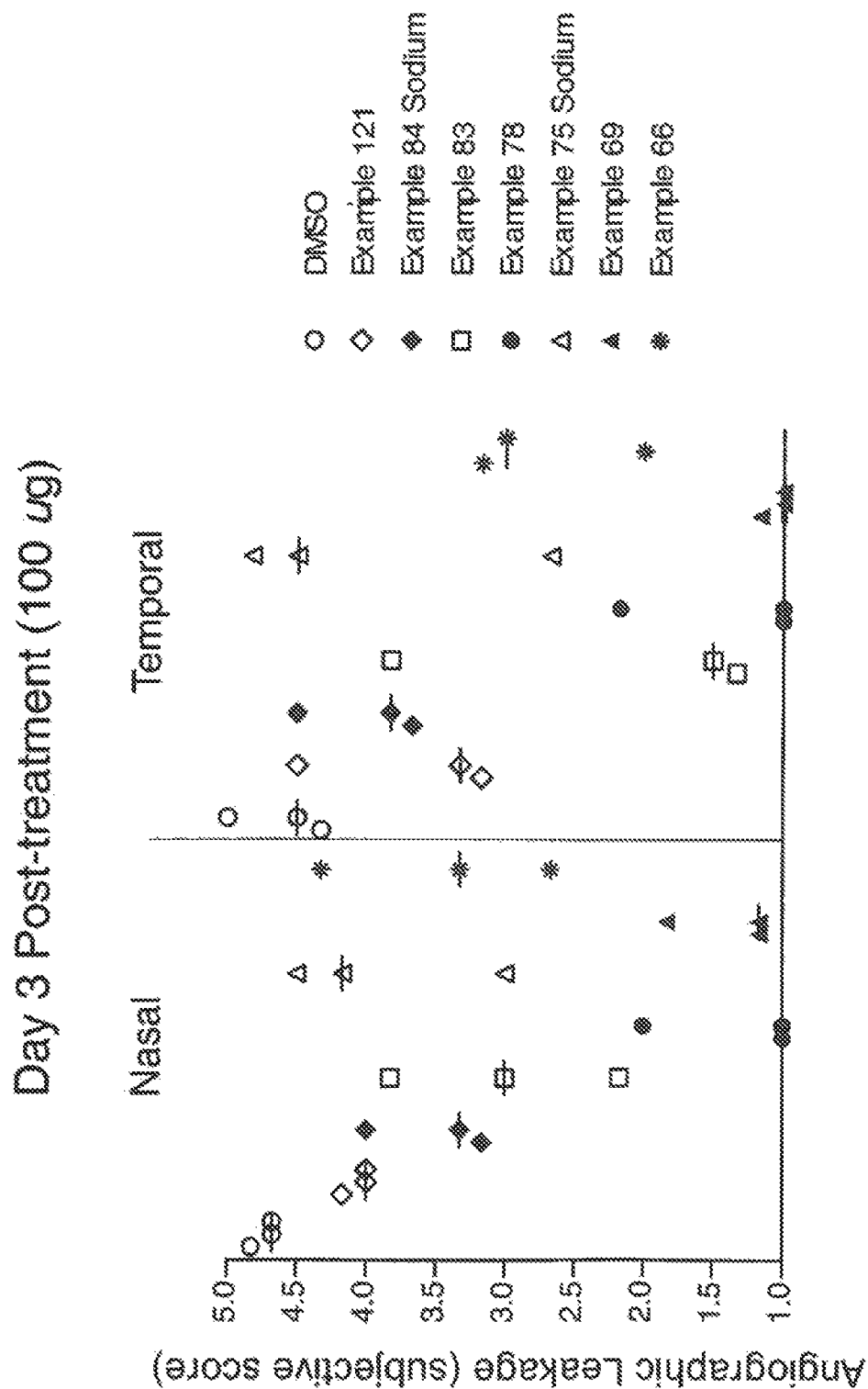
FIG. 3 shows a fluorescein angiography (blood-retinal barrier breakdown) of Example 121, Example 84 Sodium, Example 83, Example 78, Example 75 Sodium, Example 69, and Example 66.
Figure 4:
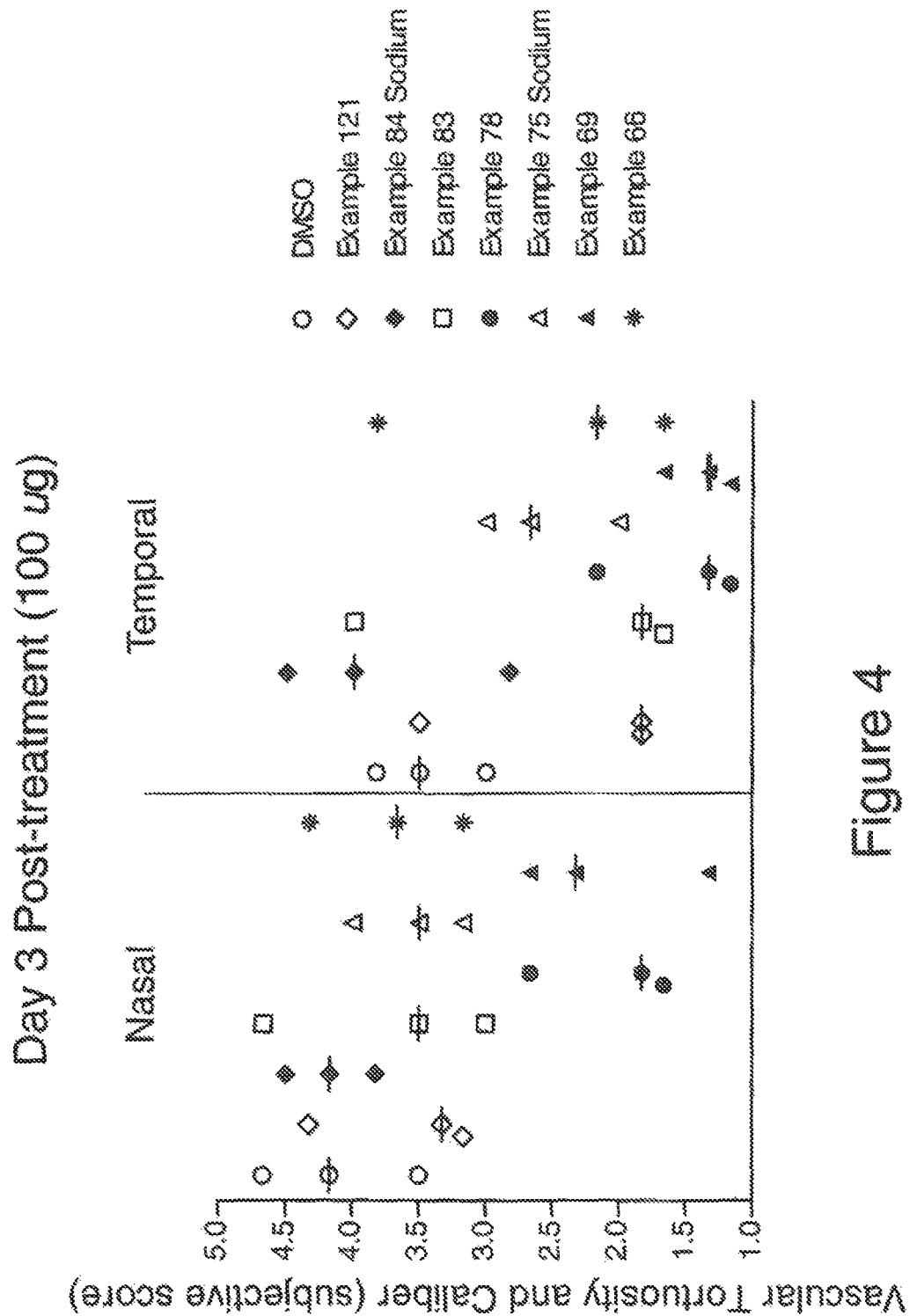
FIG. 4 shows a fundus photography (retinal vasodilation and vessel tortuosity) of Example 121, Example 84 Sodium, Example 83, Example 78, Example 75 Sodium, Example 69, and Example 66.

The present invention is directed to a series of compounds with multiple aromatic components useful as protein tyrosine kinase inhibitors. The compounds of the present invention are useful for treating diseases related to unregulated tyrosine kinase signal transduction, for example, cancer, blood vessel proliferative disorders, fibrotic disorders, and neurodegenerative diseases. In particular, compounds of the present invention are useful for the treatment of colorectal cancer, lung cancer, hematological cancer, renal cancer, liver cancer, breast cancer, diabetic retinopathy, macular degeneration, age-related macular degeneration, retinopathy of prematurity, ocular angiogenesis, retinal edema, retinal ischemia, diabetic macular edema, cystoid macular edema, retinal vein occlusion, branch vein occlusion, preretinal neovascularization, laser-induced choroidal neovascularization, neovascularization associated with keratoplasty, glaucoma and ocular tumors, arthritis, restenosis, hepatic cirrhosis, atherosclerosis, psoriasis, diabetes mellitus, wound healing, transplant rejection, inflammation, neurodegenerative diseases and immune disorders.

1. COMPOUNDS OF THE INVENTION

In one aspect of the invention, the compounds of the present invention can be represented by the general formula I:

Formula I wherein
X is selected from the group consisting of $NR^1$, O, and $S(O)_n$;
n is 0 or an integer of from 1 to 2;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkylsulfonyl, aryl sulfonyl, haloalkylsulfonyl, and heterocyclylsulfonyl; alternatively $R^2$ and $R^3$ and may be taken together to form a 5-7 membered heterocyclic ring with N;
$R^I$ is selected from the group consisting of hydrogen, halogen, $C_1$ to $C_8$ alkyl, $S(O)_fR^4$, $(CR^5R^6)_dC(O)OR^4$, $S(O)_f(CR^5R^6)_dC(O)OR^4$, $(CR^5R^6)_dAr$, $NR^4(CR^5R^6)_d$ Ar, $O(CR^5R^6)_dAr$, $S(O)_f(CR^5R^6)_dAr$, $(CR^5R^6)_dS(O)_f$ $R^4$, $NR^4(CR^5R^6)_dS(O)_fR^4$, $O(CR^5R^6)_d S(O)_fR^4$, $S(O)_f(CR^5R^6)_eS(O)_fR^4$, $(CR^5R^6)_dC(O)N(R^4)_2$, $NR^4(CR^5R^6)_d C(O)N(R^4)_2$, $O(CR^5R^6)_dC(O)N(R^4)_2$, $S(O)_f(CR^5R^6)_eC(O)N(R^4)_2$, $(CR^5 R^6)_dOR^4$, $S(O)_f(CR^5R^6)_d OR^4$, $(CR^5R^6)_dOSO_2R^4$, $S(O)_f(CR^5 R^6)_eOSO_2R^4$, $(CR^5 R^6)_dP(O)(OR^4)_2$, $S(O)_f(CR^5 R^6)_eP(O)(OR^4)_2$, $OC(O)(CR^5R^6)_dN(R^4)_2$, $C(O)(CR^5R^6)_dN(R^4)_2$, $C(O)N=S(O)R^5 R^6$, $NR^2C(O)(CR^5R^6)_dN(R^4)_2$, $(CR^5R^6)_d R^5$, $S(O)_f(CR^5R^6)_dR^5$, $HNC(O)R^4$, $HN—C(O)OR^4$, $(CR^5R^6)_dN(R^4)_2$, $S(O)_f(CR^5R^6)_dN(R^4)_2$, $OC(O)OR^4$, $(CR^5R^6)_dC(O)(CR^5R^6)_dR^4$, $(CR^5R^6)_dC(O)(CR^5R^6)_d OR^4$, and $(CR^5R^6)_dC(O)(CR^5R^6)_dN(R^4)_2$, wherein each $R^4$ is independently selected from the group consisting of hydrogen, hydroxyl, $C_1$-$C_8$ alkyl, aryl, $C_1$-$C_8$ hydroxyalkyl, $C_1$-$C_8$ alkoxyalkyl, $(CR^5R^6)_d$ and $N(R^4)_2$ may form a 3-7 membered heterocyclic ring, comprising of aziridine, azetidine, pyrrolidine, 5-fluoropyrrolidine, piperidine, 6-fluoropiperidine, N-methylpiperazine, morpholine, 2,6-dimethylmorpholine, thiomorpholine, and wherein said heterocyclic ring may be optionally substituted with up to three of $R^5$; wherein $R^5$ and $R^6$ are independently selected from the group consisting of hydrogen, halo, hydroxyl, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl, sulfonate and $CR^5R^6$ may represent a carbocyclic or heterocyclic ring of from 5 to 6 carbons or alternatively, $(CR^5R^6)_d$ and $(CR^5R^6)$, may form a 3-7 membered carbocyclic or heterocyclic ring, wherein the ring may be optionally substituted with up to three of hydroxyl, halo, $C_1$-$C_8$ alkyl, $C_1$-$C_8$ hydroxyalkyl, $C_1$-$C_8$ alkoxyalkyl, alkoxycarbonylalkyl, alkoxycarbonyl, hydroxycarbonyl, hydroxycarbonylalkyl, amide, alkylamide, amidoalkyl and sulfonate;
a is 0 or an integer of from 1 to 3;
d is 0 or an integer of from 1 to 5;
e is an integer of from 1 to 4;
f is 0 or an integer of from 1 to 2;
$R^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, $(NR^2R^3)$alkoxy, $(NR^2R^3)$alkenyl, $(NR^2R^3)$alkyl, $(NR^2R^3)$carbonylalkenyl, and $(NR^2R^3)$ carbonylalkyl, wherein $R^2$ and $R^3$ are independently selected from the group consisting of hydrogen, alkyl, alkylcarbonyl, alkyl sulfonyl, arylsulfonyl, haloalkylsulfonyl, and heterocyclylsulfonyl; alternatively $R^2$ and $R^3$ and may be taken together to form a 5-7 membered heterocyclic ring with N;
b is 0 or an integer of from 1 to 2;
Y is selected from the group consisting of:
(1') $—(CH_2)g-O—(CH_2)h-$;
(2') $—(CH_2)g-NR^1—(CH_2)h-$;
(3') $—(CH_2)g-S(O)_n—(CH_2)h-$;
(4') $—(CH_2)g-SO_2N R^2—(CH_2)h-$;
(5') $—(CH_2)g-NR^2SO_2—(CH_2)h-$;
(6') $—(CH_2)g-CO—(CH_2)h-$;
(7') $—(CH_2)g-C(O)NR^2—(CH_2)h-$;
(8') $—(CH_2)g-NR^2C(O)—(CH_2)h-$;
(9') $—(CH_2)g-C≡C—(CH_2)h-$;
(10') $—(CH_2)g-NR^2C(O)NR^3—(CH_2)h-$;
(11') $—(CH_2)g-(CH_2)h-$;
(12') $—(CH_2)g-CF_2—(CH_2)h-$;
(13') $—(CH_2)g-CCl_2—(CH_2)h-$;
(14') $—(CH_2)g-CHF—(CH_2)h-$;
(15') $—(CH_2)g-CH(OH)—(CH_2)h-$;
(16') $—(CH_2)g-CR^2R^3—(CH_2)h-$;
(17') $—(CH_2)g-C=C—(CH_2)h-$;
and (18') a single bond.
wherein
g is 0 or an integer of from 1 to 3;
h is 0 or an integer of from 1 to 3;
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered heterocyclic ring with N;
$R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered cyclic ring;
Ring A is selected from the group consisting of:

(i) Phenyl;
(ii) Naphthyl;

(iii) A 5 or 6 membered monocyclic heteroaryl group which have 1-5 heteroatoms independently selected from the group consisting of O, N and S;
and (iv) An 8 to 10 membered bicyclic heteroaryl group which have 1-6 heteroatoms independently selected from the group consisting of O, N and S;
Ring A can be illustrated but not limited to the following:

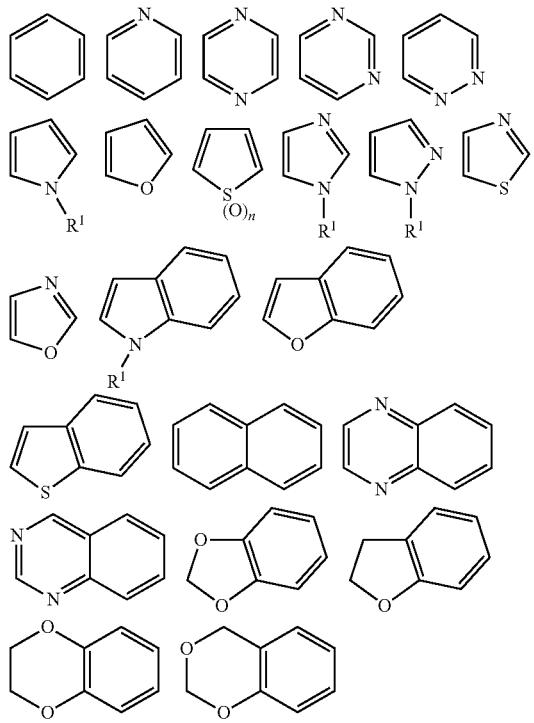

wherein
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered heterocyclic ring with N.
$R^{III}$ represents optionally 1-3 substituents independently selected from the group consisting of $C_1$-$C_5$ linear or branched alkyl, $C_1$-$C_5$ linear or branched haloalkyl, $C_1$-$C_5$ alkoxy, hydroxy, amino, $C_1$-$C_5$ alkylamino, C1-C6 dialkylamino, halogen, cyano, and nitro;
Z is selected from the group consisting of
(1') $(CH_2)_iN(R^7)C(O)N(R^8)(CH_2)_j$;
(2') $(CH_2)_iN(R^7)C(S)N(R^8)(CH_2)_j$;
(3') $(CH_2)_iN(R^7)C(O)$;
(4') $C(O)N(R^8)(CH_2)_j$;
(5') $(CH_2)_iN(R^7)S(O)_2$;
and (6') $S(O)_2N(R^8)(CH_1)_j$;
wherein
i is 0 or 1;
j is 0 or 1;
$R^7$ and $R^8$ are independently selected from the group consisting of hydrogen and alkyl;

Ring B is selected from the group consisting of:

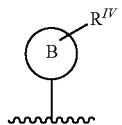

(i') Phenyl;
(ii') Naphthyl;
(iii') A 5 or 6 membered monocyclic heteroaryl group which have 1-3 heteroatoms independently selected from the group consisting of O, N and S;
and (iv') An 8 to 10 membered bicyclic heteroaryl group which have 1-3 heteroatoms independently selected from the group consisting of O, N and S;
Ring B can be illustrated but not limited to the following:

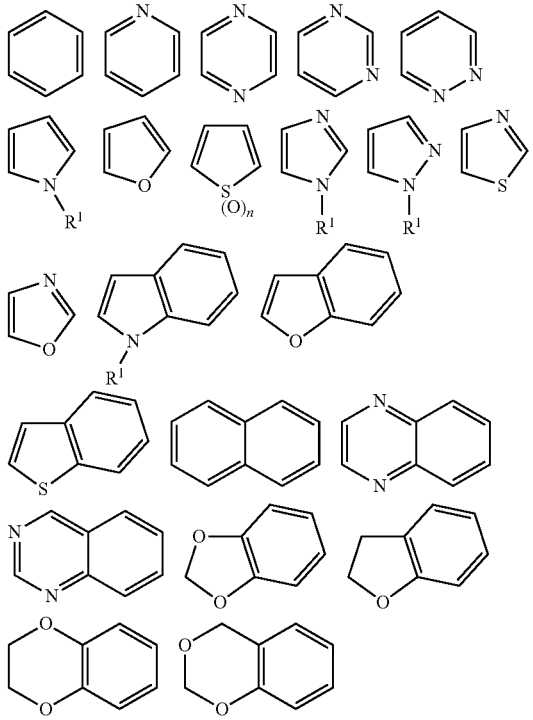

wherein
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered heterocyclic ring with N;
$R^{IV}$ represents optionally 1-3 substituents, independently selected from the group consisting of hydrogen, alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^9R^{10}$; wherein $R^9$ and $R^{10}$ are independently selected from the group consisting of hydrogen, alkyl, alkylcarbonyl, aryl, arylalkyl, cycloalkyl, cycloalkylalkyl, heterocyclyl, and heterocyclylalkyl;
In another aspect of the invention, the compounds of the present invention can be represented by the general formula II:

Formula II

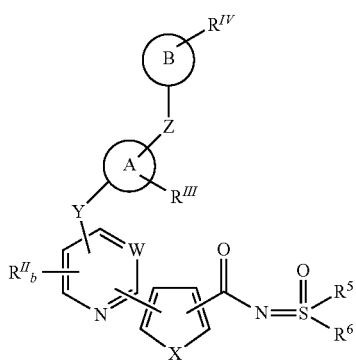

wherein
W is C or N;
X is selected from the group consisting of NR$^1$, O, and S(O)$_n$;
n is 0 or an integer of from 1 to 2;
R$^1$ is independently selected from the group consisting of hydrogen, alkenyl, alkoxyalkyl, CF$_3$, alkyl, alkylcarbonyl, alkoxycarbonyl, aryl, heterocycloalkyl, hydroxyalkyl, and alkyl(N R$^2$R$^3$), wherein R$^2$ and R$^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively R$^2$ and R$^3$ and may be taken together to form a 5-7 membered heterocyclic ring with N;
R$^5$ and R$^6$ are independently selected from the group consisting of hydrogen, halo, hydroxyl, C$_1$-C$_8$ alkyl, C$_1$-C$_8$ hydroxyalkyl, C$_1$-C$_8$ alkoxyalkyl, alkoxycarbonylalkyl, alkoxycarbonyl, hydroxycarbonyl, hydroxycarbonylalkyl, amide, alkylamide, amidoalkyl, and sulfonate;
R$^{II}$ is independently selected from the group consisting of hydrogen, alkoxy, alkoxyalkoxy, alkoxyalkyl, alkyl, aryloxy, aryloxyalkyl, halo, haloalkoxy, haloalkyl, hydroxy, hydroxyalkoxy, hydroxyalkyl, (NR$^2$R$^3$)alkoxy, (NR$^2$R$^3$)alkenyl, (NR$^2$R$^3$)alkyl, (NR$^2$R$^3$)carbonylalkenyl, and (NR$^2$R$^3$)carbonylalkyl, wherein R$^2$ and R$^3$ are independently selected from the group consisting of hydrogen, alkyl, alkylcarbonyl, alkyl sulfonyl, arylsulfonyl, haloalkylsulfonyl, and heterocyclylsulfonyl; alternatively R$^2$ and R$^3$ and may be taken together to form a 5-7 membered heterocyclic ring with N;
b is 0 or an integer of from 1 to 2;
Y is selected from the group consisting of:
  (1') —(CH$_2$)g-O—(CH$_2$)h-;
  (2') —(CH$_2$)g-NR$^1$—(CH$_2$)h-;
  (3') —(CH$_2$)g-S(O)$_n$—(CH$_2$)h-;
  (4') —(CH$_2$)g-SO$_2$N R$^2$—(CH$_2$)h-;
  (5') —(CH$_2$)g-NR$^2$SO$_2$—(CH$_2$)h-;
  (6') —(CH$_2$)g-CO—(CH$_2$)h-;
  (7') —(CH$_2$)g-C(O)NR$^2$—(CH$_2$)h-;
  (8') —(CH$_2$)g-NR$^2$C(O)—(CH$_2$)h-;
  (9') —(CH$_2$)g-C≡C—(CH$_2$)h-;
  (10') —(CH$_2$)g-NR$^2$C(O)NR$^3$—(CH$_2$)h-;
  (11') —(CH$_2$)g-(CH$_2$)h-;
  (12') —(CH$_2$)g-CF$_2$—(CH$_2$)h-;
  (13') —(CH$_2$)g-CCl$_2$—(CH$_2$)h-;
  (14') —(CH$_2$)g-CHF—(CH$_2$)h-;
  (15') —(CH$_2$)g-CH(OH)—(CH$_2$)h-;
  (16') —(CH$_2$)g-CR$^2$R$^3$—(CH$_2$)h-;
  (17') —(CH$_2$)g-C═C—(CH$_2$)h-;
  and (18') a single bond;

wherein
g is 0 or an integer of from 1 to 3;
h is 0 or an integer of from 1 to 3;
R$^1$ is independently selected from the group consisting of hydrogen, alkenyl, alkoxyalkyl, CF$_3$, alkyl, alkylcarbonyl, alkoxycarbonyl, aryl, heterocycloalkyl, hydroxyalkyl, and alkyl(N R$^2$R$^3$), wherein R$^2$ and R$^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively R$^2$ and R$^3$ and may be taken together to form a 5-7 membered heterocyclic ring with N;
R$^2$ and R$^3$ are independently selected from the group consisting of hydrogen, alkyl, alkylcarbonyl, alkoxycarbonyl, alkyl sulfonyl, aryl sulfonyl, haloalkyl sulfonyl, and heterocyclylsulfonyl; alternatively R$^2$ and R$^3$ and may be taken together to form a 5-7 membered cyclic ring;
Ring A is selected from the group consisting of:

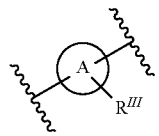

(i) Phenyl;
(ii) Naphthyl;
(iii) A 5 or 6 membered monocyclic heteroaryl group which have 1-5 heteroatoms independently selected from the group consisting of O, N and S;
and (iv) An 8 to 10 membered bicyclic heteroaryl group which have 1-6 heteroatoms independently selected from the group consisting of O, N and S;
Ring A can be illustrated but not limited to the following:

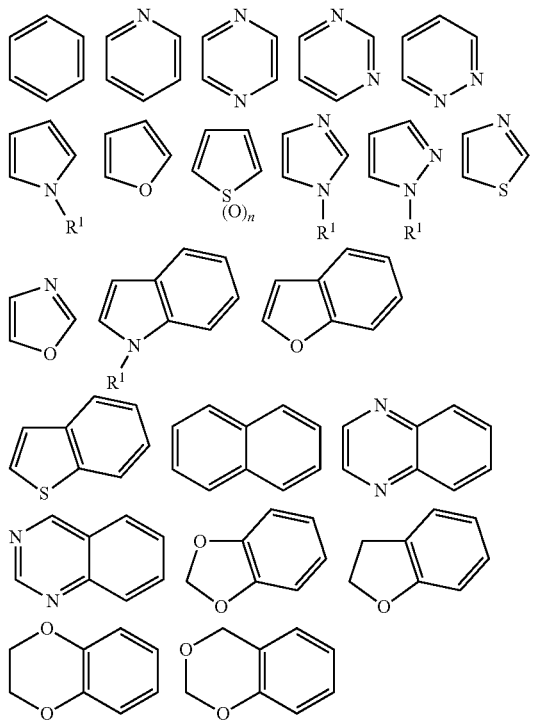

wherein
R is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered heterocyclic ring with N;

$R^{III}$ represents optionally 1-3 substituents independently selected from the group consisting of $C_1$-$C_5$ linear or branched alkyl, $C_1$-$C_5$ linear or branched haloalkyl, $C_1$-$C_5$ alkoxy, hydroxy, amino, $C_1$-$C_5$ alkylamino, C1-C6 dialkylamino, halogen, cyano, and nitro;

Z is selected from the group consisting of
(1') $(CH_2)_iN(R^7)C(O)N(R^8)(CH_2)_j$;
(2') $(CH_2)_iN(R^7)C(S)N(R^8)(CH_2)_j$;
(3') $(CH_2)_iN(R^7)C(O)$;
(4') $C(O)N(R^8)(CH_2)_j$;
(5') $(CH_2)_iN(R^7)S(O)_2$;
and (6') $S(O)_2N(R^8)(CH_2)_j$;
wherein
i is 0 or 1;
j is 0 or 1;
$R^7$ and $R^8$ are independently selected from the group consisting of hydrogen and alkyl.

Ring B is selected from the group consisting of:

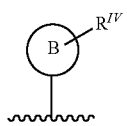

(i') Phenyl;
(ii') Naphthyl;
(iii') A 5 or 6 membered monocyclic heteroaryl group which have 1-3 heteroatoms independently selected from the group consisting of O, N and S;
and (iv') An 8 to 10 membered bicyclic heteroaryl group which have 1-3 heteroatoms independently selected from the group consisting of O, N and S;

Ring B can be illustrated but not limited to the following:

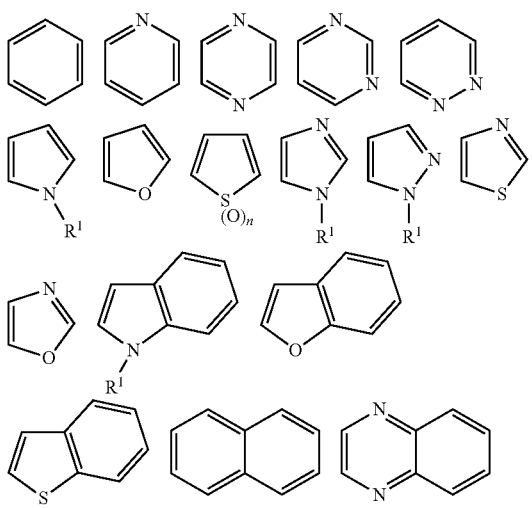

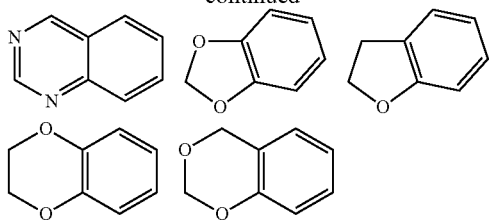

wherein
$R^1$ is independently selected from the group consisting of hydrogen, alkenyl, alkoxyalkyl, $CF_3$, alkyl, alkylcarbonyl, alkoxycarbonyl, aryl, heterocycloalkyl, hydroxyalkyl, and alkyl(N $R^2R^3$), wherein $R^2$ and $R^3$ are independently selected from the group consisting of hydrogen, alkyl, alkylcarbonyl, alkoxycarbonyl, alkyl sulfonyl, aryl sulfonyl, haloalkylsulfonyl, and heterocyclylsulfonyl; alternatively $R^2$ and $R^3$ and may be taken together to form a 5-7 membered heterocyclic ring with N;

$R^{IV}$ represents optionally 1-3 substituents, independently selected from the group consisting of alkoxy, alkoxyalkyl, alkoxycarbonyl, alkyl, aryloxy, arylalkyl, carboxy, cyano, halo, haloalkoxy, haloalkyl, hydroxy, hydroxyalkyl, nitro, and —$NR^9R^{10}$; wherein $R^9$ and $R^{10}$ are independently selected from the group consisting of hydrogen, alkyl, alkylcarbonyl, aryl, arylalkyl, cycloalkyl, cycloalkylalkyl, heterocyclyl, and heterocyclylalkyl; and including any pharmaceutically acceptable salt or prodrug.

Unless otherwise indicated, reference to a compound should be construed broadly to include compounds, pharmaceutically acceptable salts, prodrugs, tautomers, stereoisomers, diastereoisomers, alternate solid forms, crystal forms, polymorphic forms, hydrates, solvates, metabolites, mixtures of stereoisomers, mixtures of crystal forms, non-covalent complexes, and combinations thereof, of a chemical entity of a depicted structure or a chemical name. Whenever there is a conflict between chemical name and its structure drawing, the structure drawing should be used to interpret the compound of the present invention.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counterions. Salts can form from or incorporate one or more deprotonated acidic groups (e.g. carboxylic acids), one or more protonated basic groups (e.g. amines), or both (e.g. zwitterions).

A "prodrug" is a compound, which when administered to the body of a subject (such as a mammal), breaks down in the subject's metabolic pathway to provide an active compound of Formula I. More specifically, a prodrug is an active or inactive "masked" compound that is modified chemically through in vivo physiological action, such as hydrolysis, metabolism and the like, into a compound of this invention following administration of the prodrug to a subject or patient. One common form of a prodrug is a masked carboxylic acid group. Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

Tautomers are isomers that are in rapid equilibrium with one another. For example, tautomers may be related by transfer of a proton, hydrogen atom, or hydride ion. Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be amorphous forms, crystal forms, polymorphs, and the mixtures thereof.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

2. USES, FORMULATION AND ADMINISTRATION

The present invention is also directed to the use of the compounds as protein tyrosine kinase modulators and inhibitors. These compounds can be used to treat diseases related to unregulated tyrosine kinase signal transduction, for example, various cancers, blood vessel proliferative disorders, fibrotic disorders, and neurodegenerative diseases. In particular, compounds of the present invention are useful for the treatment and/or prevention of colorectal cancer, lung cancer, hematological cancer, renal cancer, liver cancer, breast cancer, diabetic retinopathy, macular degeneration, age-related macular degeneration, retinopathy of prematurity, ocular angiogenesis, retinal edema, retinal ischemia, diabetic macular edema, cystoid macular edema, retinal vein occlusion, branch vein occlusion, preretinal neovascularization, laser-induced choroidal neovascularization, neovascularization associated with keratoplasty, glaucoma and ocular tumors, arthritis, restenosis, hepatic cirrhosis, atherosclerosis, psoriasis, diabetes mellitus, wound healing, transplant rejection, inflammation, neurodegenerative diseases and immune disorders in the human being.

For the purposes of this disclosure, "treat," "treating," or "treatment" refer to the diagnosis, cure, mitigation, treatment, or prevention of disease or other undesirable condition.

The present invention is also directed to the preparation of a medicament for the treatment and prevention of diseases and conditions related with abnormal activities of tyrosine kinase receptors. The medicament contains a pharmaceutical acceptable composition, which comprises the therapeutic effective amount of the compounds of present invention, together with a pharmaceutical acceptable carrier.

The pharmaceutical acceptable compositions contain therapeutic effective amount of the compounds of the present invention. These compositions can be used as a medicament and administered to a mammal, such as a person, in need thereof. Different types of suitable dosage forms and medicaments are well known in the art, and can be readily adapted for delivery of the compounds of the present invention, such as, but not limited to, systematic, parenteral, local and topical delivery. The dosage forms can be tablets, capsules, intravenous injections, intramuscular injections, local injections, topical creams, gels and ointments, eye drops, ophthalmic solutions, ophthalmic suspensions, ophthalmic emulsions, intravitreal injections, subtenon injections, ophthalmic biodrodible implant, and non-bioeordible ophthalmic inserts or depots, nasal sprays and ointment, various rectal or vaginal preparations.

3. EXAMPLES

Some of the compounds of the present invention are listed in Table I.

TABLE 1

Exemplified Compounds of the Present Invention

| Example # | Chemical Structure | MW | Chemical Name |
|---|---|---|---|
| 1 | 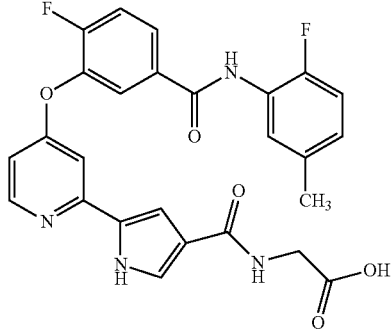 [SMILES: Cc1ccc(F)c(NC(=O)c2ccc(F)c(Oc3ccnc(-c4cc(C(=O)NCC(=O)O)c[nH]4)c3)c2)c1] | 506 | [({5-[4-(2-fluoro-5-{[(2-fluoro-5-methylphenyl)amino]carbonyl}phenoxy)pyridin-2-yl]-1H-pyrrol-3-yl}carbonyl)amino]acetic acid |

TABLE 1-continued

Exemplified Compounds of the Present Invention

| Example # | Chemical Structure | MW | Chemical Name |
|---|---|---|---|
| 2 | | 520 | methyl [({5-[4-(2-fluoro-5-{[(2-fluoro-5-methylphenyl)amino]carbonyl}phenoxy)pyridin-2-yl]-1H-pyrrol-3-yl}carbonyl)amino]acetate |
| 3 | | 460 | ({[5-(4-{3-[(3-methyl-2-furoyl)amino]phenoxy}pyridin-2-yl)-1H-pyrrol-3-yl]carbonyl}amino)acetic acid |
| 4 | | 474 | methyl ({[5-(4-{3-[(3-methyl-2-furoyl)amino]phenoxy}pyridin-2-yl)-1H-pyrrol-3-yl]carbonyl}amino)acetate |
| 5 | | 402 | 5-[4-({3-[(3-methyl-2-furoyl)amino]phenyl}amino)pyridin-2-yl]-1H-pyrrole-3-carboxylic acid |

TABLE 1-continued

Exemplified Compounds of the Present Invention

| Example # | Chemical Structure | MW | Chemical Name |
|---|---|---|---|
| 6 | | 416 | methyl 5-[4-({3-[(3-methyl-2-furoyl)amino]phenyl}amino)pyridin-2-yl]-1H-pyrrole-3-carboxylate |
| 7 | | 464 | 5-[4-(2-fluoro-5-{[(2-fluoro-5-methylphenyl)amino]carbonyl}phenoxy)pyridin-2-yl]-N-hydroxy-1H-pyrrole-3-carboxamide |
| 8 | | 533 | 4-fluoro-N-(2-fluoro-5-methylphenyl)-3-[(2-{4-[(3-hydroxypiperidin-1-yl)carbonyl]-1H-pyrrol-2-yl}pyridin-4-yl)oxy]benzamide |
| 9 | | 505 | N-(2,3-dihydroxypropyl)-5-[4-(3-{[(2-fluoro-5-methylphenyl)amino]carbonyl}phenoxy)pyridin-2-yl]-1H-pyrrole-3-carboxamide |

TABLE 1-continued

Exemplified Compounds of the Present Invention

| Example # | Chemical Structure | MW | Chemical Name |
|---|---|---|---|
| 10 | | 501 | N-(2-fluoro-5-methylphenyl)-3-[(2-{4-[(3-hydroxypyrrolidin-1-yl)carbonyl]-1H-pyrrol-2-yl}pyridin-4-yl)oxy]benzamide |
| 11 | | 446 | 5-[4-(3-{[(2-fluoro-5-methylphenyl)amino]carbonyl}phenoxy)pyridin-2-yl]-N-hydroxy-1H-pyrrole-3-carboxamide |
| 12 | | 463 | methyl 5-[4-(2-fluoro-5-{[(2-fluoro-5-methylphenyl)amino]carbonyl}phenoxy)pyridin-2-yl]-1H-pyrrole-3-carboxylate |
| 13 | | 449 | 5-[4-(2-fluoro-5-{[(2-fluoro-5-methylphenyl)amino]carbonyl}phenoxy)pyridin-2-yl]-1H-pyrrole-3-carboxylic acid |
| 14 | | 430 | N-ethyl-5-(4-{3-[(3-methyl-2-furoyl)amino]phenoxy}pyridin-2-yl)-1H-pyrrole-3-carboxamide |

TABLE 1-continued

Exemplified Compounds of the Present Invention

| Example # | Chemical Structure | MW | Chemical Name |
|---|---|---|---|
| 15 | | 476 | N-(2,3-dihydroxypropyl)-5-(4-{3-[(3-methyl-2-furoyl)amino]phenoxy}pyridin-2-yl)-1H-pyrrole-3-carboxamide |
| 16 | | 402 | 5-(4-{3-[(3-methyl-2-furoyl)amino]phenoxy}pyridin-2-yl)-1H-pyrrole-3-carboxamide |
| 17 | | 418 | N-hydroxy-5-(4-{3-[(3-methyl-2-furoyl)amino]phenoxy}pyridin-2-yl)-1H-pyrrole-3-carboxamide |
| 18 | Chiral | 472 | N-(3-{[2-(4-{[(3R)-3-hydroxypyrrolidin-1-yl]carbonyl}-1H-pyrrol-2-yl)pyridin-4-yl]oxy}phenyl)-3-methyl-2-furamide |

TABLE 1-continued

Exemplified Compounds of the Present Invention

| Example # | Chemical Structure | MW | Chemical Name |
|---|---|---|---|
| 19 | | 431 | 5-[4-(3-{[(2-fluoro-5-methylphenyl)amino]carbonyl}phenoxy)pyridin-2-yl]-1H-pyrrole-3-carboxylic acid |
| 20 | | 445 | methyl 5-[4-(3-{[(2-fluoro-5-methylphenyl)amino]carbonyl}phenoxy)pyridin-2-yl]-1H-pyrrole-3-carboxylate |
| 21 | | 477 | 2,3-dihydroxypropyl 5-(4-{3-[(3-methyl-2-furoyl)amino]phenoxy}pyridin-2-yl)-1H-pyrrole-3-carboxylate |
| 22 | | 413 | 5-[4-(3-{[(3-methylphenyl)amino]carbonyl}phenoxy)pyridin-2-yl]-1H-pyrrole-3-carboxylic acid |
| 23 | | 427 | methyl 5-[4-(3-{[(3-methylphenyl)amino]carbonyl}phenoxy)pyridin-2-yl]-1H-pyrrole-3-carboxylate |

TABLE 1-continued

Exemplified Compounds of the Present Invention

| Example # | Chemical Structure | MW | Chemical Name |
|---|---|---|---|
| 24 | | 464 | 2-hydroxyethyl 5-[4-(3-{[(3-methyl-2-thienyl)carbonyl]amino}phenoxy)pyridin-2-yl]-1H-pyrrole-3-carboxylate |
| 25 | | 447 | 2-hydroxyethyl 5-(4-{3-[(3-methyl-2-furoyl)amino]phenoxy}pyridin-2-yl)-1H-pyrrole-3-carboxylate |
| 26 | | 419 | 5-[4-(3-{[(3-methyl-2-thienyl)carbonyl]amino}phenoxy)pyridin-2-yl]-1H-pyrrole-3-carboxylic acid |
| 27 | | 433 | methyl 5-[4-(3-{[(3-methyl-2-thienyl)carbonyl]amino}phenoxy)pyridin-2-yl]-1H-pyrrole-3-carboxylate |
| 28 | | 421 | 5-(4-{4-fluoro-3-[(3-methyl-2-furoyl)amino]phenoxy}pyridin-2-yl)-1H-pyrrole-3-carboxylic acid |

TABLE 1-continued

Exemplified Compounds of the Present Invention

| Example # | Chemical Structure | MW | Chemical Name |
|---|---|---|---|
| 29 | | 435 | methyl 5-(4-{4-fluoro-3-[(3-methyl-2-furoyl)amino]phenoxy}pyridin-2-yl)-1H-pyrrole-3-carboxylate |
| 30 | | 479 | N-[dimethyl(oxido)-lambda~4~-sulfanylidene]-5-(4-{3-[(3-methyl-2-furoyl)amino]phenoxy}pyridin-2-yl)-1H-pyrrole-3-carboxamide |
| 31 | Chiral | 472 | N-(3-{[2-(4-{[(3S)-3-hydroxypyrrolidin-1-yl]carbonyl}-1H-pyrrol-2-yl)pyridin-4-yl]oxy}phenyl)-3-methyl-2-furamide |
| 32 | | 403 | 5-(4-{3-[(3-methyl-2-furoyl)amino]phenoxy}pyridin-2-yl)-1H-pyrrole-3-carboxylic acid |

TABLE 1-continued
Exemplified Compounds of the Present Invention
| Example # | Chemical Structure | MW | Chemical Name |
|---|---|---|---|
| 33 | 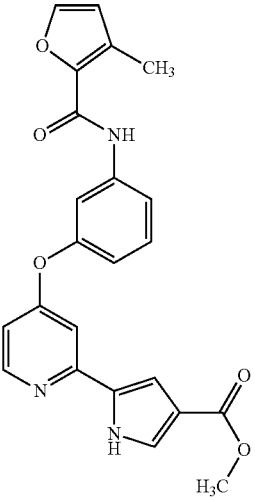 [SMILES: COC(=O)c1c[nH]c(-c2cc(Oc3cccc(NC(=O)c4occc4C)c3)ccn2)c1] | 417 | methyl 5-(4-{3-[(3-methyl-2-furoyl)amino]phenoxy}pyridin-2-yl)-1H-pyrrole-3-carboxylate |
| 34 | 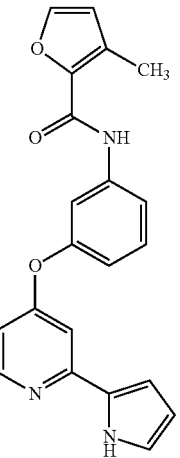 | 359 | 3-methyl-N-(3-{[2-(1H-pyrrol-2-yl)pyridin-4-yl]oxy}phenyl)-2-furamide |
| 35 | 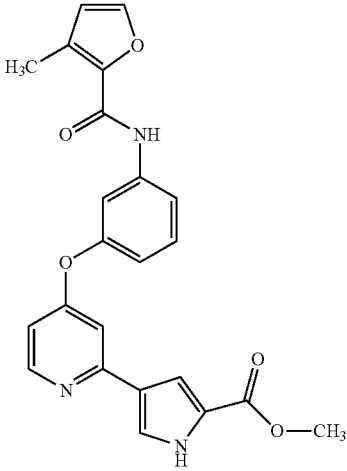 [SMILES: COC(=O)c1cc(-c2cc(Oc3cccc(NC(=O)c4occc4C)c3)ccn2)c[nH]1] | 417 | methyl 4-(4-{3-[(3-methyl-2-furoyl)amino]phenoxy}pyridin-2-yl)-1H-pyrrole-2-carboxylate |

TABLE 1-continued

Exemplified Compounds of the Present Invention

| Example # | Chemical Structure | MW | Chemical Name |
|---|---|---|---|
| 36 | | 387 | 2-fluoro-5-methyl-N-(4-{[2-(1H-pyrrol-2-yl)pyridin-4-yl]oxy}phenyl)benzamide |
| 37 | | 359 | 3-methyl-N-(4-{[2-(1H-pyrrol-2-yl)pyridin-4-yl]oxy}phenyl)-2-furamide |
| 38 | | 573 | 5-{4-[4-({[(2-fluoro-5-methylphenyl)amino]carbonyl}amino)phenoxy]pyridin-2-yl}-N-(3-morpholin-4-ylpropyl)-1H-pyrrole-3-carboxamide |
| 39 | | 479 | 5-{4-[3-fluoro-4-({[(2-fluoro-5-methylphenyl)amino]carbonyl}amino)phenoxy]pyridin-2-yl}-N-hydroxy-1H-pyrrole-3-carboxamide |

TABLE 1-continued

Exemplified Compounds of the Present Invention

| Example # | Chemical Structure | MW | Chemical Name |
|---|---|---|---|
| 40 | 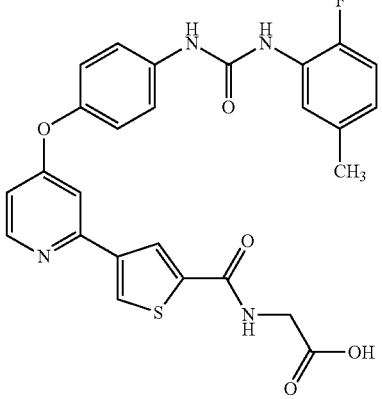 | 521 | {[(4-{4-[4-({[(2-fluoro-5-methylphenyl)amino]carbonyl}amino)phenoxy]pyridin-2-yl}-2-thienyl)carbonyl]amino}acetic acid |
| 41 | 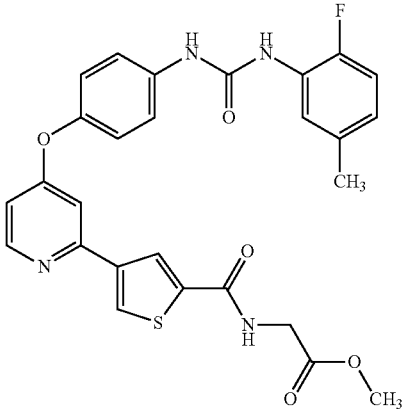 [SMILES: COC(=O)CNC(=O)c1cc(-c2cc(Oc3ccc(NC(=O)Nc4cc(C)ccc4F)cc3)ccn2)cs1] | 535 | methyl {[(4-{4-[4-({[(2-fluoro-5-methylphenyl)amino]carbonyl}amino)phenoxy]pyridin-2-yl}-2-thienyl)carbonyl]amino}acetate |
| 42 | 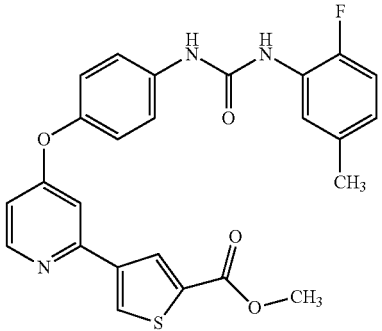 [SMILES: COC(=O)c1cc(-c2cc(Oc3ccc(NC(=O)Nc4cc(C)ccc4F)cc3)ccn2)cs1] | 478 | methyl 4-{4-[4-({[(2-fluoro-5-methylphenyl)amino]carbonyl}amino)phenoxy]pyridin-2-yl}thiophene-2-carboxylate |

TABLE 1-continued

Exemplified Compounds of the Present Invention

| Example # | Chemical Structure | MW | Chemical Name |
|---|---|---|---|
| 43 | Chiral | 603 | (4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid |
| 44 | Chiral | 659 | tert-butyl (4S)-5-ethylamino-4-{[(5-{4-[3-fluoro-4-({[(3-methylphenyl)amino]carbonyl}amino)phenoxy]pyridin-2-yl}-pyrrol-3-yl)carbonyl]amino}-5-oxopentanoate |
| 45 | Chiral | 632 | (2S)-5-tert-butoxy-2-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid |

TABLE 1-continued

Exemplified Compounds of the Present Invention

| Example # | Chemical Structure | MW | Chemical Name |
|---|---|---|---|
| 46 | | 646 | 5-tert-butyl 1-methyl 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate |
| 47 | | 664 | bis(2-hydroxyethyl) 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate |
| 48 | | 518 | 3-{[(5-{4-[3-fluoro-4-({[(3-methylphenyl)amino]carbonyl}amino)phenoxy]pyridin-2-yl}-1H-pyrrol-3-yl)carbonyl]amino}propanoic acid |

TABLE 1-continued

Exemplified Compounds of the Present Invention

| Example # | Chemical Structure | MW | Chemical Name |
|---|---|---|---|
| 49 | | 576 | 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioic acid |
| 50 | | 615 | methyl 1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylate |
| 51 | Chiral | 573 | 5-{4-[4-({[(2-fluoro-5-methylphenyl)amino]carbonyl}amino)phenoxy]pyridin-2-yl}-N-{2-[(3S)-3-hydroxypyrrolidin-1-yl]-2-oxoethyl}-1H-pyrrole-3-carboxamide |

TABLE 1-continued

Exemplified Compounds of the Present Invention

| Example # | Chemical Structure | MW | Chemical Name |
|---|---|---|---|
| 52 | | 619 | N-{4-[(2,3-dihydroxypropyl)(methyl)amino]-4-oxobutyl}-5-{4-[4-({(2-fluoro-5-methylphenyl)amino]carbonyl}amino)phenoxy]pyridin-2-yl}-1H-pyrrole-3-carboxamide |
| 53 | | 615 | 5-{4-[4-({[(2-fluoro-5-methylphenyl)amino]carbonyl}amino)phenoxy]pyridin-2-yl}-N-[4-(3-hydroxypiperidin-1-yl)-4-oxobutyl]-1H-pyrrole-3-carboxamide |
| 54 | | 605 | N-{4-[(2,3-dihydroxypropyl)amino]-4-oxobutyl}-5-{4-[4-({[(2-fluoro-5-methylphenyl)amino]carbonyl}amino)phenoxy]pyridin-2-yl}-1H-pyrrole-3-carboxamide |

TABLE 1-continued

Exemplified Compounds of the Present Invention

| Example # | Chemical Structure | MW | Chemical Name |
|---|---|---|---|
| 55 | | 531 | N-(4-amino-4-oxobutyl)-5-{4-[4-({[2-fluoro-5-methylphenyl)amino]carbonyl}amino)phenoxy]pyridin-2-yl}-1H-pyrrole-3-carboxamide |
| 56 | | 577 | N-{2-[(2,3-dihydroxypropyl)amino]-2-oxoethyl}-5-{4-[4-({[(2-fluoro-5-methylphenyl)amino]carbonyl}amino)phenoxy]pyridin-2-yl}-1H-pyrrole-3-carboxamide |
| 57 | | 664 | 5-(2,3-dihydroxypropyl) 1-methyl 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate |

TABLE 1-continued

Exemplified Compounds of the Present Invention

| Example # | Chemical Structure | MW | Chemical Name |
|---|---|---|---|
| 58 | | 724 | bis(2,3-dihydroxypropyl) 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate |
| 59 | | 590 | 4-{[(5-{4-[4-({[(2-fluoro-5-methylphenyl)amino]carbonyl}amino)phenoxy]pyridin-2-yl}-1H-pyrrol-3-yl)carbonyl]amino}-5-methoxy-5-oxopentanoic acid |
| 60 | | 559 | N-[4-(ethylamino)-4-oxobutyl]-5-{4-[4-({[(2-fluoro-5-methylphenyl)amino]carbonyl}amino)phenoxy]pyridin-2-yl}-1H-pyrrole-3-carboxamide |

TABLE 1-continued

Exemplified Compounds of the Present Invention

| Example # | Chemical Structure | MW | Chemical Name |
|---|---|---|---|
| 61 | | 601 | 5-{4-[4-({[(2-fluoro-5-methylphenyl)amino]carbonyl}amino)phenoxy]pyridin-2-yl}-N-[4-(3-hydroxypyrrolidin-1-yl)-4-oxobutyl]-1H-pyrrole-3-carboxamide |
| 62 | | 547 | 5-{4-[4-({[(2-fluoro-5-methylphenyl)amino]carbonyl}amino)phenoxy]pyridin-2-yl}-N-[4-(hydroxyamino)-4-oxobutyl]-1H-pyrrole-3-carboxamide |
| 63 | | 576 | 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioic acid |

TABLE 1-continued

Exemplified Compounds of the Present Invention

| Example # | Chemical Structure | MW | Chemical Name |
|---|---|---|---|
| 64 | | 604 | dimethyl 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate |
| 65 | | 562 | 1-[(5-{4-[3-fluoro-4-({[(2-fluoro-5-methylphenyl)amino]carbonyl}amino)phenoxy]pyridin-2-yl}-1H-pyrrol-3-yl)carbonyl]pyrrolidine-3-carboxylic acid |
| 66 | | 550 | 4-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}butanoic acid |

TABLE 1-continued

Exemplified Compounds of the Present Invention

| Example # | Chemical Structure | MW | Chemical Name |
|---|---|---|---|
| 67 | | 578 | ethyl 4-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}butanoate |
| 68 | | 532 | 4-{[(5-{4-[3-fluoro-4-({[(3-methylphenyl)amino]carbonyl}amino)phenoxy]pyridin-2-yl}-1H-pyrrol-3-yl)carbonyl]amino}butanoic acid |
| 69 | | 536 | 3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propanoic acid |
| 70 | | 474 | N-ethyl-5-{4-[3-fluoro-4-({[(3-methylphenyl)amino]carbonyl}amino)phenoxy]pyridin-2-yl}-1H-pyrrole-3-carboxamide |

TABLE 1-continued

Exemplified Compounds of the Present Invention

| Example # | Chemical Structure | MW | Chemical Name |
|---|---|---|---|
| 71 | | 503 | {[(5-{4-[3-fluoro-4-({[(3-methylphenyl)amino]carbonyl} amino)phenoxy]pyridin-2-yl}-1H-pyrrol-3-yl)carbonyl] amino}acetic acid |
| 72 | | 518 | methyl {[(5-{4-[3-fluoro-4-({[(3-methylphenyl)amino]carbonyl} amino)phenoxy]pyridin-2-yl}-1H-pyrrol-3-yl)carbonyl] amino}acetate |
| 73 | Chiral | 516 | 1-(2-fluoro-4-{[2-(4-{[(3R)-3-hydroxypyrrolidin-1-yl] carbonyl}-1H-pyrrol-2-yl) pyridin-4-yl]oxy}phenyl)-3-(3-methylphenyl)urea |

TABLE 1-continued

Exemplified Compounds of the Present Invention

| Example # | Chemical Structure | MW | Chemical Name |
|---|---|---|---|
| 74 | | 530 | 1-{2-fluoro-4-[(2-{4-[(3-hydroxypiperidin-1-yl)carbonyl-1H-pyrrol-2-yl}pyridin-4-yl)oxy]phenyl}-3-(3-methyphenyl)urea |
| 75 | | 446 | 5-{4-[3-fluoro-4-({[(3-methylphenyl)amino]carbonyl}amino)phenoxy]pyridin-2-yl}-1H-pyrrole-3-carboxylic acid |
| 76 | | 460 | methyl 5-{4-[3-fluoro-4-({[(3-methylphenyl)amino]carbonyl}amino)phenoxy]pyridin-2-yl}-1H-pyrrole-3-carboxylate |
| 77 | | 622 | 5-{4-[4-({[(2-fluoro-5-methylphenyl)amino]carbonyl}amino)phenoxy]pyridin-2-yl}-N-(2-{2-[2-(2-hydroxyethoxy)ethoxy]ethoxy}ethyl)-1H-pyrrole-3-carboxamide |

TABLE 1-continued

Exemplified Compounds of the Present Invention

| Example # | Chemical Structure | MW | Chemical Name |
|---|---|---|---|
| 78 | | 532 | 4-{[(5-{4-[4-({[(2-fluoro-5-methylphenyl)amino]carbonyl}amino)phenoxy]pyridin-2-yl}-1H-pyrrol-3-yl)carbonyl]amino}butanoic acid |
| 79 | | 560 | ethyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate |
| 80 | | 463 | 5-(4-{[4-({[(2-fluoro-5-methylphenyl)amino]carbonyl}amino)phenyl]thio}pyridin-2-yl)-1H-pyrrole-3-carboxylic acid |
| 81 | | 518 | 3-{[(5-{4-[4-({[(2-fluoro-5-methylphenyl)amino]carbonyl}amino)phenoxy]pyridin-2-yl}-1H-pyrrol-3-yl)carbonyl]amino}propanoic acid |

TABLE 1-continued

Exemplified Compounds of the Present Invention

| Example # | Chemical Structure | MW | Chemical Name |
|---|---|---|---|
| 82 | | 576 | 4-{S-methyl-N-[(5-{4-[4-({[(3-methylphenyl)amino]carbonyl}amino)phenoxy]pyridin-2-yl}-1H-pyrrol-3-yl)carbonyl]sulfonimidoyl}butanoic acid |
| 83 | | 544 | 1-[(5-{4-[4-({[(2-fluoro-5-methylphenyl)amino]carbonyl}amino)phenoxy]pyridin-2-yl}-1H-pyrrol-3-yl)carbonyl]pyrrolidine-3-carboxylic acid |
| 84 | | 503 | {[(5-{4-[4-({[(2-fluoro-5-methylphenyl)amino]carbonyl}amino)phenoxy]pyridin-2-yl}-1H-pyrrol-3-yl)carbonyl]amino}acetic acid |

TABLE 1-continued

Exemplified Compounds of the Present Invention

| Example # | Chemical Structure | MW | Chemical Name |
|---|---|---|---|
| 85 | | 518 | methyl {[(5-{4-[4-({[(2-fluoro-5-methylphenyl)amino]carbonyl}amino)phenoxy]pyridin-2-yl}-1H-pyrrol-3-yl)carbonyl]amino}acetate |
| 86 | | 594 | 1-[(5-{4-[4-({[(2-fluoro-5-methylphenyl)amino]carbonyl}amino)phenoxy]pyridin-2-yl}-1H-pyrrol-3-yl)carbonyl]piperidine-4-sulfonic acid |
| 87 | | 590 | methyl 4-{S-methyl-N-[(5-{4-[4-({[(3-methylphenyl)amino]carbonyl}amino)phenoxy]pyridin-2-yl}-1H-pyrrol-3-yl)carbonyl]sulfonimidoyl}butanoate |

TABLE 1-continued

Exemplified Compounds of the Present Invention

| Example # | Chemical Structure | MW | Chemical Name |
|---|---|---|---|
| 88 | | 477 | methyl 5-(4-{[4-({[(2-fluoro)-5-methylphenyl)amino]carbonyl}amino)phenyl]thio}pyridin-3-yl)-1H-pyrrole-3-carboxylate |
| 89 | | 441 | N-methyl-5-(4-[4-({[(3-methylphenyl)amino]carbonyl}amino)phenoxy)pyridin-2-yl]-1H-pyrrole-3-carboxamide |
| 90 | | 512 | 1-{4-[(2-{4-[(3-hydroxypiperidin-1-yl)carbonyl]-1H-pyrrol-2-yl}pyridin-4-yl)oxy]phenyl}-3-(3-methylphenyl)urea |
| 91 | | 498 | 1-{4-[(2-{4-[(3-hydroxypyrrolidin-1-yl)carbonyl]-1H-pyrrol-2-yl}pyridin-4-yl)oxy]phenyl}-3-(3-methylphenyl)urea |

TABLE 1-continued

Exemplified Compounds of the Present Invention

| Example # | Chemical Structure | MW | Chemical Name |
|---|---|---|---|
| 92 | | 502 | N-(2,3-dihydroxypropyl)-5-{4-[4-({[(3-methylphenyl)amino]carbonyl}amino)phenoxy]pyridin-2-yl}-1H-pyrrole-3-carboxamide |
| 93 | | 456 | N-ethyl-5-{4-[4-({[(3-methylphenyl)amino]carbonyl}amino)phenoxy]pyridin-2-yl}-1H-pyrrole-3-carboxamide |
| 94 | | 427 | 5-{4-[4-({[(3-methylphenyl)amino]carbonyl}amino)phenoxy]pyridin-2-yl}-1H-pyrrole-3-carboxamide |
| 95 | | 443 | N-hydroxy-5-{4-[4-({[(3-methylphenyl)amino]carbonyl}amino)phenoxy]pyridin-2-yl}-1H-pyrrole-3-carboxamide |

TABLE 1-continued

Exemplified Compounds of the Present Invention

| Example # | Chemical Structure | MW | Chemical Name |
|---|---|---|---|
| 96 | | 464 | 5-{4-[3-fluoro-4-({[(2-fluoro-5-methylphenyl)amino]carbonyl}amino)phenoxy]pyridin-2-yl}-1H-pyrrole-3-carboxlic acid |
| 97 | | 504 | N-[dimethyl(oxido)-lambda~4~-sulfanylidene]-5-{4-[4-({[(3-methylphenyl)amino]carbonyl}amino)phenoxy]pyridin-2-yl}-1H-pyrrole-3-carboxamide |
| 98 | | 561 | 2-hydroxyethyl 5-(4-{4-[({[4-chloro-3-(trifluoromethyl)phenyl]amino}carbonyl)amino]phenoxy}pyridin-2-yl)-1H-pyrrole-3-carboxylate |
| 99 | | 592 | 5-(4-{4-[({[4-chloro-3-(trifluoromethyl)phenyl]amino}carbonyl)amino]phenoxy}pyridin-2-yl)-N-[dimethyl(oxido)-lambda~4~-sulfanylidene]-1H-pyrrole-3-carboxamide |

TABLE 1-continued

Exemplified Compounds of the Present Invention

| Example # | Chemical Structure | MW | Chemical Name |
|---|---|---|---|
| 100 | | 608 | methyl 4-{N-[(5-{4-[4-({[(2-fluoro-5-methylphenyl)amino]carbonyl}amino)phenoxy]pyridin-2-yl}-1H-pyrrol-3-yl)carbonyl]-S-methylsulfonimidoyl}butanoate |
| 101 | | 522 | N-[dimethyl(oxido)-lambda~4~-sulfanylidene]-5-{4-[4-({[(2-fluoro-5-methylphenyl)amino]carbonyl}amino)phenoxy]pyridin-2-yl}-1H-pyrrole-3-carboxamide |
| 102 | Chiral | 601 | methyl (2S)-1-(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)pyrrolidine-2-carboxylate |
| 103 | | 502 | N,N-diethyl-5-{4-[4-({[(2-fluoro-5-methylphenyl)amino]carbonyl}amino)phenoxy]pyridin-2-yl}-1H-pyrrole-3-carboxamide |

TABLE 1-continued

Exemplified Compounds of the Present Invention

| Example # | Chemical Structure | MW | Chemical Name |
|---|---|---|---|
| 104 | | 529 | 1-(2-fluoro-5-methylphenyl)-3-{4-[(2-{4-[(4-methylpiperazin-1-yl)carbonyl]-1H-pyrrol-2-yl}pyridin-4-yl)oxy]phenyl}urea |
| 105 | | 543 | 5-{4-[4-({[(2-fluoro-5-methylphenyl)amino]carbonyl}amino)phenoxy]pyridin-2-yl}-N-(2-pyrrolidin-1-ylethyl)-1H-pyrrole-3-carboxamide |
| 106 | | 471 | 1-[4-({2-[4-(aziridin-1-ylcarbonyl)-1H-pyrrol-2-yl]pyridin-4-yl}oxy)phenyl]-3-(2-fluoro-5-methylphenyl)urea |
| 107 | | 445 | 5-{4-[4-({[(2-fluoro-5-methylphenyl)amino]carbonyl}amino)phenoxy]pyridin-2-yl}-1H-pyrrole-3-carboxamide |

TABLE 1-continued

Exemplified Compounds of the Present Invention

| Example # | Chemical Structure | MW | Chemical Name |
|---|---|---|---|
| 108 | | 461 | 5-{4-[4-({[(2-fluoro-5-methylphenyl)amino]carbonyl}amino)phenoxy]pyridin-2-yl}-N-hydroxy-1H-pyrrole-3-carboxamide |
| 109 | | 486 | 1-[4-({2-[4-(azetidin-1-ylcarbonyl)-1H-pyrrol-2-yl]pyridin-4-yl}oxy)phenyl]-3-(2-fluoro-5-methylphenyl)urea |
| 110 | | 504 | 5-{4-[4-({[(2-fluoro-5-methylphenyl)amino]carbonyl}amino)phenoxy]pyridin-2-yl}-N-(3-hydroxypropyl)-1H-pyrrole-3-carboxamide |
| 111 | | 549 | 2-(2-methoxyethoxy)ethyl 5-{4-[4-({[(2-fluoro-5-methylphenyl)amino]carbonyl}amino)phenoxy]pyridin-2-yl}-1H-pyrrole-3-carboxylate |

TABLE 1-continued

Exemplified Compounds of the Present Invention

| Example # | Chemical Structure | MW | Chemical Name |
|---|---|---|---|
| 112 | | 474 | N-ethyl-5-{4-[4-({[(2-fluoro-5-methylphenyl)amino]carbonyl}amino)phenoxy]pyridin-2-yl}-1H-pyrrole-3-carboxamide |
| 113 | | 505 | 2-methoxyethyl 5-{4-[4-({[(2-fluoro-5-methylphenyl)amino]carbonyl}amino)phenoxy]pyridin-2-yl}-pyrrole-3-carboxylate |
| 114 | | 504 | 5-{4-[4-({[(2-fluoro-5-methylphenyl)amino]carbonyl}amino)phenoxy]pyridin-2-yl}-N-(2-methoxyethyl)-1H-pyrrole-3-carboxamide |
| 115 | | 428 | 5-{4-[4-({[(3-methylphenyl)amino]carbonyl}amino)phenoxy]pyridin-2-yl}-1H-pyrrole-3-carboxylic acid |

TABLE 1-continued

Exemplified Compounds of the Present Invention

| Example # | Chemical Structure | MW | Chemical Name |
|---|---|---|---|
| 116 | | 442 | methyl 5-{4-[4-({[(3-methylphenyl)amino]carbonyl}amino)phenoxy]pyridin-2-yl}-1H-pyrrole-3-carboxylate |
| 117 | | 464 | 5-{4-[2-fluoro-4-({[(2-fluoro-5-methylphenyl)amino]carbonyl}amino)phenoxy]pyridin-2-yl}-1H-pyrrole-3-carboxylic acid |
| 118 | | 478 | methyl 5-{4-[2-fluoro-4-({[(2-fluoro-5-methylphenyl)amino]carbonyl}amino)phenoxy]pyridin-2-yl}-1H-pyrrole-3-carboxylate |
| 119 | | 500 | 5-(4-{4-[({[4-fluoro-3-(trifluoromethyl)phenyl]amino}carbonyl)amino]phenoxy}pyridin-2-yl)-1H-pyrrole-3-carboxylic acid |

TABLE 1-continued

Exemplified Compounds of the Present Invention

| Example # | Chemical Structure | MW | Chemical Name |
|---|---|---|---|
| 120 | | 514 | methyl 5-(4-{4-[({[4-fluoro-3-(trifluoromethyl)phenyl]amino}carbonyl)amino]phenoxy}pyridin-2-yl)-1H-pyrrole-3-carboxylate |
| 121 | | 517 | 5-(4-{4-[({[4-chloro-3-(trifluoromethyl)phenyl]amino}carbonyl)amino]phenoxy}pyridin-2-yl)-1H-pyrrole-3-carboxylic acid |
| 122 | | 531 | methyl 5-(4-{4-[({[4-chloro-3-(trifluoromethyl)phenyl]amino}carbonyl)amino]phenoxy}pyridin-2-yl)-1H-pyrrole-3-carboxylate |
| 123 | | 463 | 4-{4-[4-({[(2-fluoro-5-methylphenyl)amino]carbonyl}amino)phenoxy]pyridin-2-yl}thiophene-2-carboxylic acid |

TABLE 1-continued

Exemplified Compounds of the Present Invention

| Example # | Chemical Structure | MW | Chemical Name |
|---|---|---|---|
| 124 | | 490 | 2-hydroxyethyl 4-{4-[4-({[(2-fluoro-5-methylphenyl)amino]carbonyl}amino)phenoxy]pyridin-2-yl}-1H-pyrrole-2-carboxylate |
| 125 | | 572 | {1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetic acid |
| 126 | | 586 | methyl {1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetate |

TABLE 1-continued

Exemplified Compounds of the Present Invention

| Example # | Chemical Structure | MW | Chemical Name |
|---|---|---|---|
| 127 | | 520 | N-(2,3-dihydroxypropyl)-5-{4-[4-({[(2-fluoro-5-methylphenyl)amino]carbonyl}amino)phenoxy]pyridin-2-yl}-1H-pyrrole-3-carboxamide |
| 128 | | 490 | 5-{4-[4-({[(2-fluoro-5-methylphenyl)amino]carbonyl}amino)phenoxy]pyridin-2-yl}-N-(2-hydroxyethyl)-1H-pyrrole-3-carboxamide |
| 129 | | 530 | 1-(2-fluoro-5-methylphenyl)-3-{4-[(2-{4-[(4-hydroxypiperidin-1-yl)carbonyl]-1H-pyrrol-2-yl}pyridin-4-yl)oxy]phenyl}urea |
| 130 | | 521 | 2,3-dihydroxypropyl 5-{4-[4-({[(2-fluoro-5-methylphenyl)amino]carbonyl}amino)phenoxy]pyridin-2-yl}-1H-pyrrole-3-carboxylate |

TABLE 1-continued

Exemplified Compounds of the Present Invention

| Example # | Chemical Structure | MW | Chemical Name |
|---|---|---|---|
| 131 | | 490 | 2-hydroxyethyl 5-{4-[4-({[(2-fluoro-5-methylphenyl)amino]carbonyl}amino)phenoxy]pyridin-2-yl}-1H-pyrrole-3-carboxylate |
| 132 | Chiral | 516 | 1-(2-fluoro-5-methylphenyl)-3-(4-{[2-(4-{[(3R)-3-hydroxypyrrolidin-1-yl]carbonyl}-1H-pyrrol-2-yl)pyridin-4-yl]oxy}phenyl)urea |
| 133 | Chiral | 516 | 1-(2-fluoro-5-methylphenyl)-3-(4-{[2-(4-{[(3S)-3-hydroxypyrrolidin-1-yl]carbonyl}-1H-pyrrol-2-yl)pyridin-4-yl]oxy}phenyl)urea |
| 134 | | 446 | 5-{4-[4-({[(2-fluoro-5-methylphenyl)amino]carbonyl}amino)phenoxy]pyridin-2-yl}-1H-pyrrole-3-carboxylic acid |

TABLE 1-continued

Exemplified Compounds of the Present Invention

| Example # | Chemical Structure | MW | Chemical Name |
|---|---|---|---|
| 135 | | 460 | methyl 5-{4-[4-({[(2-fluoro-5-methylphenyl)amino]carbonyl}amino)phenoxy]pyridin-2-yl}-1H-pyrrole-3-carboxylate |
| 136 | | 460 | methyl 4-{4-[3-({[(2-fluoro-5-methylphenyl)amino]carbonyl}amino)phenoxy]pyridin-2-yl}-1H-pyrrole-2-carboxylate |
| 137 | | 522 | N-[dimethyl(oxido)-lambda~4~-sulfanylidene]-4-{4-[4-({[(2-fluoro-5-methylphenyl)amino]carbonyl}amino)phenoxy]pyridin-2-yl}-1H-pyrrole-2-carboxamide |

TABLE 1-continued

Exemplified Compounds of the Present Invention

| Example # | Chemical Structure | MW | Chemical Name |
|---|---|---|---|
| 138 | | 474 | 4-{4-[4-({[(2-fluoro-5-methylphenyl)amino]carbonyl}amino)phenoxy]pyridin-2-yl}-N,N-dimethyl-1H-pyrrole-2-carboxamide |
| 139 | | 459 | 4-{4-[4-({[(2-fluoro-5-methylphenyl)amino]carbonyl}amino)phenoxy]pyridrin-2-yl}-N-methyl-1H-pyrrole-2-carboxamide |
| 140 | | 576 | 1-tert-butyl 2-methyl 4-{6-amino-4-[4-({[(2-fluoro-5-methylphenyl)amino]carbonyl}amino)phenoxy]pyridin-2-yl}-1H-pyrrole-1,2-dicarboxylate |
| 141 | | 417 | 1-(4-{[2-amino-6-(1H-pyrrol-2-yl)pyridin-4-yl]oxy}phenyl)-3-(2-fluoro-5-methylphenyl)urea |

TABLE 1-continued

Exemplified Compounds of the Present Invention

| Example # | Chemical Structure | MW | Chemical Name |
|---|---|---|---|
| 142 | | 446 | 4-{4-[4-({[(2-fluoro-5-methylphenyl)amino]carbonyl}amino)phenoxy]pyridin-2-yl}-1H-pyrrole-2-carboxylic acid |
| 143 | | 460 | methyl 4-{4-[4-({[(2-fluoro-5-methylphenyl)amino]carbonyl}amino)phenoxy]pyridin-2-yl}-1H-pyrrole-2-carboxylate |
| 144 | | 402 | 1-(2-fluoro-5-methylphenyl)-3-(4-{[2-1H-pyrrol-2-yl)pyridin-4-yl]oxy}phenyl)urea |
| 145 | | 354 | 1-phenyl-3-{4-[6-(1H-pyrrol-2-yl)pyridin-3-yl]phenyl}urea |

TABLE 1-continued

Exemplified Compounds of the Present Invention

| Example # | Chemical Structure | MW | Chemical Name |
|---|---|---|---|
| 146 | | 386 | 1-(2-fluoro-5-methylphenyl)-3-{3-[2-(1H-pyrrol-2-yl)pyridin-4-yl]phenyl}urea |
| 147 | | 386 | 1-(2-fluoro-5-methylphenyl)-3-{4-[2-(1H-pyrrol-3-yl)pyridin-4-yl]phenyl}urea |
| 148 | | 386 | 1-(2-fluoro-5-methylphenyl)-3-{4-[2-(1H-pyrrol-2-yl)pyridin-4-yl]phenyl}urea |

3.1 Compound Synthesis and Characterization

Preparation of methyl 5-(4,4,5,5-tetramethyl-1,3,2-dioxaborolan-2-yl)-1H-pyrrole-3-carboxylate

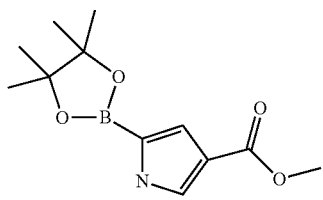

To a mixture of methyl-1H-pyrrole-3-carboxylate (5.0 g, 39.9 mmol), bis(pinacolato)diboron (5.37 g, 21.1 mmol), 4,4'-di-tert-butyl-2,2'-bipyridine (0.054 g, 0.20 mmol) and [Ir(OMe)(COD)]$_2$ (0.067 g, 0.099 mmol) was added cyclohexane (60 mL). The mixture stirred at 90° C. for 5 hours. The mixture was cooled to room temperature and filtered, washing with ample amounts of water and twice with hexanes. The light orange solid was collected and dried in a vacuum oven at 55° C. to afford methyl 5-(4,4,5,5-tetramethyl-1,3,2-dioxaborolan-2-yl)-1H-pyrrole-3-carboxylate (6.99 g, 70% yield).

Preparation of 3-(2-Bromo-pyridin-4-yloxy)-benzoic acid

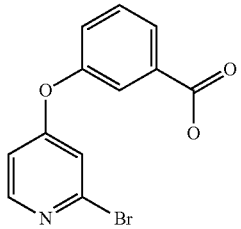 [SMILES: O=C(O)c1cccc(Oc2ccnc(Br)c2)c1]

A mixture of 2-bromo-4-chloro-pyridine (200 mg, 1.04 mmol), methyl-3-hydroxybenzoate (158 mg, 1.04 mmol), cesium carbonate (507 mg, 1.56 mmol) in 10 ml of anhydrous DMSO was heated at 66° C. for 5 hours. The mixture was diluted with ethyl acetate (100 ml), washed with brine (3×50 ml), dried over Na$_2$SO$_4$ and evaporated to give a colorless oil. The oil was dissolved in MeOH (8 ml), and 2M NaOH solution (4 ml, 8 mmol) was added. The mixture was heated at 60° C. for 20 minutes, poured into 50 ml of water, and acidified to pH=4. The precipitates were filtered, washed with water and dried in vacuo to give 3-(2-bromo-pyridin-4-yloxy)-benzoic acid as white solid. Yield: 170 mg, 56%.

$^1$H NMR (DMSO-d$_6$) δ: 13.24 (br. s., 1H), 8.27 (d, J=5.9 Hz, 1H), 7.87 (d, J=7.6 Hz, 1H), 7.58-7.68 (m, 2H), 7.45-7.52 (m, 1H), 7.19 (d, J=2.1 Hz, 1H), 7.00 (dd, J=5.7, 2.2 Hz, 1H)

LR MS (ES-): 292 (M-H), 294

Preparation of 3-(2-Bromo-pyridin-4-yloxy)-N-m-tolyl-benzamide

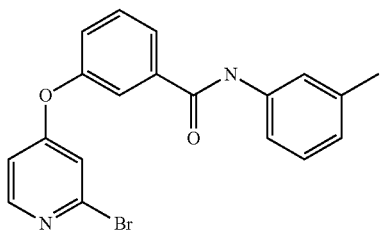 [SMILES: Cc1cccc(NC(=O)c2cccc(Oc3ccnc(Br)c3)c2)c1]

A mixture of 3-(2-bromo-pyridin-4-yloxy)-benzoic acid (170 mg, 0.58 mmol), HATU (265 mg, 0.69 mmol),) m-toluidine (93 mg, 0.87 mmol) and N,N-diisopropylethylamine (164 mg, 1.28 mmol) in anhydrous DMF (10 ml) was stirred at room temperature for 20 minutes. The mixture was poured into 100 ml of water. The precipitates were filtered, washed with water and dried in vacuo to give 3-(2-Bromo-pyridin-4-yloxy)-N-m-tolyl-benzamide as off-white solid. Yield: 150 mg, 68%.

$^1$H NMR (DMSO-d$_6$) δ: 10.18 (s, 1H), 8.29 (d, J=5.9 Hz, 1H), 7.91 (d, J=7.6 Hz, 1H), 7.78 (s, 1H), 7.65 (t, J=7.9 Hz, 1H), 7.50-7.60 (m, 2H), 7.45 (dd, J=7.9, 1.8 Hz, 1H), 7.16-7.25 (m, 2H), 7.02 (dd, J=5.7, 2.2 Hz, 1H), 6.92 (d, J=7.6 Hz, 1H), 2.29 (s, 3H)

LR MS (ES+): 405 (M+Na$^+$), 407

LR MS (ES-): 381 (M-H), 383

Preparation of 3-(2-Bromo-pyridin-4-yloxy)-N-(2-fluoro-5-methyl-phenyl)-benzamide

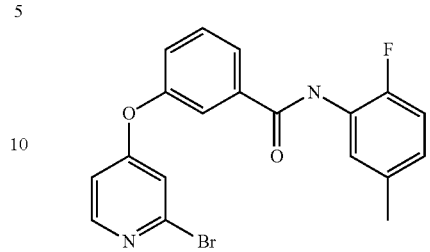

A mixture of 3-(2-bromo-pyridin-4-yloxy)-benzoic acid (200 mg, 0.68 mmol), HATU (312 mg, 0.82 mmol),) 2-fluoro-5-methylaniline (125 mg, 1.0 mmol) and N,N-diisopropylethylamine (193 mg, 1.5 mmol) in anhydrous DMF (10 ml) was stirred at 60° C. for 90 minutes. The mixture was poured into 100 ml of water. The precipitates were filtered, washed with water and dried in vacuo to give 3-(2-bromo-pyridin-4-yloxy)-N-(2-fluoro-5-methyl-phenyl)-benzamide as off-white solid. Yield: 200 mg, 74%.

Example 1

[({5-[4-(2-fluoro-5-{[(2-fluoro-5-methylphenyl)amino]carbonyl}phenoxy)pyridin-2-yl]-1H-pyrrol-3-yl}carbonyl)amino]acetic acid

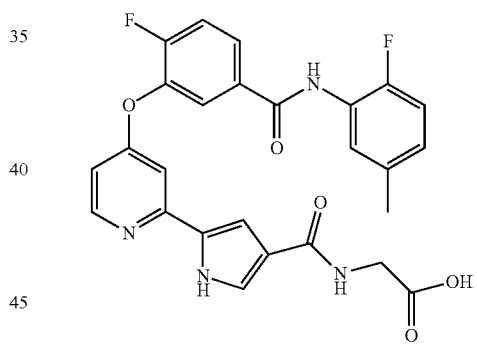

To a stirred solution of methyl [({5-[4-(2-fluoro-5-{[(2-fluoro-5-methylphenyl)amino]carbonyl}phenoxy)pyridin-2-yl]-1H-pyrrol-3-yl}carbonyl)amino]acetate (110 mg, 0.21 mmol) in a mixture of solvents THF/MeOH (5 ml/5 ml) was added 1M NaOH solution (1 ml, 1 mmol). The mixture was stirred at room temperature for 1 hour, and poured into 100 ml of water. 2M HCl was added until pH=4. The precipitates were filtered, washed with water and dried in vacuo to give [({5-[4-(2-fluoro-5-{[(2-fluoro-5-methylphenyl)amino]carbonyl}phenoxy)pyridin-2-yl]-1H-pyrrol-3-yl}carbonyl)amino]acetic acid as white solid. Yield: 100 mg, 93%.

$^1$H NMR (DMSO-d$_6$) δ: 12.41 (br. s., 1H), 11.87 (br. s., 1H), 10.12 (s, 1H), 8.42 (d, J=5.6 Hz, 1H), 8.19 (t, J=6.0 Hz, 1H), 7.95-8.04 (m, 2H), 7.63 (dd, J=10.1, 8.7 Hz, 1H), 7.41 (dd, J=3.1, 1.6 Hz, 1H), 7.35 (dd, J=7.3, 1.8 Hz, 1H), 7.27 (d, J=2.3 Hz, 1H), 7.09-7.18 (m, 2H), 7.04 (td, J=5.3, 2.3 Hz, 1H), 6.81 (dd, J=5.9, 2.3 Hz, 1H), 3.82 (d, J=5.9 Hz, 2H), 2.27 (s, 3H)

LR MS (ES-): 505 (M-H)

Example 2 methyl [({5-[4-(2-fluoro-5-{[(2-fluoro-5-methylphenyl)amino]carbonyl}phenoxy)pyridin-2-yl]-1H-pyrrol-3-yl}carbonyl)amino]acetate

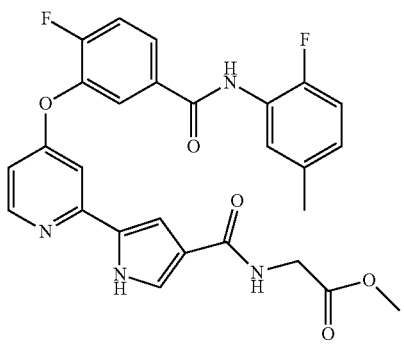 [SMILES: COC(=O)CNC(=O)c1c[nH]c(-c2cc(Oc3cc(C(=O)Nc4cc(C)ccc4F)ccc3F)ccn2)c1]

Similar procedure as Example 1.

¹H NMR (DMSO-d$_6$) δ: 11.95 (br. s., 1H), 10.12 (s, 1H), 8.44 (d, J=5.9 Hz, 1H), 8.33 (t, J=5.9 Hz, 1H), 7.97-8.03 (m, 2H), 7.61-7.67 (m, 1H), 7.45 (br. s., 1H), 7.33-7.37 (m, 1H), 7.30 (s, 1H), 7.18 (br. s., 1H), 7.14 (dd, J=10.3, 8.5 Hz, 1H), 7.02-7.08 (m, 1H), 6.86 (br. s., 1H), 3.91 (d, J=5.9 Hz, 2H), 3.61 (s, 3H), 2.27 (s, 3H)

LR MS (ES+): 521 (MH), 543 (M+Na$^+$)

LR MS (ES−): 519 (M−H)

Preparation of 4-(3-Aminophenoxy)-2-chloropyridine

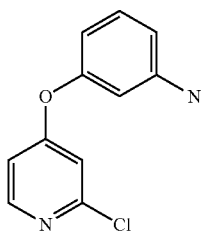 [SMILES: Nc1cccc(Oc2ccnc(Cl)c2)c1]

To a mixture of 3-aminophenol (3.7 g, 34.09 mmol) in DMSO (50 mL) was added Cs2CO3 (30.7 g, 94.46 mmol). The mixture stirred for 10 minutes and then 2,4-dichloropyridine (5.0 g, 33.79 mmol) was added. The mixture was stirred at 120° C. for 1.5 h. The mixture was cooled and diluted with water. The aqueous solution was extracted with EtOAc (3×100 mL). The organic extracts were combined, dried over MgSO4 and concentrated to afford a dark oil. The oil was purified via column chromatography, eluting with 30-40% EtOAc/hexanes, to afford 4-(3-Aminophenoxy)-2-chloropyridine (6.63 g, 89%) as a brown solid.

Preparation of methyl 5-[4-(3-aminophenoxy)pyridin-2-yl]-1H-pyrrole-3-carboxylate

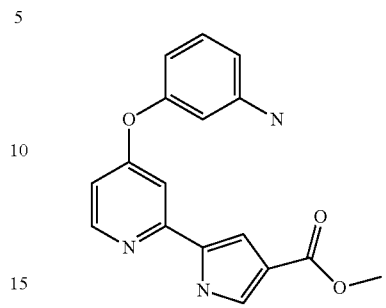

A mixture of 4-(3-aminophenoxy)-2-chloropyridine (4.0 g, 18.13 mmol), methyl-(5-(4,4,5,5-tetramethyl-1,3,2-dioxaborolan-2-yl)-1H-pyrrole-3-carboxylate (6.82 g, 27.16 mmol) and Pd(PPh3)4 (4.20 g, 3.63 mmol) was added to a thick walled reaction vessel and purged with N2. A solution of 2M K2CO3 (13.59 mL) was added, followed by DME (70 mL). The reaction vessel was sealed and the mixture stirred at 92° C. for 18 h. The reaction vessel was cooled to room temperature and the mixture was filtered over celite, washing with EtOAc. The filtrate was concentrated and the resultant dark oil was purified via column chromatography, eluting with 40-80% EtOAc/hexanes to afford methyl 5-[4-(3-aminophenoxy)pyridin-2-yl]-1H-pyrrole-3-carboxylate (2.85 g, 51% yield).

Example 3

({[5-(4-{3-[(3-methyl-2-furoyl)amino]phenoxy}pyridin-2-yl)-1H-pyrrol-3-yl]carbonyl}amino)acetic acid

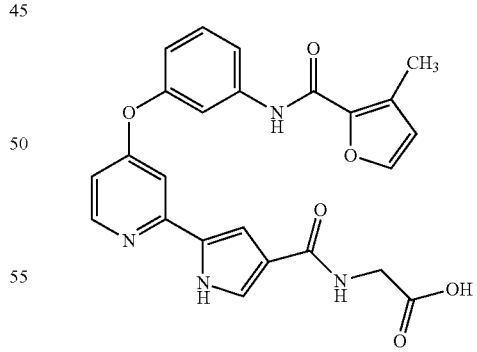

Similar procedure as Example 1.

¹H NMR (DMSO-d$_6$) δ: 12.42 (br. s., 1H), 11.91 (br. s., 1H), 10.20 (s, 1H), 8.41 (d, J=5.6 Hz, 1H), 8.21 (t, J=5.4 Hz, 1H), 7.76 (s, 1H), 7.65-7.73 (m, 2H), 7.36-7.47 (m, 2H), 7.26 (br. s., 1H), 7.12 (br. s., 1H), 6.86-6.98 (m, 1H), 6.77 (br. s., 1H), 6.56 (s, 1H), 3.81 (d, J=5.9 Hz, 2H), 2.29 (s, 3H)

LR MS (ES−): 459 (M−H)

Example 4 methyl ({[5-(4-{3-[(3-methyl-2-furoyl)amino]phenoxy}pyridin-2-yl)-1H-pyrrol-3-yl]carbonyl}amino)acetate

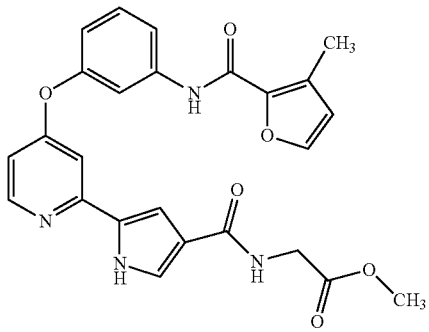 [SMILES: COC(=O)CNC(=O)c1c[nH]c(-c2cc(Oc3cccc(NC(=O)c4occc4C)c3)ccn2)c1]

Similar procedure as Example 3.

¹H NMR (DMSO-d₆) δ: 11.88 (br. s., 1H), 10.19 (s, 1H), 8.40 (d, J=5.6 Hz, 1H), 8.32 (t, J=5.6 Hz, 1H), 7.76 (s, 1H), 7.65-7.72 (m, 2H), 7.36-7.44 (m, 2H), 7.23 (d, J=2.1 Hz, 1H), 7.08 (br. s., 1H), 6.90 (d, J=7.3 Hz, 1H), 6.75 (dd, J=5.6, 1.8 Hz, 1H), 6.56 (s, 1H), 3.89 (d, J=5.6 Hz, 2H), 3.60 (s, 3H), 2.29 (s, 3H)

LR MS (ES+): 475 (MH), 497 (M+Na⁺)

LR MS (ES−): 473 (M−H)

Preparation of 2-Chloro-N-(3-nitrophenyl)pyridine-4-amine

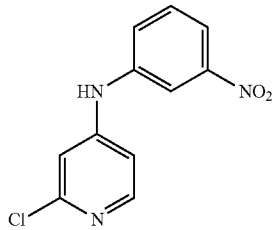 [SMILES: O=[N+]([O-])c1cccc(Nc2ccnc(Cl)c2)c1]

To a degassed (15 min, N₂) suspension of 2-chloro-4-iodopyridine (3.0 g, 12.53 mmol), 3-nitroaniline (1.82 g, 13.18 mmol), BINAP (0.39 g, 0.626 mmol) and Cs₂CO₃ (8.16 g, 25.04 mmol) in toluene (72 mL) was added Pd(OAc)₂ (0.084 g, 0.374 mmol). The reaction tube was sealed and the mixture stirred at 90° C. for 18 h. The mixture was cooled to rt and filtered, washing with EtOAc. The orange/yellow solid collected was washed with CH₂Cl₂ until all the product washed through into the filtrate. The filtrate was concentrated to afford 2-Chloro-N-(3-nitrophenyl)pyridine-4-amine as a bright yellow solid. Additional product was collected from the solid collected upon concentration of the previous filtrate, after washing with CH₂Cl₂. No further purification. Total amount of product collected was 2.85 g (91% yield).

Preparation of tert-Butyl 2-chloropyridin-4-yl(3-nitrophenyl)carbamate

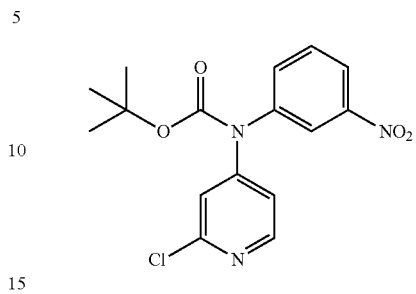

To a stirring solution of 2-Chloro-N-(3-nitrophenyl)pyridine-4-amine (2.70 g, 10.82 mmol) in THF (45 mL) was added Et₃N (6.32 mL, 45.3 mmol). The mixture was cooled to 0° C., and DMAP (0.0135 g, 0.110 mmol) and BOC₂O (2.84 g, 12.99 mmol) were added. The mixture was warmed to rt and stirred for 18 h. The mixture was quenched with ice and diluted with water. Extracted with EtOAc (3×200 mL), washed with brine and water, dried (MgSO₄), and concentrated. A dark oil was afforded, which was passed through a pad of silica gel, eluting with 1:1 EtOAc/hexanes. Concentrated and dried under high vacuum to afford tert-Butyl 2-chloropyridin-4-yl(3-nitrophenyl)carbamate (3.65 g, 96.5% yield).

Preparation of methyl 5-(4-(tert-butoxycarbonyl(3-nitrophenyl)amino)pyridine-2-yl)-1H-pyrrole-3-carboxylate

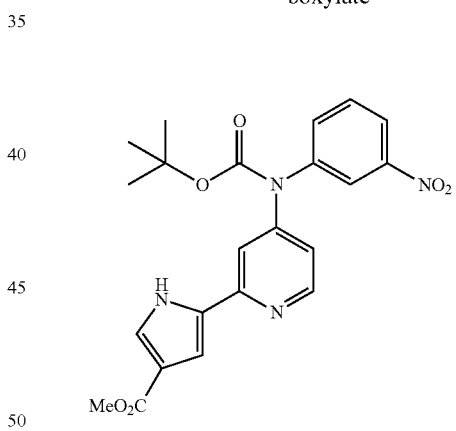

A mixture of tert-Butyl 2-chloropyridin-4-yl(3-nitrophenyl)carbamate (3.65 g, 10.43 mmol), methyl-(5-(4,4,5,5-tetramethyl-1,3,2-dioxaborolan-2-yl)-1H-pyrrole-3-carboxylate (5.48 g, 21.82 mmol), xantphos (0.72 g, 1.25 mmol) and Pd₂dba₃ (0.72 g, 0.79 mmol) was added to a thick walled reaction vessel and purged with N₂. A solution of 2M K₂CO₃ (8.76 mL) was added, followed by dioxane (67 mL). The reaction vessel was sealed and the mixture stirred at 105° C. for 18 h. The reaction vessel was cooled to rt and the mixture was filtered over celite, washing with EtOAc. The filtrate was concentrated to afford a dark oil, which was purified via column chromatography eluting with 30-50% EtOAc/hexanes to afford methyl 5-(4-(tert-butoxycarbonyl(3-nitrophenyl)amino)pyridine-2-yl)-1H-pyrrole-3-carboxylate (2.98 g, 65% yield) as an orange oil.

Preparation of methyl 5-(4-((3-nitrophenyl)amino)pyridin-2-yl)-1H-pyrrole-3-carboxylate

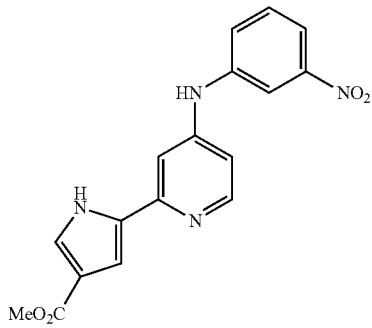 [SMILES: COC(=O)c1c[nH]c(-c2cc(Nc3cccc([N+](=O)[O-])c3)ccn2)c1]

Methyl 5-(4-(tert-butoxycarbonyl(3-nitrophenyl)amino)pyridine-2-yl)-1H-pyrrole-3-carboxylate (0.40 g, 0.91 mmol) was taken up in toluene (38 mL) and SiO$_2$ (9.0 g) was added. The mixture stirred at reflux for 20 h. The mixture was cooled to rt and filtered over celite, washing with EtOAc. The filtrate was concentrated to a bright orange color. The solid was taken up in hexanes and filtered. The solid was then washed with CH$_2$Cl$_2$/hexanes to afford methyl 5-(4-((3-nitrophenyl)amino)pyridin-2-yl)-1H-pyrrole-3-carboxylate (0.15 g, 49% yield) as a bright yellow solid.

Preparation of methyl 5-(4-((3-aminophenyl)amino)pyridin-2-yl)-1H-pyrrole-3-carboxylate

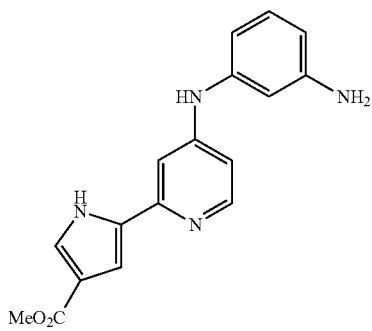

Methyl 5-(4-((3-nitrophenyl)amino)pyridin-2-yl)-1H-pyrrole-3-carboxylate (1.32 g, 3.9 mmol) was taken up in EtOAc/EtOH (1:1; 90 mL) and purged with N$_2$. Pd/C (10%, 0.145 g) was added and the mixture was stirred under an atmosphere of H$_2$ at rt for 18 h. The mixture was filtered over celite, washing with EtOAc/EtOH. The filtrate was concentrated, taken back up in EtOAc and filtered over celite again to remove any residual catalyst. The filtrate was concentrated again and taken back up in EtOAc. The solution was filtered and the filtrate was concentrated to afford a tan solid. The solid was washed with CH$_2$Cl$_2$/hexanes (1:2) and dried under high vacuum to afford methyl 5-(4-((3-aminophenyl)amino)pyridin-2-yl)-1H-pyrrole-3-carboxylate (1.15 g, 96% yield) as a tan solid.

Example 5

5-[4-({3-[(3-methyl-2-furoyl)amino]phenyl}amino)pyridin-2-yl]-1H-pyrrole-3-carboxylic acid

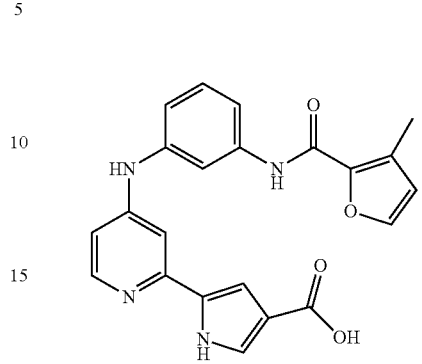

To a stirred solution of methyl 5-[4-({3-[(3-methyl-2-furoyl)amino]phenyl}amino)pyridin-2-yl]-1H-pyrrole-3-carboxylate (10 mg, 0.024 mmol) in a mixture of solvents THF/MeOH (5 ml/5 ml) was added 2 ml of 1M NaOH (2 mmol) solution. The mixture was heated in a 60° C. bath for 16 hours, cooled to room temperature and poured into 100 ml of water. 2M HCl was added until pH=5. The resulting precipitates were filtered, washed with water, and dried in vacuo to give 5-[4-({3-[(3-methyl-2-furoyl)amino]phenyl}amino)pyridin-2-yl]-1H-pyrrole-3-carboxylic acid as light brown solid. Yield: 2 mg.

Example 6 methyl 5-[4-({3-[(3-methyl-2-furoyl)amino]phenyl}amino)pyridin-2-yl]-1H-pyrrole-3-carboxylate

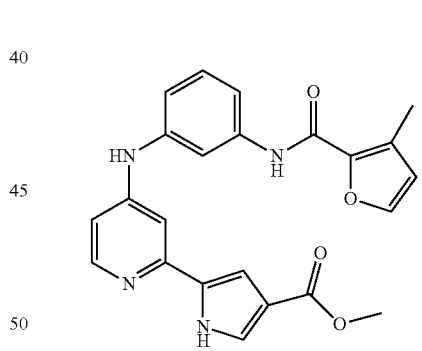

A mixture of 3-methyl-2-furoic acid (22 mg, 0.18 mmol), HATU (73 mg, 0.19 mmol) and N,N-diisopropylethylamine (45 mg, 0.35 mmol) in anhydrous DMF (10 ml) was stirred at room temperature for 10 minutes, followed by addition of methyl 5-(4-((3-aminophenyl)amino)pyridin-2-yl)-1H-pyrrole-3-carboxylate (50 mg, 0.16 mmol). The mixture was stirred at room temperature for 3 hours and poured into 100 ml of water. The precipitates were filtered, washed with water and dried in vacuo to give methyl 5-[4-({3-[(3-methyl-2-furoyl)amino]phenyl}amino)pyridin-2-yl]-1H-pyrrole-3-carboxylate as off-white solid. Yield: 10 mg, 15%.

$^1$H NMR (DMSO-d$_6$) δ: 13.60 (br. s., 1H), 12.37 (br. s., 1H), 10.14 (s, 1H), 8.15 (d, J=6.5 Hz, 1H), 7.86 (t, J=1.9 Hz, 1H), 7.77 (d, J=1.8 Hz, 1H), 7.58 (br. s., 1H), 7.52 (d, J=7.6 Hz, 1H), 7.32-7.38 (m, 2H), 7.22 (br. s., 1H), 6.97 (d, J=7.6

Hz, 1H), 6.86 (dd, J=6.2, 2.1 Hz, 1H), 6.57 (d, J=1.8 Hz, 1H), 3.71 (s, 3H), 2.32 (s, 3H)

LR MS (ES+): 417 (MH)

LR MS (ES−): 415 (M−H)

Example 7

5-[4-(2-fluoro-5-{[(2-fluoro-5-methylphenyl)amino]carbonyl}phenoxy)pyridin-2-yl]-N-hydroxy-1H-pyrrole-3-carboxamide

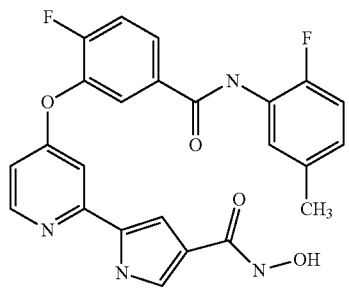 [SMILES: Cc1ccc(F)c(NC(=O)c2ccc(F)c(Oc3ccnc(-c4cc(C(=O)NO)c[nH]4)c3)c2)c1]

Similar procedure as Example 1.

$^1$H NMR (DMSO-$d_6$) δ: 11.85 (br. s., 1H), 10.56 (br. s., 1H), 10.12 (s, 1H), 8.66 (br. s., 1H), 8.41 (d, J=5.6 Hz, 1H), 7.99 (d, J=7.3 Hz, 2H), 7.63 (t, J=9.4 Hz, 1H), 7.30-7.40 (m, 2H), 7.27 (br. s., 1H), 7.10-7.18 (m, 1H), 7.01-7.10 (m, 2H), 6.75-6.85 (m, 1H), 2.26 (s, 3H)

LR MS (ES+): 487 (M+Na$^+$)

LR MS (ES−): 463 (M−H)

Example 8

4-fluoro-N-(2-fluoro-5-methylphenyl)-3-[(2-{4-[(3-hydroxypiperidin-1-yl)carbonyl]-1H-pyrrol-2-yl}pyridin-4-yl)oxy]benzamide

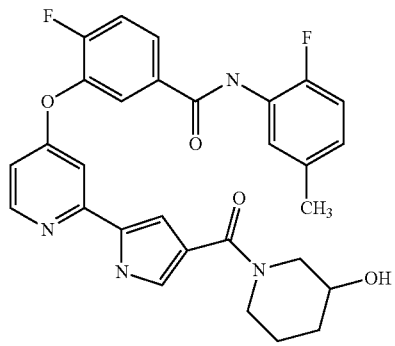 [SMILES: Cc1ccc(F)c(NC(=O)c2ccc(F)c(Oc3ccnc(-c4cc(C(=O)N5CCCC(O)C5)c[nH]4)c3)c2)c1]

Similar procedure as Example 1.

LR MS (ES+): 533 (MH), 555 (M+Na$^+$)

LR MS (ES−): 531 (M−H)

Example 9

N-(2,3-dihydroxypropyl)-5-[4-(3-{[(2-fluoro-5-methylphenyl)amino]carbonyl}phenoxy)pyridin-2-yl]-1H-pyrrole-3-carboxamide

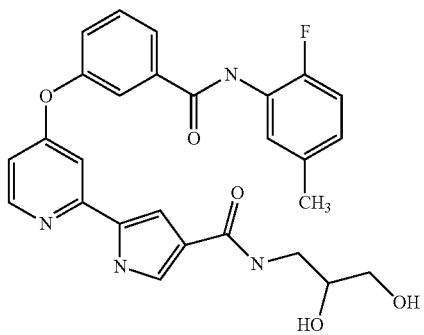 [SMILES: Cc1ccc(F)c(NC(=O)c2cccc(Oc3ccnc(-c4cc(C(=O)NCC(O)CO)c[nH]4)c3)c2)c1]

Similar procedure as Example 1.

$^1$H NMR (DMSO-$d_6$) δ: 11.83 (br. s., 1H), 10.11 (s, 1H), 8.41 (d, J=5.6 Hz, 1H), 7.89 (d, J=7.0 Hz, 1H), 7.83 (t, J=5.6 Hz, 1H), 7.77 (s, 1H), 7.63 (t, J=7.9 Hz, 1H), 7.42-7.46 (m, 1H), 7.39 (d, J=1.5 Hz, 1H), 7.35 (d, J=7.3 Hz, 1H), 7.25 (d, J=2.1 Hz, 1H), 7.09-7.16 (m, 2H), 7.02-7.06 (m, 1H), 6.76 (dd, J=5.7, 2.5 Hz, 1H), 4.77 (d, J=5.0 Hz, 1H), 4.53 (t, J=6.0 Hz, 1H), 3.50-3.56 (m, 1H), 3.25-3.30 (m, 3H), 3.08-3.14 (m, 1H), 2.27 (s, 3H)

LR MS (ES+): 505 (MH), 527 (M+Na$^+$)

LR MS (ES−): 503 (M−H)

Example 10

N-(2-fluoro-5-methylphenyl)-3-[(2-{4-[(3-hydroxypyrrolidin-1-yl)carbonyl]-1H-pyrrol-2-yl}pyridin-4-yl)oxy]benzamide

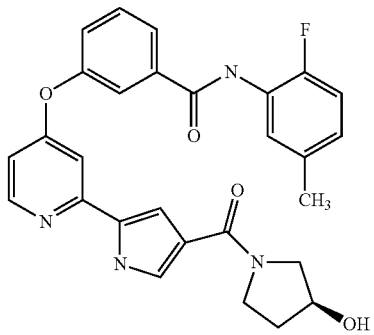 [SMILES: Cc1ccc(F)c(NC(=O)c2cccc(Oc3ccnc(-c4cc(C(=O)N5CC[C@H](O)C5)c[nH]4)c3)c2)c1]

A mixture of 5-{4-[3-(2-Fluoro-5-methyl-phenylcarbamoyl)-phenoxy]-pyridin-2-yl}-1H-pyrrole-3-carboxylic acid (50 mg, 0.12 mmol), HATU (55 mg, 0.14 mmol) and N,N-diisopropylethylamine (34 mg, 0.26 mmol) in anhydrous DMF (8 ml) was stirred at room temperature for 10 minutes, followed by addition of (S)-3-pyrrolidinol (16 mg, 0.18 mmol). The mixture was stirred for another 10 minutes and poured into 100 ml of water. The precipitates were filtered, washed with water and dried in vacuo to give N-(2-fluoro-5-methylphenyl)-3-[(2-{4-[(3-hydroxypyrrolidin-1-yl)carbonyl]-1H-pyrrol-2-yl}pyridin-4-yl)oxy]benzamide as white solid. Yield: 40 mg, 69%.

¹H NMR (DMSO-d₆) δ: 11.91 (br. s., 1H), 10.12 (s, 1H), 8.42 (d, J=5.6 Hz, 1H), 7.89 (d, J=7.6 Hz, 1H), 7.76 (s, 1H), 7.63 (t, J=7.9 Hz, 1H), 7.32-7.51 (m, 3H), 7.26 (d, J=6.7 Hz, 1H), 6.99-7.20 (m, 3H), 6.73 (dd, 1H), 4.91 (br. s., 1H), 4.30 (br. s., 1H), 3.76 (br. s., 2H), 3.50 (br. s., 2H), 2.28 (s, 3H), 1.86 (br. s., 2H)

LR MS (ES+): 501 (MH), 523 (M+Na⁺)
LR MS (ES−): 499 (M−H)

Example 11

5-[4-(3-{[(2-fluoro-5-methylphenyl)amino]carbonyl}phenoxy)pyridin-2-yl]-N-hydroxy-1H-pyrrole-3-carboxamide

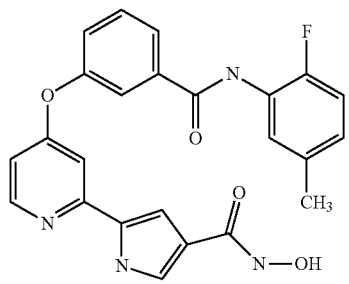 [SMILES: Cc1ccc(F)c(NC(=O)c2cccc(Oc3ccnc(-c4cc(C(=O)NO)c[nH]4)c3)c2)c1]

Similar procedure as Example 10.

¹H NMR (DMSO-d₆) δ: 11.84 (br. s., 1H), 10.56 (br. s., 1H), 10.10 (s, 1H), 8.65 (br. s., 1H), 8.40 (d, J=5.6 Hz, 1H), 7.89 (d, J=7.6 Hz, 1H), 7.76 (br. s., 1H), 7.63 (t, J=7.9 Hz, 1H), 7.44 (dd, J=7.9, 1.5 Hz, 1H), 7.35 (d, J=6.7 Hz, 1H), 7.31 (br. s., 1H), 7.25 (d, J=1.8 Hz, 1H), 7.13 (dd, J=10.3, 8.5 Hz, 1H), 7.01-7.07 (m, 2H), 6.75 (dd, J=5.7, 2.2 Hz, 1H), 2.27 (s, 3H)

LR MS (ES+): 469 (M+Na⁺)
LR MS (ES−): 445 (M−H)

Preparation of 3-(2-Chloropyridin-4-yloxy)-4-fluorobenzoic acid methyl ester

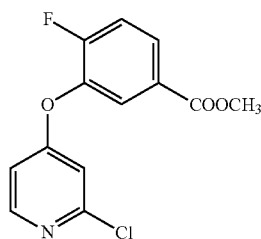 [SMILES: COC(=O)c1ccc(F)c(Oc2ccnc(Cl)c2)c1]

4-Fluoro-3-hydroxybenzoic acid methyl ester (1.70 g, 10.0 mmol) was dissolved in dimethylformamide (9 mL) under nitrogen at room temperature. Sodium hydride (60% oil dispersion, 0.48 g, 12 mmol) was added in portions over 30 min. The reaction was stirred for 90 minutes and then cooled in an ice bath. 2-Chloro-4-nitropyridine (1.58 g, 10.0 mmol) was added in small portions over 50 min. The reaction was stirred at room temperature for 17.5 h. Water (200 ml) was added and the mixture stirred until a brown lump formed. The water was decanted and the residue dissolved in EtOAc (150 mL). The solution was washed with brine, dried (MgSO₄), filtered and evaporated to give 3-(2-Chloropyridin-4-yloxy)-4-fluorobenzoic acid methyl ester. Yield: 3.10 g.

Preparation of 3-(2-Chloropyridin-4-yloxy)-4-fluorobenzoic acid

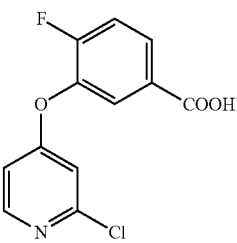 [SMILES: O=C(O)c1ccc(F)c(Oc2ccnc(Cl)c2)c1]

3-(2-Chloropyridin-4-yloxy)-4-fluorobenzoic acid methyl ester (2.81 g, 10.0 mmol) was dissolved in tetrahydrofuran (15 mL) and mixed with 2M lithium hydroxide (15 mL, 30 mmol). The suspension was stirred for 5 h. To the reaction was added water, then extracted with EtOAc. The aqueous layer was treated with 6M HCl (5 mL, 30 mmol) and then extracted with EtOAc (3×25 mL). The extract was dried (MgSO₄), filtered and evaporated to 3-(2-Chloropyridin-4-yloxy)-4-fluorobenzoic acid. Yield: 2.22 g, 83%.

Preparation of 3-(2-Chloropyridin-4-yloxy)-4-fluoro-N-(2-fluoro-5-methylphenyl)benzamide

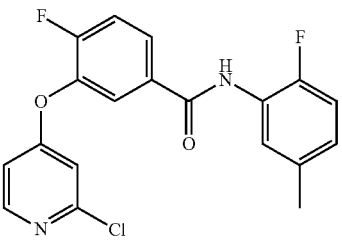 [SMILES: Cc1ccc(F)c(NC(=O)c2ccc(F)c(Oc3ccnc(Cl)c3)c2)c1]

A solution of 3-(2-Chloropyridin-4-yloxy)-4-fluorobenzoic acid (2.22 g, 8.29 mmol), 2-fluoro-5-methylaniline (1.56 g, 12.4 mmol), O-(7-azabenzotriazol-1-yl)-N,N,N',N'-tetramethyluronium hexafluorophosphate (HATU, 3.78 g, 9.95 mmol) and N-methylmorpholine (2.00 mL, 18.2 mmol) in dimethylformamide (22 mL) was heated at 90° C. for 2 h. The solvent was evaporated in vacuo at 50° C. To the residue was added water resulting in a thick oil. The water was decanted and the oil dissolved in EtOAc then extracted twice with water, 1M hydrochloric acid and brine. The organic layer was dried (MgSO₄), filtered and evaporated to crude 6 (3.37 g). Trituration with dichloromethane (25 mL) gave 3-(2-Chloropyridin-4-yloxy)-4-fluoro-N-(2-fluoro-5-methylphenyl)benzamide as white solid. Yield: 1.788 g, 58%.

Example 12 methyl 5-[4-(2-fluoro-5-{[(2-fluoro-5-methylphenyl)amino]carbonyl}phenoxy)pyridin-2-yl]-1H-pyrrole-3-carboxylate

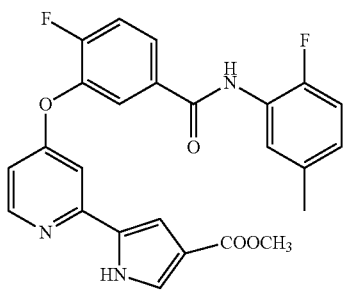 [SMILES: COC(=O)c1c[nH]c(-c2cc(Oc3cc(C(=O)Nc4cc(C)ccc4F)ccc3F)ccn2)c1]

A mixture of 3-(2-Chloropyridin-4-yloxy)-4-fluoro-N-(2-fluoro-5-methylphenyl)benzamide (1.217 g, 3.25 mmol), methyl 5-(4,4,5,5-tetramethyl-1,3,2-dioxaborolan-2-yl)-1H-pyrrole-3-carboxylate (1.63 g, 6.50 mmol) and potassium carbonate (0.67 g, 4.87 mmol) in water (2.5 mL) and dioxane (15 mL) was purged with nitrogen for several minutes. To the mixture was added tetrakis-triphenylphosphine palladium(0) (0.18 g, (0.16 mmol). The reaction was sealed under nitrogen and heated at 100° C. for 15 h. The cooled reaction was mixed with dichloromethane and filtered through Celite. The red solution was evaporated. The resulting oil was dissolved in dichloromethane, put on a column of silica gel (80 g) and eluted with hexane/EtOAc (1:1) to afford methyl 5-[4-(2-fluoro-5-{[(2-fluoro-5-methylphenyl)amino]carbonyl}phenoxy)pyridin-2-yl]-1H-pyrrole-3-carboxylate as white solid. Yield: 1.162 g, 77%.

Example 13

5-[4-(2-fluoro-5-{[(2-fluoro-5-methylphenyl)amino]carbonyl}phenoxy)pyridin-2-yl]-1H-pyrrole-3-carboxylic acid

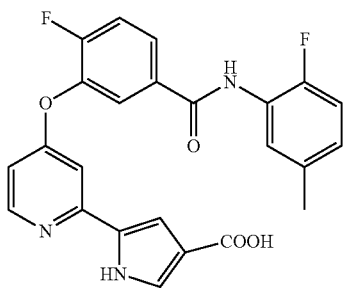 [SMILES: Cc1ccc(F)c(NC(=O)c2ccc(F)c(Oc3ccnc(-c4cc(C(=O)O)c[nH]4)c3)c2)c1]

Similar procedure as Example 12.

$^1$H NMR (DMSO-$d_6$) δ: 12.03 (br. s., 1H), 11.85 (br. s., 1H), 10.11 (s, 1H), 8.42 (d, J=5.6 Hz, 1H), 7.98 (d, J=6.2 Hz, 2H), 7.62 (t, J=9.4 Hz, 1H), 7.43 (br. s., 1H), 7.30-7.39 (m, 2H), 7.08-7.19 (m, 2H), 7.04 (br. s., 1H), 6.79 (d, J=3.2 Hz, 1H), 2.26 (s, 3H)

LR MS (ES−): 448 (M−H)

Example 14

N-ethyl-5-(4-{3-[(3-methyl-2-furoyl)amino]phenoxy}pyridin-2-yl)-1H-pyrrole-3-carboxamide

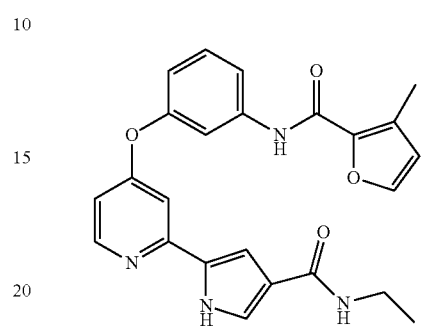

Similar procedure as Example 31.

LR MS (ES+): 453 (M+Na$^+$)

Example 15

N-(2,3-dihydroxypropyl)-5-(4-{3-[(3-methyl-2-furoyl)amino]phenoxy}pyridin-2-yl)-1H-pyrrole-3-carboxamide

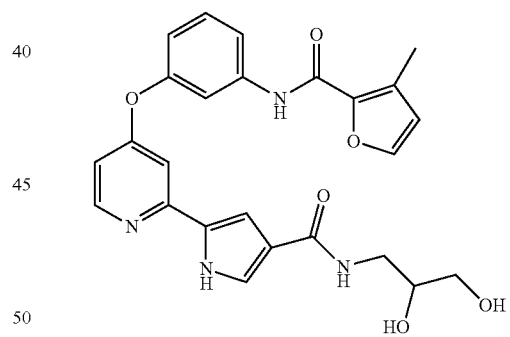

Similar procedure as Example 31.

$^1$H NMR (DMSO-$d_6$) δ: 11.83 (br. s., 1H), 10.21 (s, 1H), 8.40 (d, J=5.9 Hz, 1H), 7.85 (t, J=6.0 Hz, 1H), 7.78 (s, 1H), 7.63-7.74 (m, 2H), 7.35-7.48 (m, 2H), 7.23 (d, J=2.1 Hz, 1H), 7.10 (s, 1H), 6.85-6.96 (m, 1H), 6.75 (dd, J=5.7, 2.2 Hz, 1H), 6.57 (s, 1H), 4.78 (d, J=4.7 Hz, 1H), 4.53 (t, J=5.9 Hz, 1H), 3.48-3.61 (m, 1H), 3.24-3.33 (m, 3H), 3.04-3.19 (m, 1H), 2.30 (s, 3H)

LR MS (ES+): 499 (M+Na$^+$)

LR MS (ES−): 475 (M−H)

Example 16

5-(4-{3-[(3-methyl-2-furoyl)amino]phenoxy}pyridin-2-yl)-1H-pyrrole-3-carboxamide

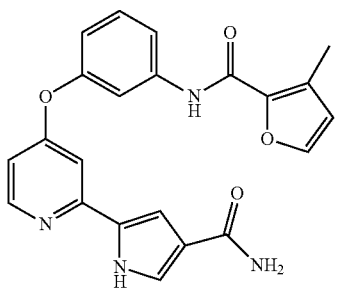 [SMILES: Cc1ccoc1C(=O)Nc1cccc(Oc2ccnc(-c3cc(C(N)=O)c[nH]3)c2)c1]

Similar procedure as Example 31.

$^1$H NMR (DMSO-d$_6$) δ: 11.83 (br. s., 1H), 10.21 (s, 1H), 8.40 (d, J=5.9 Hz, 1H), 7.77 (s, 1H), 7.65-7.74 (m, 2H), 7.31-7.48 (m, 3H), 7.23 (d, J=1.2 Hz, 1H), 7.07 (br. s., 1H), 6.86-6.95 (m, 1H), 6.75 (d, J=3.5 Hz, 2H), 6.57 (s, 1H), 2.30 (s, 3H)

LR MS (ES−): 401 (M−H)

Example 17

N-hydroxy-5-(4-{3-[(3-methyl-2-furoyl)amino]phenoxy}pyridin-2-yl)-1H-pyrrole-3-carboxamide

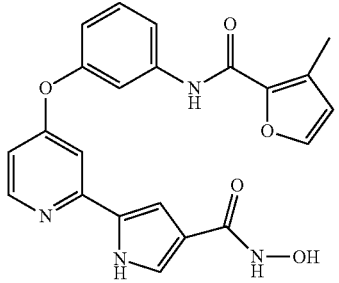 [SMILES: Cc1ccoc1C(=O)Nc1cccc(Oc2ccnc(-c3cc(C(=O)NO)c[nH]3)c2)c1]

Similar procedure as Example 31.

$^1$H NMR (DMSO-d$_6$) δ: 11.84 (br. s., 1H), 10.49-10.64 (m, 1H), 10.20 (s, 1H), 8.60-8.74 (m, 1H), 8.39 (d, J=5.9 Hz, 1H), 7.65-7.81 (m, 3H), 7.41 (t, J=7.9 Hz, 1H), 7.32 (br. s., 1H), 7.23 (s, 1H), 7.02 (br. s., 1H), 6.85-6.94 (m, 1H), 6.69-6.78 (m, 1H), 6.57 (s, 1H), 2.30 (s, 3H)

LR MS (ES−): 417 (M−H)

Example 18

N-(3-{[2-(4-{[(3R)-3-hydroxypyrrolidin-1-yl]carbonyl}-1H-pyrrol-2-yl)pyridin-4-yl]oxy}phenyl)-3-methyl-2-furamide

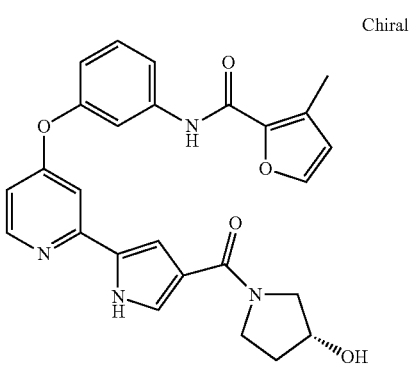 [SMILES: Cc1ccoc1C(=O)Nc1cccc(Oc2ccnc(-c3cc(C(=O)N4CC[C@@H](O)C4)c[nH]3)c2)c1]

Similar procedure as Example 31.

$^1$H NMR (DMSO-d$_6$) δ: 11.90 (br. s., 1H), 10.20 (s, 1H), 8.40 (d, J=5.6 Hz, 1H), 7.77 (d, J=1.5 Hz, 1H), 7.64-7.73 (m, 2H), 7.36-7.46 (m, 2H), 7.21-7.30 (m, 1H), 7.03-7.13 (m, 1H), 6.85-6.93 (m, 1H), 6.70 (dd, J=5.7, 2.2 Hz, 1H), 6.57 (d, J=1.5 Hz, 1H), 4.90 (br. s., 1H), 4.30 (m, 1H), 3.76 (m, 1H), 3.49 (m, 2H), 2.30 (s, 3H), 1.86 (m, 2H)

LR MS (ES−): 471 (M−H)

Example 19

5-{4-[3-(2-Fluoro-5-methyl-phenylcarbamoyl)-phenoxy]-pyridin-2-yl}-1H-pyrrole-3-carboxylic acid

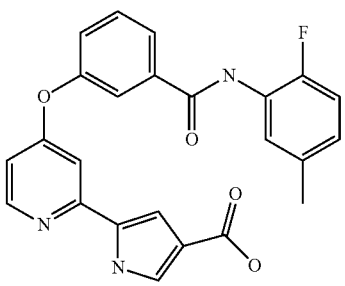 [SMILES: Cc1ccc(F)c(NC(=O)c2cccc(Oc3ccnc(-c4cc(C(=O)O)c[nH]4)c3)c2)c1]

To a stirred solution of 5-{4-[3-(2-Fluoro-5-methyl-phenylcarbamoyl)-phenoxy]-pyridin-2-yl}-1H-pyrrole-3-carboxylic acid methyl ester (140 mg, 0.31 mmol) in THF (8 ml) was added 5M NaOH solution (1 ml, 5 mmol). The mixture was heated at 70° C. for 3 hours, cooled to room temp, and poured into 100 ml of water. 2M HCl was added until pH=4. The precipitates were filtered, washed with water, and dried to give 5-{4-[3-(2-Fluoro-5-methyl-phenylcarbamoyl)-phenoxy]-pyridin-2-yl}-1H-pyrrole-3-carboxylic acid as white solid. Yield: 120 mg, 92%.

$^1$H NMR (d$_6$-DMSO): 12.03 (br. s., 1H), 11.89 (br. s., 1H), 10.11 (s, 1H), 8.42 (d, J=5.6 Hz, 1H), 7.89 (d, J=7.3 Hz, 1H), 7.77 (s, 1H), 7.56-7.71 (m, 1H), 7.30-7.54 (m, 4H), 6.97-7.23 (m, 3H), 6.75 (dd, J=5.6, 2.1 Hz, 1H), 2.28 (s, 3H)

LR MS (ES+): 454 (M+Na$^+$)

LR MS (ES−): 430 (M−H)

Example 20

5-{4-[3-(2-Fluoro-5-methyl-phenylcarbamoyl)-phenoxy]-pyridin-2-yl}-1H-pyrrole-3-carboxylic acid methyl ester

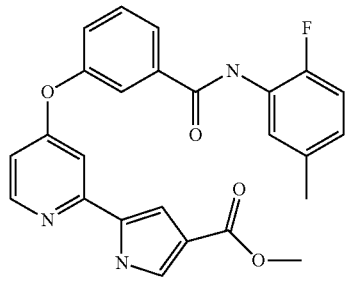 [SMILES: COC(=O)c1c[nH]c(-c2cc(Oc3cccc(C(=O)Nc4cc(C)ccc4F)c3)ccn2)c1]

A mixture of 3-(2-bromo-pyridin-4-yloxy)-N-(2-fluoro-5-methyl-phenyl)-benzamide (200 mg, 0.50 mmol), methyl-(5-(4,4,5,5-tetramethyl-1,3,2-dioxaborolan-2-yl)-1H-pyrrole-3-carboxylate (251 mg, 1.0 mmol) and PdCl$_2$(dppf).CH$_2$Cl$_2$ (10 mg, 0.012 mmol) was added to a thick-walled reaction vessel and purged with N$_2$. A solution of 2M Na$_2$CO$_3$ (0.5 mL) was added, followed by DMSO (8 mL). The reaction vessel was sealed and the mixture stirred at 95° C. for 16 h. The reaction vessel was cooled to room temperature and the mixture was poured into 100 ml of water. The precipitates were filtered, washed with water and dried to give the crude, which was purified via column chromatography eluting with 30-40% EtOAc/hexanes to afford 5-{4-[3-(2-Fluoro-5-methyl-phenylcarbamoyl)-phenoxy]-pyridin-2-yl}-1H-pyrrole-3-carboxylic acid methyl ester (150 mg, 58% yield).

$^1$H NMR (d$_6$-DMSO): 12.14 (br. s., 1H), 10.11 (s, 1H), 8.43 (d, J=5.6 Hz, 1H), 7.89 (d, J=7.9 Hz, 1H), 7.77 (s, 1H), 7.64 (t, J=7.9 Hz, 1H), 7.41-7.50 (m, 3H), 7.35 (s, 1H), 7.09-7.21 (m, 2H), 7.06 (dd, J=5.1, 1.9 Hz, 1H), 6.76 (dd, J=5.6, 2.3 Hz, 1H), 3.70 (s, 3H), 2.28 (s, 3H)

LR MS (ES+): 468 (M+Na$^+$)

LR MS (ES−): 4-(4 (M−H)

Example 21

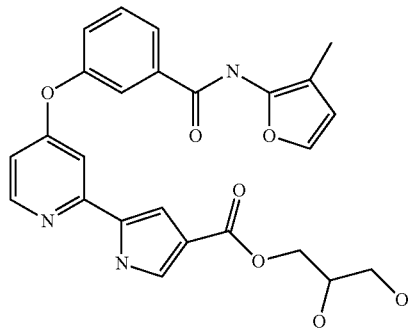 [SMILES: Cc1ccoc1NC(=O)c1cccc(Oc2ccnc(-c3cc(C(=O)OCC(O)CO)c[nH]3)c2)c1]

Similar procedure as Example 25.

2,3-dihydroxypropyl 5-(4-{3-[(3-methyl-2-furoyl)amino]phenoxy}pyridin-2-yl)-1H-pyrrole-3-carboxylate

Example 22

5-[4-(3-m-Tolylcarbamoyl-phenoxy)-pyridin-2-yl]-1H-pyrrole-3-carboxylic acid

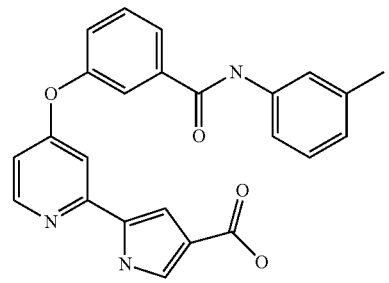 [SMILES: Cc1cccc(NC(=O)c2cccc(Oc3ccnc(-c4cc(C(=O)O)c[nH]4)c3)c2)c1]

Similar procedure as Example 19.

$^1$H NMR (DMSO-d$_6$) δ: 12.03 (br. s., 1H), 11.86 (br. s., 1H), 10.19 (s, 1H), 8.42 (d, J=5.6 Hz, 1H), 7.88 (d, J=7.9 Hz, 1H), 7.78 (s, 1H), 7.50-7.69 (m, 3H), 7.32-7.46 (m, 3H), 7.21 (t, J=7.8 Hz, 1H), 7.06 (s, 1H), 6.91 (d, J=7.3 Hz, 1H), 6.74 (dd, J=5.6, 2.3 Hz, 1H), 2.28 (s, 3H)

Example 23

5-[4-(3-m-Tolylcarbamoyl-phenoxy)-pyridin-2-yl]-1H-pyrrole-3-carboxylic acid methyl ester

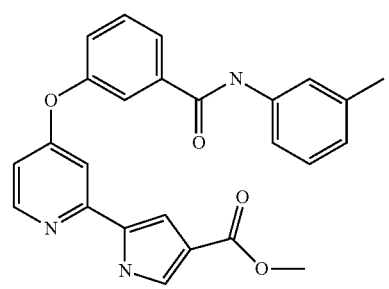 [SMILES: COC(=O)c1c[nH]c(-c2cc(Oc3cccc(C(=O)Nc4cccc(C)c4)c3)ccn2)c1]

Similar procedure as Example 20.

$^1$H NMR (DMSO-d$_6$) δ: 12.14 (br. s., 1H), 10.18 (s, 1H), 8.43 (d, J=5.6 Hz, 1H), 7.89 (d, J=7.9 Hz, 1H), 7.78 (s, 1H), 7.50-7.68 (m, 3H), 7.38-7.48 (m, 3H), 7.21 (t, J=7.8 Hz, 1H), 7.12 (s, 1H), 6.91 (d, J=7.6 Hz, 1H), 6.75 (dd, J=5.7, 2.2 Hz, 1H), 3.70 (s, 3H), 2.28 (s, 3H)

LR MS (ES+): 450 (M+Na$^+$)

LR MS (ES−): 426 (M−H)

Example 24

2-hydroxyethyl 5-[4-(3-{[(3-methyl-2-thienyl)carbonyl]amino}phenoxy)pyridin-2-yl]-1H-pyrrole-3-carboxylate

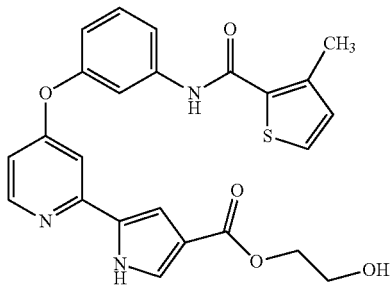 [SMILES: Cc1ccsc1C(=O)Nc1cccc(Oc2ccnc(-c3cc(C(=O)OCCO)c[nH]3)c2)c1]

Similar procedure as Example 25.

$^1$H NMR (d$_6$-DMSO): 12.13 (br. s., 1H), 10.13 (s, 1H), 8.43 (d, J=5.9 Hz, 1H), 7.68 (d, J=5.0 Hz, 1H), 7.56-7.64 (m, 2H), 7.40-7.52 (m, 3H), 7.14 (s, 1H), 7.03 (d, J=5.0 Hz, 1H), 6.89-6.98 (m, 1H), 6.76 (dd, J=5.7, 2.2 Hz, 1H), 4.83 (t, J=5.9 Hz, 1H), 4.15 (t, J=5.1 Hz, 2H), 3.64 (q, J=5.6 Hz, 2H), 2.44 (s, 3H)

LR MS (ES+): 486 (M+Na$^+$)
LR MS (ES−): 462 (M−H)

Example 25

2-hydroxyethyl 5-(4-{3-[(3-methyl-2-furoyl)amino]phenoxy}pyridin-2-yl)-1H-pyrrole-3-carboxylate

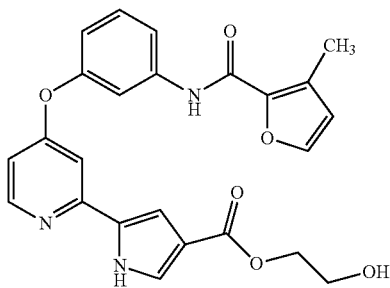 [SMILES: Cc1ccoc1C(=O)Nc1cccc(Oc2ccnc(-c3cc(C(=O)OCCO)c[nH]3)c2)c1]

A mixture of 5-(4-{3-[(3-methyl-2-furoyl)amino]phenoxy}pyridin-2-yl)-1H-pyrrole-3-carboxylic acid (70 mg, 0.17 mmol), ethylene glycol (1 ml), 1-ethyl-3-(3-dimethylaminopropyl)carbodiimide hydrochloride (EDC.HCl, 40 mg, 0.21 mmol) and 4-dimethylaminopyridine (DMAP, 10 mg, 0.08 mmol) in anhydrous DMF (10 ml) was stirred at 70° C. for 3 hours then room temperature for 16 hours. The mixture was poured into 100 ml of water. Saturated NaHCO$_3$ solution was added until pH=9. The precipitates were filtered, washed with water and dried in vacuo to give the crude, which was purified by silica gel chromatography eluting with a gradient of 3~4% MeOH/CHCl$_3$ to give 2-hydroxyethyl 5-(4-{3-[(3-methyl-2-furoyl)amino]phenoxy}pyridin-2-yl)-1H-pyrrole-3-carboxylate as white solid. Yield: 40 mg, 51%.

$^1$H NMR (d$_6$-DMSO): 12.13 (br. s., 1H), 10.22 (s, 1H), 8.43 (d, J=5.9 Hz, 1H), 7.79 (s, 1H), 7.70 (s, 2H), 7.36-7.54 (m, 3H), 7.13 (br. s., 1H), 6.86-6.97 (m, 1H), 6.72-6.80 (m, 1H), 6.59 (s, 1H), 5.75 (s, 1H), 4.83 (t, J=5.3 Hz, 1H), 4.14 (t, J=4.7 Hz, 2H), 3.58-3.69 (m, 2H), 2.32 (s, 3H)

LR MS (ES+): 470 (M+Na$^+$)
LR MS (ES−): 446 (M−H)

Example 26

5-[4-(3-{[(3-methyl-2-thienyl)carbonyl]amino}phenoxy)pyridin-2-yl]-1H-pyrrole-3-carboxylic acid

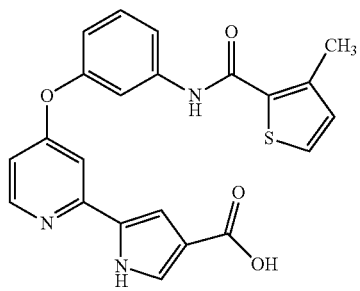 [SMILES: Cc1ccsc1C(=O)Nc1cccc(Oc2ccnc(-c3cc(C(=O)O)c[nH]3)c2)c1]

Similar procedure as Example 32.

$^1$H NMR (d$_6$-DMSO): 12.04 (br. s., 1H), 11.87 (s, 1H), 10.13 (s, 1H), 8.42 (d, J=6.2 Hz, 1H), 7.68 (d, J=4.7 Hz, 1H), 7.57-7.64 (m, 2H), 7.40-7.49 (m, 2H), 7.38 (dd, J=3.2, 1.5 Hz, 1H), 7.05-7.09 (m, 1H), 7.03 (d, J=5.0 Hz, 1H), 6.90-6.97 (m, 1H), 6.75 (dd, J=5.7, 2.5 Hz, 1H), 2.44 (s, 3H)

LR MS (ES+): 442 (M+Na$^+$)
LR MS (ES−): 418 (M−H)

Example 27 methyl 5-[4-(3-{[(3-methyl-2-thienyl)carbonyl]amino}phenoxy)pyridin-2-yl]-1H-pyrrole-3-carboxylate

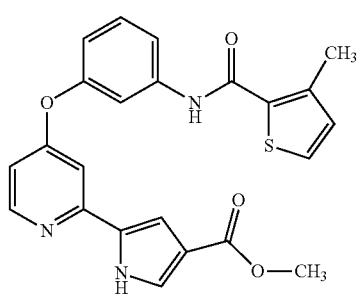 [SMILES: COC(=O)c1c[nH]c(-c2cc(Oc3cccc(NC(=O)c4sccc4C)c3)ccn2)c1]

Similar procedure as Example 33.

$^1$H NMR (DMSO-d$_6$) δ: 12.12 (br. s., 1H), 10.10 (s, 1H), 8.35-8.45 (m, 1H), 7.65 (d, J=5.0 Hz, 1H), 7.55-7.60 (m, 2H), 7.37-7.45 (m, 3H), 7.10 (s, 1H), 7.00 (d, J=5.0 Hz, 1H), 6.87-6.93 (m, 1H), 6.73 (dd, J=5.6, 2.3 Hz, 1H), 3.69 (s, 3H), 2.41 (s, 3H)

LR MS (ES+): 456 (M+Na$^+$)
LR MS (ES−): 432 (M−H)

Example 28

5-(4-{4-fluoro-3-[(3-methyl-2-furoyl)amino]phenoxy}pyridin-2-yl)-1H-pyrrole-3-carboxylic acid

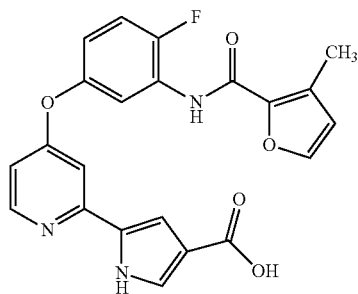 [SMILES: Cc1ccoc1C(=O)Nc1cc(Oc2ccnc(-c3cc(C(=O)O)c[nH]3)c2)ccc1F]

To a stirred solution of methyl 5-(4-{4-fluoro-3-[(3-methyl-2-furoyl)amino]phenoxy}pyridin-2-yl)-1H-pyrrole-3-carboxylate (20 mg, 0.046 mmol) in a mixture of solvents THF/MeOH (5 ml/5 ml) was added 3 ml of 1M NaOH (3 mmol) solution. The mixture was heated in a 72° C. bath for 3 hours, cooled to room temperature and poured into 50 ml of water. 2M HCl was added until pH=4. The resulting precipitates were filtered, washed with water, and dried in vacuo to give 5-(4-{4-fluoro-3-[(3-methyl-2-furoyl)amino]phenoxy}pyridin-2-yl)-1H-pyrrole-3-carboxylic acid as light gray solid. Yield: 19 mg, 100%.

LR MS (ES−): 420 (M−H)

Example 29 methyl 5-(4-{4-fluoro-3-[(3-methyl-2-furoyl)amino]phenoxy}pyridin-2-yl)-1H-pyrrole-3-carboxylate

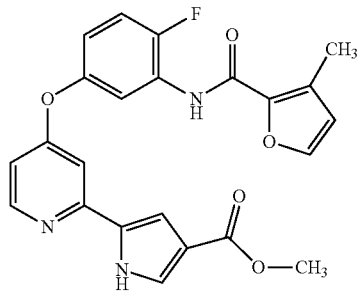 [SMILES: COC(=O)c1c[nH]c(-c2cc(Oc3ccc(F)c(NC(=O)c4occc4C)c3)ccn2)c1]

Similar procedure as Example 33.

$^1$H NMR ($d_6$-DMSO): 12.15 (br. s., 1H), 9.74 (s, 1H), 8.43 (d, J=5.6 Hz, 1H), 7.81 (d, J=1.8 Hz, 1H), 7.60 (dd, J=6.4, 2.9 Hz, 1H), 7.34-7.50 (m, 3H), 7.02-7.18 (m, 2H), 6.75 (dd, J=5.6, 2.3 Hz, 1H), 6.60 (d, J=1.5 Hz, 1H), 3.72 (s, 3H), 2.31 (s, 3H)

LR MS (ES+): 458 (M+Na$^+$)
LR MS (ES−): 434 (M−H)

Example 30

N-[dimethyl(oxido)-lambda~4~-sulfanylidene]-5-(4-{3-[(3-methyl-2-furoyl)amino]phenoxy}pyridin-2-yl)-1H-pyrrole-3-carboxamide

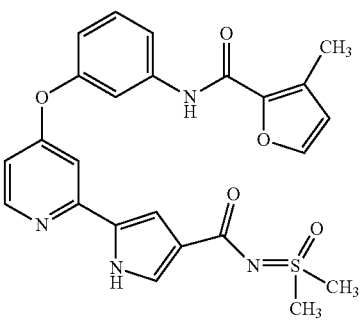 [SMILES: Cc1ccoc1C(=O)Nc1cccc(Oc2ccnc(-c3cc(C(=O)N=S(C)(C)=O)c[nH]3)c2)c1]

Similar procedure as Example 101.

$^1$H NMR ($d_6$-DMSO): 11.83 (br. s., 1H), 10.20 (s, 1H), 8.39 (d, J=5.6 Hz, 1H), 7.77 (d, J=1.5 Hz, 1H), 7.65-7.72 (m, 2H), 7.37-7.45 (m, 1H), 7.32 (d, J=2.1 Hz, 1H), 7.27 (dd, J=2.9, 1.5 Hz, 1H), 6.96-6.99 (m, 1H), 6.87-6.92 (m, 1H), 6.71 (dd, J=5.6, 2.3 Hz, 1H), 6.57 (d, J=1.8 Hz, 1H), 3.35 (s, 6H), 2.30 (s, 3H)

LR MS (ES+): 501 (M+Na$^+$)
LR MS (ES−): 477 (M−H)

Example 31

N-(3-{[2-(4-{[(3S)-3-hydroxypyrrolidin-1-yl]carbonyl}-1H-pyrrol-2-yl)pyridin-4-yl]oxy}phenyl)-3-methyl-2-furamide

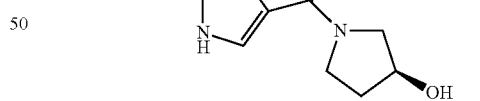

A mixture of 5-(4-{3-[(3-methyl-2-furoyl)amino]phenoxy}pyridin-2-yl)-1H-pyrrole-3-carboxylic acid (60 mg, 0.15 mmol), HATU (68 mg, 0.18 mmol) and N,N-diisopropylethylamine (43 mg, 0.33 mmol) in anhydrous DMF (10 ml) was stirred at room temperature for 10 minutes, followed by addition of (S)-3-pyrrolidinol (16 mg, 0.18 mmol). The mixture was stirred for another 10 minutes and poured into 100 ml of water. 2M HCl was added dropwise until pH=4~5. The precipitates were filtered, washed with water and dried in vacuo to give N-(3-{[2-(4-{[(3S)-3-hydroxypyrrolidin-1-yl]carbonyl}-1H-pyrrol-2-yl)pyridin-4-yl]oxy}phenyl)-3-methyl-2-furamide as white solid. Yield: 40 mg, 56%.

¹H NMR (d₆-DMSO): 11.95 (br. s., 1H), 10.21 (s, 1H), 8.41 (d, J=5.6 Hz, 1H), 7.77 (d, J=1.8 Hz, 1H), 7.64-7.74 (m, 2H), 7.35-7.51 (m, 2H), 7.29 (br. s., 1H), 7.12 (br. s., 1H), 6.90 (dd, J=8.1, 1.3 Hz, 1H), 6.73 (dd, J=5.7, 2.2 Hz, 1H), 6.57 (d, J=1.8 Hz, 1H), 4.20-4.36 (m, 1H), 3.66-3.88 (m, 2H), 3.42-3.60 (m, 3H), 2.30 (s, 3H), 1.66-2.03 (m, 2H)

LR MS (ES+): 495 (M+Na⁺)

LR MS (ES−): 471 (M−H)

Example 32

5-(4-{3-[(3-methyl-2-furoyl)amino]phenoxy}pyridin-2-yl)-1H-pyrrole-3-carboxylic acid

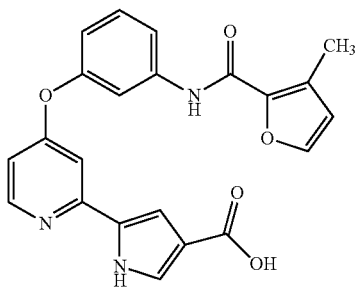

To a stirred solution of methyl 5-(4-{3-[(3-methyl-2-furoyl)amino]phenoxy}pyridin-2-yl)-1H-pyrrole-3-carboxylate (1.30 g, 3.12 mmol) in a mixture of solvents THF/MeOH (10 ml/10 ml) was added 2 ml of 5M NaOH (10 mmol) solution. The mixture was heated in a 68° C. bath for 8 hours, cooled to room temperature and poured into 200 ml of water. 2M HCl was added until pH=3. The resulting precipitates were filtered, washed with water, and dried in vacuo to give 5-(4-{3-[(3-methyl-2-furoyl)amino]phenoxy}pyridin-2-yl)-1H-pyrrole-3-carboxylic acid as white solid. Yield: 1.20 g, 95%.

¹H NMR (d₆-DMSO): 11.98 (br. s., 1H), 10.22 (s, 1H), 8.42 (d, J=5.6 Hz, 1H), 7.79 (d, J=1.2 Hz, 1H), 7.61-7.76 (m, 2H), 7.27-7.51 (m, 3H), 7.04 (br. s., 1H), 6.85-6.98 (m, 1H), 6.73 (dd, J=5.7, 2.2 Hz, 1H), 6.59 (d, J=1.5 Hz, 1H), 2.32 (s, 3H)

LR MS (ES−): 402 (M−H)

Example 33 methyl 5-(4-{3-[(3-methyl-2-furoyl)amino]phenoxy}pyridin-2-yl)-1H-pyrrole-3-carboxylate

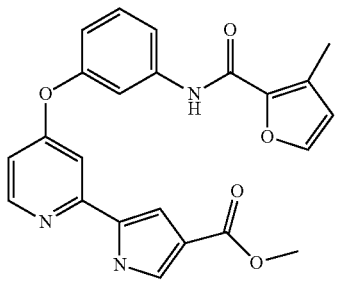 [SMILES: COC(=O)c1c[nH]c(-c2cc(Oc3cccc(NC(=O)c4occc4C)c3)ccn2)c1]

A mixture of 3-methyl-2-furoic acid (490 mg, 3.88 mmol), HATU (1.71 g, 4.5 mmol) and N,N-diisopropylethylamine (1.0 g, 7.8 mmol) in anhydrous DMF (10 ml) was stirred at room temperature for 10 minutes, followed by addition of methyl 5-[4-(3-aminophenoxy)pyridin-2-yl]-1H-pyrrole-3-carboxylate (1.0 g, 3.24 mmol). The mixture was stirred at 50° C. for 2 hours and poured into 100 ml of water. 2M HCl was added dropwise until pH=4~5. The precipitates were filtered, washed with water and dried in vacuo to give methyl 5-(4-{3-[(3-methyl-2-furoyl)amino]phenoxy}pyridin-2-yl)-1H-pyrrole-3-carboxylate as white solid. Yield: 1.30 g, 96%.

¹H NMR (d₆-DMSO): 12.15 (br. s., 1H), 10.22 (s, 1H), 8.43 (d, J=5.9 Hz, 1H), 7.79 (d, J=1.5 Hz, 1H), 7.68-7.74 (m, 2H), 7.38-7.47 (m, 3H), 7.09-7.14 (m, 1H), 6.88-6.94 (m, 1H), 6.75 (dd, J=5.6, 2.3 Hz, 1H), 6.59 (d, J=1.5 Hz, 1H), 3.72 (s, 3H), 2.32 (s, 3H)

LR MS (ES+): 440 (M+Na⁺)

LR MS (ES−): 416 (M−H)

Example 34

3-methyl-N-(3-{[2-(1H-pyrrol-2-yl)pyridin-4-yl]oxy}phenyl)-2-furamide

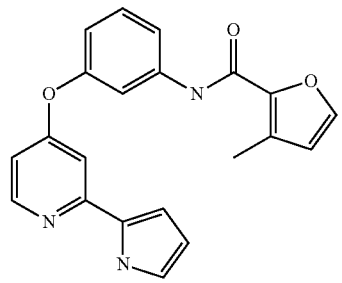 [SMILES: Cc1ccoc1C(=O)Nc1cccc(Oc2ccnc(-c3ccc[nH]3)c2)c1]

A mixture of 3-methyl-2-furoic acid (60 mg, 0.48 mmol), HBTU (198 mg, 0.52 mmol) and N,N-diisopropylethylamine (129 mg, 1.0 mmol) in anhydrous DMF (10 ml) was stirred at room temperature for 10 minutes, followed by addition of 3-{[2-(1H-pyrrol-2-yl)pyridin-4-yl]oxy}aniline (100 mg, 0.40 mmol). The mixture was stirred at 70° C. for 3 hours and poured into 100 ml of water. The precipitates were filtered, washed with water and dried in vacuo to give the crude, which was purified by silica gel chromatography eluting with 3-5% MeOH/CHCl₃ to give 3-methyl-N-(3-{[2-(1H-pyrrol-2-yl)pyridin-4-yl]oxy}phenyl)-2-furamide as white solid. Yield: 52 mg, 36%.

¹H NMR (d₆-DMSO): 11.46 (br. s., 1H), 10.19 (s, 1H), 8.36 (d, J=6.2 Hz, 1H), 7.77 (d, J=1.8 Hz, 1H), 7.64-7.72 (m, 2H), 7.35-7.44 (m, 1H), 7.28 (d, J=2.1 Hz, 1H), 6.86-6.91 (m, 1H), 6.81-6.86 (m, 1H), 6.68-6.74 (m, 1H), 6.65 (dd, J=5.7, 2.5 Hz, 1H), 6.57 (d, J=1.8 Hz, 1H), 6.06-6.13 (m, 1H), 2.30 (s, 3H)

LR MS (ES+): 360 (M+H)

LR MS (ES−): 358 (M−H)

Example 35 methyl 4-(4-{3-[(3-methyl-2-furoyl)amino]phenoxy}pyridin-2-yl)-1H-pyrrole-2-carboxylate

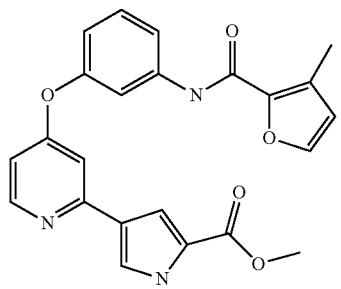 [SMILES: COC(=O)c1cc(-c2cc(Oc3cccc(NC(=O)c4occc4C)c3)ccn2)c[nH]1]

Similar procedure as Example 33.

$^1$H NMR (d$_6$-DMSO): 12.18 (br. s., 1H), 10.19 (s, 1H), 8.37 (d, J=5.6 Hz, 1H), 7.77 (d, J=1.8 Hz, 1H), 7.59-7.72 (m, 3H), 7.33-7.44 (m, 2H), 7.25-7.32 (m, 1H), 6.83-6.93 (m, 1H), 6.66 (dd, J=5.6, 2.3 Hz, 1H), 6.57 (d, J=1.2 Hz, 1H), 3.76 (s, 3H), 2.30 (s, 3H)

LR MS (ES+): 440 (M+Na$^+$)

LR MS (ES−): 416 (M−H)

Example 36

2-fluoro-5-methyl-N-(4-{[2-(1H-pyrrol-2-yl)pyridin-4-yl]oxy}phenyl)benzamide

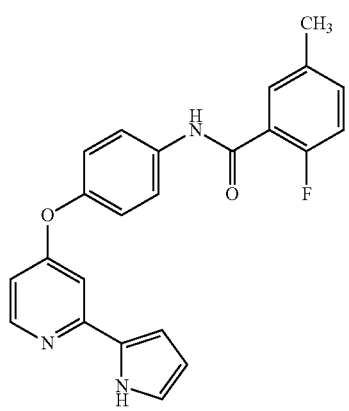 [SMILES: Cc1ccc(F)c(C(=O)Nc2ccc(Oc3ccnc(-c4ccc[nH]4)c3)cc2)c1]

Similar procedure as Example 37.

$^1$H NMR (d$_6$-DMSO): 11.44 (br. s., 1H), 10.47 (s, 1H), 8.33 (d, J=5.6 Hz, 1H), 7.76-7.86 (m, 2H), 7.46 (dd, J=6.4, 2.1 Hz, 1H), 7.36 (ddd, J=7.9, 5.3, 2.1 Hz, 1H), 7.13-7.27 (m, 4H), 6.80-6.87 (m, 1H), 6.66-6.73 (m, 1H), 6.60 (dd, J=5.6, 2.3 Hz, 1H), 6.06-6.15 (m, 1H), 2.34 (s, 3H)

LR MS (ES+): 388 (M+H)

LR MS (ES−): 386 (M−H)

Example 37

3-methyl-N-(4-{[2-(1H-pyrrol-2-yl)pyridin-4-yl]oxy}phenyl)-2-furamide

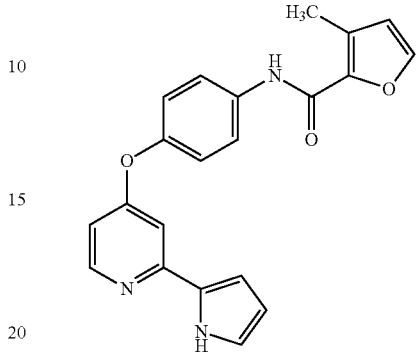

A mixture of 3-methyl-2-furoic acid (70 mg, 0.55 mmol), HATU (243 mg, 0.64 mmol),) tert-butyl 2-[4-(4-aminophenoxy)pyridin-2-yl]-1H-pyrrole-1-carboxylate (160 mg, 0.46 mmol) and N,N-diisopropylethylamine (148 mg, 1.15 mmol) in anhydrous DMF (10 ml) was stirred at 45° C. for 2 hours. The mixture was poured into 100 ml of water. The precipitates were filtered, washed with water and dried in vacuo to give the crude, which was dissolved in 5 ml of methylene chloride, followed by addition of trifluoroacetic acid (3 ml). The mixture was stirred at room temperature for 16 hours. The solvents were evaporated under reduced pressure. The residue was purified by reversed-phase chromatography with a gradient of 1050% acetonitrile/water to give 3-methyl-N-(4-{[2-(1H-pyrrol-2-yl)pyridin-4-yl]oxy}phenyl)-2-furamide as white solid. Yield: 56 mg, 34%.

LR MS (ES+): 360 (M+H)

LR MS (ES−): 358 (M−H)

Preparation of 4-((2-chloropyridin-4-yl)oxy)aniline

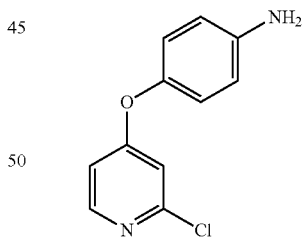

A stirred solution of 4-aminophenol (740 mg, 6.8 mmol) in anhydrous DMSO (8 ml) was flushed with nitrogen and treated with 1M KOBu$^t$/THF solution (10 ml, 10 mmol). The mixture was stirred at room temperature under nitrogen for 10 minutes. 2,4-dichloropyridine (1.0 g, 6.8 mmol) was added and the mixture was heated at 60° C. for 30 minutes, cooled to room temperature and poured into 100 ml of water. The resulting precipitates were filtered, washed with water and dried to give 4-((2-chloropyridin-4-yl)oxy)aniline as light brown solid. The material was used for the following reactions without further purification. Yield: 1.15 g, 77%.

$^1$H NMR (d$_6$-DMSO): 8.21 (d, 1H), 6.77-6.91 (m, 4H), 6.54-6.68 (m, 2H), 5.16 (s, 2H)

133

Preparation of methyl 5-[4-(4-aminophenoxy)pyridin-2-yl]-1H-pyrrole-3-carboxylate

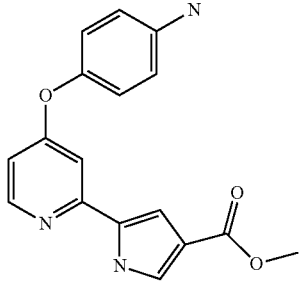 [SMILES: COC(=O)c1c[nH]c(-c2cc(Oc3ccc(N)cc3)ccn2)c1]

A mixture of 4-((2-chloropyridin-4-yl)oxy)aniline (2.6 g, 11.78 mmol), methyl-(5-(4,4,5,5-tetramethyl-1,3,2-dioxaborolan-2-yl)-1H-pyrrole-3-carboxylate (6.0 g, 23.90 mmol) and Pd(PPh3)4 (2.72 g, 2.35 mmol) was added to a thick walled reaction vessel and purged with $N_2$. A solution of 2M $K_2CO_3$ (17.68 mL) was added, followed by DME (90 mL). The reaction vessel was sealed and the mixture stirred at 92° C. for 18 h. The reaction vessel was cooled to room temperature and the mixture was filtered over celite, washing with EtOAc. The filtrate was concentrated to afford a dark oil, which was purified via column chromatography eluting with 40-80% EtOAc/hexanes to afford methyl 5-[4-(4-aminophenoxy)pyridin-2-yl]-1H-pyrrole-3-carboxylate (2.4 g, 65% yield).

Example 38

5-{4-[4-({[(2-fluoro-5-methylphenyl)amino]carbonyl}amino)phenoxy]pyridin-2-yl}-N-(3-morpholin-4-ylpropyl)-1H-pyrrole-3-carboxamide

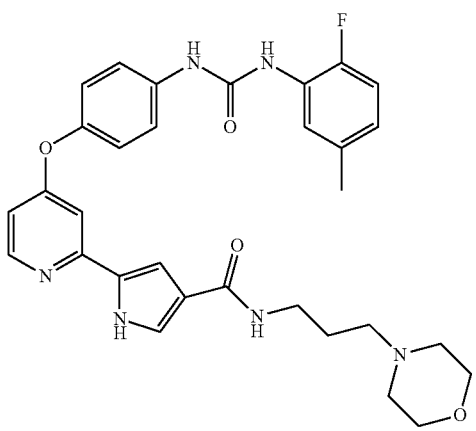 [SMILES: Cc1ccc(F)c(NC(=O)Nc2ccc(Oc3ccnc(-c4cc(C(=O)NCCCN5CCOCC5)c[nH]4)c3)cc2)c1]

Similar procedure as Example 132.
LR MS (ES+): 573 (MH)

134

Example 39

5-{4-[3-fluoro-4-({[(2-fluoro-5-methylphenyl)amino]carbonyl}amino)phenoxy]pyridin-2-yl}-N-hydroxy-1H-pyrrole-3-carboxamide

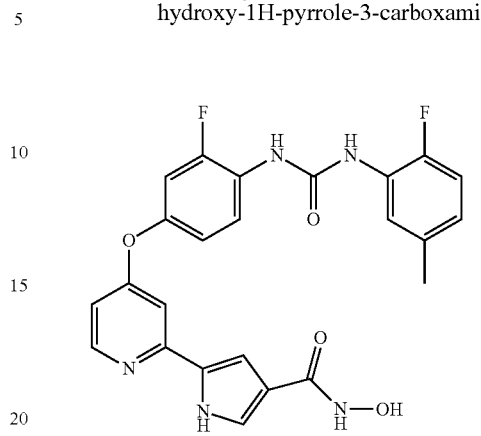

Similar procedure as Example 132.
$^1$H NMR (DMSO-$d_6$) δ: 11.82 (br. s., 1H), 10.55 (br. s., 1H), 9.05 (d, J=1.8 Hz, 1H), 8.94 (d, J=2.3 Hz, 1H), 8.64 (br. s., 1H), 8.37 (d, J=5.6 Hz, 1H), 8.23 (t, J=9.2 Hz, 1H), 7.98 (dd, J=7.8, 1.9 Hz, 1H), 7.31 (br. s., 1H), 7.26 (dd, J=11.7, 2.6 Hz, 1H), 7.19 (d, J=2.3 Hz, 1H), 7.09 (dd, J=11.3, 8.4 Hz, 1H), 6.98-7.05 (m, 2H), 6.76-6.83 (m, 1H), 6.73 (dd, J=5.7, 2.5 Hz, 1H), 2.25 (s, 3H)
LR MS (ES−): 478 (M−H)

Example 40

{[(4-{4-[4-({[(2-fluoro-5-methylphenyl)amino]carbonyl}amino)phenoxy]pyridin-2-yl}-2-thienyl)carbonyl]amino}acetic acid

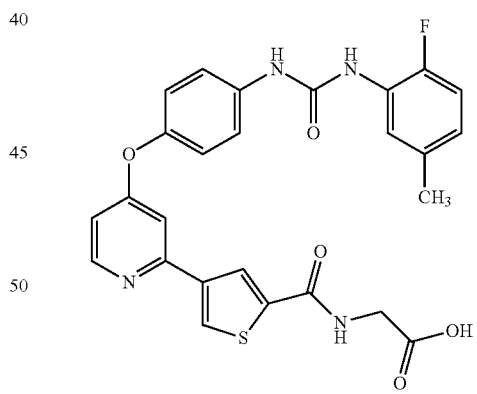

To a stirred solution of methyl {[(4-{4-[4-({[(2-fluoro-5-methylphenyl)amino]carbonyl}amino)phenoxy]pyridin-2-yl}-2-thienyl)carbonyl]amino}acetate (60 mg, 0.11 mmol) in a mixture of solvents THF/MeOH (5 ml/5 ml) was added 1 ml of 1M NaOH (1.0 mmol) solution. The mixture was stirred at room temperature for 1 hour and poured into 100 ml of water. 2M HCl was added until pH=3. The resulting precipitates were filtered, washed with water, and dried in vacuo to give {[(4-{4-[4-({[(2-fluoro-5-methylphenyl)amino]carbonyl}amino)phenoxy]pyridin-2-yl}-2-thienyl)carbonyl]amino}acetic acid as white solid. Yield: 50 mg, 86%.

¹H NMR (DMSO-d₆) δ: 12.61 (br s, 1H), 9.15 (s, 1H), 8.98 (t, J=5.9 Hz, 1H), 8.43-8.48 (m, 2H), 8.40 (d, J=1.5 Hz, 1H), 8.36 (d, J=1.2 Hz, 1H), 7.95 (dd, J=7.6, 1.8 Hz, 1H), 7.50-7.58 (m, 2H), 7.40 (d, J=2.3 Hz, 1H), 7.12-7.19 (m, 2H), 7.08 (dd, J=11.3, 8.4 Hz, 1H), 6.73-6.81 (m, 2H), 3.88 (d, J=5.9 Hz, 2H), 2.25 (s, 3H)

LR MS (ES–): 519 (M–H)

Example 41 methyl {[(4-{4-[4-({[(2-fluoro-5-methylphenyl)amino]carbonyl}amino)phenoxy]pyridin-2-yl}-2-thienyl)carbonyl]amino}acetate

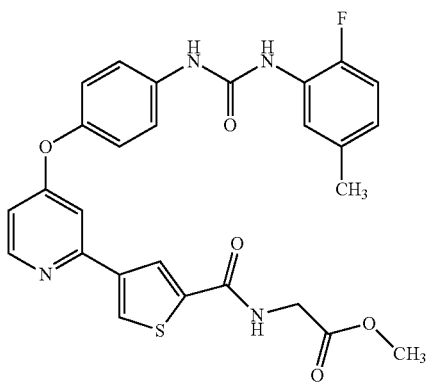 [SMILES: COC(=O)CNC(=O)c1cc(-c2cc(Oc3ccc(NC(=O)Nc4cc(C)ccc4F)cc3)ccn2)cs1]

A mixture of 4-{4-[4-({[(2-fluoro-5-methylphenyl)amino]carbonyl}amino)phenoxy]pyridin-2-yl}thiophene-2-carboxylic acid (100 mg, 0.22 mmol), HATU (100 mg, 0.26 mmol) and N,N-diisopropylethylamine (85 mg, 0.66 mmol) in anhydrous DMF (10 ml) was stirred at room temperature for 10 minutes, followed by addition of glycine methyl ester hydrochloride (41 mg, 0.33 mmol). The mixture was stirred for another 10 minutes and poured into 100 ml of water. 2M HCl was added dropwise until pH=4~5. The precipitates were filtered, washed with water and dried in vacuo to give methyl {[(4-{4-[4-({[(2-fluoro-5-methylphenyl)amino]carbonyl}amino)phenoxy]pyridin-2-yl}-2-thienyl)carbonyl]amino}acetate as white solid. Yield: 90 mg, 78%.

¹H NMR (DMSO-d₆) δ: 9.17 (s, 1H), 9.10 (t, J=5.9 Hz, 1H), 8.44-8.49 (m, 2H), 8.37-8.42 (m, 2H), 7.92-7.98 (m, 1H), 7.55 (d, J=8.8 Hz, 2H), 7.43 (d, J=2.1 Hz, 1H), 7.16 (d, J=8.8 Hz, 2H), 7.08 (dd, J=11.3, 8.4 Hz, 1H), 6.75-6.84 (m, 2H), 3.98 (d, J=5.9 Hz, 2H), 3.63 (s, 3H), 2.25 (s, 3H)

LR MS (ES+): 557 (M+Na⁺)

LR MS (ES–): 533 (M–H)

Preparation of methyl 4-(4-(4-aminophenoxy)pyridine-2-yl)thiophene-2-carboxylate

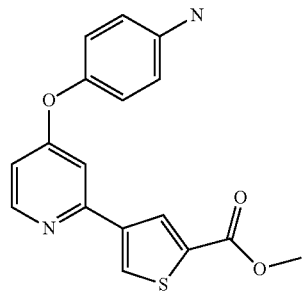 [SMILES: COC(=O)c1cc(-c2cc(Oc3ccc(N)cc3)ccn2)cs1]

A mixture of 4-(4-aminophenoxy)-2-chloropyridine (5.0 g, 22.66 mmol), methyl-(4-(4,4,5,5-tetramethyl-1,3,2-dioxaborolan-2-yl)-thiophene-2-carboxylate (9.73 g, 36.25 mmol) and Pd(PPh₃)₄ (5.24 g, 4.53 mmol) was added to a thick walled reaction vessel and purged with N₂. A solution of 2M K₂CO₃ (17.0 mL) was added, followed by dioxane (120 mL). The reaction vessel was sealed and the mixture stirred at 92° C. for 18 h. The reaction vessel was cooled to room temperature and the mixture was filtered over celite, washing with EtOAc. The filtrate was concentrated and the resultant dark oil was purified via column chromatography, eluting with 40-60% EtOAc/hexanes to afford methyl 4-(4-(4-aminophenoxy)pyridine-2-yl)thiophene-2-carboxylate (6.1 g, 82% yield).

Example 42 methyl 4-{4-[4-({[(2-fluoro-5-methylphenyl)amino]carbonyl}amino)phenoxy]pyridin-2-yl}thiophene-2-carboxylate

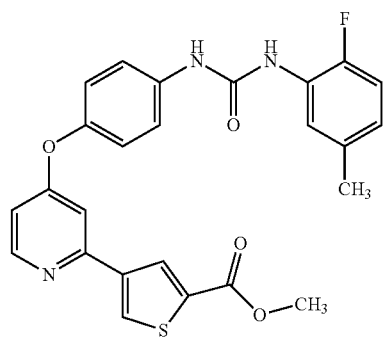 [SMILES: COC(=O)c1cc(-c2cc(Oc3ccc(NC(=O)Nc4cc(C)ccc4F)cc3)ccn2)cs1]

To a stirred solution of methyl 4-[4-(4-aminophenoxy)pyridin-2-yl]thiophene-2-carboxylate (500 mg, 1.53 mmol) in anhydrous THF (10 ml) was added 2-fluoro-5-methylphenylisocyanate (255 mg, 1.68 mmol). The mixture was stirred at room temperature for one hour and poured into 200 ml of water. The resulting precipitates were filtered, washed with water and dried in vacuo to give the crude, which was purified by silica gel chromatography eluting with 3-5% MeOH/CHCl₃ to give methyl 4-{4-[4-({[(2-fluoro-5-methylphenyl)amino]carbonyl}amino)phenoxy]pyridin-2-yl}thiophene-2-carboxylate as off-white solid. Yield: 560 mg, 76%.

¹H NMR (DMSO-d₆) δ: 9.14 (s, 1H), 8.51 (d, J=1.5 Hz, 1H), 8.41-8.47 (m, 2H), 8.33 (d, J=1.8 Hz, 1H), 7.96 (d, J=6.2 Hz, 1H), 7.48-7.57 (m, 3H), 7.13 (d, J=9.1 Hz, 2H), 7.08 (dd, J=11.4, 8.5 Hz, 1H), 6.76-6.81 (m, 1H), 6.74 (dd, J=5.6, 2.3 Hz, 1H), 3.83 (s, 3H), 2.25 (s, 3H)

LR MS (ES+): 500 (M+Na⁺)

LR MS (ES−): 476 (M−H)

Example 43

(4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid

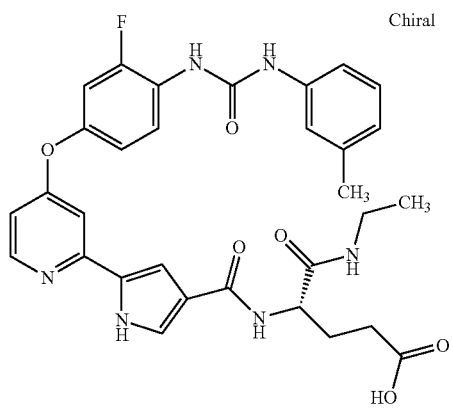 [SMILES: CCNC(=O)[C@H](CCC(=O)O)NC(=O)c1c[nH]c(-c2cc(Oc3ccc(NC(=O)Nc4cccc(C)c4)c(F)c3)ccn2)c1]

To a stirred solution of tert-butyl (4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoate (30 mg, 0.046 mmol) in 5 ml of methylene chloride was added 2 ml of TFA. The mixture was stirred at room temperature for 1 hour, and evaporated to dryness. The residue was dissolved in MeOH (3 ml), which was added dropwise into 100 ml of water with vigorous stirring. The precipitates were filtered, washed with water and dried to give (4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid as white solid. Yield: 20 mg, 74%.

¹H NMR (DMSO-d₆) δ: 12.04 (br. s., 1H), 11.86 (br. s., 1H), 8.97 (s, 1H), 8.57 (d, J=2.1 Hz, 1H), 8.39 (d, J=5.9 Hz, 1H), 8.20 (t, J=9.1 Hz, 1H), 7.82 (t, J=5.6 Hz, 1H), 7.79 (d, J=8.2 Hz, 1H), 7.46 (br. s., 1H), 7.12-7.29 (m, 5H), 6.99-7.04 (m, 1H), 6.79 (d, J=7.3 Hz, 1H), 6.74 (d, J=4.7 Hz, 1H), 4.31 (td, J=8.6, 5.4 Hz, 1H), 2.97-3.11 (m, 2H), 2.26 (s, 3H), 2.17-2.25 (m, 2H), 1.87-1.98 (m, 1H), 1.74-1.84 (m, 1H), 0.97 (t, J=7.2 Hz, 3H)

LR MS (ES−): 601 (M−H)

Example 44 tert-butyl (4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoate

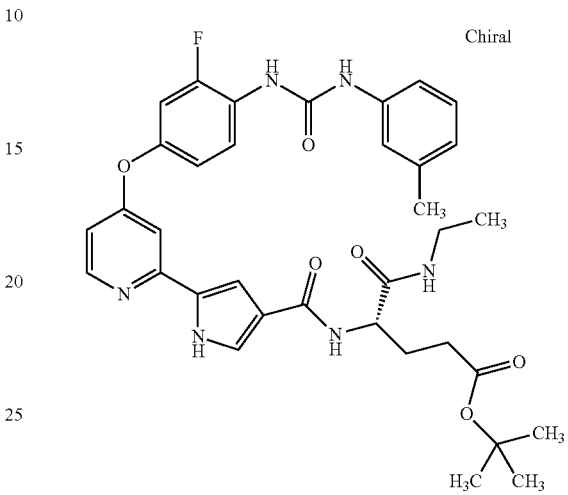

A mixture of (2S)-5-tert-butoxy-2-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid (80 mg, 0.13 mmol), HATU (57 mg, 0.15 mmol) and N,N-diisopropylethylamine (49 mg, 0.38 mmol) in anhydrous DMF (8 ml) was stirred at room temperature for 10 minutes, followed by addition of 2M ethylamine in THF solution (0.1 ml, 0.2 mmol). The mixture was stirred for another 10 minutes and poured into 100 ml of water. 2M HCl was added dropwise until pH=5. The precipitates were filtered, washed with water and dried in vacuo to give the crude, which was purified by silica gel chromatography eluting with 4~5% MeOH/CHCl₃ to give tert-butyl (4S)-5-(ethylamino)-4-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoate as white solid. Yield: 40 mg, 48%.

¹H NMR (DMSO-d₆) δ: 11.83 (br. s., 1H), 8.95 (s, 1H), 8.56 (br. s., 1H), 8.38 (d, J=5.6 Hz, 1H), 8.20 (t, J=9.1 Hz, 1H), 7.81 (t, J=5.3 Hz, 1H), 7.77 (d, J=8.2 Hz, 1H), 7.45 (d, J=1.5 Hz, 1H), 7.23-7.30 (m, 2H), 7.18-7.23 (m, 2H), 7.12-7.18 (m, 2H), 6.98-7.04 (m, 1H), 6.79 (d, J=7.6 Hz, 1H), 6.73 (dd, J=5.6, 2.3 Hz, 1H), 4.27-4.35 (m, 1H), 3.01-3.08 (m, 2H), 2.26 (s, 3H), 2.17-2.23 (m, 2H), 1.87-1.95 (m, 1H), 1.78 (m, 1H), 1.34 (s, 9H), 0.97 (t, J=7.2 Hz, 3H)

LR MS (ES+): 681 (M+Na⁺)

LR MS (ES−): 657 (M−H)

Example 45

(2S)-5-tert-butoxy-2-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid

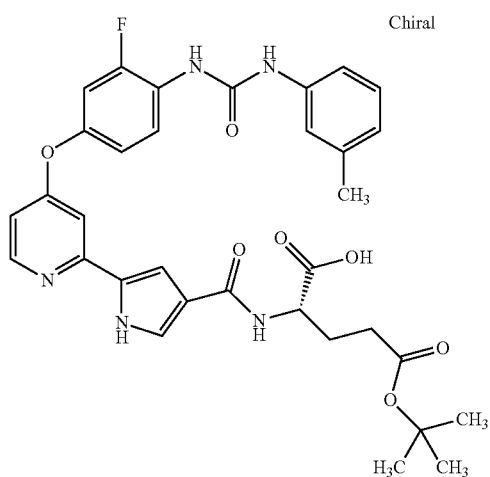 [SMILES: Cc1cccc(NC(=O)Nc2ccc(Oc3ccnc(-c4cc(C(=O)N[C@@H](CCC(=O)OC(C)(C)C)C(=O)O)c[nH]4)c3)cc2F)c1]

To a stirred solution of (S)-5-tert-butyl 1-methyl 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate (120 mg, 0.19 mmol) in a mixture of solvents THF/MeOH (5 ml/5 ml) was added 1 ml of 1M NaOH (1 mmol) solution. The mixture was stirred at room temperature for 30 minutes, and poured into 100 ml of water. 2M HCl was added dropwise until pH=4. The resulting precipitates were filtered, washed with water, and dried in vacuo to give (2S)-5-tert-butoxy-2-{[(5-{4-[3-fluoro-4-({[(3-methylphenyl)amino]carbonyl}amino)phenoxy]pyridin-2-yl}-1H-pyrrol-3-yl)carbonyl]amino}-5-oxopentanoic acid as white solid. Yield: 100 mg, 85%.

$^1$H NMR (DMSO-$d_6$) δ: 12.49 (br. s., 1H), 11.84 (br. s., 1H), 8.98 (s, 1H), 8.58 (d, J=2.3 Hz, 1H), 8.38 (d, J=5.6 Hz, 1H), 8.20 (t, J=9.1 Hz, 1H), 7.89 (br. s., 1H), 7.42 (br. s., 1H), 7.28 (s, 1H), 7.25 (dd, J=11.7, 2.6 Hz, 1H), 7.20-7.23 (m, 2H), 7.11-7.18 (m, 2H), 7.01 (dd, J=9.0, 1.6 Hz, 1H), 6.79 (d, J=7.3 Hz, 1H), 6.73 (dd, J=5.6, 2.3 Hz, 1H), 4.23-4.34 (m, 1H), 2.23-2.28 (m, 2H), 2.26 (s, 3H), 1.95-2.03 (m, 1H), 1.80-1.88 (m, 1H), 1.35 (s, 9H)

LR MS (ES+): 654 (M+Na$^+$)
LR MS (ES−): 630 (M−H)

Example 46

(S)-5-tert-butyl 1-methyl 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate

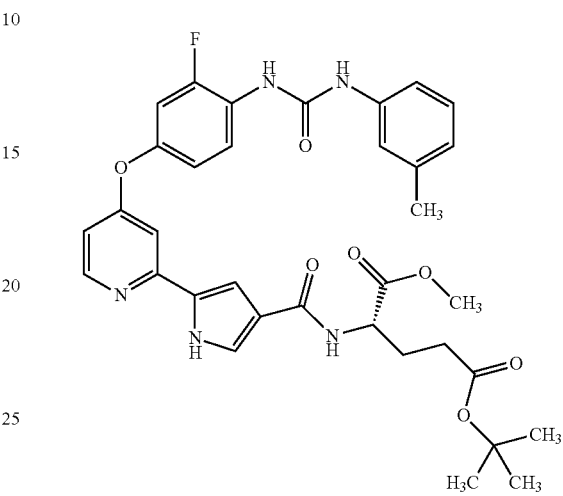

A mixture of 5-{4-[3-fluoro-4-({[(3-methylphenyl)amino]carbonyl}amino)phenoxy]pyridin-2-yl}-1H-pyrrole-3-carboxylic acid (500 mg, 1.1 mmol), HATU (500 mg, 1.32 mmol) and N,N-diisopropylethylamine (426 mg, 3.3 mmol) in anhydrous DMF (8 ml) was stirred at room temperature for 10 minutes, followed by addition of L-Glutamic acid 5-tert-butyl 1-methyl ester hydrochloride (334 mg, 1.32 mmol). The mixture was stirred for another 10 minutes and poured into 200 ml of water. 2M HCl was added dropwise until pH=5. The precipitates were filtered, washed with water and dried in vacuo to give the crude, which was purified by silica gel chromatography eluting with 3~5% MeOH/CHCl$_3$ to give (S)-5-tert-butyl 1-methyl 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate as off-white solid. Yield: 380 mg, 52%.

$^1$H NMR (DMSO-$d_6$) δ: 11.87 (br. s., 1H), 8.96 (s, 1H), 8.56 (br. s., 1H), 8.38 (d, J=5.6 Hz, 1H), 8.20 (t, J=8.9 Hz, 1H), 8.08 (d, J=7.0 Hz, 1H), 7.44 (br. s., 1H), 7.23-7.29 (m, 2H), 7.18-7.23 (m, 2H), 7.11-7.17 (m, 2H), 7.01 (d, J=8.8 Hz, 1H), 6.79 (d, J=7.0 Hz, 1H), 6.70-6.76 (m, 1H), 4.32-4.41 (m, 1H), 3.60 (s, 3H), 2.23-2.31 (m, 5H), 1.93-2.03 (m, 1H), 1.81-1.91 (m, 1H), 1.35 (s, 9H)

LR MS (ES+): 646 (MH), 668 (M+Na$^+$)
LR MS (ES−): 644 (M−H)

Example 47 bis(2-hydroxyethyl) 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate

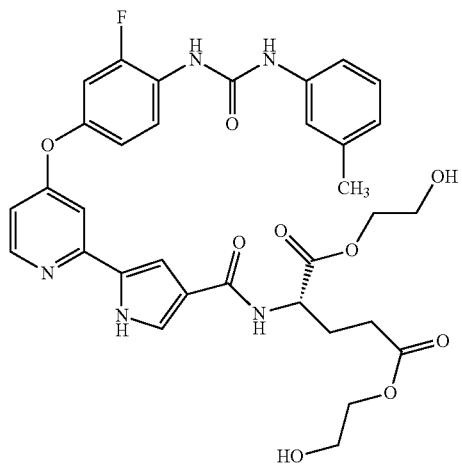 [SMILES: Cc1cccc(NC(=O)Nc2ccc(Oc3ccnc(-c4cc(C(=O)N[C@@H](CCC(=O)OCCO)C(=O)OCCO)c[nH]4)c3)cc2F)c1]

LR MS (ES+): 686 (M+Na⁺)
LR MS (ES−): 662 (M−H), 561

Example 48

3-{[(5-{4-[3-fluoro-4-({[(3-methylphenyl)amino]carbonyl}amino)phenoxy]pyridin-2-yl}-1H-pyrrol-3-yl)carbonyl]amino}propanoic acid

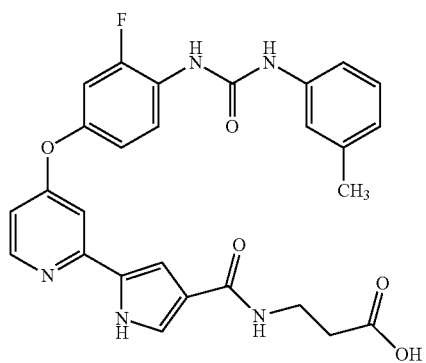 [SMILES: Cc1cccc(NC(=O)Nc2ccc(Oc3ccnc(-c4cc(C(=O)NCCC(=O)O)c[nH]4)c3)cc2F)c1]

Similar procedure as Example 132.
$^1$H NMR (DMSO-$d_6$) δ: 11.90 (br. s., 1H), 8.99 (s, 1H), 8.59 (br. s., 1H), 8.40 (d, J=5.9 Hz, 1H), 8.22 (t, J=9.0 Hz, 1H), 7.90-7.96 (m, 1H), 7.40 (br. s., 1H), 7.25-7.30 (m, 2H), 7.21 (d, J=7.0 Hz, 2H), 7.15 (t, J=7.8 Hz, 2H), 7.03 (d, J=9.1 Hz, 1H), 6.79 (d, J=7.0 Hz, 2H), 3.32-3.37 (m, 2H), 2.43 (t, J=7.0 Hz, 2H), 2.26 (s, 3H)

LR MS (ES−): 516 (M−H)

Example 49

2-{[(5-{4-[3-fluoro-4-({[(3-methylphenyl)amino]carbonyl}amino)phenoxy]pyridin-2-yl}-1H-pyrrol-3-yl)carbonyl]amino}pentanedioic acid

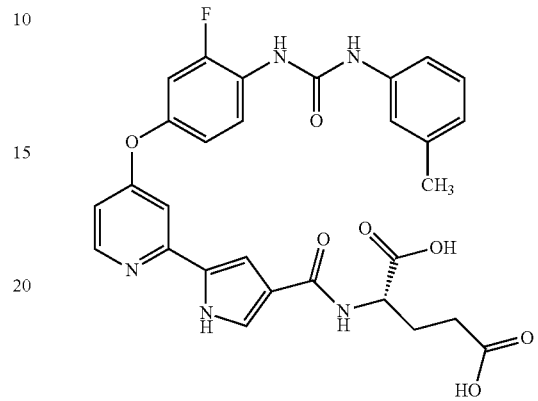

$^1$H NMR (DMSO-$d_6$) δ: 12.43 (br. s., 2H), 11.89 (br. s., 1H), 8.97 (br. s., 1H), 8.57 (br. s., 1H), 8.39 (d, J=5.3 Hz, 1H), 8.20 (t, J=8.8 Hz, 1H), 7.97 (d, J=7.6 Hz, 1H), 7.46 (br. s., 1H), 7.11-7.31 (m, 4H), 7.02 (d, J=9.1 Hz, 1H), 6.79 (d, J=7.0 Hz, 1H), 6.75 (br. s., 1H), 4.32 (br. s., 1H), 2.30 (t, J=7.2 Hz, 2H), 2.26 (s, 3H), 2.01 (m, 2H), 1.86 (m, 2H)

LR MS (ES−): 574 (M−H)

Example 50 methyl 1-(3-{[(5-{4-[4-({[(2-fluoro-5-methylphenyl)amino]carbonyl}amino)phenoxy]pyridin-2-yl}-1H-pyrrol-3-yl)carbonyl]amino}propyl)pyrrolidine-2-carboxylate

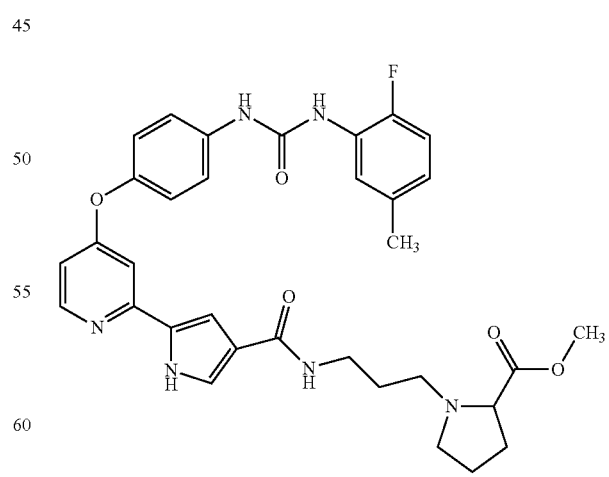

Similar procedure as Example 132.
LR MS (ES+): 615 (MH), 637 (M+Na⁺)
LR MS (ES−): 613 (M−H)

Example 51

5-{4-[4-({[(2-fluoro-5-methylphenyl)amino]carbonyl}amino)phenoxy]pyridin-2-yl}-N-{2-[(3S)-3-hydroxypyrrolidin-1-yl]-2-oxoethyl}-1H-pyrrole-3-carboxamide

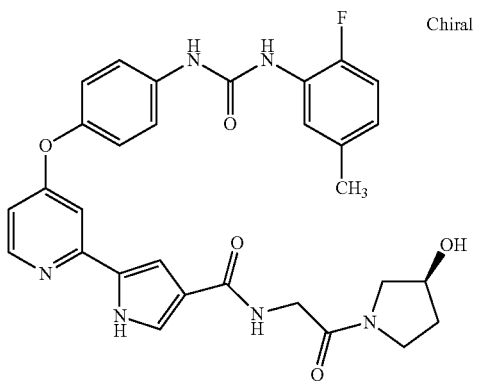 [SMILES: Cc1ccc(F)c(NC(=O)Nc2ccc(Oc3ccnc(-c4cc(C(=O)NCC(=O)N5CC[C@H](O)C5)c[nH]4)c3)cc2)c1]

Similar procedure as Example 132.
LR MS (ES+): 573 (MH), 595 (M+Na⁺)
LR MS (ES−): 571 (M−H)

Example 52

N-{4-[(2,3-dihydroxypropyl)(methyl)amino]-4-oxobutyl}-5-{4-[4-({[(2-fluoro-5-methylphenyl)amino]carbonyl}amino)phenoxy]pyridin-2-yl}-1H-pyrrole-3-carboxamide

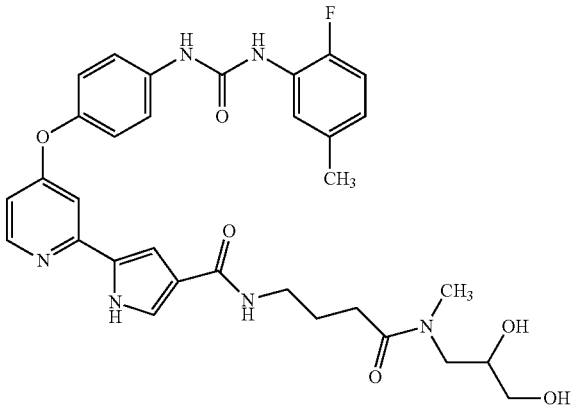 [SMILES: Cc1ccc(F)c(NC(=O)Nc2ccc(Oc3ccnc(-c4cc(C(=O)NCCCC(=O)N(C)CC(O)CO)c[nH]4)c3)cc2)c1]

Similar procedure as Example 61.
$^1$H NMR (DMSO-$d_6$) δ: 11.70-11.82 (m, 1H), 9.24 (s, 1H), 8.50 (d, J=2.1 Hz, 1H), 8.35 (d, J=5.9 Hz, 1H), 7.93-7.98 (m, 1H), 7.85 (dt, J=14.5, 5.5 Hz, 1H), 7.54 (d, J=9.1 Hz, 2H), 7.34 (br. s., 1H), 7.10-7.15 (m, 3H), 7.08 (dd, J=11.2, 8.5 Hz, 1H), 7.01-7.05 (m, 1H), 6.73-6.82 (m, 1H), 6.67 (dd, J=5.6, 2.3 Hz, 1H), 4.87 (d, J=5.3 Hz, 1H), 4.60-4.69 (m, 1H), 4.46 (t, J=5.9 Hz, 1H), 3.55-3.65 (m, 2H), 3.20-3.27 (m, 2H), 3.10-3.19 (m, 2H), 2.96 (s, 1H), 2.79 (s, 2H), 2.27-2.35 (m, 1H), 2.24 (s, 3H), 1.62-1.72 (m, 2H)
LR MS (ES+): 619 (MH), 641 (M+Na⁺)
LR MS (ES−): 617 (M−H)

Example 53

5-{4-[4-({[(2-fluoro-5-methylphenyl)amino]carbonyl}amino)phenoxy]pyridin-2-yl}-N-[4-(3-hydroxypiperidin-1-yl)-4-oxobutyl]-1H-pyrrole-3-carboxamide

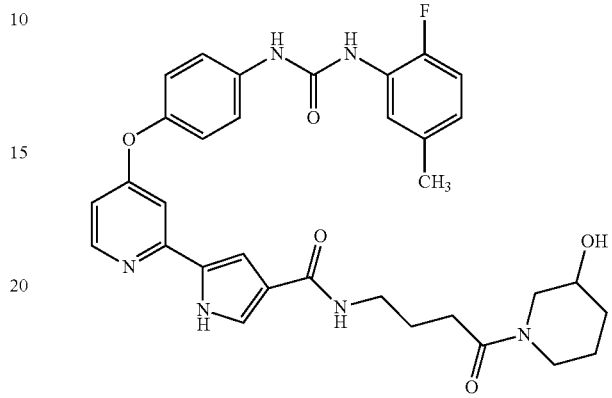

Similar procedure as Example 61.
LR MS (ES+): 637 (M+Na⁺)
LR MS (ES−): 613 (M−H)

Example 54

N-{4-[(2,3-dihydroxypropyl)amino]-4-oxobutyl}-5-{4-[4-({[(2-fluoro-5-methylphenyl)amino]carbonyl}amino)phenoxy]pyridin-2-yl}-1H-pyrrole-3-carboxamide

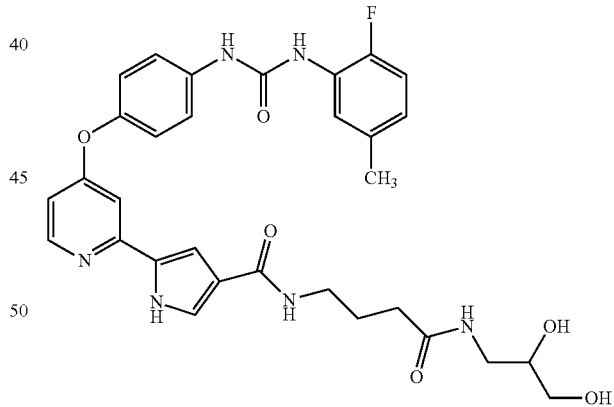

Similar procedure as Example 61.
$^1$H NMR (DMSO-$d_6$) δ: 11.77 (br. s., 1H), 9.14 (s, 1H), 8.46 (d, J=2.3 Hz, 1H), 8.35 (d, J=5.9 Hz, 1H), 7.96 (dd, J=7.9, 2.1 Hz, 1H), 7.84 (t, J=5.6 Hz, 1H), 7.77 (t, J=5.9 Hz, 1H), 7.51-7.57 (m, 2H), 7.33 (dd, J=3.1, 1.6 Hz, 1H), 7.11-7.16 (m, 3H), 7.08 (dd, J=11.3, 8.4 Hz, 1H), 7.01-7.05 (m, 1H), 6.75-6.82 (m, 1H), 6.68 (dd, J=5.7, 2.5 Hz, 1H), 4.68 (d, J=5.0 Hz, 1H), 4.46 (t, J=5.9 Hz, 1H), 3.41-3.47 (m, 1H), 3.20-3.26 (m, 2H), 3.09-3.19 (m, 3H), 2.90-2.97 (m, 1H), 2.25 (s, 3H), 2.10 (t, J=7.6 Hz, 2H), 1.66 (quin, J=7.3 Hz, 2H)
LR MS (ES+): 605 (MH), 627 (M+Na⁺)
LR MS (ES−): 603 (M−H)

Example 55

N-(4-amino-4-oxobutyl)-5-{4-[4-({[(2-fluoro-5-methylphenyl)amino]carbonyl}amino)phenoxy]pyridin-2-yl}-1H-pyrrole-3-carboxamide

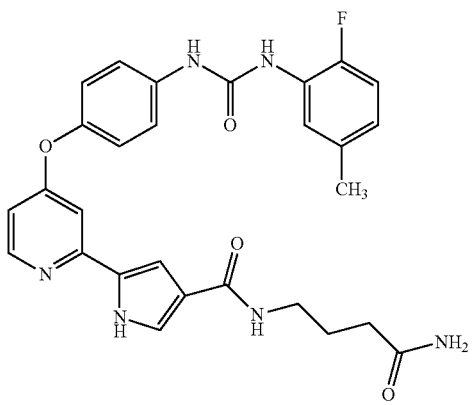 [SMILES: Cc1ccc(F)c(NC(=O)Nc2ccc(Oc3ccnc(-c4cc(C(=O)NCCCC(N)=O)c[nH]4)c3)cc2)c1]

Similar procedure as Example 61.

$^1$H NMR (DMSO-$d_6$) δ: 11.92 (br. s., 1H), 9.20 (br. s., 1H), 8.48 (d, J=1.8 Hz, 1H), 8.39 (d, J=5.9 Hz, 1H), 7.95 (dd, J=7.8, 1.9 Hz, 1H), 7.89 (br. s., 1H), 7.56 (d, J=8.8 Hz, 2H), 7.42 (br. s., 1H), 7.18-7.28 (m, 2H), 7.15 (d, J=8.8 Hz, 2H), 7.08 (dd, J=11.4, 8.5 Hz, 1H), 6.78 (ddd, J=7.5, 5.0, 2.2 Hz, 2H), 6.68 (br. s., 1H), 3.14 (q, J=6.7 Hz, 2H), 2.25 (s, 3H), 2.05 (t, J=7.5 Hz, 2H), 1.66 (quin, J=7.3 Hz, 2H)

LR MS (ES+): 553 (M+Na$^+$)
LR MS (ES−): 529 (M−H)

Example 56

N-{2-[(2,3-dihydroxypropyl)amino]-2-oxoethyl}-5-{4-[4-({[(2-fluoro-5-methylphenyl)amino]carbonyl}amino)phenoxy]pyridin-2-yl}-1H-pyrrole-3-carboxamide

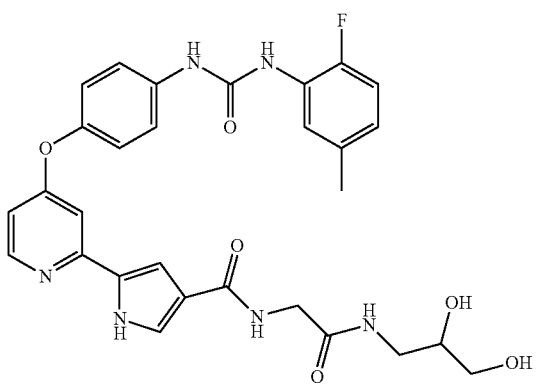 [SMILES: Cc1ccc(F)c(NC(=O)Nc2ccc(Oc3ccnc(-c4cc(C(=O)NCC(=O)NCC(O)CO)c[nH]4)c3)cc2)c1]

Similar procedure as Example 132.

$^1$H NMR (DMSO-$d_6$) δ: 11.83 (br. s., 1H), 9.15 (s, 1H), 8.46 (br. s., 1H), 8.36 (d, J=5.9 Hz, 1H), 8.14 (t, J=6.0 Hz, 1H), 7.95 (d, J=7.6 Hz, 1H), 7.67 (t, J=5.6 Hz, 1H), 7.54 (d, J=8.8 Hz, 2H), 7.38 (br. s., 1H), 7.13 (d, J=8.8 Hz, 3H), 7.03-7.11 (m, 2H), 6.75-6.82 (m, 1H), 6.69 (dd, J=5.6, 2.3 Hz, 1H), 4.70 (d, J=5.0 Hz, 1H), 4.47 (t, J=5.7 Hz, 1H), 3.76 (d, J=5.6 Hz, 2H), 3.45 (dq, J=11.2, 5.5 Hz, 1H), 3.16-3.27 (m, 3H), 2.93-3.00 (m, 1H), 2.25 (s, 3H)

LR MS (ES+): 577 (MH), 599 (M+Na$^+$)
LR MS (ES−): 575 (M−H)

Example 57

5-(2,3-dihydroxypropyl) 1-methyl 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate

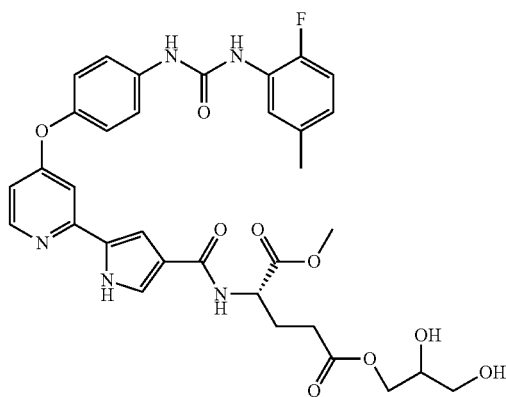 [SMILES: COC(=O)[C@H](CCC(=O)OCC(O)CO)NC(=O)c1c[nH]c(-c2cc(Oc3ccc(NC(=O)Nc4cc(C)ccc4F)cc3)ccn2)c1]

Similar procedure as Example 58.

$^1$H NMR (DMSO-$d_6$) δ: 11.86 (br. s., 1H), 9.14 (s, 1H), 8.46 (d, J=2.3 Hz, 1H), 8.36 (d, J=5.6 Hz, 1H), 8.08-8.17 (m, 1H), 7.96 (dd, J=7.9, 1.8 Hz, 1H), 7.54 (d, J=8.5 Hz, 2H), 7.43 (br. s., 1H), 7.04-7.21 (m, 4H), 6.78 (dt, J=5.7, 2.7 Hz, 1H), 6.68 (dd, J=5.6, 2.3 Hz, 1H), 4.83 (d, J=5.3 Hz, 1H), 4.58 (t, J=5.7 Hz, 1H), 4.36-4.45 (m, 1H), 3.95-4.06 (m, 2H), 3.88 (dd, J=11.0, 6.6 Hz, 1H), 3.60 (s, 3H), 3.28-3.35 (m, 2H), 2.40 (t, J=7.6 Hz, 2H), 2.25 (s, 3H), 1.99-2.10 (m, 1H), 1.88-1.95 (m, 1H), 1.15 (t, J=7.0 Hz, 1H)

LR MS (ES+): 664 (MH), 686 (M+Na$^+$)

Example 58 bis(2,3-dihydroxypropyl) 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate

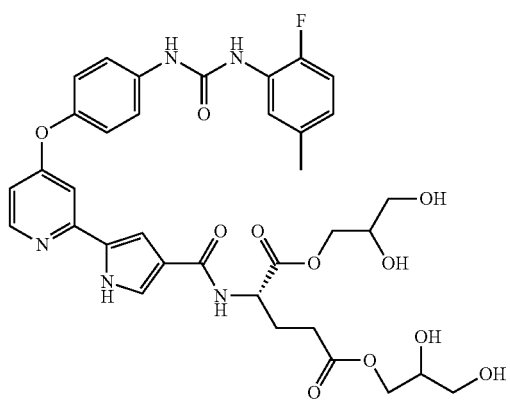 [SMILES: Cc1ccc(F)c(NC(=O)Nc2ccc(Oc3ccnc(-c4cc(C(=O)N[C@@H](CCC(=O)OCC(O)CO)C(=O)OCC(O)CO)c[nH]4)c3)cc2)c1]

A mixture of 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioic acid (60 mg, 0.10 mmol), glycerol (0.5 ml), 1-Ethyl-3-(3-dimethylaminopropyl)carbodiimide hydrochloride (EDC.HCl, 37 mg, 0.19 mmol) and 4-dimethylaminopyridine (DMAP, 5 mg, 0.04 mmol) in anhydrous THF (10 ml) was stirred at 60° C. for 3 hours. The mixture was cooled to room temperature, concentrated and purified by silica gel chromatography eluting with a gradient of 10~15% MeOH/CHCl$_3$ to give bis(2,3-dihydroxypropyl) 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate as colorless oil. Yield: 40 mg, 53%.

LR MS (ES+): 746 (M+Na$^+$)
LR MS (ES−): 722 (M−H)

Example 59

4-{[(5-{4-[4-({[(2-fluoro-5-methylphenyl)amino]carbonyl}amino)phenoxy]pyridin-2-yl}-1-H-pyrrol-3-yl)carbonyl]amino}-5-methoxy-5-oxopentanoic acid

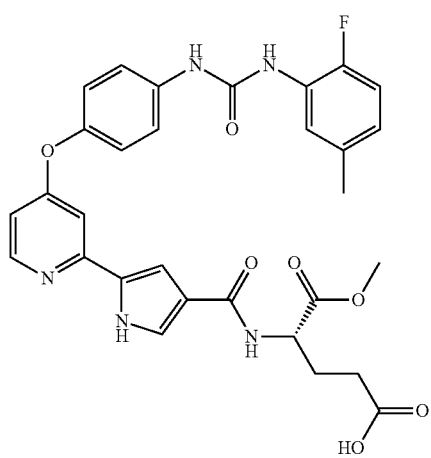 [SMILES: COC(=O)[C@H](CCC(=O)O)NC(=O)c1c[nH]c(-c2cc(Oc3ccc(NC(=O)Nc4cc(C)ccc4F)cc3)ccn2)c1]

Similar procedure as Example 132.
$^1$H NMR (DMSO-d$_6$) δ: 11.98 (br. s., 1H), 9.19 (s, 1H), 8.48 (d, J=2.6 Hz, 1H), 8.39 (d, J=5.9 Hz, 1H), 8.13 (d, J=7.3 Hz, 1H), 7.95 (dd, J=7.8, 1.9 Hz, 1H), 7.53-7.57 (m, 2H), 7.47-7.52 (m, 1H), 7.24 (br. s., 1H), 7.19 (br. s., 1H), 7.15 (d, J=8.8 Hz, 2H), 7.08 (dd, J=11.3, 8.4 Hz, 1H), 6.72-6.81 (m, 2H), 4.38 (ddd, J=9.5, 7.5, 5.3 Hz, 1H), 3.60 (s, 3H), 2.31 (t, J=7.6 Hz, 2H), 2.25 (s, 3H), 1.95-2.05 (m, 1H), 1.82-1.93 (m, J=14.0, 9.6, 7.0, 7.0 Hz, 1H)

LR MS (ES−): 588 (M−H)

Example 60

N-[4-(ethylamino)-4-oxobutyl]-5-{4-[4-({[(2-fluoro-5-methylphenyl)amino]carbonyl}amino)phenoxy]pyridin-2-yl}-1H-pyrrole-3-carboxamide

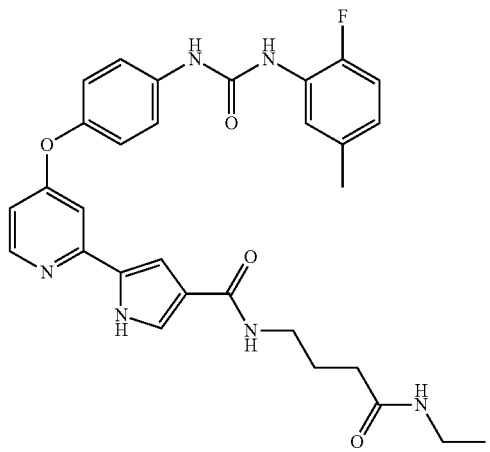 [SMILES: CCNC(=O)CCCNC(=O)c1c[nH]c(-c2cc(Oc3ccc(NC(=O)Nc4cc(C)ccc4F)cc3)ccn2)c1]

Similar procedure as Example 61.
$^1$H NMR (DMSO-d$_6$) δ: 11.96 (br. s., 1H), 9.20 (s, 1H), 8.48 (d, J=2.6 Hz, 1H), 8.39 (d, J=5.9 Hz, 1H), 7.95 (dd, J=7.8, 1.9 Hz, 1H), 7.89 (br. s., 1H), 7.76 (t, J=5.3 Hz, 1H), 7.53-7.58 (m, 2H), 7.44 (br. s., 1H), 7.23 (br. s., 1H), 7.13-7.19 (m, 3H), 7.08 (dd, J=11.3, 8.4 Hz, 1H), 6.75-6.84 (m, 2H), 3.11-3.17 (m, 2H), 3.01 (qd, J=7.2, 5.6 Hz, 2H), 2.25 (s, 3H), 2.05 (t, J=7.5 Hz, 2H), 1.66 (quin, J=7.3 Hz, 2H), 0.96 (t, J=7.2 Hz, 3H)
LR MS (ES+): 559 (MH), 581 (M+Na$^+$)
LR MS (ES−): 557 (M−H)

Example 61

5-{4-[4-({[(2-fluoro-5-methylphenyl)amino]carbonyl}amino)phenoxy]pyridin-2-yl}-N-[4-(3-hydroxypyrrolidin-1-yl)-4-oxobutyl]-1H-pyrrole-3-carboxamide

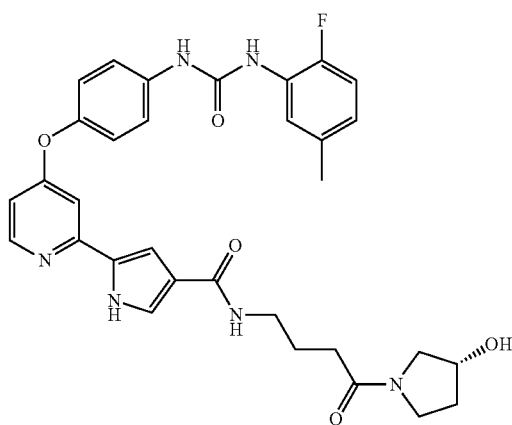 [SMILES: Cc1ccc(F)c(NC(=O)Nc2ccc(Oc3ccnc(-c4cc(C(=O)NCCCC(=O)N5CC[C@@H](O)C5)c[nH]4)c3)cc2)c1]

A mixture of 4-{[(5-{4-[4-({[(2-fluoro-5-methylphenyl)amino]carbonyl}amino)phenoxy]pyridin-2-yl}-1H-pyrrol- 3-yl)carbonyl]amino}butanoic acid (60 mg, 0.11 mmol), HATU (50 mg, 0.13 mmol) and N,N-diisopropylethylamine (43 mg, 0.33 mmol) in anhydrous DMF (8 ml) was stirred at room temperature for 10 minutes, followed by addition of (R)-3-pyrrolidinol (14 mg, 0.16 mmol). The mixture was stirred for another 10 minutes and poured into 100 ml of water. 2M HCl was added dropwise until pH=4~5. The precipitates were filtered, washed with water and dried in vacuo to give 5-{4-[4-({[(2-fluoro-5-methylphenyl)amino]carbonyl}amino)phenoxy]pyridin-2-yl}-N-[4-(3-hydroxy-pyrrolidin-1-yl)-4-oxobutyl]-1H-pyrrole-3-carboxamide as white solid. Yield: 40 mg, 59%.

$^1$H NMR (DMSO-d$_6$) δ: 11.97 (br. s., 1H), 9.31 (s, 1H), 8.53 (d, J=2.3 Hz, 1H), 8.39 (d, J=5.9 Hz, 1H), 7.95 (dd, J=7.8, 1.9 Hz, 1H), 7.91 (d, J=4.4 Hz, 1H), 7.54-7.59 (m, 2H), 7.42-7.48 (m, 1H), 7.24 (br. s., 1H), 7.16 (d, J=8.8 Hz, 2H), 7.05-7.10 (m, 1H), 6.78 (ddd, J=7.5, 5.0, 2.2 Hz, 2H), 4.24-4.28 (m, OH), 4.16-4.21 (m, 1H), 3.40-3.48 (m, 2H), 3.35 (ddd, J=11.6, 8.4, 3.5 Hz, 1H), 3.25-3.30 (m, 1H), 3.14-3.25 (m, 4H), 2.25 (s, 3H), 2.23-2.27 (m, 1H), 2.20 (t, J=7.9 Hz, 1H), 1.84-1.92 (m, 1H), 1.75-1.82 (m, 1H), 1.65-1.73 (m, 2H)

LR MS (ES+): 601 (MH), 623 (M+Na$^+$)

LR MS (ES-): 599 (M-H)

Example 62

5-{4-[4-({[(2-fluoro-5-methylphenyl)amino]carbonyl}amino)phenoxy]pyridin-2-yl}-N-[4-(hydroxyamino)-4-oxobutyl]-1H-pyrrole-3-carboxamide

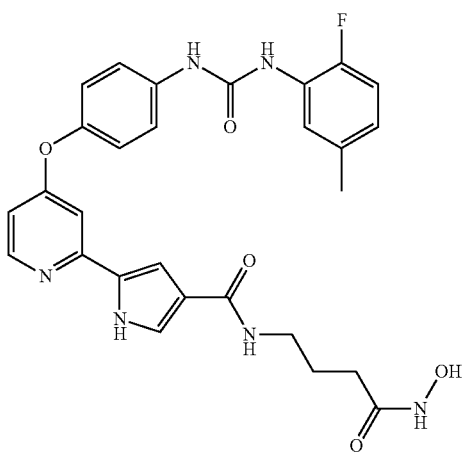 [SMILES: Cc1ccc(F)c(NC(=O)Nc2ccc(Oc3ccnc(-c4cc(C(=O)NCCCC(=O)NO)c[nH]4)c3)cc2)c1]

Similar procedure as Example 61.

$^1$H NMR (DMSO-d$_6$) δ: 11.92 (br. s., 1H), 10.33 (s, 1H), 9.18 (s, 1H), 8.47 (d, J=2.6 Hz, 1H), 8.39 (d, J=5.9 Hz, 1H), 7.95 (dd, J=7.9, 1.8 Hz, 1H), 7.87-7.92 (m, 1H), 7.51-7.58 (m, 2H), 7.38-7.46 (m, 1H), 7.21 (br. s., 1H), 7.11-7.18 (m, 3H), 7.05-7.11 (m, 1H), 6.72-6.82 (m, 2H), 3.14 (q, J=6.7 Hz, 2H), 2.25 (s, 3H), 1.96 (t, J=7.6 Hz, 2H), 1.66 (quin, J=7.3 Hz, 2H)

LR MS (ES+): 547 (MH), 569 (M+Na$^+$)

LR MS (ES-): 545 (M-H)

Example 63

2-{[(5-{4-[4-({[(2-fluoro-5-methylphenyl)amino]carbonyl}amino)phenoxy]pyridin-2-yl}-1H-pyrrol-3-yl)carbonyl]amino}pentanedioic acid

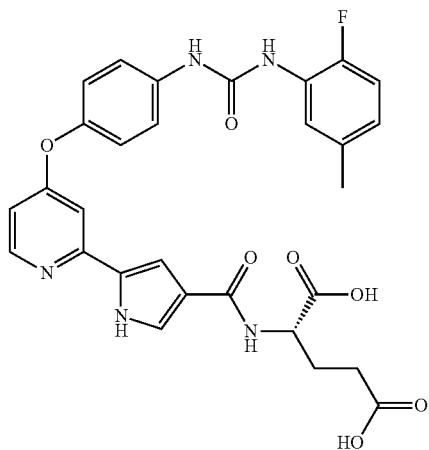 [SMILES: Cc1ccc(F)c(NC(=O)Nc2ccc(Oc3ccnc(-c4cc(C(=O)N[C@@H](CCC(=O)O)C(=O)O)c[nH]4)c3)cc2)c1]

Similar procedure as Example 132.

$^1$H NMR (DMSO-d$_6$) δ: 12.42 (br. s., 1H), 12.12 (br. s., 1H), 11.86 (br. s., 1H), 9.15 (s, 1H), 8.46 (d, J=2.6 Hz, 1H), 8.37 (d, J=5.6 Hz, 1H), 7.93-8.01 (m, 2H), 7.51-7.58 (m, 2H), 7.44 (br. s., 1H), 7.18 (s, 1H), 7.11-7.16 (m, 3H), 7.08 (dd, J=11.3, 8.4 Hz, 1H), 6.75-6.82 (m, 1H), 6.69 (d, J=3.8 Hz, 1H), 4.32 (ddd, J=9.7, 7.9, 5.0 Hz, 1H), 2.30 (t, J=7.6 Hz, 2H), 2.25 (s, 3H), 1.96-2.05 (m, 1H), 1.80-1.91 (m, J=14.0, 9.8, 7.2, 7.2 Hz, 1H)

LR MS (ES-): 574 (M-H)

Example 64 dimethyl 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate

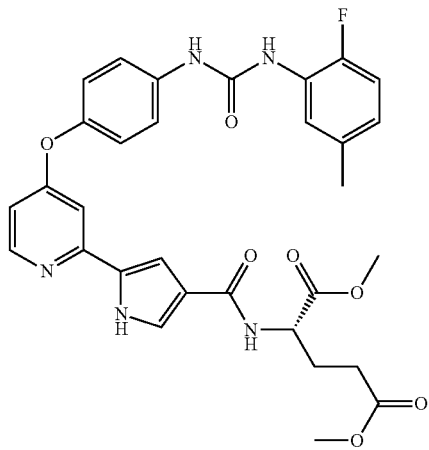 [SMILES: COC(=O)CC[C@H](NC(=O)c1c[nH]c(-c2cc(Oc3ccc(NC(=O)Nc4cc(C)ccc4F)cc3)ccn2)c1)C(=O)OC]

Similar procedure as Example 132.

$^1$H NMR (DMSO-d$_6$) δ: 12.27 (br. s., 1H), 9.33 (br. s., 1H), 8.50-8.57 (m, 1H), 8.44 (d, J=6.2 Hz, 1H), 8.23 (d,

J=6.7 Hz, 1H), 7.95 (d, J=6.5 Hz, 1H), 7.64 (br. s., 1H), 7.58 (d, J=8.8 Hz, 2H), 7.39 (br. s., 2H), 7.19 (d, J=8.8 Hz, 2H), 7.08 (dd, J=11.2, 8.2 Hz, 1H), 6.92 (br. s., 1H), 6.79 (d, J=5.6 Hz, 1H), 4.35-4.43 (m, 1H), 3.60 (s, 3H), 3.55 (s, 3H), 2.40 (t, J=7.5 Hz, 2H), 2.22-2.28 (m, 3H), 2.00-2.10 (m, 1H), 1.88-1.97 (m, 1H)

LR MS (ES+): 626 (M+Na⁺)
LR MS (ES−): 602 (M−H)

Example 65

1-[(5-{4-[3-fluoro-4-({[(2-fluoro-5-methylphenyl)amino]carbonyl}amino)phenoxy]pyridin-2-yl}-1H-pyrrol-3-yl)carbonyl]pyrrolidine-3-carboxylic acid

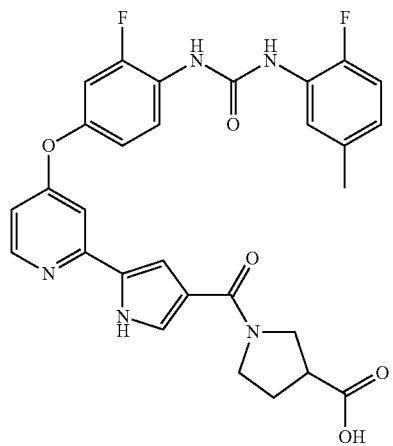 [SMILES: Cc1ccc(F)c(NC(=O)Nc2ccc(Oc3ccnc(-c4cc(C(=O)N5CCC(C(=O)O)C5)c[nH]4)c3)cc2F)c1]

Similar procedure as Example 132.

$^1$H NMR (DMSO-d$_6$) δ: 12.47 (br. s., 1H), 11.85-12.01 (m, 1H), 9.05 (d, J=1.8 Hz, 1H), 8.94 (d, J=2.3 Hz, 1H), 8.39 (d, J=5.9 Hz, 1H), 8.22 (t, J=9.1 Hz, 1H), 7.98 (dd, J=7.8, 1.9 Hz, 1H), 7.41 (br. s., 1H), 7.21-7.32 (m, 2H), 7.06-7.14 (m, 2H), 7.01 (dd, J=9.0, 1.6 Hz, 1H), 6.79 (ddd, J=7.6, 5.1, 1.9 Hz, 1H), 6.65-6.76 (m, 1H), 2.97-3.93 (m, 5H), 2.25 (s, 3H), 1.93-2.19 (m, 2H)

LR MS (ES+): 562 (MH), 584 (M+Na⁺)
LR MS (ES−): 560 (M−H)

Example 66

4-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}butanoic acid

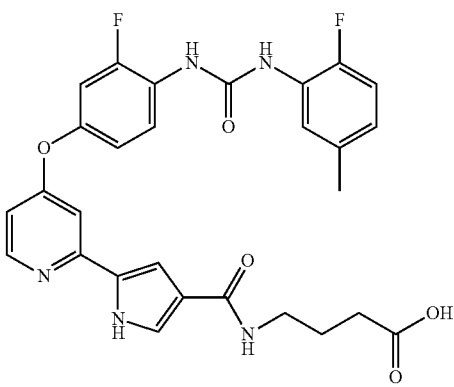 [SMILES: Cc1ccc(F)c(NC(=O)Nc2ccc(Oc3ccnc(-c4cc(C(=O)NCCCC(=O)O)c[nH]4)c3)cc2F)c1]

To a stirred solution of ethyl 4-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}butanoate (45 mg, 0.078 mmol) in 10 ml of THF was added 3 ml of 1M NaOH (3.0 mmol). The mixture was heated at 60° C. for 3 hours, cooled to room temperature and poured into 100 ml of water. 2M HCl was added until pH=5. The precipitates were filtered, washed with water, and dried to give 4-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}butanoic acid as grey solid. Yield: 40 mg, 93%.

$^1$H NMR (DMSO-d$_6$) δ: 11.99 (br. s., 1H), 11.82 (br. s., 1H), 9.06 (d, J=2.1 Hz, 1H), 8.94 (d, J=2.6 Hz, 1H), 8.38 (d, J=5.9 Hz, 1H), 8.23 (t, J=9.1 Hz, 1H), 7.98 (dd, J=7.9, 2.1 Hz, 1H), 7.85 (t, J=5.7 Hz, 1H), 7.37 (br. s., 1H), 7.27 (dd, J=11.7, 2.6 Hz, 1H), 7.19 (s, 1H), 7.09 (dd, J=11.3, 8.4 Hz, 2H), 7.02 (dd, J=8.9, 1.6 Hz, 1H), 6.77-6.82 (m, 1H), 6.73-6.77 (m, 1H), 3.16 (q, J=6.7 Hz, 2H), 2.25 (s, 3H), 2.22 (t, J=7.3 Hz, 2H), 1.67 (quin, J=7.2 Hz, 2H)

LR MS (ES−): 548 (M−H)

Example 67 ethyl 4-{[(5-{4-[3-fluoro-4-({[(2-fluoro-5-methyl-phenyl)amino]carbonyl}amino)phenoxy]pyridin-2-yl}-1H-pyrrol-3-yl)carbonyl]amino}butanoate

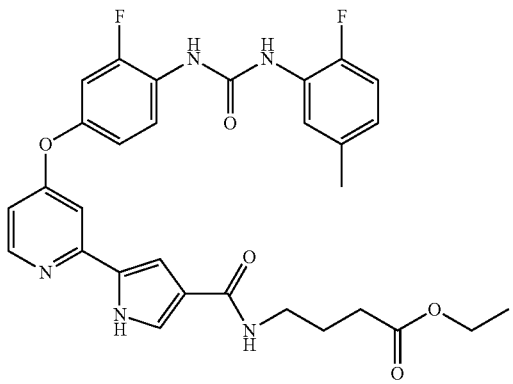 [SMILES: CCOC(=O)CCCNC(=O)c1c[nH]c(-c2cc(Oc3ccc(NC(=O)Nc4cc(C)ccc4F)c(F)c3)ccn2)c1]

Similar procedure as Example 132.
¹H NMR (DMSO-d₆) δ: 11.99 (br. s., 1H), 9.09 (d, J=1.5 Hz, 1H), 8.96 (d, J=2.3 Hz, 1H), 8.42 (d, J=6.2 Hz, 1H), 8.26 (t, J=9.1 Hz, 1H), 7.98 (dd, J=7.8, 2.2 Hz, 1H), 7.86-7.94 (m, 1H), 7.46 (br. s., 1H), 7.25-7.34 (m, 2H), 7.22 (br. s., 1H), 7.09 (dd, J=11.3, 8.4 Hz, 1H), 7.02-7.07 (m, 1H), 6.87 (br. s., 1H), 6.76-6.82 (m, 1H), 4.01 (q, J=7.1 Hz, 2H), 3.13-3.21 (m, 2H), 2.30 (t, J=7.5 Hz, 2H), 2.25 (s, 3H), 1.70 (quin, J=7.2 Hz, 2H), 1.14 (t, J=7.04 Hz, 3H)
LR MS (ES+): 578 (MH), 600 (M+Na⁺)
LR MS (ES−): 576 (M−H)

Example 68

4-{[(5-{4-[3-fluoro-4-({[(3-methylphenyl)amino]carbonyl}amino)phenoxy]pyridin-2-yl}-1H-pyrrol-3-yl)carbonyl]amino}butanoic acid

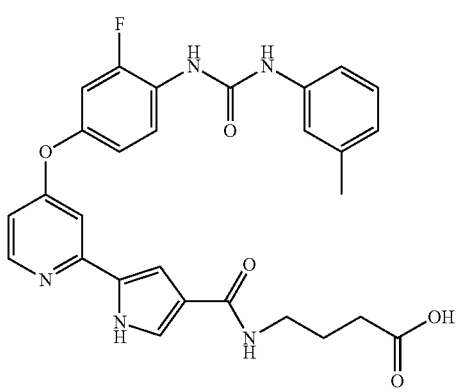 [SMILES: Cc1cccc(NC(=O)Nc2ccc(Oc3ccnc(-c4cc(C(=O)NCCCC(=O)O)c[nH]4)c3)cc2F)c1]

Similar procedure as Example 66.
¹H NMR (DMSO-d₆) δ: 12.00 (br. s., 1H), 11.82 (br. s., 1H), 8.97 (s, 1H), 8.57 (d, J=2.3 Hz, 1H), 8.38 (d, J=5.9 Hz, 1H), 8.21 (t, J=9.1 Hz, 1H), 7.85 (t, J=5.7 Hz, 1H), 7.37 (br. s., 1H), 7.24-7.29 (m, 2H), 7.17-7.23 (m, 2H), 7.13-7.17 (m, 1H), 7.10 (br. s., 1H), 7.02 (dd, J=8.8, 1.8 Hz, 1H), 6.79 (d, J=7.3 Hz, 1H), 6.75 (br. s., 1H), 3.16 (q, J=6.7 Hz, 2H), 2.26 (s, 3H), 2.22 (t, J=7.3 Hz, 2H), 1.67 (quin, J=7.2 Hz, 2H)
LR MS (ES+): 532 (MH), 554 (M+Na⁺)
LR MS (ES−): 530 (M−H)

Example 69

3-{[(5-{4-[3-fluoro-4-({[(2-fluoro-5-methylphenyl)amino]carbonyl}amino)phenoxy]pyridin-2-yl}-1H-pyrrol-3-yl)carbonyl]amino}propanoic acid

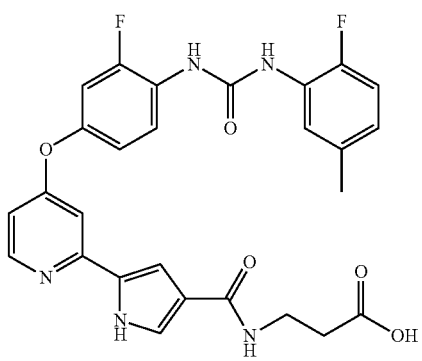 [SMILES: Cc1ccc(F)c(NC(=O)Nc2ccc(Oc3ccnc(-c4cc(C(=O)NCCC(=O)O)c[nH]4)c3)cc2F)c1]

Similar procedure as Example 66.
¹H NMR (DMSO-d₆) δ: 11.93 (br. s., 2H), 9.08 (br. s., 1H), 8.96 (d, J=1.8 Hz, 1H), 8.41 (d, J=5.9 Hz, 1H), 8.25 (t, J=8.9 Hz, 1H), 7.98 (d, J=7.9 Hz, 1H), 7.94 (br. s., 1H), 7.43 (d, J=2.1 Hz, 1H), 7.29 (d, J=10.3 Hz, 1H), 7.24 (br. s., 1H), 7.17 (br. s., 1H), 7.09 (dd, J=11.3, 8.4 Hz, 1H), 7.04 (d, J=8.5 Hz, 1H), 6.83 (br. s., 1H), 6.76-6.81 (m, 1H), 3.33-3.38 (m, 2H), 2.44 (t, J=7.0 Hz, 2H), 2.25 (s, 3H)
LR MS (ES−): 534 (M−H)

Example 70

N-ethyl-5-{4-[3-fluoro-4-({[(3-methylphenyl)amino]carbonyl}amino)phenoxy]pyridin-2-yl}-1H-pyrrole-3-carboxamide

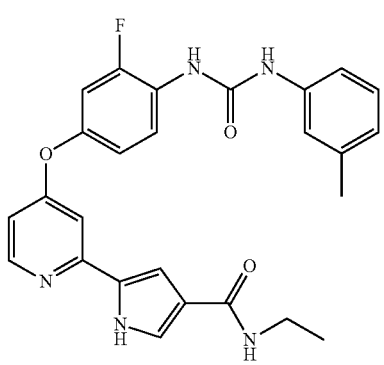 [SMILES: CCNC(=O)c1c[nH]c(-c2cc(Oc3ccc(NC(=O)Nc4cccc(C)c4)c(F)c3)ccn2)c1]

Similar procedure as Example 132.
¹H NMR (DMSO-d₆) δ: 11.98 (br. s., 1H), 9.11 (s, 1H), 8.67 (br. s., 1H), 8.41 (d, J=5.9 Hz, 1H), 8.23 (t, J=9.1 Hz, 1H), 7.87 (t, J=5.0 Hz, 1H), 7.44 (br. s., 1H), 7.25-7.32 (m, 3H), 7.18-7.25 (m, 2H), 7.12-7.17 (m, 1H), 7.04 (dd, J=9.0, 1.6 Hz, 1H), 6.85 (br. s., 1H), 6.79 (d, J=7.3 Hz, 1H), 3.15-3.22 (m, 2H), 2.26 (s, 3H), 1.05 (t, J=7.2 Hz, 3H)
LR MS (ES+): 474 (MH), 496 (M+Na⁺)
LR MS (ES−): 472 (M−H)

Example 71

{[(5-{4-[3-fluoro-4-({[(3-methylphenyl)amino]carbonyl}amino)phenoxy]pyridin-2-yl}-1H-pyrrol-3-yl)carbonyl]amino}acetic acid

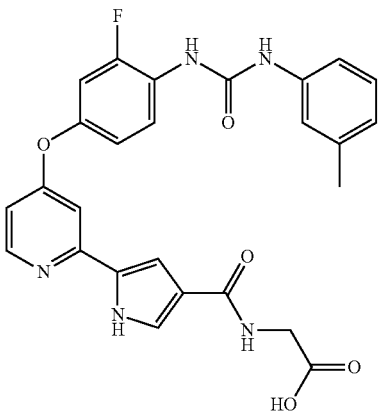 [SMILES: Cc1cccc(NC(=O)Nc2ccc(Oc3ccnc(-c4cc(C(=O)NCC(=O)O)c[nH]4)c3)cc2F)c1]

Similar procedure as Example 66.

$^1$H NMR (DMSO-d$_6$) δ: 11.84 (br. s., 1H), 9.23 (s, 1H), 8.73 (d, J=1.5 Hz, 1H), 8.38 (d, J=5.6 Hz, 1H), 8.18 (t, J=9.1 Hz, 1H), 8.12 (t, J=5.4 Hz, 1H), 7.38 (dd, J=2.9, 1.8 Hz, 1H), 7.28 (s, 1H), 7.21-7.26 (m, 2H), 7.19 (d, J=2.3 Hz, 1H), 7.14 (t, J=7.8 Hz, 1H), 7.08-7.11 (m, 1H), 7.01 (dd, J=9.0, 2.5 Hz, 1H), 6.78 (d, J=7.3 Hz, 1H), 6.73 (dd, J=5.9, 2.3 Hz, 1H), 3.78 (d, J=5.9 Hz, 2H), 2.25 (s, 3H)

LR MS (ES−): 502 (M−H)

Example 72 methyl {[(5-{4-[3-fluoro-4-({[(3-methylphenyl)amino]carbonyl}amino)phenoxy]pyridin-2-yl}-1H-pyrrol-3-yl)carbonyl]amino}acetate

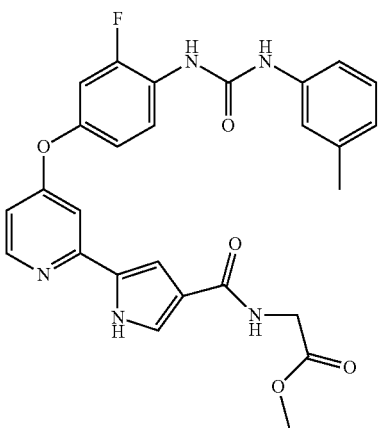 [SMILES: COC(=O)CNC(=O)c1c[nH]c(-c2cc(Oc3ccc(NC(=O)Nc4cccc(C)c4)c(F)c3)ccn2)c1]

Similar procedure as Example 132.

$^1$H NMR (DMSO-d$_6$) δ: 11.87 (br. s., 1H), 8.96 (s, 1H), 8.56 (d, J=2.3 Hz, 1H), 8.38 (d, J=5.9 Hz, 1H), 8.31 (t, J=6.0 Hz, 1H), 8.20 (t, J=9.1 Hz, 1H), 7.39 (dd, J=3.2, 1.8 Hz, 1H), 7.24-7.29 (m, 2H), 7.21 (d, J=8.2 Hz, 1H), 7.19 (d, J=2.3 Hz, 1H), 7.13-7.17 (m, 1H), 7.08-7.10 (m, 1H), 7.01 (dd, J=8.5, 2.1 Hz, 1H), 6.79 (d, J=7.3 Hz, 1H), 6.74 (dd, J=5.9, 2.3 Hz, 1H), 3.90 (d, J=5.9 Hz, 2H), 3.60 (s, 3H), 2.26 (s, 3H)

LR MS (ES+): 518 (MH), 540 (M+Na$^+$)
LR MS (ES−): 516 (M−H)

Example 73

1-(2-fluoro-4-{[2-(4-{[(3R)-3-hydroxypyrrolidin-1-yl]carbonyl}-1H-pyrrol-2-yl)pyridin-4-yl]oxy}phenyl)-3-(3-methylphenyl)urea

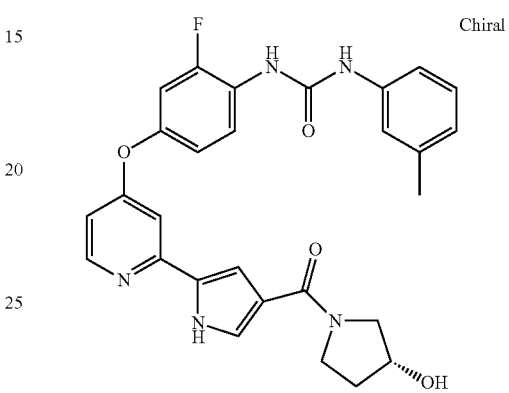

Similar procedure as Example 132.

$^1$H NMR (DMSO-d$_6$) δ: 11.87 (br. s., 1H), 8.97 (s, 1H), 8.56 (d, J=2.1 Hz, 1H), 8.37 (d, J=5.9 Hz, 1H), 8.18 (t, J=9.1 Hz, 1H), 7.38 (d, J=2.3 Hz, 1H), 7.18-7.30 (m, 4H), 7.12-7.17 (m, 1H), 7.08 (d, J=18.8 Hz, 1H), 6.99 (dt, J=7.6, 1.5 Hz, 1H), 6.78 (d, J=7.6 Hz, 1H), 6.68 (dd, J=5.6, 2.3 Hz, 1H), 4.90 (d, J=9.4 Hz, 1H), 4.30 (br. s., 1H), 3.68-3.82 (m, 2H), 3.42-3.54 (m, 2H), 2.26 (s, 3H), 1.72-1.97 (m, 2H)

LR MS (ES+): 516 (MH), 538 (M+Na$^+$)
LR MS (ES−): 514 (M−H)

Example 74

1-{2-fluoro-4-[(2-{4-[(3-hydroxypiperidin-1-yl)carbonyl]-1H-pyrrol-2-yl}pyridin-4-yl)oxy]phenyl}-3-(3-methylphenyl)urea

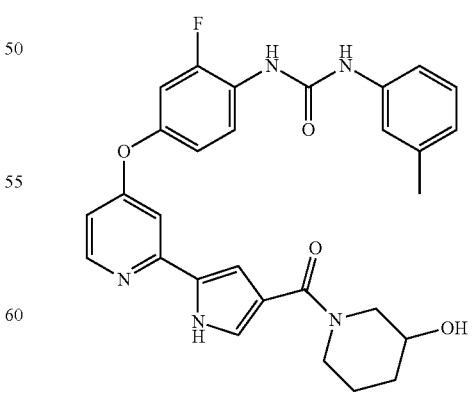

Similar procedure as Example 132.

$^1$H NMR (DMSO-d$_6$) δ: 11.83 (br. s., 1H), 8.96 (s, 1H), 8.55 (d, J=2.3 Hz, 1H), 8.37 (d, J=5.6 Hz, 1H), 8.19 (t, J=9.1

Hz, 1H), 7.34 (d, J=2.3 Hz, 1H), 7.27 (s, 1H), 7.19-7.25 (m, 2H), 7.15 (t, J=7.8 Hz, 1H), 7.12 (br. s., 1H), 6.97-7.01 (m, 1H), 6.90 (s, 1H), 6.79 (d, J=7.6 Hz, 1H), 6.68 (dd, J=5.7, 2.2 Hz, 1H), 4.87 (br. s., 1H), 4.04 (br. s., 1H), 3.85 (br. s., 1H), 3.41-3.52 (m, 1H), 3.07 (t, J=10.1 Hz, 1H), 2.26 (s, 3H), 1.78-1.90 (m, 1H), 1.67 (td, J=8.8, 4.7 Hz, 1H), 1.30-1.43 (m, 2H)

LR MS (ES+): 530 (MH), 552 (M+Na⁺)
LR MS (ES−): 528 (M−H)

Example 75

5-{4-[3-fluoro-4-({[(3-methylphenyl)amino]carbonyl}amino)phenoxy]pyridin-2-yl}-1H-pyrrole-3-carboxylic acid

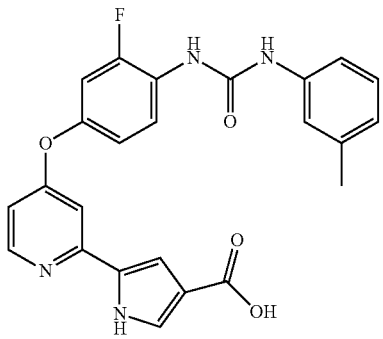 [SMILES: Cc1cccc(NC(=O)Nc2ccc(Oc3ccnc(-c4cc(C(=O)O)c[nH]4)c3)cc2F)c1]

Similar procedure as Example 134.
¹H NMR (DMSO-d₆) δ: 12.04 (br. s., 1H), 11.87 (br. s., 1H), 8.97 (br. s., 1H), 8.56 (br. s., 1H), 8.39 (d, J=5.9 Hz, 1H), 8.20 (t, J=9.1 Hz, 1H), 7.36 (br. s., 2H), 7.19-7.30 (m, 3H), 7.12-7.17 (m, 1H), 7.08 (br. s., 1H), 7.00 (d, J=8.8 Hz, 1H), 6.79 (d, J=7.3 Hz, 1H), 6.73 (br. s., 1H), 2.26 (s, 3H)

LR MS (ES+): 469 (MH)

Example 76 methyl 5-{4-[3-fluoro-4-({[(3-methylphenyl)amino]carbonyl}amino)phenoxy]pyridin-2-yl}-1H-pyrrole-3-carboxylate

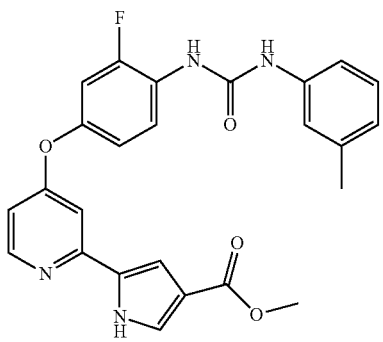 [SMILES: COC(=O)c1c[nH]c(-c2cc(Oc3ccc(NC(=O)Nc4cccc(C)c4)c(F)c3)ccn2)c1]

Similar procedure as Example 135.
¹H NMR (DMSO-d₆) δ: 12.11 (br. s., 1H), 8.96 (s, 1H), 8.55 (s, 1H), 8.38 (d, J=5.9 Hz, 1H), 8.19 (t, J=9.1 Hz, 1H), 7.42 (dd, J=3.1, 1.6 Hz, 1H), 7.37 (d, J=2.1 Hz, 1H), 7.28 (s, 1H), 7.19-7.26 (m, 2H), 7.12-7.17 (m, 1H), 7.09-7.12 (m, 1H), 7.00 (dd, J=9.1, 2.3 Hz, 1H), 6.79 (d, J=7.3 Hz, 1H), 6.72 (dd, J=5.6, 2.3 Hz, 1H), 3.69 (s, 3H), 2.26 (s, 3H)

LR MS (ES+): 461 (MH), 483 (M+Na⁺)
LR MS (ES−): 459 (M−H)

Example 77

5-{4-[4-({[(2-fluoro-5-methylphenyl)amino]carbonyl}amino)phenoxy]pyridin-2-yl}-N-(2-{2-[2-(2-hydroxyethoxy)ethoxy]ethoxy}ethyl)-1H-pyrrole-3-carboxamide

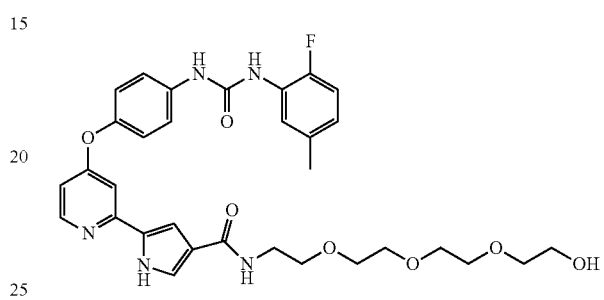

Similar procedure as Example 132.
¹H NMR (DMSO-d₆) δ: 11.92 (br. s., 1H), 9.20 (s, 1H), 8.48 (br. s., 1H), 8.38 (d, J=5.6 Hz, 1H), 7.96 (d, J=7.9 Hz, 1H), 7.92 (br. s., 1H), 7.55 (d, J=8.8 Hz, 2H), 7.43 (br. s., 1H), 7.20 (br. s., 1H), 7.11-7.17 (m, 3H), 7.08 (dd, J=11.2, 8.5 Hz, 1H), 6.73-6.81 (m, 2H), 3.41-3.48 (m, 12H), 3.34-3.39 (m, 2H), 3.31 (q, J=5.8 Hz, 2H), 2.25 (s, 3H)

LR MS (ES+): 622 (MH), 644 (M+Na⁺)
LR MS (ES−): 620 (M−H)

Example 78

4-{[(5-{4-[4-({[(2-fluoro-5-methylphenyl)amino]carbonyl}amino)phenoxy]pyridin-2-yl}-1H-pyrrol-3-yl)carbonyl]amino}butanoic acid

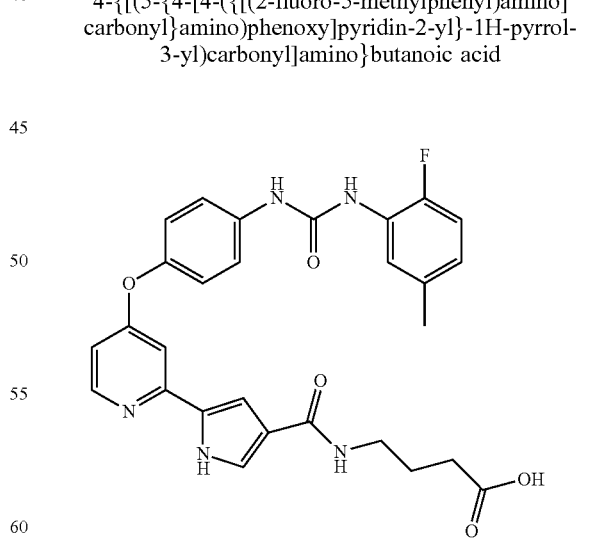

Similar procedure as Example 66.
¹H NMR (DMSO-d₆) δ: 11.83 (br. s., 1H), 9.17 (s, 1H), 8.49 (d, J=2.3 Hz, 1H), 8.39 (d, J=5.9 Hz, 1H), 7.95-8.02 (m, 1H), 7.88 (t, J=5.6 Hz, 1H), 7.57 (d, J=9.1 Hz, 2H), 7.38 (br. s., 1H), 7.16 (d, J=9.1 Hz, 2H), 7.06-7.17 (m, 3H), 6.77-6.85

(m, 1H), 6.67-6.76 (m, 1H), 3.16-3.22 (m, 2H), 2.28 (s, 3H), 2.25 (t, J=7.3 Hz, 2H), 1.70 (quin, J=7.2 Hz, 2H)

LR MS (ES+): 532 (MH)
LR MS (ES−): 530 (M−H)

Example 79 ethyl 4-{[(5-{4-[4-({[(2-fluoro-5-methylphenyl)amino]carbonyl}amino)phenoxy]pyridin-2-yl}-1H-pyrrol-3-yl)carbonyl]amino}butanoate

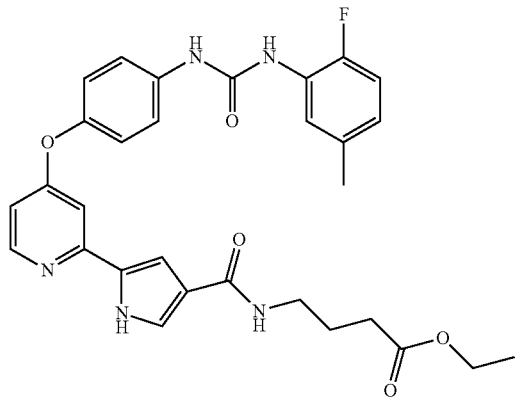 [SMILES: CCOC(=O)CCCNC(=O)c1c[nH]c(-c2cc(Oc3ccc(NC(=O)Nc4cc(C)ccc4F)cc3)ccn2)c1]

Similar procedure as Example 132.
LR MS (ES+): 560 (MH), 582 (M+Na⁺)
LR MS (ES−): 558 (M−H)

Preparation of 4-(2-Chloro-pyridin-4-ylsulfanyl)-phenylamine

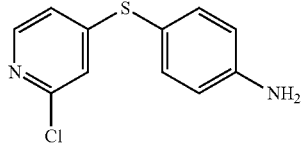 [SMILES: Nc1ccc(Sc2ccnc(Cl)c2)cc1]

2,4-Dichloropyrdine (4.44 g, 30.0 mmol) and potassium carbonate (8.28 g, 60.0 mmol) in dimethylformamide (60 mL) was purged with nitrogen for 10 min. 4-Aminothiophenol (3.76 g, 30.0 mmol) was added and the mixture stirred under nitrogen at room temperature for 18 h. Water (300 mL) was added and the slurry stirred for 30 min. The resulting solid was filtered, washed with water and vacuum dried at room temperature. Recrystallization from ethyl acetate (35 mL), filtered hot, then cooled gave 4-(2-Chloro-pyridin-4-ylsulfanyl)-phenylamine (3.946 g, 56% yield).

Preparation of 1-[4-(2-Chloro-pyridin-4-ylsulfanyl)-phenyl]-3-(2-fluoro-5-methyl-phenyl)-urea

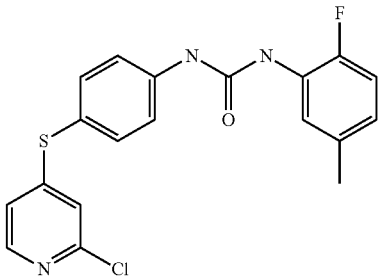 [SMILES: Cc1ccc(F)c(NC(=O)Nc2ccc(Sc3ccnc(Cl)c3)cc2)c1]

To a stirred solution of 4-(2-Chloro-pyridin-4-ylsulfanyl)-phenylamine (300 mg, 1.27 mmol) in anhydrous THF (10 ml) was added 2-fluoro-5-methyl-phenylisocyanate (210 mg, 1.39 mmol). The mixture was stirred at 60° C. for 5 hours, and poured into 100 ml of water. The precipitates were filtered, washed with water (50 ml), and dried to give the crude, which was purified by silica gel chromatography eluting with 2-3% MeOH/CHCl₃ to give 1-[4-(2-Chloro-pyridin-4-ylsulfanyl)-phenyl]-3-(2-fluoro-5-methyl-phenyl)-urea as white solid. Yield: 410 mg, 83%.

$^1$H NMR (DMSO-d₆) δ: 9.37 (s, 1H), 8.57 (d, J=2.1 Hz, 1H), 8.17 (d, J=5.9 Hz, 1H), 7.89-8.01 (m, 1H), 7.58-7.70 (m, 2H), 7.47-7.59 (m, 2H), 7.10 (dd, J=11.4, 8.2 Hz, 1H), 6.94-7.03 (m, 2H), 6.82 (dd, J=4.8, 2.2 Hz, 1H), 2.26 (s, 3H)

Example 80

5-(4-{[4-({[(2-fluoro-5-methylphenyl)amino]carbonyl}amino)phenyl]thio}pyridin-2-yl)-1H-pyrrole-3-carboxylic acid

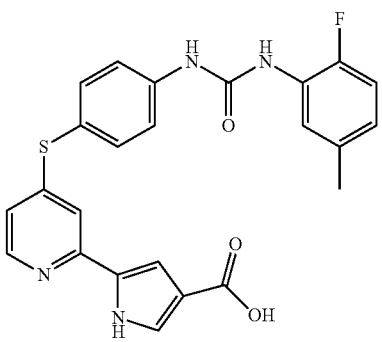 [SMILES: Cc1ccc(F)c(NC(=O)Nc2ccc(Sc3ccnc(-c4cc(C(=O)O)c[nH]4)c3)cc2)c1]

To a stirred solution of methyl 5-(4-{[4-({[(2-fluoro-5-methylphenyl)amino]carbonyl}amino)phenyl]thio}pyridin-2-yl)-1H-pyrrole-3-carboxylate (86 mg, 0.18 mmol) in a mixture of solvents THF/MeOH (5 ml/5 ml) was added 2 ml of 1M NaOH (2 mmol) solution. The mixture was heated in a 66° C. bath for 7 hours, cooled to room temperature and poured into 100 ml of water. 2M HCl was added until pH=3. The resulting precipitates were filtered, washed with water, and dried in vacuo to give 5-(4-{[4-({[(2-fluoro-5-methylphenyl)amino]carbonyl}amino)phenyl]thio}pyridin-2-yl)-1H-pyrrole-3-carboxylic acid as light brown solid. Yield: 73 mg, 88%.

¹H NMR (DMSO-d₆) δ: 12.01 (br. s., 1H), 9.37 (s, 1H), 8.56 (d, J=1.8 Hz, 1H), 8.27 (d, J=5.6 Hz, 1H), 7.95 (s, 1H), 7.44-7.68 (m, 5H), 7.36 (br. s., 1H), 7.10 (dd, J=11.1, 8.5 Hz, 1H), 6.94 (br. s., 1H), 6.81 (br. s., 1H), 6.69 (d, J=5.3 Hz, 1H), 2.26 (s, 3H)

LR MS (ES−): 461 (M−H)

Example 81

3-{[(5-{4-[4-({[(2-fluoro-5-methylphenyl)amino] carbonyl}amino)phenoxy]pyridin-2-yl}-1H-pyrrol-3-yl)carbonyl]amino}propanoic acid

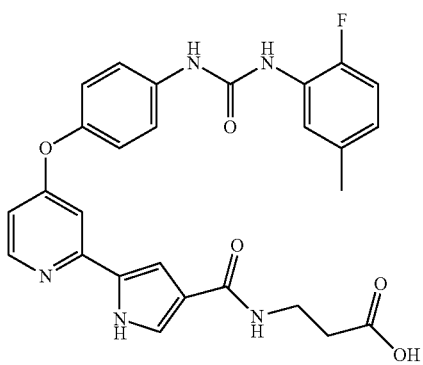 [SMILES: Cc1ccc(F)c(NC(=O)Nc2ccc(Oc3ccnc(-c4cc(C(=O)NCCC(=O)O)c[nH]4)c3)cc2)c1]

Similar procedure as Example 66.

¹H NMR (DMSO-d₆) δ: 12.12 (br. s., 1H), 11.81 (br. s., 1H), 9.15 (s, 1H), 8.46 (br. s., 1H), 8.36 (d, J=5.6 Hz, 1H), 7.96 (d, J=7.6 Hz, 1H), 7.92 (t, J=5.3 Hz, 1H), 7.54 (d, J=8.8 Hz, 2H), 7.35 (br. s., 1H), 7.13 (dd, J=6.6, 2.2 Hz, 3H), 7.08 (dd, J=11.2, 8.5 Hz, 1H), 7.04 (br. s., 1H), 6.75-6.82 (m, 1H), 6.70 (d, J=3.2 Hz, 1H), 3.32-3.41 (m, 2H), 2.43 (t, J=7.0 Hz, 2H), 2.25 (s, 3H)

LR MS (ES+): 518 (MH), 540 (M+Na⁺)
LR MS (ES−): 516 (M−H)

Example 82

4-{S-methyl-N-[(5-{4-[4-({[(3-methylphenyl)amino] carbonyl}amino)phenoxy]pyridin-2-yl}-1H-pyrrol-3-yl)carbonyl]sulfonimidoyl}butanoic acid

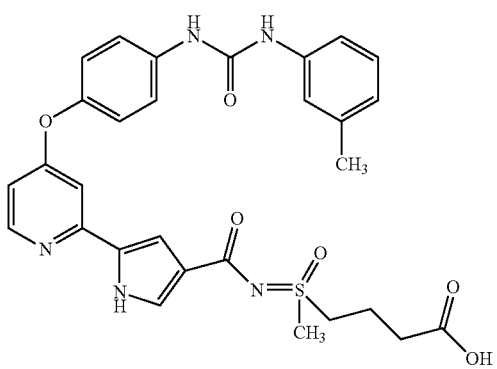 [SMILES: Cc1cccc(NC(=O)Nc2ccc(Oc3ccnc(-c4cc(C(=O)N=S(C)(=O)CCCC(=O)O)c[nH]4)c3)cc2)c1]

To a stirred solution of methyl 4-{S-methyl-N-[(5-{4-[4-({[(3-methylphenyl)amino]carbonyl}amino)phenoxy]pyridin-2-yl}-1H-pyrrol-3-yl)carbonyl] sulfonimidoyl}butanoate (5 mg, 0.0087 mol) in MeOH (3 ml) was added 1M NaOH (0.5 ml, 0.5 mmol). The mixture was stirred at room temperature for 30 minutes, and poured into 30 ml of water. 2M HCl was added dropwise until pH=4. The precipitates were filtered, washed with water and dried to give 4-{S-methyl-N-[(5-{4-[4-({[(3-methylphenyl) amino]carbonyl}amino)phenoxy]pyridin-2-yl}-1H-pyrrol-3-yl)carbonyl]sulfonimidoyl}butanoic acid as off-white solid. Yield: 5 mg, 100%.

LR MS (ES+): 576 (MH), 598 (M+Na⁺)
LR MS (ES−): 574 (M−H)

Example 83

1-[(5-{4-[4-({[(2-fluoro-5-methylphenyl)amino] carbonyl}amino)phenoxy]pyridin-2-yl}-1H-pyrrol-3-yl)carbonyl]pyrrolidine-3-carboxylic acid

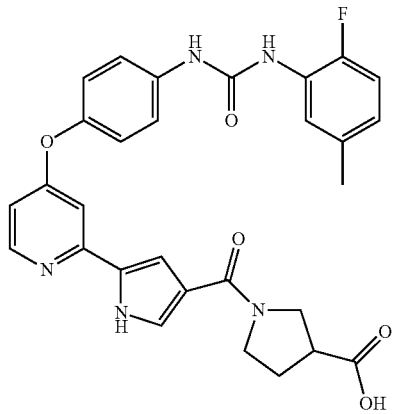 [SMILES: Cc1ccc(F)c(NC(=O)Nc2ccc(Oc3ccnc(-c4cc(C(=O)N5CCC(C(=O)O)C5)c[nH]4)c3)cc2)c1]

Similar procedure as Example 132.

¹H NMR (DMSO-d₆) δ: 12.04 (br. s., 1H), 9.16 (s, 1H), 8.46 (d, J=2.3 Hz, 1H), 8.39 (d, J=5.6 Hz, 1H), 7.93-7.99 (m, 1H), 7.54 (d, J=9.1 Hz, 2H), 7.41 (br. s., 1H), 7.33 (br. s., 1H), 7.14 (d, J=8.8 Hz, 2H), 7.08 (dd, J=11.3, 8.4 Hz, 1H), 6.75-6.82 (m, 1H), 6.72 (br. s., 1H), 2.98-3.93 (m, 5H), 2.25 (s, 3H), 1.93-2.19 (m, 2H)

LR MS (ES+): 544 (MH), 566 (M+Na⁺)
LR MS (ES−): 542 (M−H)

Example 84

{[(5-{4-[4-({[(2-fluoro-5-methylphenyl)amino]carbonyl}amino)phenoxy]pyridin-2-yl}-1H-pyrrol-3-yl)carbonyl]amino}acetic acid

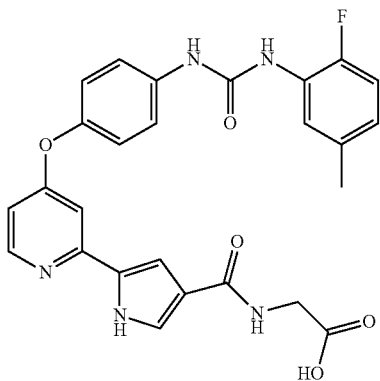 [SMILES: Cc1ccc(F)c(NC(=O)Nc2ccc(Oc3ccnc(-c4cc(C(=O)NCC(=O)O)c[nH]4)c3)cc2)c1]

Similar procedure as Example 66.

$^1$H NMR (DMSO-$d_6$) δ: 12.42 (br. s., 1H), 11.85 (br. s., 1H), 9.15 (s, 1H), 8.47 (d, J=2.1 Hz, 1H), 8.37 (d, J=5.9 Hz, 1H), 8.21 (t, J=6.0 Hz, 1H), 7.90-8.03 (m, 1H), 7.55 (d, J=8.8 Hz, 2H), 7.38 (br. s., 1H), 7.02-7.21 (m, 5H), 6.74-6.84 (m, 1H), 6.70 (dd, J=5.6, 2.3 Hz, 1H), 3.82 (d, J=5.9 Hz, 2H), 2.26 (s, 3H)

LR MS (ES+): 504 (MH), 526 (M+Na$^+$)

LR MS (ES−): 502 (M−H)

Example 85 methyl {[(5-{4-[4-({[(2-fluoro-5-methylphenyl)amino]carbonyl}amino)phenoxy]pyridin-2-yl}-1H-pyrrol-3-yl)carbonyl]amino}acetate

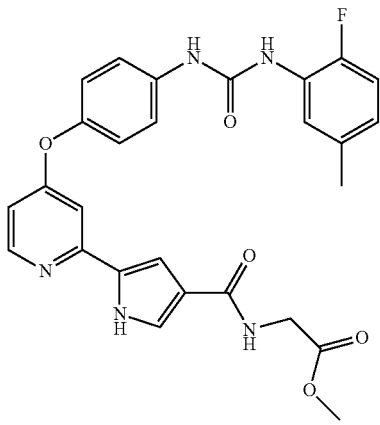 [SMILES: COC(=O)CNC(=O)c1c[nH]c(-c2cc(Oc3ccc(NC(=O)Nc4cc(C)ccc4F)cc3)ccn2)c1]

Similar procedure as Example 132.

$^1$H NMR (DMSO-$d_6$) δ: 12.00 (br. s., 1H), 9.18 (s, 1H), 8.48 (d, J=2.1 Hz, 1H), 8.29-8.44 (m, 2H), 7.97 (d, J=7.9 Hz, 1H), 7.56 (d, J=9.1 Hz, 2H), 7.46 (br. s., 1H), 7.02-7.27 (m, 5H), 6.79 (d, J=2.1 Hz, 2H), 3.91 (d, J=6.2 Hz, 2H), 3.61 (s, 3H), 2.26 (s, 3H)

LR MS (ES+): 518 (MH), 540 (M+Na$^+$)

LR MS (ES−): 516 (M−H)

Example 86

1-[(5-{4-[4-({[(2-fluoro-5-methylphenyl)amino]carbonyl}amino)phenoxy]pyridin-2-yl}-1H-pyrrol-3-yl)carbonyl]piperidine-4-sulfonic acid

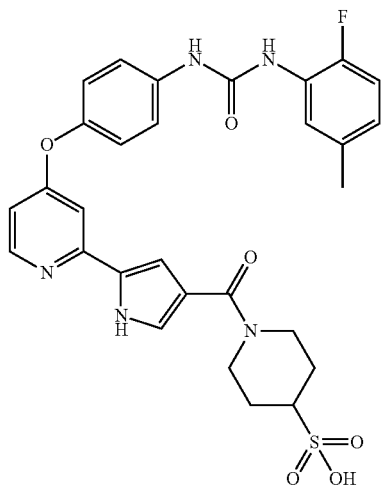 [SMILES: Cc1ccc(F)c(NC(=O)Nc2ccc(Oc3ccnc(-c4cc(C(=O)N5CCC(S(=O)(=O)O)CC5)c[nH]4)c3)cc2)c1]

Similar procedure as Example 132.

$^1$H NMR (DMSO-$d_6$) δ: 12.41 (br. s., 1H), 9.24 (s, 1H), 8.46-8.53 (m, 2H), 7.91-7.98 (m, 1H), 7.54-7.64 (m, 3H), 7.45 (br. s., 1H), 7.30 (br. s., 1H), 7.22 (d, J=8.8 Hz, 2H), 7.08 (dd, J=11.2, 8.2 Hz, 1H), 7.02 (br. s., 1H), 6.75-6.82 (m, 1H), 4.29 (br. s., 2H), 3.52 (br. s., 2H), 2.48-2.56 (m, 1H), 2.25 (s, 3H), 1.93 (d, J=12.6 Hz, 2H), 1.45 (br. s., 2H)

LR MS (ES+): 616 (M+Na$^+$)

LR MS (ES−): 592 (M−H)

Example 87 methyl 4-{S-methyl-N-[(5-{4-[4-({[(3-methylphenyl)amino]carbonyl}amino)phenoxy]pyridin-2-yl}-1H-pyrrol-3-yl)carbonyl]sulfonimidoyl}butanoate

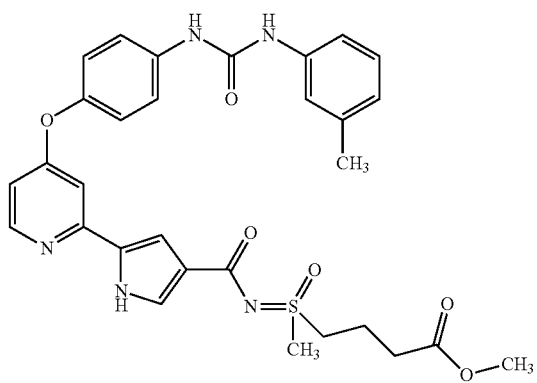 [SMILES: COC(=O)CCCS(C)(=O)=NC(=O)c1c[nH]c(-c2cc(Oc3ccc(NC(=O)Nc4cccc(C)c4)cc3)ccn2)c1]

Similar procedure as Example 101.

LR MS (ES+): 590 (MH), 612 (M+Na$^+$)

Example 88 methyl 5-(4-{[4-({[(2-fluoro-5-methylphenyl)amino]carbonyl}amino)phenyl]thio}pyridin-2-yl)-1H-pyrrole-3-carboxylate

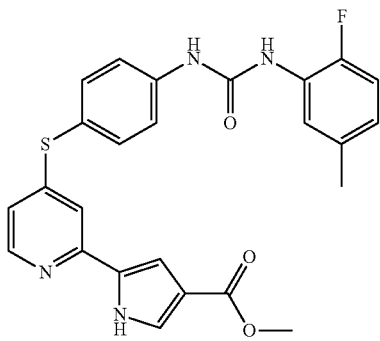 [SMILES: COC(=O)c1c[nH]c(-c2cc(Sc3ccc(NC(=O)Nc4cc(C)ccc4F)cc3)ccn2)c1]

A mixture of 1-[4-(2-Chloro-pyridin-4-ylsulfanyl)-phenyl]-3-(2-fluoro-5-methyl-phenyl)-urea (410 mg, 1.06 mmol), methyl-(5-(4,4,5,5-tetramethyl-1,3,2-dioxaborolan-2-yl)-1H-pyrrole-3-carboxylate (532 mg, 2.12 mmol) and PdCl$_2$(dppf).CH$_2$Cl$_2$ (10 mg, 0.012 mmol) was added to a thick-walled reaction vessel and purged with N$_2$. A solution of 2M Na$_2$CO$_3$ (1.0 mL) was added, followed by DMSO (10 mL). The reaction vessel was sealed and the mixture stirred at 95° C. for 16 h. The reaction vessel was cooled to room temperature and the mixture was poured into 100 ml of water. The precipitates were filtered, washed with water and dried to give the crude, which was purified via silica gel chromatography eluting with 2-5% MeOH/CHCl$_3$ to afford methyl 5-(4-{[4-({[(2-fluoro-5-methylphenyl)amino]carbonyl}amino)phenyl]thio}pyridin-2-yl)-1H-pyrrole-3-carboxylate as off-white solid. Yield: 100 mg, 20% yield.

LR MS (ES+): 477 (MH), 499 (M+Na$^+$)

Example 89

N-methyl-5-{4-[4-({[(3-methylphenyl)amino]carbonyl}amino)phenoxy]pyridin-2-yl}-1H-pyrrole-3-carboxamide

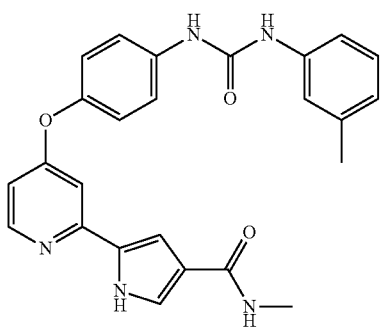 [SMILES: CNC(=O)c1c[nH]c(-c2cc(Oc3ccc(NC(=O)Nc4cccc(C)c4)cc3)ccn2)c1]

Similar procedure as Example 132.

$^1$H NMR (DMSO-d$_6$) δ: 11.88 (br. s., 1H), 8.89 (s, 1H), 8.69 (s, 1H), 8.37 (d, J=5.9 Hz, 1H), 7.82 (d, J=4.4 Hz, 1H), 7.52-7.58 (m, 2H), 7.37 (br. s., 1H), 7.27 (s, 1H), 7.22 (d, J=8.2 Hz, 1H), 7.18 (br. s., 1H), 7.11-7.15 (m, 3H), 7.08 (br. s., 1H), 6.71-6.80 (m, 2H), 2.67 (d, J=4.7 Hz, 3H), 2.25 (s, 3H)

LR MS (ES+): 442 (MH), 464 (M+Na$^+$)
LR MS (ES-): 440 (M-H)

Example 90

1-{4-[(2-{4-[(3-hydroxypiperidin-1-yl)carbonyl]-1H-pyrrol-2-yl}pyridin-4-yl)oxy]phenyl}-3-(3-methylphenyl)urea

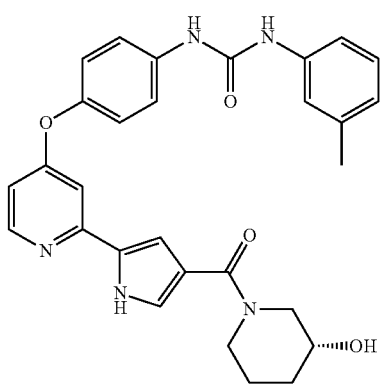 [SMILES: Cc1cccc(NC(=O)Nc2ccc(Oc3ccnc(-c4cc(C(=O)N5CCC[C@@H](O)C5)c[nH]4)c3)cc2)c1]

Similar procedure as Example 132.
LR MS (ES+): 512 (MH), 534 (M+Na$^+$)
LR MS (ES-): 510 (M-H)

Example 91

1-{4-[(2-{4-[(3-hydroxypyrrolidin-1-yl)carbonyl]-1H-pyrrol-2-yl}pyridin-4-yl)oxy]phenyl}-3-(3-methylphenyl)urea

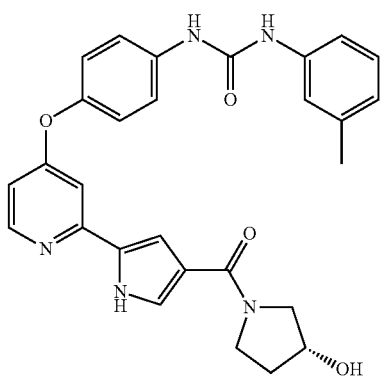 [SMILES: Cc1cccc(NC(=O)Nc2ccc(Oc3ccnc(-c4cc(C(=O)N5CC[C@@H](O)C5)c[nH]4)c3)cc2)c1]

Similar procedure as Example 132.

$^1$H NMR (DMSO-d$_6$) δ: 11.88 (br. s., 1H), 8.74 (s, 1H), 8.58 (s, 1H), 8.36 (d, J=5.6 Hz, 1H), 7.54 (d, J=8.8 Hz, 2H), 6.99-7.39 (m, 8H), 6.78 (d, J=7.0 Hz, 1H), 6.62 (dd, J=5.6, 2.3 Hz, 1H), 4.91 (br. s., 1H), 4.31 (br. s., 1H), 3.67-3.87 (m, 2H), 3.49 (br. s., 2H), 2.26 (s, 3H), 1.88 (br. s., 2H)

LR MS (ES+): 520 (M+Na$^+$)

Example 92

N-(2,3-dihydroxypropyl)-5-{4-[4-({[(3-methylphenyl)amino]carbonyl}amino)phenoxy]pyridin-2-yl}-1H-pyrrole-3-carboxamide

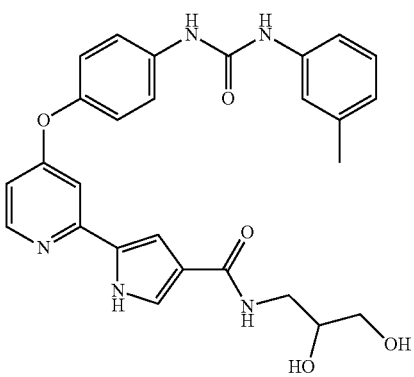 [SMILES: Cc1cccc(NC(=O)Nc2ccc(Oc3ccnc(-c4cc(C(=O)NCC(O)CO)c[nH]4)c3)cc2)c1]

Similar procedure as Example 132.

$^1$H NMR (DMSO-$d_6$) δ: 11.86 (br. s., 1H), 8.78 (s, 1H), 8.61 (s, 1H), 8.37 (d, J=5.9 Hz, 1H), 7.87 (t, J=5.7 Hz, 1H), 7.55 (d, J=8.8 Hz, 2H), 7.41 (br. s., 1H), 7.05-7.32 (m, 7H), 6.75 (dd, J=17.7, 6.6 Hz, 2H), 3.49-3.61 (m, 1H), 3.22-3.35 (m, 3H), 3.04-3.18 (m, 1H), 2.26 (s, 3H) LR MS (ES+): 524 (M+Na$^+$)

Example 93

N-ethyl-5-{4-[4-({[(3-methylphenyl)amino]carbonyl}amino)phenoxy]pyridin-2-yl}-1H-pyrrole-3-carboxamide

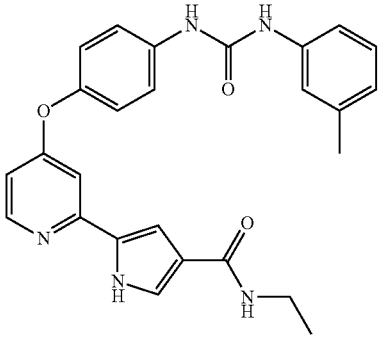 [SMILES: CCNC(=O)c1c[nH]c(-c2cc(Oc3ccc(NC(=O)Nc4cccc(C)c4)cc3)ccn2)c1]

Similar procedure as Example 132.

$^1$H NMR (DMSO-$d_6$) δ: 12.09 (br. s., 1H), 8.98 (s, 1H), 8.76 (s, 1H), 8.42 (d, J=5.9 Hz, 1H), 7.91 (br. s., 1H), 7.45-7.65 (m, 3H), 7.05-7.38 (m, 7H), 6.82-6.94 (m, 1H), 6.78 (d, J=7.6 Hz, 1H), 3.09-3.27 (m, 2H), 2.26 (s, 3H), 1.06 (t, J=7.2 Hz, 3H)

LR MS (ES+): 478 (M+Na$^+$)

LR MS (ES−): 454 (M−H)

Example 94

5-{4-[4-({[(3-methylphenyl)amino]carbonyl}amino)phenoxy]pyridin-2-yl}-1H-pyrrole-3-carboxamide

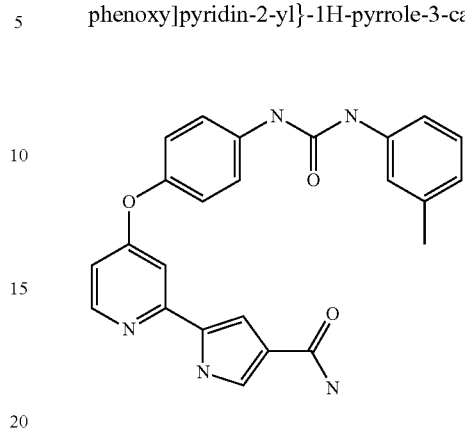

Similar procedure as Example 132.

$^1$H NMR (d$_6$-DMSO, 300 MHz) δ: 11.81 (br. s., 1H), 8.76 (s, 1H), 8.59 (s, 1H), 8.37 (d, J=5.6 Hz, 1H), 7.55 (d, J=9.1 Hz, 2H), 7.37 (br. s., 2H), 7.28 (s, 1H), 7.19-7.26 (m, 1H), 7.09-7.18 (m, 4H), 7.04 (br. s., 1H), 6.78 (d, J=7.3 Hz, 2H), 6.69 (dd, J=5.4, 1.9 Hz, 1H), 2.26 (s, 3H)

LR MS (ES+): 428 (MH), 450 (M+Na$^+$)

LR MS (ES−): 426 (M−H)

Example 95

N-hydroxy-5-{4-[4-({[(3-methylphenyl)amino]carbonyl}amino)phenoxy]pyridin-2-yl}-1H-pyrrole-3-carboxamide

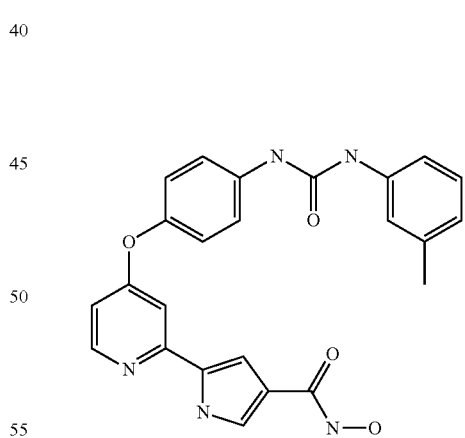

Similar procedure as Example 132.

$^1$H NMR (d$_6$-DMSO, 300 MHz): 11.98 (br. s., 1H), 10.62 (br. s., 1H), 8.87 (s, 1H), 8.68 (s, 1H), 8.41 (d, J=5.6 Hz, 1H), 7.58 (d, J=9.1 Hz, 2H), 7.04-7.46 (m, 8H), 6.80 (d, J=7.6 Hz, 2H), 2.28 (s, 3H)

LR MS (ES+): 444 (MH), 466 (M+Na$^+$)

LR MS (ES−): 442 (M−H)

Example 96

5-{4-[3-fluoro-4-({[(2-fluoro-5-methylphenyl)amino]carbonyl}amino)phenoxy]pyridin-2-yl}-1H-pyrrole-3-carboxylic acid

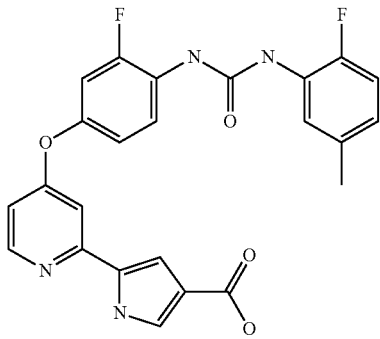 [SMILES: Cc1ccc(F)c(NC(=O)Nc2ccc(Oc3ccnc(-c4cc(C(=O)O)c[nH]4)c3)cc2F)c1]

Similar procedure as Example 134.

$^1$H NMR (d$_6$-DMSO, 300 MHz): 12.04 (br. s., 1H), 11.88 (br. s., 1H), 9.08 (s, 1H), 8.97 (s, 1H), 8.41 (d, J=5.6 Hz, 1H), 8.25 (t, J=9.2 Hz, 1H), 8.01 (d, J=7.6 Hz, 1H), 7.38 (s, 2H), 7.27 (dd, J=11.9, 2.5 Hz, 1H), 6.95-7.18 (m, 3H), 6.78-6.88 (m, 1H), 6.74 (dd, J=5.6, 2.1 Hz, 1H), 2.28 (s, 3H)

LR MS (ES+): 465 (MH), 487 (M+Na$^+$)

LR MS (ES−): 463 (M−H)

Example 97

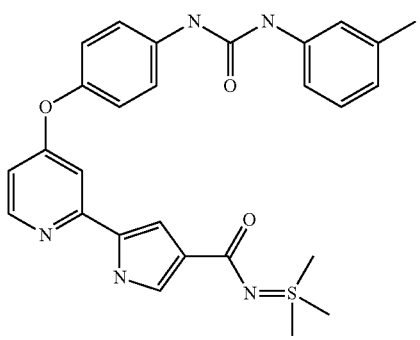

N-[dimethyl(oxido)-lambda~4~-sulfanylidene]-5-{4-[4-({[(3-methylphenyl)amino]carbonyl}amino)phenoxy]pyridin-2-yl}-1H-pyrrole-3-carboxamide Similar procedure as Example 101.

$^1$H NMR (d$_6$-DMSO, 300 MHz): 11.82 (none, 1H), 11.83 (br. s., 1H), 8.76 (s, 1H), 8.60 (s, 1H), 8.37 (d, J=5.9 Hz, 1H), 7.56 (d, J=9.1 Hz, 2H), 7.21-7.35 (m, 4H), 7.08-7.20 (m, 3H), 6.95 (s, 1H), 6.79 (d, J=7.0 Hz, 1H), 6.66 (dd, J=5.6, 2.3 Hz, 1H), 3.37 (s, 6H), 2.28 (s, 3H)

LR MS (ES+): 526 (M+Na$^+$)

LR MS (ES−): 502 (M−H)

Example 98

2-hydroxyethyl 5-{4-[4-({[(4-chloro-3-(trifluoromethyl)phenyl)amino]carbonyl}amino)phenoxy]pyridin-2-yl}-1H-pyrrole-3-carboxylate

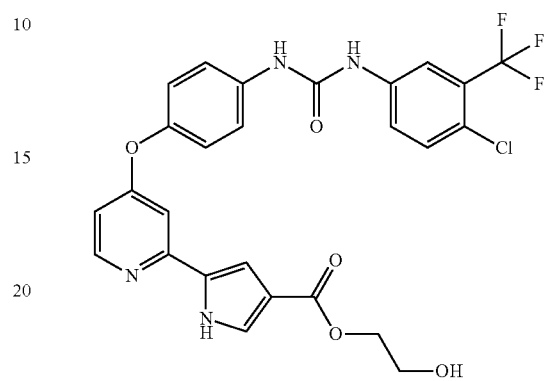

Similar procedure as Example 131.

$^1$H NMR (d$_6$-DMSO, 300 MHz): 12.12 (br. s., 1H), 9.19 (s, 1H), 8.97 (s, 1H), 8.40 (d, J=5.9 Hz, 1H), 8.12 (d, J=2.1 Hz, 1H), 7.53-7.70 (m, 4H), 7.48 (dd, J=3.1, 1.6 Hz, 1H), 7.35 (d, J=2.1 Hz, 1H), 7.16 (d, J=9.1 Hz, 2H), 7.09 (d, J=2.3 Hz, 1H), 6.68 (dd, J=5.6, 2.3 Hz, 1H), 4.83 (t, J=5.9 Hz, 1H), 4.15 (t, J=5.0 Hz, 2H), 3.59-3.69 ppm (m, 2H)

LR MS (ES+): 583 (M+Na$^+$), 585

LR MS (ES−): 559 (M−H), 561

Example 99

N-[dimethyl(oxido)-lambda~4~-sulfanylidene]-5-{4-[4-({[(4-chloro-3-(trifluoromethyl)phenyl)amino]carbonyl}amino)phenoxy]pyridin-2-yl}-1H-pyrrole-3-carboxamide

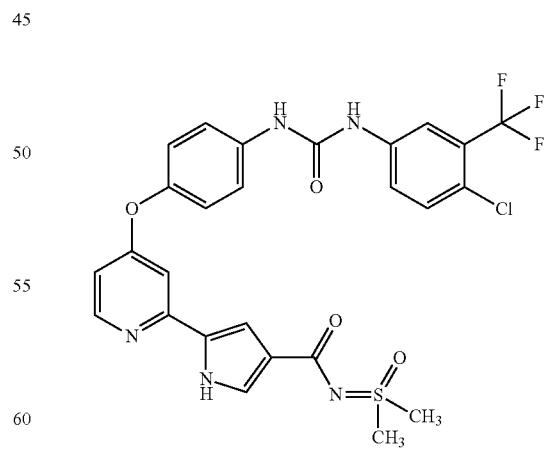

Similar procedure as Example 101.

$^1$H NMR (d$_6$-DMSO, 300 MHz) 11.83 (br. s., 1H), 9.19 (s, 1H), 8.97 (s, 1H), 8.37 (d, J=5.9 Hz, 1H), 8.12 (d, J=2.3 Hz, 1H), 7.54-7.69 (m, 4H), 7.23-7.31 (m, 2H), 7.12-7.19 (m,

2H), 6.93-6.97 (m, 1H), 6.67 (dd, J=5.9, 2.3 Hz, 1H), 3.37 ppm (s, 6H)

LR MS (ES−): 590 (M−H)

Example 100 methy 4-(N-5-{4-[4-({[(2-fluoro-5-methylphenyl)amino]carbonyl}amino)phenoxy]pyridin-2-yl}-1H-pyrrole-3-carboxyl)-S-methylsulfonimidoyl)butanoate

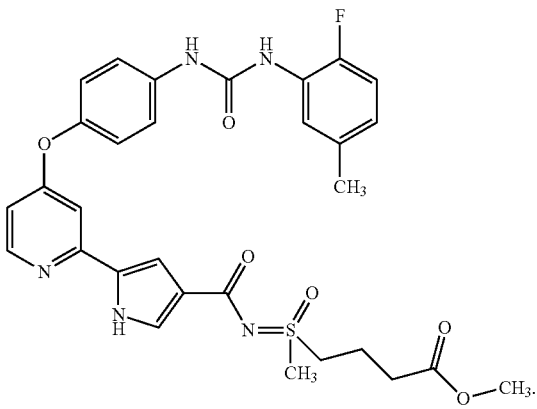 [SMILES: COC(=O)CCCS(C)(=O)=NC(=O)c1c[nH]c(-c2cc(Oc3ccc(NC(=O)Nc4cc(C)ccc4F)cc3)ccn2)c1]

LR MS (ES+): 630 (M+Na⁺)
LR MS (ES−): 606 (M−H)

Example 101

N-[dimethyl(oxido)-lambda~4~-sulfanylidene]-5-{4-[4-({[(2-fluoro-5-methylphenyl)amino]carbonyl}amino)phenoxy]pyridin-2-yl}-1H-pyrrole-3-carboxamide

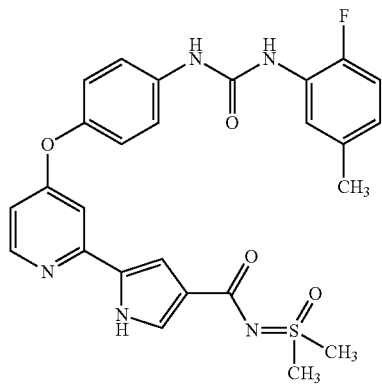 [SMILES: Cc1ccc(F)c(NC(=O)Nc2ccc(Oc3ccnc(-c4cc(C(=O)N=S(C)(C)=O)c[nH]4)c3)cc2)c1]

A mixture of 5-{4-[4-({[(2-fluoro-5-methylphenyl)amino]carbonyl}amino)phenoxy]pyridin-2-yl}-1H-pyrrole-3-carboxylic acid (60 mg, 0.13 mmol), HATU (60 mg, 0.16 mmol), sulfonimidoyldimethane (24 mg, 0.26 mmol), N,N-diisopropylethylamine (37 mg, 0.29 mmol), 200 mg of 4 Å molecular sieves and 5 ml of anhydrous 1,4-dioxane was added to a thick walled reaction vessel and purged with N₂. The reaction vessel was sealed and the mixture stirred at 90° C. for 18 hours. The reaction vessel was cooled to room temperature and the mixture was poured into 100 ml of water. The precipitates were filtered, washed with water and dried to give the crude, which was purified by silica gel chromatography eluting with 3~5% MeOH/CHCl₃ to give N-[dimethyl(oxido)-lambda~4~-sulfanylidene]-5-{4-[4-({[(2-fluoro-5-methylphenyl)amino]carbonyl}amino)phenoxy]pyridin-2-yl}-1H-pyrrole-3-carboxamide as white solid. Yield: 38 mg, 54%.

¹H NMR (d₆-DMSO): 11.83 (br. s., 1H), 9.16 (s, 1H), 8.48 (br. s., 1H), 8.37 (d, J=5.9 Hz, 1H), 7.98 (d, J=6.7 Hz, 1H), 7.56 (d, J=8.8 Hz, 2H), 7.26 (dd, J=8.6, 1.6 Hz, 2H), 7.05-7.19 (m, 3H), 6.96 (s, 1H), 6.75-6.85 (m, 1H), 6.66 (dd, J=5.4, 1.6 Hz, 1H), 3.37 (s, 6H), 2.27 (s, 3H)

LR MS (ES+): 544 (M+Na⁺)
LR MS (ES−): 520 (M−H)

Example 102 methyl (2S)-1-(2-{[(5-{4-[4-({[(2-fluoro-5-methylphenyl)amino]carbonyl}amino)phenoxy]pyridin-2-yl}-1H-pyrrol-3-yl)carbonyl]amino}ethyl)pyrrolidine-2-carboxylate

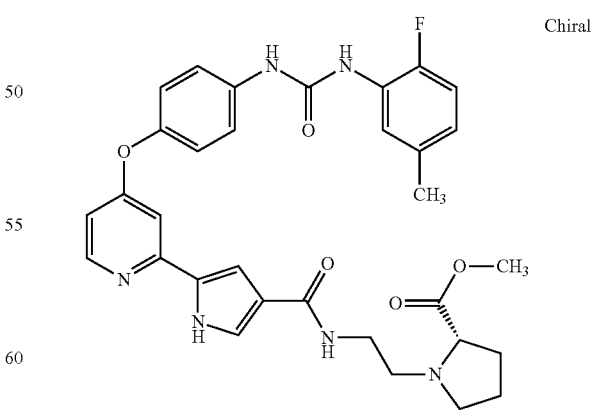

Similar procedure as Example 132.
LR MS (ES+): 623 (M+Na⁺)
LR MS (ES−): 599 (M−H)

Example 103

N,N-diethyl-5-{4-[4-({[(2-fluoro-5-methylphenyl)amino]carbonyl}amino)phenoxy]pyridin-2-yl}-1H-pyrrole-3-carboxamide

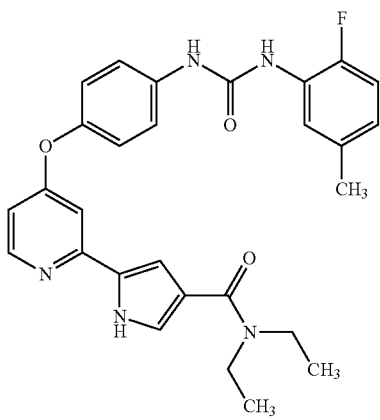 [SMILES: CCN(CC)C(=O)c1c[nH]c(-c2cc(Oc3ccc(NC(=O)Nc4cc(C)ccc4F)cc3)ccn2)c1]

Similar procedure as Example 132.

$^1$H NMR (d$_6$-DMSO): 11.97 (br. s., 1H), 9.19 (s, 1H), 8.49 (d, J=2.6 Hz, 1H), 8.40 (d, J=6.2 Hz, 1H), 7.98 (dd, J=7.8, 1.9 Hz, 1H), 7.53-7.61 (m, 2H), 7.40 (d, J=1.5 Hz, 1H), 7.05-7.25 (m, 4H), 7.01 (br. s., 1H), 6.76-6.86 (m, 1H), 6.67-6.76 (m, 1H), 3.26-3.64 (m, 4H), 2.27 (s, 3H), 1.13 (t, J=7.0 Hz, 6H)

LR MS (ES+): 524 (M+Na$^+$)

LR MS (ES−): 500 (M−H)

Example 104

1-(2-fluoro-5-methylphenyl)-3-{4-[(2-{4-[(4-methylpiperazin-1-yl)carbonyl]-1H-pyrrol-2-yl}pyridin-4-yl)oxy]phenyl}urea Similar procedure as Example 132.

$^1$H NMR (d$_6$-DMSO): 11.87 (br. s., 1H), 9.16 (s, 1H), 8.47 (d, J=2.6 Hz, 1H), 8.37 (d, J=5.6 Hz, 1H), 7.98 (dd, J=8.1, 1.9 Hz, 1H), 7.50-7.59 (m, 2H), 7.35 (d, J=2.3 Hz, 1H), 7.08-7.19 (m, 4H), 6.87-6.95 (m, 1H), 6.80 (ddd, J=7.7, 5.1, 2.2 Hz, 1H), 6.63 (dd, J=5.9, 2.3 Hz, 1H), 3.60 (d, J=4.1 Hz, 4H), 2.23-2.35 (m, 7H), 2.18 (s, 3H)

LR MS (ES+): 551 (M+Na$^+$)

LR MS (ES−): 527 (M−H)

Example 105

5-{4-[4-({[(2-fluoro-5-methylphenyl)amino]carbonyl}amino)phenoxy]pyridin-2-yl}-N-(2-pyrrolidin-1-ylethyl)-1H-pyrrole-3-carboxamide

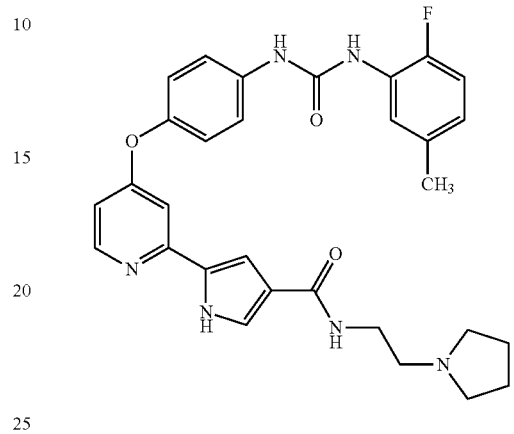

Similar procedure as Example 132.

$^1$H NMR (d$_6$-DMSO): 11.80 (br. s., 1H), 9.17 (s, 1H), 8.48 (d, J=2.6 Hz, 1H), 8.37 (d, J=5.6 Hz, 1H), 7.98 (dd, J=7.9, 2.1 Hz, 1H), 7.82 (t, J=5.7 Hz, 1H), 7.50-7.63 (m, 2H), 7.35 (dd, J=2.9, 1.8 Hz, 1H), 7.00-7.20 (m, 5H), 6.80 (dt, J=7.9, 2.2 Hz, 1H), 6.70 (dd, J=5.9, 2.3 Hz, 1H), 3.21-3.35 (m, 2H), 2.37-2.57 (m, 6H), 2.27 (s, 3H), 1.65 (dt, J=6.6, 3.1 Hz, 4H)

LR MS (ES+): 565 (M+Na$^+$)

LR MS (ES−): 541 (M−H)

Example 106

1-[4-({2-[4-(aziridin-1-ylcarbonyl)-1H-pyrrol-2-yl]pyridin-4-yl}oxy)phenyl]-3-(2-fluoro-5-methylphenyl)urea

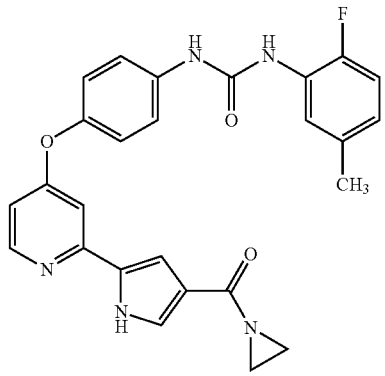 [SMILES: Cc1ccc(F)c(NC(=O)Nc2ccc(Oc3ccnc(-c4cc(C(=O)N5CC5)c[nH]4)c3)cc2)c1]

Similar procedure as Example 132.

$^1$H NMR (d$_6$-DMSO): 11.90 (br. s., 1H), 9.15 (s, 1H), 8.47 (d, J=2.6 Hz, 1H), 8.36 (d, J=5.9 Hz, 1H), 7.97 (dd, J=8.2, 2.1 Hz, 1H), 7.50-7.58 (m, 2H), 7.28 (d, J=2.1 Hz, 1H), 7.23 (br. s., 1H), 7.04-7.17 (m, 3H), 6.97 (br. s., 1H), 6.79 (ddd, J=7.5, 5.1, 2.3 Hz, 1H), 6.65 (dd, J=5.7, 2.5 Hz, 1H), 4.17-4.31 (m, 2H), 3.82 (t, J=9.2 Hz, 2H), 2.26 (s, 3H)
LR MS (ES+): 494 (M+Na⁺)
LR MS (ES−): 470 (M−H)

Example 107

5-{4-[4-({[(2-fluoro-5-methylphenyl)amino]carbonyl}amino)phenoxy]pyridin-2-yl}-1H-pyrrole-3-carboxamide

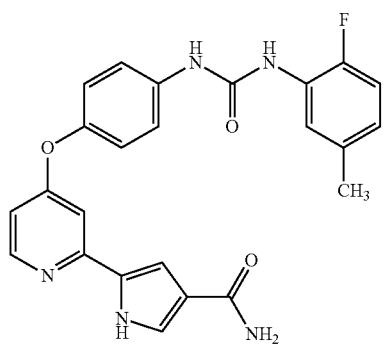 [SMILES: Cc1ccc(F)c(NC(=O)Nc2ccc(Oc3ccnc(-c4cc(C(N)=O)c[nH]4)c3)cc2)c1]

Similar procedure as Example 132.
¹H NMR (d₆-DMSO): 11.89 (br. s., 1H), 9.21 (s, 1H), 8.50 (d, J=2.3 Hz, 1H), 8.39 (d, J=5.9 Hz, 1H), 7.98 (dd, J=8.1, 1.9 Hz, 1H), 7.53-7.62 (m, 2H), 7.43 (br. s., 2H), 7.05-7.24 (m, 5H), 6.71-6.86 (m, 3H), 2.27 (s, 3H)
LR MS (ES+): 468 (M+Na⁺)
LR MS (ES−): 444 (M−H)

Example 108

5-{4-[4-({[(2-fluoro-5-methylphenyl)amino]carbonyl}amino)phenoxy]pyridin-2-yl}-N-hydroxy-1H-pyrrole-3-carboxamide

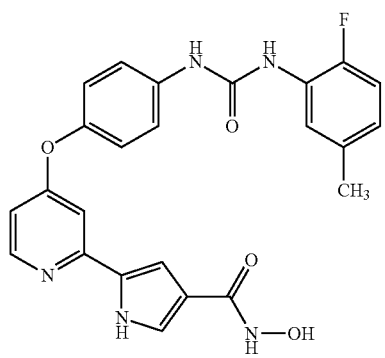 [SMILES: Cc1ccc(F)c(NC(=O)Nc2ccc(Oc3ccnc(-c4cc(C(=O)NO)c[nH]4)c3)cc2)c1]

Similar procedure as Example 132.
¹H NMR (d₆-DMSO): 12.10 (br. s., 1H), 10.66 (br. s., 1H), 9.29 (s, 1H), 8.53 (br. s., 1H), 8.43 (d, J=6.2 Hz, 1H), 7.93-8.03 (m, 1H), 7.59 (d, J=8.8 Hz, 2H), 7.39-7.50 (m, 1H), 7.30 (br. s., 1H), 7.05-7.26 (m, 4H), 6.75-6.91 (m, 2H), 2.27 (s, 3H)
LR MS (ES+): 484 (M+Na⁺)
LR MS (ES−): 460 (M−H)

Example 109

1-[4-({2-[4-(azetidin-1-ylcarbonyl)-1H-pyrrol-2-yl]pyridin-4-yl}oxy)phenyl]-3-(2-fluoro-5-methylphenyl)urea

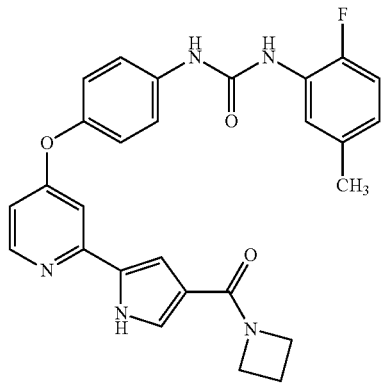 [SMILES: Cc1ccc(F)c(NC(=O)Nc2ccc(Oc3ccnc(-c4cc(C(=O)N5CCC5)c[nH]4)c3)cc2)c1]

Similar procedure as Example 132.
¹H NMR (d₆-DMSO): 11.67 (br. s., 1H), 9.16 (s, 1H), 8.47 (d, J=2.1 Hz, 1H), 8.34 (d, J=5.6 Hz, 1H), 7.97 (d, J=5.9 Hz, 1H), 7.54 (d, J=9.1 Hz, 2H), 7.02-7.23 (m, 5H), 6.86 (br. s., 1H), 6.74-6.83 (m, 1H), 6.64 (dd, J=5.9, 2.3 Hz, 1H), 4.14-4.28 (m, 2H), 3.33-3.42 (m, 2H), 2.26 (s, 3H), 1.83 (br. s., 2H)
LR MS (ES+): 486 (M+H)
LR MS (ES−): 484 (M−H)

Example 110

5-{4-[4-({[(2-fluoro-5-methylphenyl)amino]carbonyl}amino)phenoxy]pyridin-2-yl}-N-(3-hydroxypropyl)-1H-pyrrole-3-carboxamide

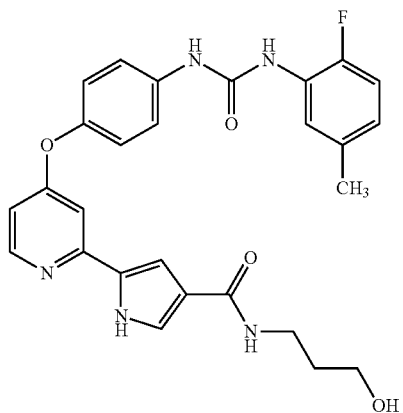 [SMILES: Cc1ccc(F)c(NC(=O)Nc2ccc(Oc3ccnc(-c4cc(C(=O)NCCCO)c[nH]4)c3)cc2)c1]

Similar procedure as Example 132.
¹H NMR (d₆-DMSO): 11.78 (br. s., 1H), 9.20 (s, 1H), 8.51 (d, J=2.1 Hz, 1H), 8.36 (d, J=5.6 Hz, 1H), 7.96 (dd, J=7.9, 1.8 Hz, 1H), 7.83 (t, J=5.7 Hz, 1H), 7.55 (d, J=9.1 Hz, 2H), 7.32-7.36 (m, 1H), 7.02-7.17 (m, 5H), 6.78 (td, J=5.3, 2.6 Hz, 1H), 6.69 (dd, J=5.6, 2.3 Hz, 1H), 4.42 (t, J=5.3 Hz, 1H), 3.41 (q, J=6.2 Hz, 2H), 3.15-3.26 (m, 2H), 2.26 (s, 3H), 1.60 (quin, J=6.7 Hz, 2H)
LR MS (ES+): 526 (M+Na⁺)
LR MS (ES−): 502 (M−H)

Example 111

2-(2-methoxyethoxy)ethyl 5-{4-[4-({[(2-fluoro-5-methylphenyl)amino]carbonyl}amino)phenoxy]pyridin-2-yl}-1H-pyrrole-3-carboxylate

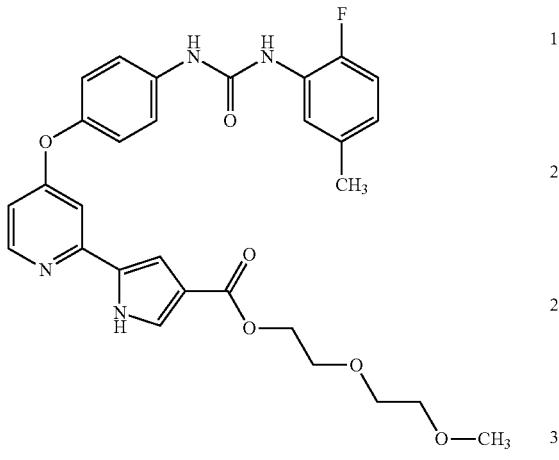

Similar procedure as Example 131.
¹H NMR (d₆-DMSO): 12.12 (br. s., 1H), 9.15 (s, 1H), 8.47 (d, J=2.3 Hz, 1H), 8.38 (d, J=5.9 Hz, 1H), 7.97 (dd, J=8.1, 1.9 Hz, 1H), 7.49-7.59 (m, 2H), 7.41 (dd, J=3.1, 1.6 Hz, 1H), 7.34 (d, J=2.3 Hz, 1H), 7.03-7.17 (m, 4H), 6.74-6.84 (m, 1H), 6.67 (dd, J=5.7, 2.5 Hz, 1H), 4.20-4.28 (m, 2H), 3.62-3.70 (m, 2H), 3.51-3.59 (m, 2H), 3.39-3.46 (m, 2H), 3.18-3.24 (m, 3H), 2.26 (s, 3H)
LR MS (ES+): 571 (M+Na⁺)
LR MS (ES−): 547 (M−H)

Example 112

N-ethyl-5-{4-[4-({[(2-fluoro-5-methylphenyl)amino]carbonyl}amino)phenoxy]pyridin-2-yl}-1H-pyrrole-3-carboxamide

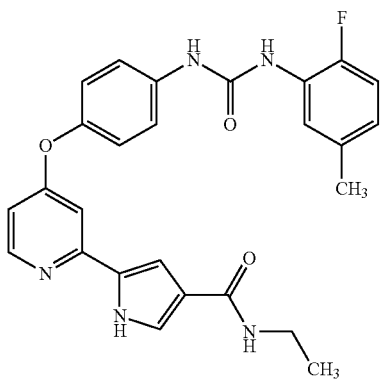 [SMILES: CCNC(=O)c1c[nH]c(-c2cc(Oc3ccc(NC(=O)Nc4cc(C)ccc4F)cc3)ccn2)c1]

Similar procedure as Example 132.
¹H NMR (d₆-DMSO): 11.93 (br. s., 1H), 9.23 (s, 1H), 8.50 (d, J=2.3 Hz, 1H), 8.39 (d, J=6.2 Hz, 1H), 7.96 (dd, J=7.9, 1.8 Hz, 1H), 7.87 (t, J=5.6 Hz, 1H), 7.57 (d, J=8.8 Hz, 2H), 7.42 (br. s., 1H), 7.02-7.27 (m, 5H), 6.72-6.86 (m, 2H), 3.09-3.25 (m, 2H), 2.26 (s, 3H), 1.06 (t, J=7.2 Hz, 3H)
LR MS (ES+): 496 (M+Na⁺)
LR MS (ES−): 472 (M−H)

Example 113

2-methoxyethyl 5-{4[(4-({[(2-fluoro-5-methylphenyl)amino]carbonyl}amino)phenoxy]pyridin-2-yl}-1H-pyrrole-3-carboxylate

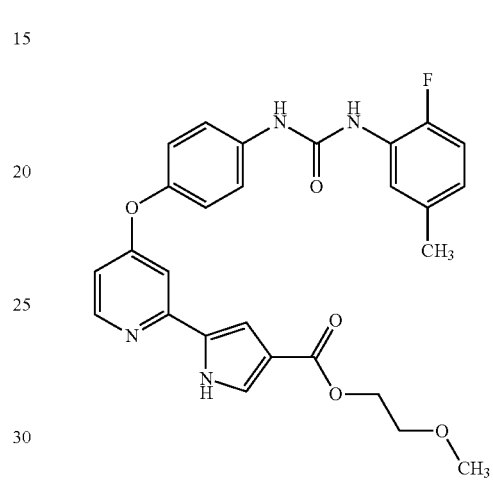

Similar procedure as Example 131.
¹H NMR (d₆-DMSO): 12.12 (br. s., 1H), 9.15 (s, 1H), 8.46 (br. s., 1H), 8.38 (d, J=5.6 Hz, 1H), 7.98 (s, 1H), 7.54 (d, J=8.8 Hz, 2H), 7.41 (d, J=1.2 Hz, 1H), 7.35 (d, J=1.8 Hz, 1H), 7.01-7.19 (m, 4H), 6.78 (d, J=5.9 Hz, 1H), 6.66 (dd, J=5.9, 2.1 Hz, 1H), 4.17-4.32 (m, 2H), 3.51-3.65 (m, 2H), 3.29 (s, 3H), 2.26 (s, 3H)
LR MS (ES+): 527 (M+Na⁺)
LR MS (ES−): 503 (M−H)

Example 114

5-{4-[4-({[(2-fluoro-5-methylphenyl)amino]carbonyl}amino)phenoxy]pyridin-2-yl}-N-(2-methoxyethyl)-1H-pyrrole-3-carboxamide

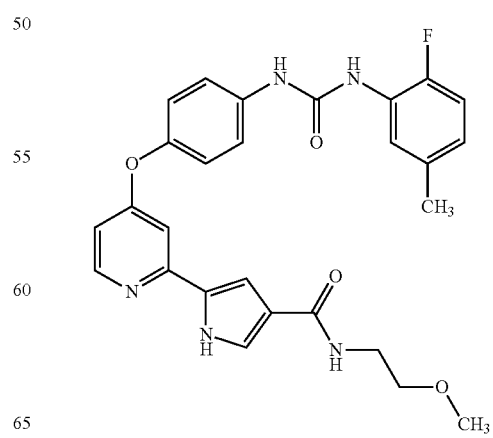

Example 115

5-{4-[4-({[(3-methylphenyl)amino]carbonyl}amino)phenoxy]pyridin-2-yl}-1H-pyrrole-3-carboxylic acid

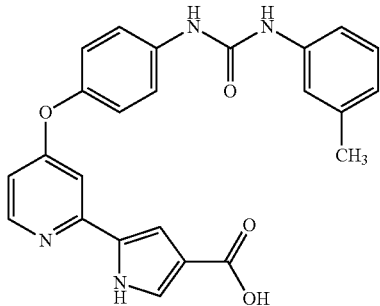 [SMILES: Cc1cccc(NC(=O)Nc2ccc(Oc3ccnc(-c4cc(C(=O)O)c[nH]4)c3)cc2)c1]

Similar procedure as Example 132.
$^1$H NMR (d$_6$-DMSO): 11.86 (br. s., 1H), 9.17 (s, 1H), 8.48 (d, J=2.3 Hz, 1H), 8.38 (d, J=5.9 Hz, 1H), 7.86-8.02 (m, 2H), 7.56 (d, J=8.8 Hz, 2H), 7.40 (br. s., 1H), 7.02-7.21 (m, 5H), 6.67-6.84 (m, 2H), 3.26-3.50 (m, 7H), 2.26 (s, 3H)
LR MS (ES+): 526 (M+Na$^+$)
LR MS (ES−): 502 (M−H)

Example 115

5-{4-[4-({[(3-methylphenyl)amino]carbonyl}amino)phenoxy]pyridin-2-yl}-1H-pyrrole-3-carboxylic acid Similar procedure as Example 134.
$^1$H NMR (d$_6$-DMSO): 12.05 (br. s., 1H), 8.79 (s, 1H), 8.62 (s, 1H), 8.39 (d, J=5.6 Hz, 1H), 7.52-7.61 (m, 2H), 7.39 (dd, J=3.1, 1.6 Hz, 1H), 7.34 (d, J=2.3 Hz, 1H), 7.30 (s, 1H), 7.21-7.27 (m, 1H), 7.10-7.20 (m, 3H), 7.05 (s, 1H), 6.79 (d, J=7.3 Hz, 1H), 6.68 (dd, J=5.6, 2.3 Hz, 1H), 2.28 (s, 3H)
LR MS (ES−): 427 (M−H)

Example 116 methyl 5-{4-[4-({[(3-methylphenyl)amino]carbonyl}amino)phenoxy]pyridin-2-yl}-1H-pyrrole-3-carboxylate

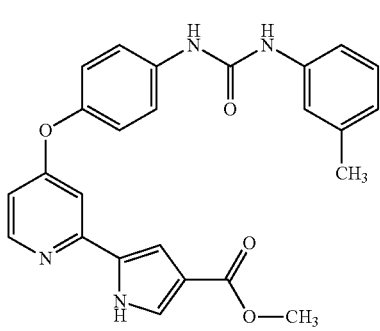 [SMILES: COC(=O)c1c[nH]c(-c2cc(Oc3ccc(NC(=O)Nc4cccc(C)c4)cc3)ccn2)c1]

Similar procedure as Example 135.
$^1$H NMR (d$_6$-DMSO): 12.12 (br. s., 1H), 9.02 (br. s., 1H), 8.85 (br. s., 1H), 8.36 (d, J=5.6 Hz, 1H), 7.50-7.59 (m, 2H), 7.41 (d, J=1.5 Hz, 1H), 7.33 (d, J=2.3 Hz, 1H), 7.29 (s, 1H), 7.24 (d, J=7.9 Hz, 1H), 7.08-7.18 (m, 3H), 7.06 (d, J=1.5 Hz, 1H), 6.77 (d, J=7.6 Hz, 1H), 6.65 (dd, J=5.6, 2.3 Hz, 1H), 3.69 (s, 3H), 2.26 (s, 3H)
LR MS (ES+): 465 (M+Na$^+$)
LR MS (ES−): 441 (M−H)

Example 117

5-{4-[2-fluoro-4-({[(2-fluoro-5-methylphenyl)amino]carbonyl}amino)phenoxy]pyridin-2-yl}-1H-pyrrole-3-carboxylic acid

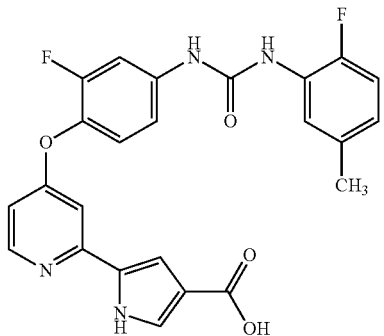 [SMILES: Cc1ccc(F)c(NC(=O)Nc2ccc(Oc3ccnc(-c4cc(C(=O)O)c[nH]4)c3)c(F)c2)c1]

Similar procedure as Example 134.
$^1$H NMR (d$_6$-DMSO): 12.03 (br. s., 1H), 11.86 (br. s., 1H), 9.62 (s, 1H), 8.65 (s, 1H), 8.38 (d, J=5.6 Hz, 1H), 7.94 (dd, J=7.9, 1.8 Hz, 1H), 7.72 (dd, J=13.2, 2.3 Hz, 1H), 7.26-7.40 (m, 3H), 7.15-7.24 (m, 1H), 7.01-7.14 (m, 2H), 6.81 (td, J=5.3, 2.3 Hz, 1H), 6.68 (dd, J=5.7, 2.2 Hz, 1H), 2.26 (s, 3H)
LR MS (ES+): 487 (M+Na$^+$)
LR MS (ES−): 463 (M−H)

Example 118 methyl 5-{4-[2-fluoro-4-({[(2-fluoro-5-methylphenyl)amino]carbonyl}amino)phenoxy]pyridin-2-yl}-1H-pyrrole-3-carboxylate

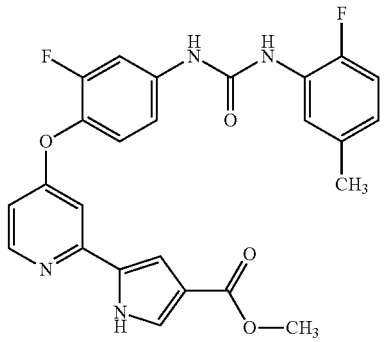 [SMILES: COC(=O)c1c[nH]c(-c2cc(Oc3ccc(NC(=O)Nc4cc(C)ccc4F)cc3F)ccn2)c1]

Similar procedure as Example 135.
$^1$H NMR (d$_6$-DMSO): 12.13 (br. s., 1H), 9.34 (s, 1H), 8.55 (d, J=2.3 Hz, 1H), 8.39 (d, J=5.9 Hz, 1H), 7.94 (dd, J=7.8, 1.6 Hz, 1H), 7.72 (dd, J=13.5, 2.3 Hz, 1H), 7.43 (dd, J=3.2, 1.8 Hz, 1H), 7.37 (d, J=2.3 Hz, 1H), 7.26-7.36 (m, 1H), 7.18 (dd, J=8.9, 1.6 Hz, 1H), 7.05-7.15 (m, 2H), 6.77-6.87 (m, 1H), 6.70 (dd, J=5.6, 2.3 Hz, 1H), 3.70 (s, 3H), 2.26 (s, 3H)
LR MS (ES+): 501 (M+Na$^+$)
LR MS (ES−): 477 (M−H)

Example 119

5-(4-{4-[({[4-fluoro-3-(trifluoromethyl)phenyl]amino}carbonyl)amino]phenoxy}pyridin-2-yl)-1H-pyrrole-3-carboxylic acid

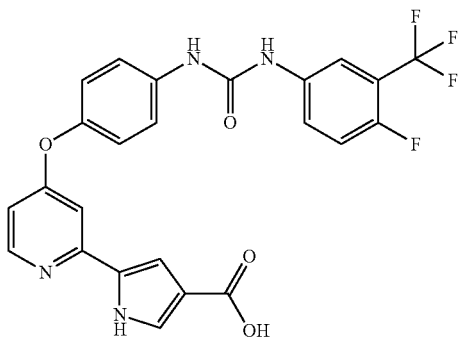 [SMILES: O=C(Nc1ccc(Oc2ccnc(-c3cc(C(=O)O)c[nH]3)c2)cc1)Nc1ccc(F)c(C(F)(F)F)c1]

Similar procedure as Example 134.

$^1$H NMR (d$_6$-DMSO): 12.05 (d, 1H), 9.11 (s, 1H), 8.96 (s, 1H), 8.38 (d, J=5.6 Hz, 1H), 7.99 (dd, J=6.4, 2.3 Hz, 1H), 7.60-7.72 (m, 1H), 7.56 (d, J=9.1 Hz, 2H), 7.27-7.49 (m, 3H), 7.14 (d, J=9.1 Hz, 2H), 7.03 (br. s., 1H), 6.67 (dd, J=5.7, 2.2 Hz, 1H)

LR MS (ES−): 499 (M−H)

Example 120 methyl 5-(4-{4-[({[4-fluoro-3-(trifluoromethyl)phenyl]amino}carbonyl)amino]phenoxy}pyridin-2-yl)-1H-pyrrole-3-carboxylate

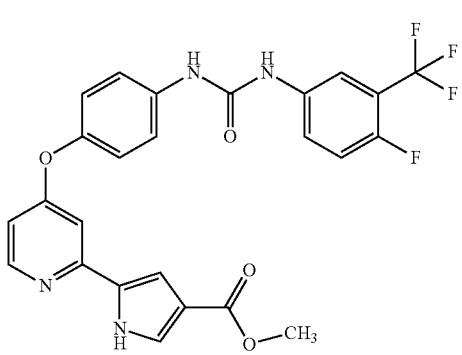 [SMILES: COC(=O)c1c[nH]c(-c2cc(Oc3ccc(NC(=O)Nc4ccc(F)c(C(F)(F)F)c4)cc3)ccn2)c1]

Similar procedure as Example 135.

$^1$H NMR (d$_6$-DMSO): 12.12 (br. s., 1H), 9.04 (s, 1H), 8.91 (s, 1H), 8.37 (d, J=6.2 Hz, 1H), 7.99 (dd, J=6.4, 2.6 Hz, 1H), 7.60-7.69 (m, 1H), 7.51-7.61 (m, 2H), 7.37-7.49 (m, 2H), 7.34 (d, J=2.1 Hz, 1H), 7.09-7.18 (m, 2H), 7.01-7.09 (m, 1H), 6.66 (dd, J=5.6, 2.3 Hz, 1H), 3.70 (s, 3H)

LR MS (ES+): 537 (M+Na$^+$)

LR MS (ES−): 513 (M−H)

Example 121

5-(4-{4-[({[4-chloro-3-(trifluoromethyl)phenyl]amino}carbonyl)amino]phenoxy}pyridin-2-yl)-1H-pyrrole-3-carboxylic acid

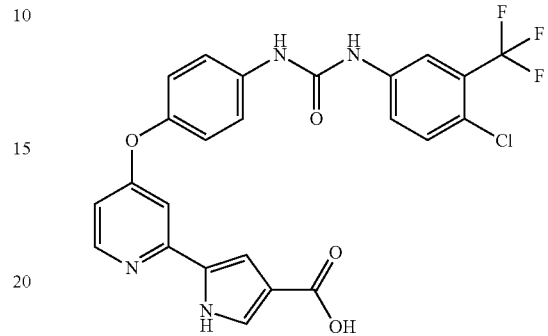

Similar procedure as Example 134.

$^1$H NMR (d$_6$-DMSO): 12.08 (br. s., 1H), 9.23 (s, 1H), 9.00 (s, 1H), 8.39 (d, J=5.6 Hz, 1H), 8.10 (s, 1H), 7.48-7.72 (m, 4H), 7.27-7.47 (m, 2H), 7.00-7.23 (m, 3H), 6.69 (br. s., 1H)

LR MS (ES−): 515 (M−H)

Example 122 methyl 5-(4-{4-[({[4-chloro-3-(trifluoromethyl)phenyl]amino}carbonyl)amino]phenoxy}pyridin-2-yl)-1H-pyrrole-3-carboxylate

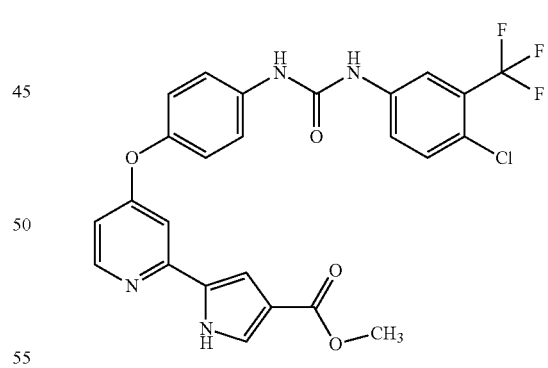

Similar procedure as Example 135.

$^1$H NMR (d$_6$-DMSO): 12.12 (br. s., 1H), 9.17 (s, 1H), 8.94 (s, 1H), 8.38 (d, J=5.9 Hz, 1H), 8.10 (d, J=2.1 Hz, 1H), 7.51-7.69 (m, 4H), 7.42 (dd, J=3.2, 1.8 Hz, 1H), 7.34 (d, J=2.3 Hz, 1H), 7.10-7.18 (m, 2H), 7.03-7.09 (m, 1H), 6.66 (dd, J=5.9, 2.3 Hz, 1H), 3.70 (s, 3H)

LR MS (ES+): 553 (M+Na$^+$)

LR MS (ES−): 529 (M−H)

Example 123

4-{4-[4-({[(2-fluoro-5-methylphenyl)amino]carbonyl}amino)phenoxy]pyridin-2-yl}thiophene-2-carboxylic acid

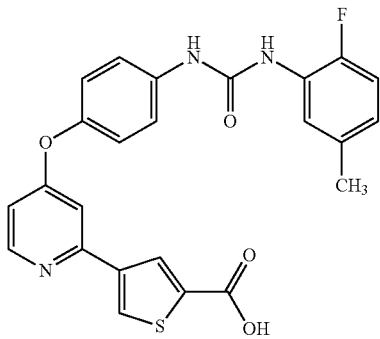 [SMILES: Cc1ccc(F)c(NC(=O)Nc2ccc(Oc3ccnc(-c4csc(C(=O)O)c4)c3)cc2)c1]

To a stirred solution of methyl 4-{4-[4-({[(2-fluoro-5-methylphenyl)amino]carbonyl}amino)phenoxy]pyridin-2-yl}thiophene-2-carboxylate (550 mg, 1.15 mmol) in a mixture of solvents—THF/MeOH (20 ml/20 ml) was added 1 ml of 5M NaOH (5 mmol) solution. The mixture was heated in a 66° C. bath for 2 hours, cooled to room temperature and poured into 200 ml of water. 2M HCl was added until pH=5. The resulting precipitates were filtered, washed with water, and dried in vacuo to give 4-{4-[4-({[(2-fluoro-5-methylphenyl)amino]carbonyl}amino)phenoxy]pyridin-2-yl}thiophene-2-carboxylic acid as off-white solid. Yield: 520 mg, 97%.

$^1$H NMR (d$_6$-DMSO): 9.30 (s, 1H), 8.59 (d, J=2.6 Hz, 1H), 8.43 (d, J=5.9 Hz, 1H), 8.35 (br. s., 1H), 8.13 (br. s., 1H), 7.95 (dd, J=7.8, 1.9 Hz, 1H), 7.51-7.59 (m, 2H), 7.45 (s, 1H), 7.03-7.18 (m, 3H), 6.75-6.83 (m, 1H), 6.72 (dd, J=5.6, 2.3 Hz, 1H), 2.25 (s, 3H)

LR MS (ES−): 462 (M−H)

Example 124

2-hydroxyethyl 4-{4-[4-({[(2-fluoro-5-methylphenyl)amino]carbonyl}amino)phenoxy]pyridin-2-yl}-1H-pyrrole-2-carboxylate

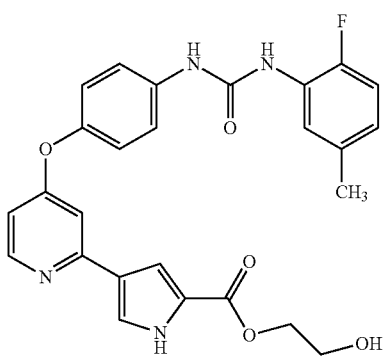 [SMILES: Cc1ccc(F)c(NC(=O)Nc2ccc(Oc3ccnc(-c4c[nH]c(C(=O)OCCO)c4)c3)cc2)c1]

Similar procedure as Example 131.

$^1$H NMR (DMSO-d$_6$) δ: 12.11 (br. s., 1H), 9.15 (s, 1H), 8.47 (d, J=2.1 Hz, 1H), 8.33 (d, J=5.6 Hz, 1H), 7.97 (dd, J=7.9, 1.8 Hz, 1H), 7.63 (dd, J=2.9, 1.8 Hz, 1H), 7.53 (d, J=8.8 Hz, 2H), 7.22-7.37 (m, 2H), 7.01-7.18 (m, 3H), 6.72-6.85 (m, 1H), 6.58 (dd, J=5.6, 2.3 Hz, 1H), 4.83 (t, J=5.9 Hz, 1H), 4.19 (t, J=5.1 Hz, 2H), 3.57-3.73 (m, 2H), 2.25 (s, 3H)

LR MS (ES+): 491 (MH), 513 (M+Na$^+$)

LR MS (ES−): 489 (M−H)

Example 125

{1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetic acid

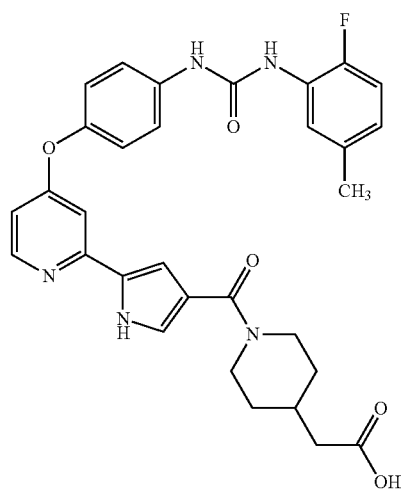 [SMILES: Cc1ccc(F)c(NC(=O)Nc2ccc(Oc3ccnc(-c4cc(C(=O)N5CCC(CC(=O)O)CC5)c[nH]4)c3)cc2)c1]

To a stirred solution of methyl {1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetate (50 mg, 0.085 mmol) in THF/MeOH (5 ml/5 ml) was added 1M NaOH solution (3 ml, 3 mmol). The mixture was stirred at room temperature for one hour, and poured into 50 ml of water. 2M HCl was added until pH=4. The resulting precipitates were filtered, washed with water, and dried in vacuo to give {1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetic acid as white solid. Yield: 47 mg, 96%.

LR MS (ES−): 570 (M−H)

Example 126 methyl {1-[(5-{4-[4-({[(2-fluoro-5-methylphenyl)amino]carbonyl}amino)phenoxy]pyridin-2-yl}-1H-pyrrol-3-yl)carbonyl]piperidin-4-yl}acetate

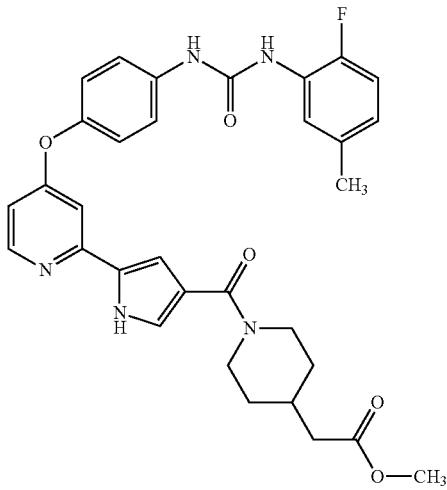 [SMILES: COC(=O)CC1CCN(C(=O)c2c[nH]c(-c3cc(Oc4ccc(NC(=O)Nc5cc(C)ccc5F)cc4)ccn3)c2)CC1]

Similar procedure as Example 132.

¹H NMR (d₆-DMSO): 11.83 (br. s., 1H), 9.14 (s, 1H), 8.46 (br. s., 1H), 8.35 (d, J=5.6 Hz, 1H), 7.97 (d, J=8.2 Hz, 1H), 7.53 (d, J=8.8 Hz, 2H), 7.33 (d, J=1.8 Hz, 1H), 7.01-7.18 (m, 4H), 6.86 (s, 1H), 6.80 (d, J=4.4 Hz, 1H), 6.61 (dd, J=5.9, 2.1 Hz, 1H), 4.26 (br. s., 2H), 3.57 (s, 3H), 2.87 (br. s., 2H), 2.18-2.32 (m, 5H), 1.93 (br. s., 1H), 1.65 (br. s., 2H), 1.14 (br. s., 2H)

LR MS (ES+): 608 (M+Na⁺)
LR MS (ES−): 584 (M−H)

Example 127

N-(2,3-dihydroxypropyl)-5-{4-[4-({[(2-fluoro-5-methylphenyl)amino]carbonyl}amino)phenoxy]pyridin-2-yl}-1H-pyrrole-3-carboxamide

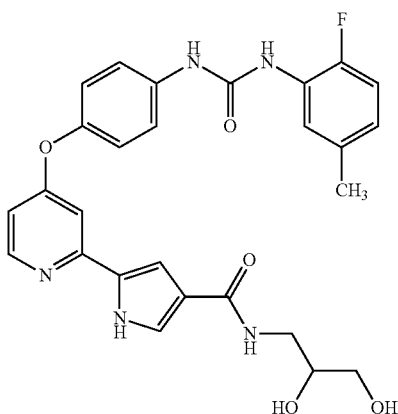 [SMILES: Cc1ccc(F)c(NC(=O)Nc2ccc(Oc3ccnc(-c4cc(C(=O)NCC(O)CO)c[nH]4)c3)cc2)c1]

Similar procedure as Example 132.

¹H NMR (d₆-DMSO): 11.81 (br. s., 1H), 9.17 (s, 1H), 8.48 (d, J=2.3 Hz, 1H), 8.36 (d, J=5.6 Hz, 1H), 7.97 (dd, J=7.8, 1.9 Hz, 1H), 7.86 (t, J=5.7 Hz, 1H), 7.51-7.60 (m, 2H), 7.38 (dd, J=3.1, 1.6 Hz, 1H), 7.10-7.19 (m, 3H), 7.07 (td, J=4.3, 2.5 Hz, 2H), 6.74-6.84 (m, 1H), 6.69 (dd, J=5.6, 2.3 Hz, 1H), 4.78 (d, J=5.0 Hz, 1H), 4.54 (t, J=5.9 Hz, 1H), 3.48-3.60 (m, 1H), 3.23-3.36 (m, 3H), 3.05-3.18 (m, 1H), 2.26 (s, 3H)

LR MS (ES+): 542 (M+Na⁺)
LR MS (ES−): 518 (M−H)

Example 128

5-{4-[4-({[(2-fluoro-5-methylphenyl)amino]carbonyl}amino)phenoxy]pyridin-2-yl}-N-(2-hydroxyethyl)-1H-pyrrole-3-carboxamide

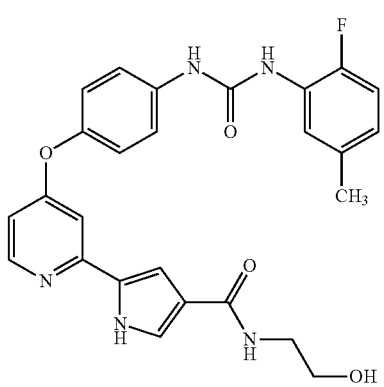 [SMILES: Cc1ccc(F)c(NC(=O)Nc2ccc(Oc3ccnc(-c4cc(C(=O)NCCO)c[nH]4)c3)cc2)c1]

Similar procedure as Example 132.

¹H NMR (d₆-DMSO): 11.79 (br. s., 1H), 9.30 (s, 1H), 8.57 (d, J=1.5 Hz, 1H), 8.36 (d, J=5.6 Hz, 1H), 7.95 (dd, J=7.9, 1.8 Hz, 1H), 7.84 (t, J=5.6 Hz, 1H), 7.50-7.63 (m, 2H), 7.35 (d, J=1.5 Hz, 1H), 7.00-7.21 (m, 5H), 6.79 (td, J=5.3, 2.5 Hz, 1H), 6.69 (dd, J=5.6, 2.3 Hz, 1H), 4.66 (t, J=5.6 Hz, 1H), 3.38-3.51 (m, 2H), 3.22 (q, J=6.1 Hz, 2H), 2.25 (s, 3H)

LR MS (ES+): 512 (M+Na⁺)
LR MS (ES−): 488 (M−H)

Example 129

1-(2-fluoro-5-methylphenyl)-3-{4-[(2-{4-[(4-hydroxypiperidin-1-yl)carbonyl]-1H-pyrrol-2-yl}pyridin-4-yl)oxy]phenyl}urea

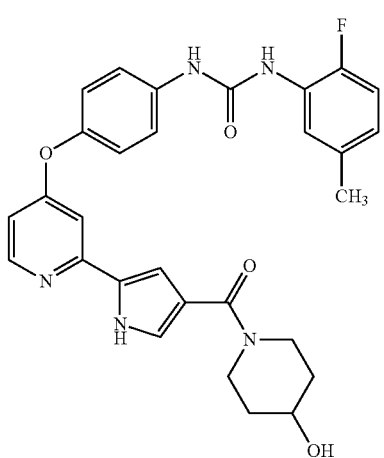 [SMILES: Cc1ccc(F)c(NC(=O)Nc2ccc(Oc3ccnc(-c4cc(C(=O)N5CCC(O)CC5)c[nH]4)c3)cc2)c1]

Similar procedure as Example 132.

¹H NMR (d₆-DMSO): 11.84 (br. s., 1H), 9.17 (s, 1H), 8.48 (d, J=2.3 Hz, 1H), 8.37 (d, J=5.6 Hz, 1H), 7.99 (dd, J=7.9, 1.8 Hz, 1H), 7.55 (d, J=8.8 Hz, 2H), 7.36 (d, J=2.3 Hz, 1H), 7.04-7.20 (m, 4H), 6.89 (s, 1H), 6.81 (td, J=5.3, 2.3 Hz, 1H), 6.63 (dd, J=5.9, 2.3 Hz, 1H), 4.73 (d, J=4.1 Hz, 1H), 3.90-4.06 (m, 2H), 3.71 (dt, J=8.4, 4.3 Hz, 1H), 3.25 (d, J=2.6 Hz, 2H), 2.27 (s, 3H), 1.73 (d, J=4.1 Hz, 2H), 1.21-1.44 (m, 2H)

LR MS (ES+): 552 (M+Na⁺)
LR MS (ES−): 528 (M−H)

Example 130

2,3-dihydroxypropyl 5-{4-[4-({[(2-fluoro-5-methylphenyl)amino]carbonyl}amino)phenoxy]pyridin-2-yl}-1H-pyrrole-3-carboxylate

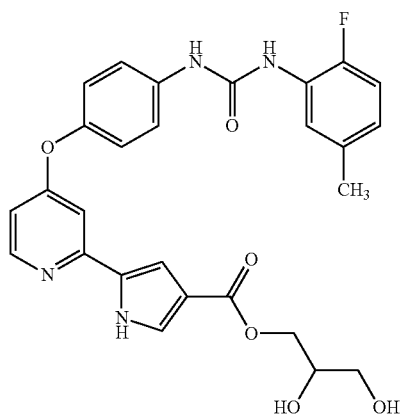 [SMILES: Cc1ccc(F)c(NC(=O)Nc2ccc(Oc3ccnc(-c4cc(C(=O)OCC(O)CO)c[nH]4)c3)cc2)c1]

Similar procedure as Example 131.

¹H NMR (d₆-DMSO): 12.12 (br. s., 1H), 9.24 (s, 1H), 8.54 (d, J=2.3 Hz, 1H), 8.39 (d, J=5.9 Hz, 1H), 7.98 (dd, J=7.8, 1.9 Hz, 1H), 7.51-7.62 (m, 2H), 7.48 (dd, J=3.1, 1.6 Hz, 1H), 7.34-7.40 (m, 1H), 7.05-7.20 (m, 4H), 6.75-6.87 (m, 1H), 6.68 (dd, J=5.9, 2.3 Hz, 1H), 4.92 (d, J=5.3 Hz, 1H), 4.64 (t, J=5.7 Hz, 1H), 4.11-4.22 (m, 1H), 3.97-4.09 (m, 1H), 3.67-3.79 (m, 1H), 3.38-3.46 (m, 2H), 2.28 (s, 3H)

LR MS (ES+): 543 (M+Na⁺)
LR MS (ES−): 519 (M−H)

Example 131

2-hydroxyethyl 5-{4-[4-({[(2-fluoro-5-methylphenyl)amino]carbonyl}amino)phenoxy]pyridin-2-yl}-1H-pyrrole-3-carboxylate

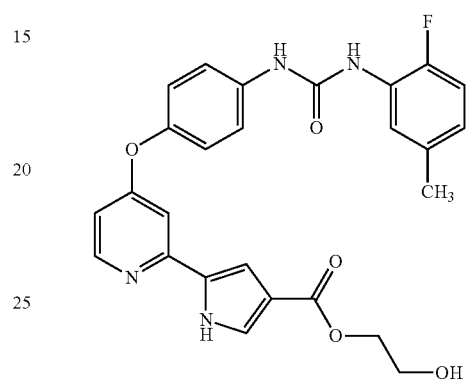

A mixture of 5-{4-[4-({[(2-fluoro-5-methylphenyl)amino]carbonyl}amino)phenoxy]pyridin-2-yl}-1H-pyrrole-3-carboxylic acid (50 mg, 0.11 mmol), ethylene glycol (1 ml), 1-Ethyl-3-(3-dimethylaminopropyl)carbodiimide hydrochloride (EDC.HCl, 25 mg, 0.13 mmol) and 4-dimethylaminopyridine (DMAP, 5 mg, 0.04 mmol) in anhydrous THF (10 ml) was stirred at 60° C. for 16 hours. The mixture was poured into 100 ml of water. 2M HCl was added dropwise until pH=4. The precipitates were filtered, washed with water and dried in vacuo to give the crude, which was purified by silica gel chromatography with a gradient of 3~5% MeOH/CHCl₃ to give 2-hydroxyethyl 5-{4-[4-({[(2-fluoro-5-methylphenyl)amino]carbonyl}amino)phenoxy]pyridin-2-yl}-1H-pyrrole-3-carboxylate as white solid. Yield: 36 mg, 67%.

¹H NMR (d₆-DMSO): 12.12 (br. s., 1H), 9.18 (s, 1H), 8.49 (d, J=1.8 Hz, 1H), 8.39 (d, J=5.6 Hz, 1H), 7.94-8.05 (m, 1H), 7.56 (d, J=9.1 Hz, 2H), 7.48 (d, J=1.5 Hz, 1H), 7.35 (d, J=2.1 Hz, 1H), 7.03-7.23 (m, 4H), 6.75-6.86 (m, 1H), 6.69 (dd, J=5.7, 2.2 Hz, 1H), 4.83 (t, J=5.7 Hz, 1H), 4.15 (t, J=5.1 Hz, 2H), 3.64 (q, J=5.4 Hz, 2H), 2.27 (s, 3H)

LR MS (ES+): 513 (M+Na⁺)
LR MS (ES−): 489 (M−H)

Example 132

1-(2-fluoro-5-methylphenyl)-3-(4-{[2-(4-{[(3R)-3-hydroxypyrrolidin-1-yl]carbonyl}-1H-pyrrol-2-yl)pyridin-4-yl]oxy}phenyl)urea

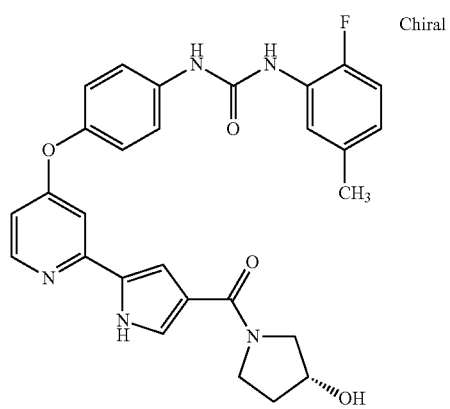 [SMILES: Cc1ccc(F)c(NC(=O)Nc2ccc(Oc3ccnc(-c4cc(C(=O)N5CC[C@@H](O)C5)c[nH]4)c3)cc2)c1]

A mixture of 5-{4-[4-({[(2-fluoro-5-methylphenyl)amino]carbonyl}amino)phenoxy]pyridin-2-yl}-1H-pyrrole-3-carboxylic acid (50 mg, 0.11 mmol), HATU (51 mg, 0.13 mmol) and N,N-diisopropylethylamine (31 mg, 0.24 mmol) in anhydrous DMF (10 ml) was stirred at room temperature for 10 minutes, followed by addition of (R)-3-pyrrolidinol (14 mg, 0.16 mmol). The mixture was stirred for another 10 minutes and poured into 100 ml of water. 2M HCl was added dropwise until pH=4~5. The precipitates were filtered, washed with water and dried in vacuo to give 1-(2-fluoro-5-methylphenyl)-3-(4-{[2-(4-{[(3R)-3-hydroxypyrrolidin-1-yl]carbonyl}-1H-pyrrol-2-yl)pyridin-4-yl]oxy}phenyl)urea as white solid. Yield: 40 mg, 71%.

$^1$H NMR (d$_6$-DMSO): 11.90 (br. s., 1H), 9.17 (s, 1H), 8.49 (d, J=2.6 Hz, 1H), 8.38 (d, J=5.9 Hz, 1H), 7.99 (dd, J=7.8, 1.9 Hz, 1H), 7.51-7.62 (m, 2H), 7.37 (d, J=2.3 Hz, 1H), 7.25 (br. s., 1H), 7.02-7.19 (m, 4H), 6.76-6.86 (m, 1H), 6.64 (dd, J=5.6, 2.3 Hz, 1H), 4.93 (br. s., 1H), 4.22-4.38 (m, 1H), 3.69-3.87 (m, 1H), 3.43-3.59 (m, 2H), 3.35-3.42 (m, 1H), 2.27 (s, 3H), 1.90 (br. s., 2H)

LR MS (ES+): 538 (M+Na$^+$)
LR MS (ES−): 514 (M−H)

Example 133

1-(2-fluoro-5-methylphenyl)-3-(4-{[2-(4-{[(3S)-3-hydroxypyrrolidin-1-yl]carbonyl}-1H-pyrrol-2-yl)pyridin-4-yl]oxy}phenyl)urea

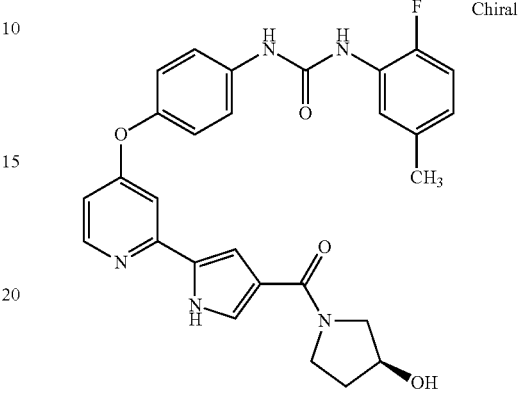

Similar procedure as Example 132.
LR MS (ES+): 538 (M+Na$^+$)
LR MS (ES−): 514 (M−H)

Example 134

5-{4-[4-({[(2-fluoro-5-methylphenyl)amino]carbonyl}amino)phenoxy]pyridin-2-yl}-1H-pyrrole-3-carboxylic acid

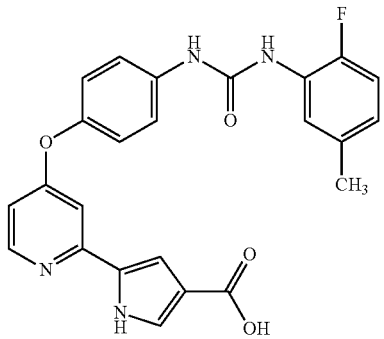 [SMILES: Cc1ccc(F)c(NC(=O)Nc2ccc(Oc3ccnc(-c4cc(C(=O)O)c[nH]4)c3)cc2)c1]

To a stirred solution of methyl 5-{4-[4-({[(2-fluoro-5-methylphenyl)amino]carbonyl}amino)phenoxy]pyridin-2-yl}-1H-pyrrole-3-carboxylate (1.38 g, 3.00 mmol) in a mixture of solvents THF/MeOH (20 ml/20 ml) was added 2 ml of 5M NaOH (10 mmol) solution. The mixture was heated in a 72° C. bath for 5 hours, cooled to room temperature and poured into 200 ml of water. 2M HCl was added until pH=3. The resulting precipitates were filtered, washed with water, and dried in vacuo to give 5-{4-[4-({[(2-fluoro-5-methylphenyl)amino]carbonyl}amino)phenoxy]pyridin-2-yl}-1H-pyrrole-3-carboxylic acid as light brown solid. Yield: 1.28 g, 96%.

$^1$H NMR (d$_6$-DMSO): 12.04 (br. s., 1H), 11.88 (br. s., 1H), 9.18 (s, 1H), 8.49 (d, J=2.3 Hz, 1H), 8.39 (d, J=5.6 Hz, 1H), 7.94-8.05 (m, 1H), 7.56 (d, J=9.1 Hz, 2H), 7.31-7.42

(m, 2H), 7.01-7.21 (m, 4H), 6.81 (td, J=5.2, 2.2 Hz, 1H), 6.68 (dd, J=5.6, 2.3 Hz, 1H), 2.27 (s, 3H)
LR MS (ES−): 467 (M−H)

Example 135 methyl 5-{4-[4-({[(2-fluoro-5-methylphenyl)amino]carbonyl}amino)phenoxy]pyridin-2-yl}-1H-pyrrole-3-carboxylate

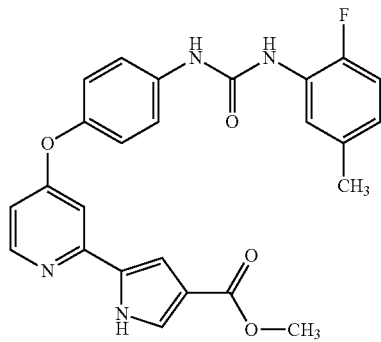 [SMILES: COC(=O)c1c[nH]c(-c2cc(Oc3ccc(NC(=O)Nc4cc(C)ccc4F)cc3)ccn2)c1]

To a stirred solution of methyl 5-[4-(4-aminophenoxy)pyridin-2-yl]-1H-pyrrole-3-carboxylate (1.0 g, 3.23 mmol) in anhydrous THF (10 ml) was added 2-fluoro-5-methyl-phenylisocyanate (488 mg, 3.23 mmol). The mixture was stirred at room temperature for one hour and poured into 200 ml of 0.02M HCl solution with vigorous stirring. The resulting precipitates were filtered, washed with water, and dried in vacuo to give methyl 5-{4-[4-({[(2-fluoro-5-methylphenyl)amino]carbonyl}amino)phenoxy]pyridin-2-yl}-1H-pyrrole-3-carboxylate as white solid. Yield: 1.38 g, 93%.

$^1$H NMR (d$_6$-DMSO): 12.14 (br. s., 1H), 9.17 (s, 1H), 8.49 (d, J=2.3 Hz, 1H), 8.39 (d, J=5.9 Hz, 1H), 7.99 (dd, J=7.9, 1.8 Hz, 1H), 7.53-7.59 (m, 2H), 7.44 (dd, J=3.2, 1.5 Hz, 1H), 7.36 (d, J=2.3 Hz, 1H), 7.06-7.18 (m, 4H), 6.77-6.85 (m, 1H), 6.68 (dd, J=5.6, 2.3 Hz, 1H), 3.72 (s, 3H), 2.28 (s, 3H)
LR MS (ES+): 483 (M+Na$^+$)
LR MS (ES−): 459 (M−H)

Preparation of 1-tert-butyl 2-methyl 4-[4-(3-aminophenoxy)pyridin-2-yl]-1H-pyrrole-1,2-dicarboxylate

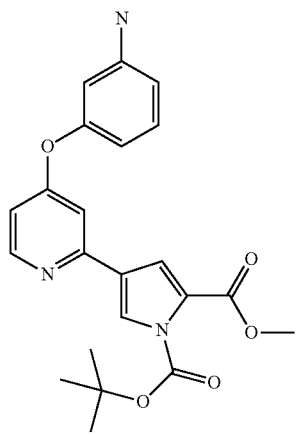 [SMILES: COC(=O)c1cc(-c2cc(Oc3cccc(N)c3)ccn2)cn1C(=O)OC(C)(C)C]

Similar procedure as 1-tert-butyl 2-methyl 4-[4-(4-aminophenoxy)pyridin-2-yl]-1H-pyrrole-1,2-dicarboxylate.

$^1$H NMR (d$_6$-DMSO): 8.38 (d, 1H), 8.01 (d, J=1.5 Hz, 1H), 7.45 (d, J=2.1 Hz, 1H), 7.37 (d, J=1.5 Hz, 1H), 7.06 (t, J=7.9 Hz, 1H), 6.67 (dd, J=5.7, 2.2 Hz, 1H), 6.43 (d, J=7.9 Hz, 1H), 6.20-6.33 (m, 2H), 5.32 (br. s., 2H), 3.72-3.85 (m, 3H), 1.53 (s, 9H)
LR MS (ES+): 432 (M+Na$^+$)

Example 136 methyl 4-{4-[3-({[(2-fluoro-5-methylphenyl)amino]carbonyl}amino)phenoxy]pyridin-2-yl}-1H-pyrrole-2-carboxylate

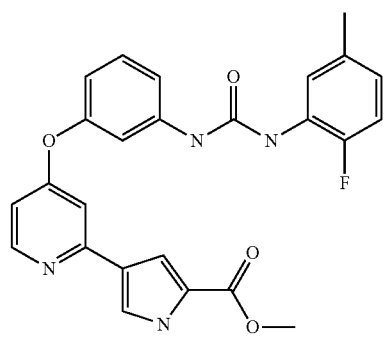 [SMILES: COC(=O)c1cc(-c2cc(Oc3cccc(NC(=O)Nc4cc(C)ccc4F)c3)ccn2)c[nH]1]

To a stirred solution of 1-tert-butyl 2-methyl 4-[4-(3-aminophenoxy)pyridin-2-yl]-1H-pyrrole-1,2-dicarboxylate (150 mg, 0.37 mmol) in anhydrous THF (10 ml) was added 2-fluoro-5-methyl-phenylisocyanate (67 mg, 0.44 mmol). The mixture was stirred at room temperature for 3 hours and poured into 100 ml of water. The resulting precipitates were filtered, washed with water, and dried in vacuo to give the Boc-protected intermediate as brown solid. This intermediate was dissolved in 5 ml of methylene chloride, and 3 ml of trifluoroacetic acid was added. Stirring was continued for 20 minutes. The mixture was evaporated to dryness to give the crude product, which was purified by silica gel chromatography eluting with 5% MeOH/CHCl$_3$ to give methyl 4-{4-[3-({[(2-fluoro-5-methylphenyl)amino]carbonyl}amino)phenoxy]pyridin-2-yl}-1H-pyrrole-2-carboxylate as white solid. Yield: 67 mg, 39%.

$^1$H NMR (d$_6$-DMSO): 12.18 (br. s., 1H), 9.23 (s, 1H), 8.47 (br. s., 1H), 8.36 (d, J=5.6 Hz, 1H), 7.91 (d, J=7.6 Hz, 1H), 7.63 (br. s., 1H), 7.25-7.47 (m, 4H), 7.16 (d, J=7.9 Hz, 1H), 7.07 (dd, J=11.4, 8.5 Hz, 1H), 6.72-6.85 (m, 2H), 6.65 (dd, J=5.6, 2.1 Hz, 1H), 3.76 (s, 3H), 2.22 (s, 3H)
LR MS (ES+): 483 (M+Na$^+$)
LR MS (ES−): 459 (M−H)

Example 137

N-[dimethyl(oxido)-lambda~4~-sulfanylidene]-4-{4-[4-({[(2-fluoro-5-methylphenyl)amino]carbonyl}amino)phenoxy]pyridin-2-yl}-1H-pyrrole-2-carboxamide

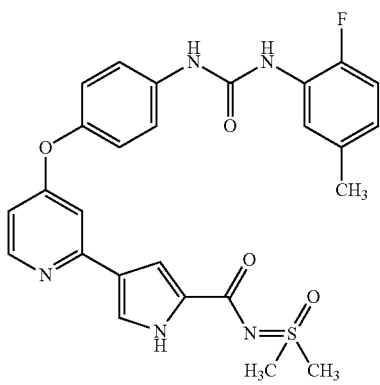 [SMILES: Cc1ccc(F)c(NC(=O)Nc2ccc(Oc3ccnc(-c4c[nH]c(C(=O)N=S(C)(C)=O)c4)c3)cc2)c1]

Similar procedure as Example 101.
LR MS (ES+): 544 (M+Na$^+$)
LR MS (ES−): 520 (M−H)

Example 138

4-{4-[4-({[(2-fluoro-5-methylphenyl)amino]carbonyl}amino)phenoxy]pyridin-2-yl}-N,N-dimethyl-1H-pyrrole-2-carboxamide

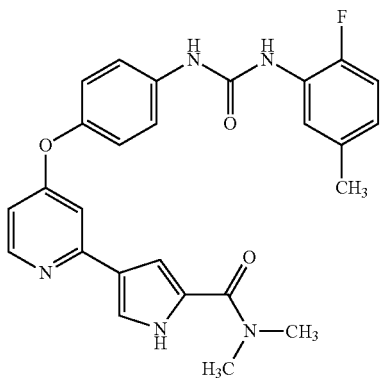 [SMILES: Cc1ccc(F)c(NC(=O)Nc2ccc(Oc3ccnc(-c4c[nH]c(C(=O)N(C)C)c4)c3)cc2)c1]

The title compound was isolated as a side product in the synthesis of Example 137.
LR MS (ES+): 474 (M+H)
LR MS (ES−): 472 (M−H

Example 139

4-{4-[4-({[(2-fluoro-5-methylphenyl)amino]carbonyl}amino)phenoxy]pyridin-2-yl}-N-methyl-1H-pyrrole-2-carboxamide

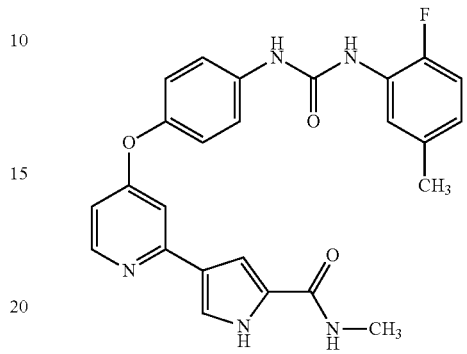

A mixture of 4-{4-[4-({[(2-fluoro-5-methylphenyl)amino]carbonyl}amino)phenoxy]pyridin-2-yl}-1H-pyrrole-2-carboxylic acid (50 mg, 0.11 mmol), HATU (50 mg, 0.13 mmol), 2M methylamine/THF solution (0.1 ml, 0.2 mmol) and N,N-diisopropylethylamine (31 mg, 0.24 mmol) in anhydrous DMF (8 ml) was stirred at room temperature for 10 minutes. The mixture was poured into 100 ml of water. The precipitates were filtered, washed with water and dried to give the crude, which was purified by silica gel chromatography with 3~5% MeOH/CHCl$_3$ to give 4-{4-[4-({[(2-fluoro-5-methylphenyl)amino]carbonyl}amino)phenoxy]pyridin-2-yl}-N-methyl-1H-pyrrole-2-carboxamide as white solid. Yield: 21 mg, 41%.
$^1$H NMR (d$_6$-DMSO): 11.69 (br. s., 1H), 9.17 (s, 1H), 8.48 (d, J=2.3 Hz, 1H), 8.32 (d, J=5.6 Hz, 1H), 8.01-8.12 (m, 1H), 7.96 (dd, J=7.8, 1.9 Hz, 1H), 7.48-7.61 (m, 2H), 7.43 (dd, J=2.9, 1.5 Hz, 1H), 7.03-7.23 (m, 5H), 6.79 (dt, J=8.1, 2.3 Hz, 1H), 6.61 (dd, J=5.6, 2.3 Hz, 1H), 2.71 (d, J=4.7 Hz, 3H), 2.26 (s, 3H)
LR MS (ES+): 482 (M+Na$^+$)
LR MS (ES−): 458 (M−H)

Preparation of 4-(4-aminophenoxy)-6-chloropyridin-2-amine

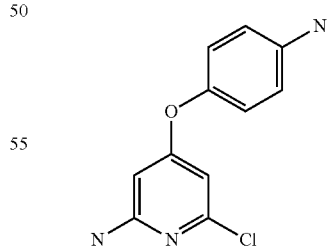

A stirred solution of 4-aminophenol (335 mg, 3.1 mmol) in anhydrous DMSO (8 ml) was flushed with nitrogen and treated with 1M KOBu$^t$/THF solution (3.1 ml, 3.1 mmol). The mixture was stirred at room temperature under nitrogen for 10 minutes. 4,6-dichloropyridin-2-ylamine (500 mg, 3.1 mmol) was added and the mixture was heated at 88° C. for 16 hours, cooled to room temperature and poured into 100 ml of water. The resulting precipitates were filtered, washed with water and dried to give the crude product, which was purified by silica gel chromatography with 2~5% MeOH/CHCl₃ to give 4-(4-aminophenoxy)-6-chloropyridin-2-amine as light brown solid. Yield: 350 mg, 49%.

Example 140

1-tert-butyl 2-methyl 4-{6-amino-4-[4-({[(2-fluoro-5-methylphenyl)amino]carbonyl}amino)phenoxy]pyridin-2-yl}-1H-pyrrole-1,2-dicarboxylate

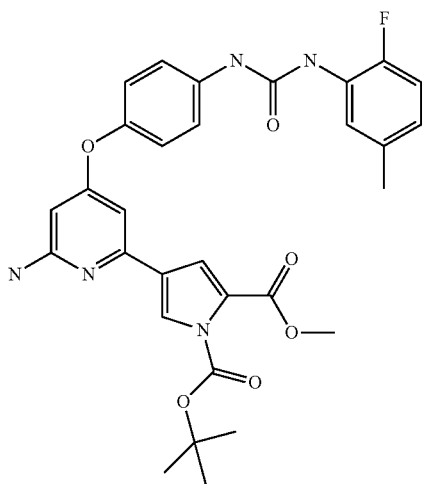 [SMILES: COC(=O)c1cc(-c2cc(Oc3ccc(NC(=O)Nc4cc(C)ccc4F)cc3)cc(N)n2)cn1C(=O)OC(C)(C)C]

Similar procedure as Example 148.
LR MS (ES+): 598 (M+Na⁺)

Example 141

1-(4-{[2-amino-6-(1H-pyrrol-2-yl)pyridin-4-yl]oxy}phenyl)-3-(2-fluoro-5-methylphenyl)urea

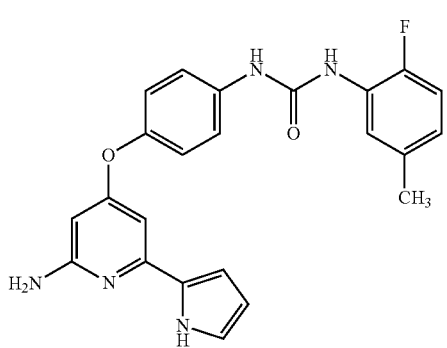 [SMILES: Cc1ccc(F)c(NC(=O)Nc2ccc(Oc3cc(N)nc(-c4ccc[nH]4)c3)cc2)c1]

Similar procedure as Example 148.
¹H NMR (d₆-DMSO): 11.02 (br. s., 1H), 9.11 (s, 1H), 8.44 (br. s., 1H), 7.97 (d, 1H), 7.50 (d, J=8.8 Hz, 2H), 6.98-7.17 (m, 3H), 6.78 (br. s., 2H), 6.53 (br. s., 2H), 6.05 (br. s., 1H), 5.74 (br. s., 2H), 5.61 (s, 1H), 2.25 (s, 3H)
LR MS (ES+): 418 (M+H)
LR MS (ES−): 416 (M−H)

Example 142

4-{4-[4-({[(2-fluoro-5-methylphenyl)amino]carbonyl}amino)phenoxy]pyridin-2-yl}-1H-pyrrole-2-carboxylic acid

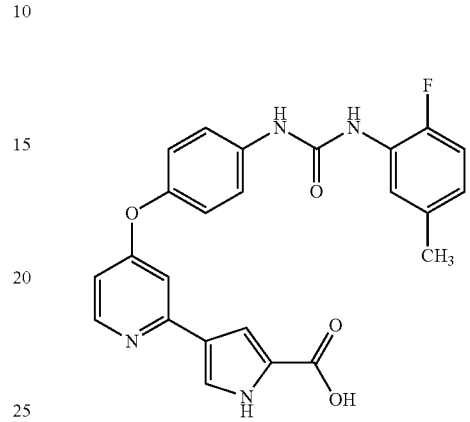

To a stirred solution of methyl 4-{4-[4-({[(2-fluoro-5-methylphenyl)amino]carbonyl}amino)phenoxy]pyridin-2-yl}-1H-pyrrole-2-carboxylate (220 mg, 0.48 mmol) in THF/MeOH (3 ml/10 ml) was added 1M NaOH (4.0 ml, 4.0 mmol). The mixture was heated at 70° C. for 2 hours, cooled to room temperature and poured into 100 ml of water. 1M HCl was added until pH=4 and the resulting precipitates were filtered, washed with water and dried in vacuo to give 4-{4-[4-({[(2-fluoro-5-methylphenyl)amino]carbonyl}amino)phenoxy]pyridin-2-yl}-1H-pyrrole-2-carboxylic acid. Yield: 200 mg, 94%.
¹H NMR (d₆-DMSO): 12.38 (br. s., 1H), 12.04 (br. s., 1H), 9.14-9.23 (m, 1H), 8.48 (d, J=2.3 Hz, 1H), 8.34 (d, J=5.6 Hz, 1H), 7.97 (dd, J=7.9, 2.1 Hz, 1H), 7.60 (br. s., 1H), 7.50-7.58 (m, 2H), 7.30 (d, J=2.1 Hz, 1H), 7.22 (s, 1H), 7.03-7.18 (m, 3H), 6.73-6.84 (m, 1H), 6.60 (dd, J=5.6, 2.3 Hz, 1H), 2.25 (s, 3H)
LR MS (ES−): 445 (M−H)

Preparation of 1-tert-butyl 2-methyl 4-[4-(4-aminophenoxy)pyridin-2-yl]-1H-pyrrole-1,2-dicarboxylate

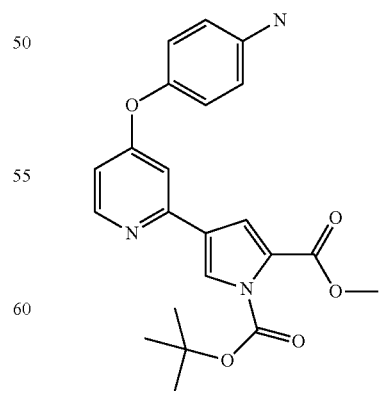

A 100 ml flask was charged with 4-((2-chloropyridin-4-yl)oxy)aniline (150 mg, 0.68 mmol), 1-tert-butyl 2-methyl 4-(4,4,5,5-tetramethyl-1,3,2-dioxaborolan-2-yl)-1H-pyrrole-1,2-dicarboxylate (260 mg, 0.81 mmol), 2M Na₂CO₃ solution (0.5 ml, 1.0 mmol), PdCl₂(PPh₃)₂ (5 mg, 0.007 mmol), 10 ml of 1,4-dioxane and 3 ml of water. The mixture was flushed with nitrogen and heated at 70° C. for 30 minutes. The mixture was cooled to room temperature and poured into 100 ml of water. The precipitates were filtered and dried to give the crude, which was further purified by silica gel chromatography eluting with 2-3% MeOH/CHCl₃ to give 1-tert-butyl 2-methyl 4-[4-(4-aminophenoxy)pyridin-2-yl]-1H-pyrrole-1,2-dicarboxylate as light brown oil. Yield: 240 mg, 86%.

Example 143

Methyl 4-{4-[4-({[(2-fluoro-5-methylphenyl)amino]carbonyl}amino)phenoxy]pyridin-2-yl}-1H-pyrrole-2-carboxylate

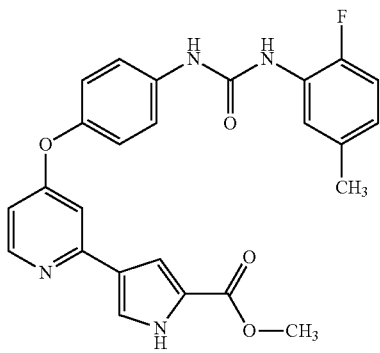 [SMILES: COC(=O)c1cc(-c2cc(Oc3ccc(NC(=O)Nc4cc(C)ccc4F)cc3)ccn2)c[nH]1]

To a stirred solution of 1-tert-butyl 2-methyl 4-[4-(4-aminophenoxy)pyridin-2-yl]-1H-pyrrole-1,2-dicarboxylate (240 mg, 0.59 mmol) in anhydrous THF (10 ml) was added 2-fluoro-5-methyl-phenylisocyanate (107 mg, 0.71 mmol). The mixture was stirred at room temperature for 30 minutes and poured into 100 ml of water. The resulting precipitates were filtered, washed with water and dried to give a brown oil. Purification by silica gel chromatography eluting with 2-3% MeOH/CHCl₃ gave the Boc-protected intermediate as light green oil, which was dissolved in 5 ml of methylene chloride, followed by addition of 3 ml of trifluoroacetic acid. The mixture was stirred at room temperature for 10 minutes, evaporated to dryness, and purified by silica gel chromatography eluting with 2-5% MeOH/CHCl₃ to give methyl 4-{4-[4-({[(2-fluoro-5-methylphenyl)amino]carbonyl}amino)phenoxy]pyridin-2-yl}-1H-pyrrole-2-carboxylate as white solid. Yield: 135 mg, 50%.

¹H NMR (d₆-DMSO): 12.17 (br. s., 1H), 9.14 (s, 1H), 8.46 (d, J=2.3 Hz, 1H), 8.33 (d, J=5.9 Hz, 1H), 7.91-8.04 (m, 1H), 7.61 (dd, J=3.1, 1.6 Hz, 1H), 7.53 (d, J=9.1 Hz, 2H), 7.22-7.31 (m, 2H), 7.02-7.17 (m, 3H), 6.73-6.85 (m, 1H), 6.58 (dd, J=5.7, 2.5 Hz, 1H), 3.76 (s, 3H), 2.26 (s, 3H)
LR MS (ES+): 483 (M+Na⁺)
LR MS (ES−): 459 (M−H)

Preparation of tert-butyl 2-[4-(4-aminophenoxy)pyridin-2-yl]-1H-pyrrole-1-carboxylate

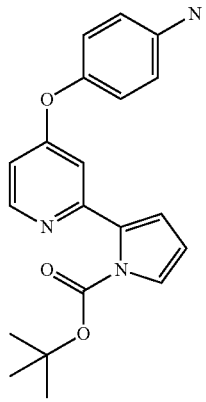 [SMILES: CC(C)(C)OC(=O)n1cccc1-c1cc(Oc2ccc(N)cc2)ccn1]

To a stirred mixture of N-Boc-pyrrole-2-boronic acid (114 mg, 0.54 mmol) and 4-((2-chloropyridin-4-yl)oxy)aniline (100 mg, 0.45 mmol) in 8 ml of 1,4-dioxane, was added PdCl₂(PPh₃)₂ (10 mg, 0.014 mmol) and 1M Na₂CO₃ aqueous solution (0.5 ml, 1.0 mmol). The mixture was heated at 72° C. under N₂ for one hour, cooled to room temperature and poured into 100 ml of water. The resulting mixture was extracted with EtOAc (2×50 ml). The organic layers were combined, washed with brine (50 ml), dried over Na₂SO₄, and evaporated to give a brown oil, which was purified by silica gel chromatography with a gradient of 20~50% EtOAc/hexanes to give tert-butyl 2-[4-(4-aminophenoxy)pyridin-2-yl]-1H-pyrrole-1-carboxylate as colorless oil. Yield: 110 mg, 70%.

Example 144

1-(2-fluoro-5-methylphenyl)-3-(4-{[2-(1H-pyrrol-2-yl)pyridin-4-yl]oxy}phenyl)urea

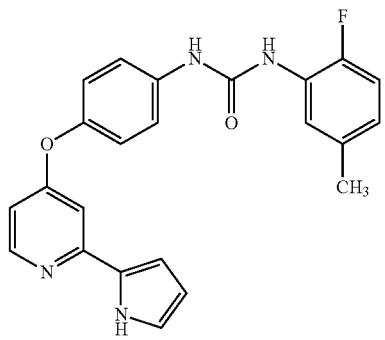 [SMILES: Cc1ccc(F)c(NC(=O)Nc2ccc(Oc3ccnc(-c4ccc[nH]4)c3)cc2)c1]

To a stirred solution of tert-butyl 2-[4-(4-aminophenoxy)pyridin-2-yl]-1H-pyrrole-1-carboxylate (100 mg, 0.28 mmol) in anhydrous THF (10 ml) was added 2-fluoro-5-methyl-phenylisocyanate (51 mg, 0.34 mmol). The mixture was stirred at room temperature for one hour and poured into 100 ml of water. The resulting mixture was extracted with EtOAc (2×50 ml). The organic layers were combined, washed with brine (50 ml), dried over Na₂SO₄, and evaporated to give a brown oil, which was purified by silica gel chromatography with 2-5% MeOH/CHCl₃ to give the Boc-protected intermediate as light green oil. The oil was dissolved in 5 ml of methylene chloride, and 3 ml of trifluoroacetic acid was added. Stirring was continued for 10 hours, and the mixture was evaporated to dryness. The brown residue was dissolved in methanol (5 ml). This methanol solution was then added dropwise into 100 ml of 1M NaHCO₃ solution with stirring. The resulting precipitates were filtered, washed with water, and dried in vacuo to give 1-(2-fluoro-5-methylphenyl)-3-(4-{[2-(1H-pyrrol-2-yl)pyridin-4-yl]oxy}phenyl)urea as light grey solid.

¹H NMR (d₆-DMSO): 11.43 (br. s., 1H), 9.14 (s, 1H), 8.46 (d, J=2.6 Hz, 1H), 8.32 (d, J=5.6 Hz, 1H), 7.96 (dd, J=7.9, 1.8 Hz, 1H), 7.48-7.58 (m, 2H), 7.20 (d, J=2.1 Hz, 1H), 7.04-7.16 (m, 3H), 6.75-6.86 (m, 2H), 6.67 (dt, J=3.8, 1.9 Hz, 1H), 6.57 (dd, J=5.9, 2.3 Hz, 1H), 6.05-6.13 (m, 1H), 2.25 (s, 3H)

Example 145

1-phenyl-3-{4-[6-(1H-pyrrol-2-yl)pyridin-3-yl]phenyl}urea

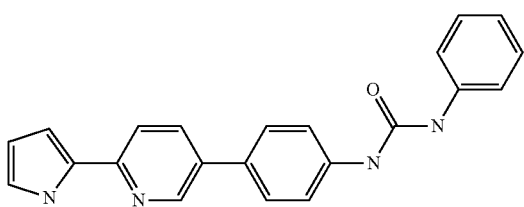 [SMILES: O=C(Nc1ccccc1)Nc1ccc(-c2ccc(-c3ccc[nH]3)nc2)cc1]

Similar procedure as Example 148.
¹H NMR (DMSO-d₆) δ: 11.46 (br. s., 1H), 8.79 (s, 1H), 8.75 (d, J=1.8 Hz, 1H), 8.67 (s, 1H), 7.98 (dd, J=8.4, 2.5 Hz, 1H), 7.70 (d, J=8.2 Hz, 1H), 7.67 (d, J=8.5 Hz, 2H), 7.56 (d, J=8.5 Hz, 2H), 7.45 (d, J=7.6 Hz, 2H), 7.27 (t, J=7.9 Hz, 2H), 6.96 (t, J=7.3 Hz, 1H), 6.84-6.88 (m, 1H), 6.77 (t, J=3.8 Hz, 1H), 6.11-6.16 (m, 1H)

Example 146

1-(2-fluoro-5-methylphenyl)-3-{3-[2-(1H-pyrrol-2-yl)pyridin-4-yl]phenyl}urea

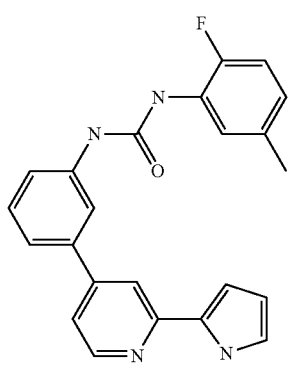 [SMILES: Cc1ccc(F)c(NC(=O)Nc2cccc(-c3ccnc(-c4ccc[nH]4)c3)c2)c1]

Similar procedure as Example 148.
LR MS (ES+): 387 (M+H⁺)

Example 147

1-(2-fluoro-5-methylphenyl)-3-{4-[2-(1H-pyrrol-3-yl)pyridin-4-yl]phenyl}urea

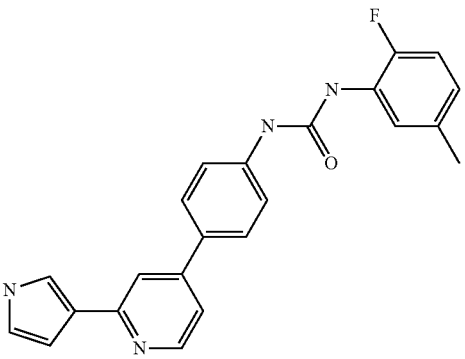 [SMILES: Cc1ccc(F)c(NC(=O)Nc2ccc(-c3ccnc(-c4cc[nH]c4)c3)cc2)c1]

Similar procedure as Example 148.
¹H NMR (d₆-DMSO): 11.72 (br. s., 1H), 9.49 (br. s., 1H), 8.63 (s, 1H), 8.53 (d, J=6.4 Hz, 1H), 8.38 (br. s., 1H), 8.07 (d, J=8.5 Hz, 2H), 8.00-8.04 (m, 1H), 7.97 (dd, J=7.9, 1.8 Hz, 1H), 7.81-7.90 (m, 1H), 7.69 (d, J=8.8 Hz, 2H), 7.13 (dd, J=11.3, 8.4 Hz, 1H), 7.03 (d, J=2.1 Hz, 1H), 6.98 (br. s., 1H), 6.84 (ddd, J=7.8, 5.3, 2.1 Hz, 1H), 2.21-2.36 (m, 3H)

LR MS (ES+): 387 (M+H)

tert-butyl (4-(2-chloropyridin-4-yl)phenyl)carbamate

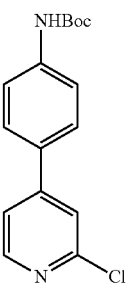 [SMILES: CC(C)(C)OC(=O)Nc1ccc(-c2ccnc(Cl)c2)cc1]

To a mixture of (4-boc-aminophenyl)boronic acid (200 mg, 0.84 mmol) and 2-chloro-4-bromopyridine (162 mg, 0.84 mmol) in 10 ml of 1,4-dioxane, was added PdCl₂(PPh₃)₂ (10 mg, 0.014 mmol) and 1M Na₂CO₃ aqueous solution (0.5 ml, 1.0 mmol). The mixture was heated at 70° C. under N₂ for 2 hours, cooled to room temperature and poured into 100 ml of water. The brown precipitates were filtered, washed with water and dried to give tert-butyl (4-(2-chloropyridin-4-yl)phenyl)carbamate as the crude product.

4-(2-(1H-pyrrol-2-yl)pyridin-4-yl)aniline

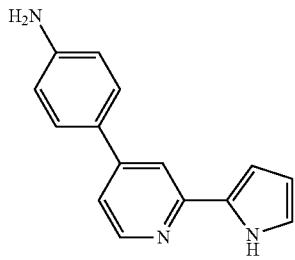 [SMILES: Nc1ccc(-c2ccnc(-c3ccc[nH]3)c2)cc1]

To a mixture of N-Boc-pyrrole-2-boronic acid (210 mg, 1.0 mmol) and tert-butyl (4-(2-chloropyridin-4-yl)phenyl)carbamate (250 mg, 0.82 mmol) in 10 ml of 1,4-dioxane, was added $PdCl_2(PPh_3)_2$ (10 mg, 0.014 mmol) and 1M $Na_2CO_3$ aqueous solution (0.75 ml, 1.5 mmol). The mixture was heated at 60° C. under $N_2$ for 3 hours, cooled to room temperature and poured into 100 ml of water. The precipitates were filtered, dried and purified by silica gel chromatography with 1-5% $MeOH/CHCl_3$ to give the intermediate as light yellow oil. This intermediate was dissolved in 10 ml of methylene chloride and 3 ml of trifluoroacetic acid was added. The mixture was stirred at room temperature for 16 hours and evaporated to dryness to give 4-(2-(1H-pyrrol-2-yl)pyridin-4-yl)aniline TFA salt as light brown solid. Yield: 290 mg, 100%.

Example 148

1-(2-fluoro-5-methylphenyl)-3-{4-[2-(1H-pyrrol-2-yl)pyridin-4-yl]phenyl}urea

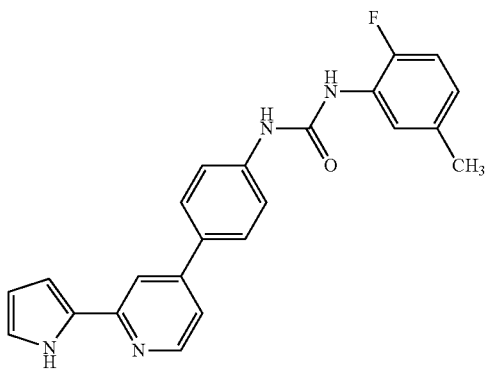 [SMILES: Cc1ccc(F)c(NC(=O)Nc2ccc(-c3ccnc(-c4ccc[nH]4)c3)cc2)c1]

To a stirred suspension of 4-(2-(1H-pyrrol-2-yl)pyridin-4-yl)aniline TFA salt (60 mg, 0.17 mmol) in anhydrous THF (10 ml) was added 2-fluoro-5-methyl-phenylisocyanate (48 mg, 0.32 mmol) and N,N-diisopropylethylamine (40 mg, 0.31 mmol). After 1 hour, the reaction mixture was evaporated and purified by silica gel chromatography with 2-3% $MeOH/CHCl_3$ to give 1-(2-fluoro-5-methylphenyl)-3-{4-[2-(1H-pyrrol-2-yl)pyridin-4-yl]phenyl}urea as off-white solid. Yield: 28 mg.

$^1$H NMR ($d_6$-DMSO): 11.49 (br. s., 1H), 9.29 (br. s., 1H), 8.52-8.60 (m, 1H), 8.48 (d, J=5.3 Hz, 1H), 7.94-8.04 (m, 2H), 7.84 (d, J=8.5 Hz, 2H), 7.62 (d, J=8.5 Hz, 2H), 7.42 (dd, J=5.3, 1.5 Hz, 1H), 7.12 (dd, J=11.4, 8.2 Hz, 1H), 6.89 (s, 2H), 6.82 (dt, J=5.4, 2.6 Hz, 1H), 6.16 (t, J=2.9 Hz, 1H), 2.29 (s, 3H)

LR MS (ES+): 409 (M+Na$^+$)
LR MS (ES−): 385 (M−H)

3.2 Biological Testing

Biological data for the compounds of the present invention was generated by the use of one or more of the following assays.

VEGF Stimulated Ca.sup.++ Signal In Vitro

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 96-well fibronectin coated black-walled plates overnight at 37.degree. C./5% CO.sub.2. Cells were loaded with calcium indicator Fluo-4 for 45 minutes at 37.degree. C. Cells were washed 4 times (Original Cell Wash, Labsystems) to remove extracellular dye. Test compounds were reconstituted in 100% DMSO and added to the cells to give a final DMSO concentration of 0.1%. For screening, cells were pre-incubated with test agents for 30 minutes, at a single concentration (10 .mu·M) or at concentrations ranging from 0.01 to 10.0 .mu·M followed by VEGF stimulation (5 ng/mL). Changes in fluorescence at 516 nm were measured simultaneously in all 96 wells using a cooled CCD camera. Data were generated by determining max-min fluorescence levels for unstimulated, stimulated, and drug treated samples. IC.sub.50 values for test compounds were calculated from % inhibition of VEGF stimulated responses in the absence of inhibitor.

VEGFR2 Kinase Assay

The cytoplasmic domain of the human VEGF receptor (VEGFR-2) was expressed as a Histidine-tagged fusion protein following infection of insect cells using an His engineered baculovirus. His-VEGFR-2 was purified to homogeneity, as determined by SDS-PAGE, using nickel resin chromatography. Kinase assays were performed in 96 well microtiter plates that were coated overnight with 30 .mu·g of poly-Glu-Tyr (4:1) in 10 mM Phosphate Buffered Saline (PBS), pH 7.2-7.4. The plates were incubated with 1% BSA and then washed four times with PBS prior to starting the reaction. Reactions were carried out in 120 .mu·L reaction volumes containing 3.6 .mu·M ATP in kinase buffer (50 mM Hepes buffer pH 7.4, 20 mM MgCl.sub.2, 0.1 mM MnCl.sub.2 and 0.2 mM Na.sub.3 VO.sub.4). Test compounds were reconstituted in 100% DMSO and added to the reaction to give a final DMSO concentration of 5%. Reactions were initiated by the addition 0.5 ng of purified protein. Following a ten minute incubation at 25.degree. C., the reactions were washed four times with PBS containing 0.05% Tween-20. 100 .mu·l of a monoclonal anti-phosphotyrosine antibody-peroxidase conjugate was diluted 1:10000 in PBS-Tween-20 and added to the wells for 30 minutes. Following four washes with PBS-Tween-20, 100 .mu·l of O-phenylenediamine Dihydrochloride in Phosphate-citrate buffer, containing urea hydrogen peroxide, was added to the wells for 7 minutes as a colorimetric substrate for the peroxidase. The reaction was terminated by the addition of 100 .mu·l of 2.5N H.sub.2 SO.sub.4 to each well and read using a microplate ELISA reader set at 492 nm. IC.sub.50 values for compound inhibition were calculated directly from graphs of optical density (arbitrary units) versus compound concentration following subtraction of blank values. Compounds of the current invention have the IC50 value in the range of 0.01 to 500 nM.

VEGF-Induced Dermal Extravasation in Guinea Pig (Miles Assay)

Male Hartley guinea pigs (300-600 g) were anesthetized with isofluorane, sheared, and given a single dose of drug or the respective vehicle. The guinea pigs were dosed orally unless indicated otherwise in Table 3. Ten minutes prior to the end of drug treatment, guinea pigs were anesthetized with isofluorane, and 0.5% Evans blue dye (EBD) in PBS (13-15 mg/kg dose of EBD) was injected intravenously. After 5 minutes, triplicate intradermal injections of 100 ng rhVEGF$_{165}$ in 100 μl PBS and of 100 μl PBS alone were administered on the flank. After 20 minutes, each animal was cuthanized with Pentosol, and the skin containing the intradermal injection sites was removed for image analysis.

Using an analog video camera coupled to a PC, an image of each trans-illuminated skin sample was captured, and the integrated optical density of each injection site was measured using ImagePro 4. For each skin sample, the difference between the mean optical density of the VEGF sites and mean optical density of the PBS sites is the measure of VEGF-induced EBD extravasation in that animal. These measured values were averaged per study group to determine the mean VEGF-induced EBD extravasation for each experimental condition, and the group means were then compared to assess inhibition of VEGF-induced EBD extravasation in the drug-treated groups relative to the vehicle-treated controls.

To determine the dose required for 50% inhibition (ID$_{50}$), the percent inhibition data was plotted as a function of oral dose, using the 'best-fit' analysis within MicroSoft Excel software. The ID$_{50}$ value was verified visually by using the plotted data (horizontal line from 50% y value, at intersection with best-fit line drop vertical line to x axis (dose).

Laser-Induced Choroidal Neovascularization (CNV) in Rat (CNV Assay).

CNV was induced and quantified in this model as previously described (Edelman and Castro. Exp. Eye Res. 2000; 71:523~533). On day 0, male Brown Norway rats (200-300 g) were anesthetized with 100 mg/kg Ketamine and 10 mg/kg Xylazine, and pupils were dilated with 1% Tropicamide. Using the blue-green setting of a Coherent Novus Argon Laser, 3 laser burns (90 mW for 0.1 s; 100 μm diameter) were given to each eye between the retinal vessels around the optic nerve head. Rats were dosed with test compounds in their indicated vehicles orally once daily.

On day 10, rats were sacrificed with 100% $CO_2$, and blood vessels were labeled by vascular perfusion with 10 mg/ml FITC-dextran (MW $2 \times 10^6$). Using an epi-fluorescence microscope (20x) coupled to a spot digital camera and a PC, images were obtained from the flat mounts of the RPE-choroid-sclera from each eye, and the area occupied by hyperfluorescent neovessels within each laser lesion was measured using ImagePro 4 software.

To determine the dose required for 50% inhibition (ID$_{50}$), the percent inhibition data was plotted as a function of oral dose, using the 'best-fit' analysis within MicroSoft Excel software. The ID$_{50}$ value was verified visually by using the plotted data (horizontal line from 50% y value, at intersection with best-fit line drop vertical line to x axis (dose).

The foregoing description can be employed to practice the present invention, and represents the best mode contemplated. It should not be construed as limiting the overall scope hereof.

Rabbit Eye VEGF Permeability Model

Assay used was detailed by Jeffrey Edelman, etc in Exp. Eye. Res. 80(2005), Pg 249-258.

PDGF Stimulated $Ca^{2+}$ Signal In Vitro

Automated FLIPR (Fluorometric Imaging Plate Reader) technology was used to screen for inhibitors of PDGF induced increases in intracellular calcium levels in fluorescent dye loaded endothelial cells. NHDF-Ad (Normal human dermal fibroblasts) (Lonza) were seeded in 384-well fibronectin coated black-walled plates overnight at 37° C./5% $CO_2$. Cells were loaded with calcium indicator Fluo-4 for 45 minutes at 37° C. Cells were washed 4 times (ELx405-CW, Bio-Tek) to remove extracellular dye. Test compounds were reconstituted in 100% DMSO and added to the cells to give a final DMSO concentration of 0.1%. For screening, cells were pre-incubated with test agents for 30 minutes, at a single concentration (10 μM) or at concentrations ranging from 0.001 nM to 10 μM followed by PDGF stimulation (10 ng/mL). Changes in fluorescence at 515 nm were measured simultaneously in all 384 wells using a cooled CCD camera. Data were generated by determining max-min fluorescence levels for unstimulated, stimulated, and drug treated samples. IC$_{50}$ values for test compounds were calculated from % inhibition of PDGF stimulated responses in the absence of inhibitor.

Table II and III present the biodata of some of the compounds of the present invention.

TABLE II

Biodata of Compounds of the Present Invention with Amide Linker

| Example# | VEGFR2 Cellular IC$_{50}$ (nM) | VEGFR2 Enzyme IC$_{50}$ (nM) | VEGFR1 Enzyme IC$_{50}$ (nM) | PDGFβ Cellular IC$_{50}$ (nM) |
|---|---|---|---|---|
| 1 |  | 28 |  |  |
| 2 | 8 | 28 |  |  |
| 3 |  | 28 |  |  |
| 4 | 6 | 29 |  |  |
| 5 |  | 2956 |  |  |
| 6 |  | 506 |  |  |
| 7 | 12 | 34 |  |  |
| 8 | 8 | 28 |  |  |
| 9 | 30 | 47 |  |  |
| 10 | 46 | 41 |  |  |
| 11 | 28 | 23 | 34 |  |
| 12 |  |  |  |  |
| 13 | 16 | 27 |  |  |
| 14 | 15 | 33 | 15 |  |
| 15 | 51 | 26 |  | 73 |
| 16 | 17 | 21 |  |  |
| 17 | 22 | 20 |  | 61 |
| 18 | 10 | 31 |  |  |
| 19 | 30 | 37 |  | 135 |
| 20 | 83 | 28 |  |  |
| 21 | 12 | 24 |  | 39 |
| 22 | 18 | 29 | 13 | 105 |
| 23 | 13 | 35 |  |  |
| 24 | 55 | 24 |  |  |
| 25 | 30 | 25 |  |  |
| 26 | 39 | 120 |  |  |
| 27 | 45 | 66 |  |  |
| 28 | 38 | 52 |  |  |
| 29 | 18 | 55 |  |  |
| 30 | 29 | 37 |  | 94 |
| 31 | 14 | 29 | 20 |  |
| 32 | 22 | 46 |  |  |
| 33 | 18 | 56 |  |  |
| 34 | 7 | 70 |  |  |
| 35 | 27 | 29 |  |  |
| 36 |  | 10028 |  |  |
| 37 | 1005 | 2610 |  |  |

TABLE 1II
Biodata of Compounds of the Present Invention with Urea Linker
| Example# | VEGFR2 Cellular IC$_{50}$ (nM) | VEGFR2 Enzyme IC$_{50}$ (nM) | VEGFR1 Enzyme IC$_{50}$ (nM) | PDGFβ Cellular IC$_{50}$ (nM) |
|---|---|---|---|---|
| 38 |  | 10 |  |  |
| 39 |  | 23 |  |  |
| 40 |  | 11 |  |  |
| 41 |  | 11 |  |  |
| 42 |  | 60 |  |  |
| 43 |  | 16 |  |  |
| 44 |  | 24 |  |  |
| 45 |  | 17 |  |  |
| 46 | 2 | 28 |  |  |
| 47 | 107 | 17 |  |  |
| 48 | 16 | 12 |  |  |
| 49 | 145 | 27 |  |  |
| 50 | 5 | 32 |  |  |
| 51 |  | 16 |  |  |
| 52 |  | 25 |  |  |
| 53 | 43 | 28 |  | 44 |
| 54 | 130 | 29 |  | 191 |
| 55 | 32 | 23 |  | 26 |
| 56 | 81 | 20 |  |  |
| 57 | 102 | 45 |  |  |
| 58 | 211 | 36 |  |  |
| 59 | 34 | 29 |  |  |
| 60 | 27 | 23 |  |  |
| 61 | 91 | 39 |  |  |
| 62 | 122 | 43 |  |  |
| 63 | 111 | 30 |  |  |
| 64 | 16 | 39 |  |  |
| 65 |  | 15 | 4 |  |
| 66 |  | 17 | 3 |  |
| 67 | 31 | 31 |  |  |
| 68 |  | 16 |  |  |
| 69 |  | 24 | 5 |  |
| 70 | 2 | 20 |  |  |
| 71 |  | 20 |  |  |
| 72 | 7 | 15 |  |  |
| 73 |  | 11 |  |  |
| 74 | 7 | 12 |  |  |
| 76 | 2 | 14 | 3 |  |
| 76 | 3 | 14 |  |  |
| 77 | 8 | 10 |  |  |
| 78 | 25 | 15 | 4 |  |
| 79 | 13 | 38 |  |  |
| 80 | 176 | 69 |  |  |
| 81 |  | 19 |  |  |
| 82 | 17 | 19 |  |  |
| 83 |  | 22 | 5 |  |
| 84 |  | 13 |  |  |
| 85 | 6 | 30 |  |  |
| 86 |  | 27 |  |  |
| 87 | 5 | 25 |  |  |
| 88 | 374 | 477 |  |  |
| 89 | 5 | 23 |  |  |
| 90 | 8 | 17 | 6 | 21 |
| 91 | 17 | 14 |  | 38 |
| 92 | 37 | 9 |  | 39 |
| 93 | 6 | 5 | 5 | 14 |
| 94 | 10 | 6 |  | 10 |
| 95 | 30 | 32 |  |  |
| 96 | 3 | 17 |  | 69 |
| 97 | 8 | 18 |  |  |
| 98 | 62 | 51 |  |  |
| 99 | 49 | 46 |  |  |
| 100 | 12 | 13 |  |  |
| 101 | 4 | 8 |  | 82 |
| 102 | 10 | 35 |  | 8 |
| 103 | 24 | 20 |  |  |
| 104 | 23 | 27 |  |  |
| 105 | 87 | 15 |  |  |
| 106 | 16 | 21 |  |  |
| 107 | 13 | 21 |  |  |
| 108 | 17 | 14 | 13 | 43 |
| 109 | 16 | 23 |  |  |
| 110 | 8 | 38 | 10 | 32 |
| 111 | 13 | 71 |  |  |
| 112 | 13 | 18 |  |  |
| 113 | 23 | 25 |  |  |
| 114 | 13 | 22 |  |  |
| 115 | 2 | 15 | 2 | 44 |
| 116 | 12 | 17 |  |  |
| 117 | 6 | 18 |  |  |
| 118 | 22 | 85 |  |  |
| 119 | 12 | 54 |  |  |
| 120 | 43 | 98 |  |  |
| 121 | 37 | 14 | 20 | 102 |
| 122 | 142 | 130 |  |  |
| 123 | 13 | 24 |  | 85 |
| 124 | 23 | 36 |  |  |
| 125 | 22 | 31 |  |  |
| 126 | 16 | 116 |  |  |
| 127 | 20 | 21 |  | 91 |
| 128 | 10 | 53 |  |  |
| 129 | 12 | 102 |  |  |
| 130 | 5 | 43 | 16 | 32 |
| 131 | 8 | 31 |  |  |
| 132 | 22 | 15 |  |  |
| 133 | 66 | 15 |  |  |
| 134 | 4 | 31 | 4 |  |
| 135 | 11 | 47 |  |  |
| 136 | 29 | 22 |  |  |
| 137 | 14 | 33 |  |  |
| 138 |  | 30 |  |  |
| 139 | 14 | 30 |  |  |
| 140 |  | 10000 |  |  |
| 141 |  | 2704 |  |  |
| 142 | 111 | 28 |  |  |
| 143 | 16 | 12 |  |  |
| 144 | 28 | 26 |  |  |
| 145 | 10000 | 10000 |  |  |
| 146 | 10000 | 7007 |  |  |
| 147 | 10000 | 3505 |  |  |
| 148 | 10000 | 1382 |  |  |
We claim:
1. A compound represented by Formula I:
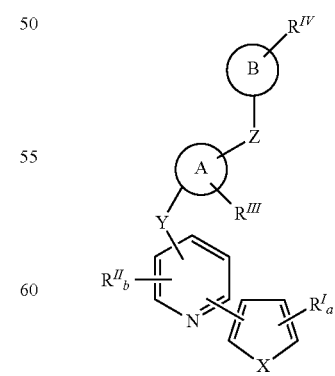
Formula I
or a pharmaceutically acceptable salt thereof, wherein:
X is NH;

$R^I$ is selected from the group consisting of:

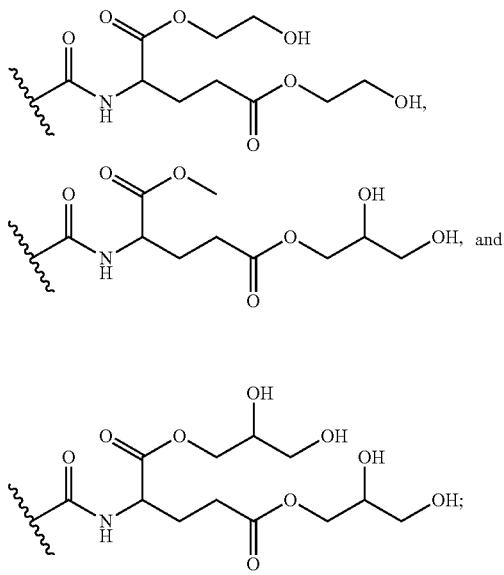

a is 1;
$R^{II}$ is hydrogen;
b is 1;
Y is

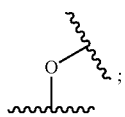 [SMILES: *O*]

Ring A in the structure

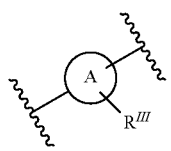

is phenyl;
$R^{III}$ represents optionally halogen;
Z is

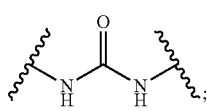 [SMILES: *NC(=O)N*]

Ring B in the structure

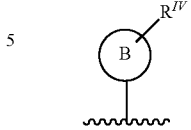

is phenyl; and
$R^{IV}$ represents optionally 1-2 substituents, independently selected from the group consisting of methyl and halogen.

2. The compound of claim 1 selected from the group consisting of:
bis(2-hydroxyethyl) 2-{[(5-{4-[3-fluoro-4-({[(3-methylphenyl)amino]carbonyl}amino)phenoxy]pyridin-2-yl}-1H-pyrrol-3-yl)carbonyl]amino}pentanedioate;
5-(2,3-dihydroxypropyl) 1-methyl 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate; and
bis(2,3-dihydroxypropyl) 2-{[(5-{4-[4-({[(2-fluoro-5-methylphenyl)amino]carbonyl}amino)phenoxy]pyridin-2-yl}-1H-pyrrol-3-yl)carbonyl]amino}pentanedioate;
or a pharmaceutically acceptable salt thereof.

3. A pharmaceutical composition comprising at least one compound of claim 1 and at least one pharmaceutically acceptable carrier.

4. The pharmaceutical composition of claim 3, wherein the composition comprises of tablets, capsules, creams, gels, ointments, drops, sprays, suspensions, and emulsions.

5. A pharmaceutical composition comprising at least one compound of claim 1 and at least one pharmaceutically acceptable carrier.

6. The pharmaceutical composition of claim 5, wherein the composition comprises of tablets, capsules, creams, gels, ointments, drops, sprays, suspensions, and emulsions.

7. A method of treating a disease or condition in a human subject, wherein said disease or condition is selected from the group consisting of diabetic retinopathy, macular degeneration, age-related macular degeneration, and retinopathy of prematurity, comprising administering to said human subject a therapeutically effective amount of at least one compound of claim 1 or a pharmaceutically acceptable salt thereof.

8. The method of claim 7, wherein said administration is through intravitreal injection, subtenon injection, ophthalmic bioerodible implant, non-bioerodible ophthalmic insert and depots.

9. A method of treating a disease or condition in a human subject, wherein said disease or condition is selected from the group consisting of diabetic retinopathy, macular degeneration, age-related macular degeneration, and retinopathy of prematurity, comprising administering to said human subject a therapeutically effective amount of at least one compound of claim 2 or a pharmaceutically acceptable salt thereof.

10. The method of claim 9, wherein said administration is through intravitreal injection, subtenon injection, ophthalmic bioerodible implant, non-bioerodible ophthalmic insert and depots.

* * * * *

UNITED STATES PATENT AND TRADEMARK OFFICE
CERTIFICATE OF CORRECTION

PATENT NO.           : 9,725,433 B2                                          Page 1 of 10
APPLICATION NO.      : 15/269612
DATED                : August 8, 2017
INVENTOR(S)          : Xialing Guo et al.

It is certified that error appears in the above-identified patent and that said Letters Patent is hereby corrected as shown below:

On the page 2, in Column 2, under "Other Publications", Line 2, delete "Chorodial" and insert -- Choroidal --, therefor.

In Column 2, Line 10, delete "phophorylation" and insert -- phosphorylation --, therefor.

In Column 2, Line 47, delete "Oncogen" and insert -- Oncogene --, therefor.

In Column 3, Line 61, delete "(N $R^2R^3$)," and insert -- ($NR^2R^3$), --, therefor.

In Column 3, Lines 63-64, delete "alkyl sulfonyl, aryl sulfonyl," and insert -- alkylsulfonyl, arylsulfonyl, --, therefor.

In Column 4, Line 8, delete "($CR^5 R^6$)$_d$" and insert -- ($CR^5R^6$)$_d$ --, therefor.

In Column 4, Line 9, delete "($CR^5 R^6$)$_d$" and insert -- ($CR^5R^6$)$_d$ --, therefor.

In Column 4, Line 9, delete "($CR^5 R^6$)$_e$" and insert -- ($CR^5R^6$)$_e$ --, therefor.

In Column 4, Line 10, delete "($CR^5 R^6$)$_d$" and insert -- ($CR^5R^6$)$_d$ --, therefor.

In Column 4, Line 10, delete "($CR^5 R^6$)$_e$" and insert -- ($CR^5R^6$)$_e$ --, therefor.

In Column 4, Line 12, delete "S(O)$R^5 R^6$," and insert -- S(O)$R^5R^6$, --, therefor.

In Column 4, Line 60, delete "$SO_2N R^2$" and insert -- $SO_2NR^2$ --, therefor.

In Column 5, Line 15, delete "(N $R^2R^3$)," and insert -- ($NR^2R^3$), --, therefor.

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*

In Column 5, Line 17, delete "alkyl sulfonyl, aryl sulfonyl," and insert -- alkylsulfonyl, arylsulfonyl, --, therefor.

In Column 5, Line 23, delete "alkyl sulfonyl, aryl sulfonyl," and insert -- alkylsulfonyl, arylsulfonyl, --, therefor.

In Column 6, Line 16, delete "(N R$^2$R$^3$)," and insert -- (NR$^2$R$^3$), --, therefor.

In Column 6, Line 18, delete "alkyl sulfonyl, aryl sulfonyl," and insert -- alkylsulfonyl, arylsulfonyl, --, therefor.

In Column 7, Line 26, delete "(N R$^2$R$^3$)," and insert -- (NR$^2$R$^3$), --, therefor.

In Column 7, Line 28, delete "alkyl sulfonyl, aryl sulfonyl," and insert -- alkylsulfonyl, arylsulfonyl, --, therefor.

In Column 7, Line 37, delete "—NR$^9$R$^{10}$," and insert -- —NR$^9$R$^{10}$; --, therefor.

In Column 7, Line 60, delete "SO$_2$N R$^2$" and insert -- SO$_2$NR$^2$ --, therefor.

In Column 9, Line 50, delete "~4~-" and insert -- -4- --, therefor.

In Column 10, Line 8, delete "SO$_2$N R$^2$" and insert -- SO$_2$NR$^2$ --, therefor.

In Column 10, Line 62, delete "(CR$^5$ R$^6$)$_d$" and insert -- (CR$^5$R$^6$)$_d$ --, therefor.

In Column 10, Line 63, delete "S(O)R$^5$ R$^6$," and insert -- S(O)R$^5$R$^6$, --, therefor.

In Column 11, Line 51, delete "(N R$^2$R$^3$)," and insert -- (NR$^2$R$^3$), --, therefor.

In Column 11, Line 53, delete "alkyl sulfonyl, aryl sulfonyl," and insert -- alkylsulfonyl, arylsulfonyl, --, therefor.

In Column 12, Line 2, delete "alkyl sulfonyl" and insert -- alkylsulfonyl, --, therefor.

In Column 12, Line 10, delete "SO$_2$N R$^2$" and insert -- SO$_2$NR$^2$ --, therefor.

In Column 12, Line 30, delete "(N R$^2$R$^3$)," and insert -- (NR$^2$R$^3$), --, therefor.

In Column 12, Lines 32-33, delete "alkyl sulfonyl, aryl sulfonyl," and insert -- alkylsulfonyl, arylsulfonyl, --, therefor.

In Column 12, Line 38, delete "alkyl sulfonyl, aryl sulfonyl," and insert -- alkylsulfonyl, arylsulfonyl, --, therefor.

CERTIFICATE OF CORRECTION (continued)
U.S. Pat. No. 9,725,433 B2

In Column 13, Line 30, delete "(N R$^2$R$^3$)," and insert -- (NR$^2$R$^3$), --, therefor.

In Column 13, Lines 32-33, delete "alkyl sulfonyl, aryl sulfonyl," and insert -- alkylsulfonyl, arylsulfonyl, --, therefor.

In Column 14, Line 41, delete "(N R$^2$R$^3$)," and insert -- (NR$^2$R$^3$), --, therefor.

In Column 14, Lines 44-45, delete "alkyl sulfonyl, aryl sulfonyl," and insert -- alkylsulfonyl, arylsulfonyl, --, therefor.

In Column 14, Line 65, delete "SO$_2$N R$^2$" and insert -- SO$_2$NR$^2$ --, therefor.

In Column 15, Line 42, delete "modulators;" and insert -- modulators. --, therefor.

In Column 15, Line 49, delete "carrier;" and insert -- carrier. --, therefor.

In Column 16, Line 17, delete "biodrodible" and insert -- bioerodible --, therefor.

In Column 16, Line 17, delete "-bioeordible" and insert -- -bioerodible --, therefor.

In Column 17, Line 25, delete "(N R$^2$R$^3$)," and insert -- (NR$^2$R$^3$), --, therefor.

In Column 17, Line 28, delete "aryl sulfonyl," and insert -- arylsulfonyl, --, therefor.

In Column 17, Line 39, delete "(CR$^5$ R$^6$)$_d$" and insert -- (CR$^5$R$^6$)$_d$ --, therefor.

In Column 17, Line 40, delete "(CR$^5$ R$^6$)$_e$" and insert -- (CR$^5$R$^6$)$_e$ --, therefor.

In Column 17, Line 41, delete "(CR$^5$ R$^6$)$_d$" and insert -- (CR$^5$R$^6$)$_d$ --, therefor.

In Column 17, Line 41, delete "(CR$^5$ R$^6$)$_e$" and insert -- (CR$^5$R$^6$)$_e$ --, therefor.

In Column 17, Line 43, delete "S(O)R$^5$ R$^6$," and insert -- S(O)R$^5$R$^6$, --, therefor.

In Column 17, Line 64, delete "(CR$^5$ R$^6$)," and insert -- (CR$^5$R$^6$)$_e$ --, therefor.

In Column 18, Line 15, delete "alkyl sulfonyl," and insert -- alkylsulfonyl, --, therefor.

In Column 18, Line 23, delete "SO$_2$N R$^2$" and insert -- SO$_2$NR$^2$ --, therefor.

In Column 18, Line 37, delete "bond." and insert -- bond; --, therefor.

In Column 18, Line 44, delete "(N R$^2$R$^3$)," and insert -- (NR$^2$R$^3$), --, therefor.

In Column 18, Lines 46-47, delete "alkyl sulfonyl, aryl sulfonyl," and insert -- alkylsulfonyl, arylsulfonyl, --, therefor.

CERTIFICATE OF CORRECTION (continued)
U.S. Pat. No. 9,725,433 B2

In Column 18, Line 53, delete "alkyl sulfonyl, aryl sulfonyl," and insert -- alkylsulfonyl, arylsulfonyl, --, therefor.

In Column 19, Line 43, delete "(N $R^2R^3$)," and insert -- ($NR^2R^3$), --, therefor.

In Column 19, Line 45, delete "alkyl sulfonyl, aryl sulfonyl," and insert -- alkylsulfonyl, arylsulfonyl, --, therefor.

In Column 19, Line 48, delete "N." and insert -- N; --, therefor.

In Column 19, Line 61, delete "$(CH_1)_j$;" and insert -- $(CH_2)_j$; --, therefor.

In Column 20, Line 53, delete "(N $R^2R^3$)," and insert -- ($NR^2R^3$), --, therefor.

In Column 20, Line 55, delete "alkyl sulfonyl, aryl sulfonyl," and insert -- alkylsulfonyl, arylsulfonyl, --, therefor.

In Column 21, Line 26, delete "(N $R^2R^3$)," and insert -- ($NR^2R^3$), --, therefor.

In Column 21, Line 28, delete "alkyl sulfonyl, aryl sulfonyl," and insert -- alkylsulfonyl, arylsulfonyl, --, therefor.

In Column 21, Line 45, delete "alkyl sulfonyl," and insert -- alkylsulfonyl, --, therefor.

In Column 21, Line 53, delete "$SO_2N\ R^2$" and insert -- $SO_2NR^2$ --, therefor.

In Column 22, Line 7, delete "(N $R^2R^3$)," and insert -- ($NR^2R^3$), --, therefor.

In Column 22, Lines 9-10, delete "alkyl sulfonyl, aryl sulfonyl," and insert -- alkylsulfonyl, arylsulfonyl, --, therefor.

In Column 22, Lines 15-16, delete "alkyl sulfonyl, aryl sulfonyl, haloalkyl sulfonyl," and insert -- alkylsulfonyl, arylsulfonyl, haloalkylsulfonyl, --, therefor.

In Column 23, Line 2, delete "R" and insert -- $R^1$ --, therefor.

In Column 23, Line 5, delete "(N $R^2R^3$)," and insert -- ($NR^2R^3$), --, therefor.

In Column 23, Lines 7-8, delete "alkyl sulfonyl, aryl sulfonyl," and insert -- alkylsulfonyl, arylsulfonyl, --, therefor.

In Column 24, Line 16, delete "(N $R^2R^3$)," and insert -- ($NR^2R^3$), --, therefor.

In Column 24, Lines 18-19, delete "alkyl sulfonyl, aryl sulfonyl," and insert -- alkylsulfonyl, arylsulfonyl, --, therefor.

CERTIFICATE OF CORRECTION (continued)

In Column 26, Line 40, delete "biodrodible" and insert -- bioerodible --, therefor.

In Column 26, Line 40, delete "-bioeordible" and insert -- -bioerodible --, therefor.

In Columns 25-26, Line 3, in table 1, delete "Sructure" and insert -- Structure --, therefor.

In Columns 25-26, Line 3, in table 1-continued, delete "Sructure" and insert -- Structure --, therefor.

In Columns 25-26, Line 17, in table 1-continued, delete "amino)" and insert -- amino] --, therefor.

In Columns 29-30, Line 3, in table 1-continued, delete "Sructure" and insert -- Structure --, therefor.

In Columns 31-32, Line 3, in table 1-continued, delete "Sructure" and insert -- Structure --, therefor.

In Columns 33-34, Line 3, in table 1-continued, delete "Sructure" and insert -- Structure --, therefor.

In Columns 35-36, Line 3, in table 1-continued, delete "Sructure" and insert -- Structure --, therefor.

In Columns 37-38, Line 3, in table 1-continued, delete "Sructure" and insert -- Structure --, therefor.

In Columns 39-40, Line 3, in table 1-continued, delete "Sructure" and insert -- Structure --, therefor.

In Columns 41-42, Line 3, in table 1-continued, delete "Sructure" and insert -- Structure --, therefor.

In Columns 43-44, Line 3, in table 1-continued, delete "Sructure" and insert -- Structure --, therefor.

In Columns 45-46, Line 3, in table 1-continued, delete "Sructure" and insert -- Structure --, therefor.

In Columns 47-48, Line 3, in table 1-continued, delete "Sructure" and insert -- Structure --, therefor.

In Columns 47-48, Line 13, in table 1-continued, delete "}-" and insert -- }-1H- --, therefor.

In Columns 49-50, Line 3, in table 1-continued, delete "Sructure" and insert -- Structure --, therefor.

In Columns 51-52, Line 3, in table 1-continued, delete "Sructure" and insert -- Structure --, therefor.

In Columns 53-54, Line 3, in table 1-continued, delete "Sructure" and insert -- Structure --, therefor.

In Columns 53-54, Line 6, in table 1-continued, delete "-({(" and insert -- -({[( --, therefor.

In Columns 55-56, Line 3, in table 1-continued, delete "Sructure" and insert -- Structure --, therefor.

In Columns 55-56, Line 5, in table 1-continued, delete "-({[" and insert -- -({[( --, therefor.

In Columns 57-58, Line 3, in table 1-continued, delete "Sructure" and insert -- Structure --, therefor.

In Columns 59-60, Line 3, in table 1-continued, delete "Sructure" and insert -- Structure --, therefor.

In Columns 61-62, Line 3, in table 1-continued, delete "Sructure" and insert -- Structure --, therefor.

In Columns 63-64, Line 3, in table 1-continued, delete "Sructure" and insert -- Structure --, therefor.

In Columns 65-66, Line 3, in table 1-continued, delete "Sructure" and insert -- Structure --, therefor.

In Columns 67-68, Line 3, in table 1-continued, delete "Sructure" and insert -- Structure --, therefor.

In Columns 67-68, Line 8, in table 1-continued, delete "-methyphenyl)" and insert -- -methylphenyl) --, therefor.

In Columns 69-70, Line 3, in table 1-continued, delete "Sructure" and insert -- Structure --, therefor.

In Columns 69-70, Line 16, in table 1-continued, delete "amino)" and insert -- amino] --, therefor.

In Columns 71-72, Line 3, in table 1-continued, delete "Sructure" and insert -- Structure --, therefor.

In Columns 71-72, Line 9, in table 1-continued, delete "I-" and insert -- 1- --, therefor.

In Columns 73-74, Line 3, in table 1-continued, delete "Sructure" and insert -- Structure --, therefor.

In Columns 73-74, Line 9, in table 1-continued, delete "I-" and insert -- 1- --, therefor.

In Columns 75-76, Line 3, in table 1-continued, delete "Sructure" and insert -- Structure --, therefor.

In Columns 75-76, Line 4, in table 1-continued, delete "-fluoro)-" and insert -- -fluoro- --, therefor.

In Columns 75-76, Line 7, in table 1-continued, delete "-3-" and insert -- -2- --, therefor.

In Columns 75-76, Line 9, in table 1-continued, delete "-(4-" and insert -- -{4- --, therefor.

In Columns 77-78, Line 3, in table 1-continued, delete "Sructure" and insert -- Structure --, therefor.

In Columns 79-80, Line 3, in table 1-continued, delete "Sructure" and insert -- Structure --, therefor.

In Columns 79-80, Line 8, delete "-carboxlic" and insert -- -carboxylic --, therefor.

In Columns 79-80, Line 9, delete "~4~-" and insert -- -4- --, therefor.

In Column 79-80, Line 23, delete "~4~-" and insert -- -4- --, therefor.

In Columns 81-82, Line 3, in table 1-continued, delete "Sructure" and insert -- Structure --, therefor.

In Columns 81-82, Line 12, in table 1-continued, delete "~4~-" and insert -- -4- --, therefor.

In Columns 83-84, Line 3, in table 1-continued, delete "Sructure" and insert -- Structure --, therefor.

In Columns 85-86, Line 3, in table 1-continued, delete "Sructure" and insert -- Structure --, therefor.

In Columns 87-88, Line 3, in table 1-continued, delete "Sructure" and insert -- Structure --, therefor.

In Columns 87-88, Line 11, in table 1-continued, delete "}-" and insert -- }-1H- --, therefor.

In Columns 89-90, Line 3, in table 1-continued, delete "Sructure" and insert -- Structure --, therefor.

In Columns 91-92, Line 3, in table 1-continued, delete "Sructure" and insert -- Structure --, therefor.

In Columns 91-92, Lines 9-13, in table 1-continued, delete " 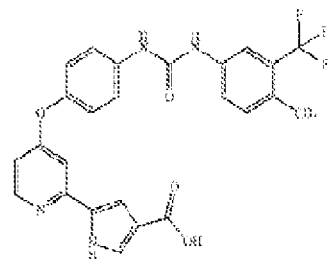 " and insert -- 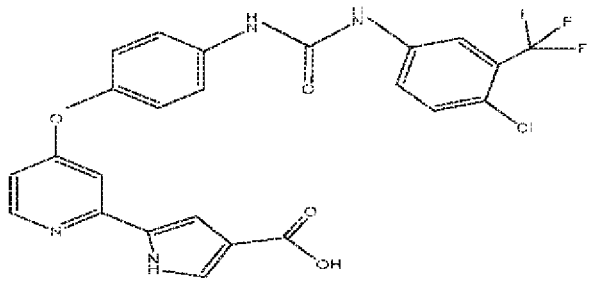 --, therefor.

In Columns 93-94, Line 3, in table 1-continued, delete "Sructure" and insert -- Structure --, therefor.

In Columns 95-96, Line 3, in table 1-continued, delete "Sructure" and insert -- Structure --, therefor.

In Columns 97-98, Line 3, in table 1-continued, delete "Sructure" and insert -- Structure --, therefor.

In Columns 99-100, Line 3, in table 1-continued, delete "Sructure" and insert -- Structure --, therefor.

In Columns 99-100, Line 12, in table 1-continued, delete "~4~-" and insert -- -4- --, therefor.

In Columns 101-102, Line 3, in table 1-continued, delete "Sructure" and insert -- Structure --, therefor.

In Columns 101-102, Line 11, in table 1-continued, delete "]pyridrin-" and insert -- ]pyridin- --, therefor.

In Columns 103-104, Line 3, in table 1-continued, delete "Sructure" and insert -- Structure --, therefor.

In Columns 103-104, Line 13, in table 1-continued, delete "-1H-" and insert -- -1H)- --, therefor.

In Columns 105-106, Line 3, in table 1-continued, delete "Sructure" and insert -- Structure --, therefor.

In Column 107, Line 52, delete "mmol),)" and insert -- mmol), --, therefor.

In Column 108, Line 17, delete "mmol),)" and insert -- mmol), --, therefor.

In Column 123, Line 46, delete "4-(4" and insert -- 444 --, therefor.

In Column 125, Lines 53-54, delete "-dimethyllaminopropyl)" and insert -- -dimethylaminopropyl) --, therefor.

In Column 127, Lines 25-34, delete "(20 mg, 0.046 mmol) in a mixture of solvents THF/MeOH (5 ml/5 ml) was added 3 ml of 1M NaOH (3 mmol) solution. The mixture was heated in a 72° C. bath for 3 hours, cooled to room temperature and poured into 50 ml of water. 2M HCl was added until pH=4. The resulting precipitates were filtered, washed with water, and dried in vacuo to give 5-(4-{4-fluoro-3-[(3-methyl-2-furoyl)amino]phenoxy}pyridin-2-yl)-1H-pyrrole-3-carboxylic acid as light gray solid. Yield: 19 mg, 100%." and insert the same on Column 127, Line 24, as a continuation of the same paragraph.

In Column 128, Line 1, delete "~4~-" and insert -- -4- --, therefor.

In Column 130, Line 43, delete "HBTU" and insert -- HATU --, therefor.

In Column 132, Line 24, delete "mmol),)" and insert -- mmol), --, therefor.

In Column 132, Line 35, delete "1050%" and insert -- 10~50% --, therefor.

In Column 147, Lines 5-6, delete "-dimethyllaminopropyl)" and insert -- -dimethylaminopropyl) --, therefor.

In Column 147, Line 29, delete "-1-H-" and insert -- -1H- --, therefor.

In Column 159, Line 54, delete "-Dichloropyrdine" and insert -- -Dichloropyridine --, therefor.

In Column 169, Line 54, delete "~4~-" and insert -- -4- --, therefor.

In Column 170, Line 40, delete "~4~-" and insert -- -4- --, therefor.

In Column 171, Line 8, delete "methy" and insert -- methyl --, therefor.
In Column 171, Line 45, delete "~4~-" and insert -- -4- --, therefor.

CERTIFICATE OF CORRECTION (continued)
U.S. Pat. No. 9,725,433 B2

In Column 172, Line 19, delete "~4~-" and insert -- -4- --, therefor.

In Column 178, Line 11, delete "4[(4-" and insert -- 4-[4- --, therefor.

In Column 188, Line 40, delete "-dimethyllaminopropyl)" and insert -- -dimethylaminopropyl) --, therefor.

In Column 190, Line 4, delete "(3 S)-" and insert -- (3S)- --, therefor.

In Column 193, Line 4, delete "~4~-" and insert -- -4- --, therefor.

In Column 193, Line 67, delete "(M-H" and insert -- (M-H) --, therefor.

In Column 202, Line 24, delete ".mu·M)" and insert -- .mu.M) --, therefor.

In Column 202, Line 25, delete ".mu·M" and insert -- .mu.M --, therefor.

In Column 202, Line 41, delete ".mu·g" and insert -- .mu.g --, therefor.

In Column 202, Line 45, delete ".mu·L" and insert -- .mu.L --, therefor.

In Column 202, Line 45, delete ".mu·M" and insert -- .mu.M --, therefor.

In Column 202, Line 53, delete ".mu·l" and insert -- .mu.l --, therefor.

In Column 202, Line 56, delete ".mu·l" and insert -- .mu.l --, therefor.

In Column 202, Line 61, delete ".mu·l" and insert -- .mu.l --, therefor.

In Column 203, Line 11, delete "100 .mu·l PBS and of 100 .mu·l" and insert -- 100 .mu.l PBS and of 100 .mu.l --, therefor.

In Column 203, Line 13, delete "cuthanized with Pentosol," and insert -- euthanized with Pentosol, --, therefor.

In Column 203, Line 41, delete "71:523~533))." and insert -- 71:523-533). --, therefor.

In Column 203, Line 45, delete ".mu·m" and insert -- .mu.m --, therefor.

In Column 205, Line 1, delete "1II" and insert -- III --, therefor.

In Column 205, Line 37, delete "76" and insert -- 75 --, therefor.

In Column 206, Line 1, delete "1II" and insert -- III --, therefor.

CERTIFICATE OF CORRECTION (continued)
U.S. Pat. No. 9,725,433 B2

In Column 208, Line 34, in Claim 5, delete "claim 1" and insert -- claim 2 --, therefor.